United States Patent
Paidi et al.

(10) Patent No.: US 9,242,976 B2
(45) Date of Patent: Jan. 26, 2016

(54) THIAZOLYL- OR THIADIAZOLYL-SUBSTITUTED PYRIDYL COMPOUNDS USEFUL AS KINASE INHIBITORS

(71) Applicant: BRISTOL-MYERS SQUIBB COMPANY, Princeton, NJ (US)

(72) Inventors: Venkatram Reddy Paidi, Bangalore (IN); Sreekantha Ratna Kumar, Bangalore (IN); Abhisek Banerjee, West Bengal (IN); Ramesh Sistla, Bangalore (IN); Satheesh Kesavan Nair, Bangalore (IN); William J. Pitts, Newtown, PA (US); John Hynes, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/371,463

(22) PCT Filed: Jan. 11, 2013

(86) PCT No.: PCT/US2013/021134
§ 371 (c)(1),
(2) Date: Jul. 10, 2014

(87) PCT Pub. No.: WO2013/106641
PCT Pub. Date: Jul. 18, 2013

(65) Prior Publication Data
US 2015/0018344 A1 Jan. 15, 2015

Related U.S. Application Data

(60) Provisional application No. 61/586,148, filed on Jan. 13, 2012.

(51) Int. Cl.
| | |
|---|---|
| *C07D 417/14* | (2006.01) |
| *C07D 413/14* | (2006.01) |
| *C07D 413/04* | (2006.01) |
| *C07D 417/04* | (2006.01) |
| *C07D 471/04* | (2006.01) |
| *C07D 487/04* | (2006.01) |

(52) U.S. Cl.
CPC ............ *C07D 417/14* (2013.01); *C07D 413/04* (2013.01); *C07D 413/14* (2013.01); *C07D 417/04* (2013.01); *C07D 471/04* (2013.01); *C07D 487/04* (2013.01)

(58) Field of Classification Search
CPC ...................................................... C07D 417/14
USPC ......................................... 546/193; 514/318
See application file for complete search history.

(56) References Cited

U.S. PATENT DOCUMENTS

| | | | |
|---|---|---|---|
| 8,586,751 B2 | 11/2013 | De Lucca et al. | |
| 2005/0272753 A1 | 12/2005 | Nagashima et al. | |
| 2006/0148800 A1 | 7/2006 | Stadtmueller et al. | |
| 2009/0082329 A1 | 3/2009 | Halley et al. | |

FOREIGN PATENT DOCUMENTS

| | | |
|---|---|---|
| EP | 2 532 656 | 12/2012 |
| GB | 2 388 596 | 11/2003 |
| WO | WO 02/102800 A1 | 12/2002 |
| WO | WO 03/013523 A1 | 2/2003 |
| WO | WO 2004/065378 A1 | 8/2004 |
| WO | WO 2005/007646 A1 | 1/2005 |
| WO | WO 2005/075468 A2 | 8/2005 |
| WO | WO 2008/148889 A1 | 12/2008 |
| WO | WO 2009/046416 A1 | 4/2009 |
| WO | WO 2011/053701 A1 | 5/2011 |
| WO | WO 2012/149567 A1 | 11/2012 |

OTHER PUBLICATIONS

Dorwald, Side Reactions in Organic Synthesis, 2005, Wiley: VCH Weinheim Preface, pp. 1-15 & Chapter 8, pp. 279-308.*
U.S. Appl. No. 14/371,281, filed Jul. 9, 2014, Dharmpal S. Dodd.
U.S. Appl. No. 14/371,456, filed Jul. 10, 2014, Paidi et al.

* cited by examiner

*Primary Examiner* — Patricia L Morris
(74) *Attorney, Agent, or Firm* — Gary D. Greenblatt

(57) ABSTRACT

Compounds having the following formula (I) or an enantiomer, diastereomer or a pharmaceutically-acceptable salt thereof, wherein X is N or C—$R^7$, are useful as kinase modulators, including IRAK-4 modulation.

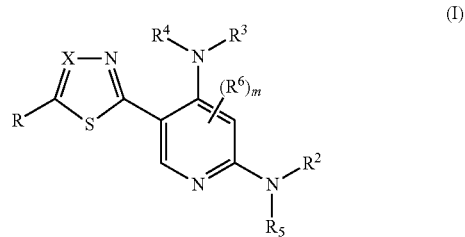

7 Claims, No Drawings

THIAZOLYL- OR THIADIAZOLYL-SUBSTITUTED PYRIDYL COMPOUNDS USEFUL AS KINASE INHIBITORS

FIELD OF THE INVENTION

This invention relates to compounds useful as kinase inhibitors, including the modulation of IRAK-4. Provided herein are heterocyclic-substituted pyridyl compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal

BACKGROUND OF THE INVENTION

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T., et al. 2010, Nature Immunol. 11:373-384). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E., et al. 2010, Nature Rev. Immunol. 10: 89-102).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S., et al., 2010, Nature 465: 885-890). IRAK4 directly phosphorylates IRAK1 to facilitate downstream signaling to the E3 ubiquitin ligase TRAF6, resulting in activation of the serine/threonine kinase TAK1 with subsequent activation of the NF kappaB pathway and MAPK cascade (Flannery, S. et al., 2010, Biochem. Pharmacol. 80: 1981-1991). A subset of human patients was identified who lack IRAK4 expression (Picard, C. et al., 2003, Science 299: 2076-2079). Cells from these patients fail to respond to all TLR agonists with the exception of TLR3 as well as to members of the IL-1 family including IL-1β and IL-18 (Ku, C. et al., 2007, J. Exp. Med. 204: 2407-2422). Deletion of IRAK4 in mice results in a severe block in IL-1, IL-18 and all TLR dependent responses with the exception of TLR3 (Suzuki, N. et al., 2002, Nature 416: 750-754). In contrast, deletion of either IRAK1 (Thomas, J. A. et al. 1999, J. Immunol. 163: 978-984; Swantek, J. L. et al., 2000, J. Immunol. 164: 4301-4306) or IRAK2 (Wan, Y. et al., 2009, J. Biol. Chem. 284: 10367-10375) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., 2007, J. Biol. Chem. 282: 13552-13560; Kawagoe, T et al., 2007, J. Exp. Med. 204: 1013-1024; and Fraczek, J. et al., 2008, J. Biol. Chem. 283: 31697-31705).

As compared to wild type animals, IRAK4 KDKI mice show greatly reduced disease severity in mouse models of multiple sclerosis (Staschke, K. A. et al., 2009, J. Immunol. 183: 568-577), rheumatoid arthritis (Koziczak-Holbro, M. et al., 2009, Arthritis Rheum. 60: 1661-1671), atherosclerosis (Kim, T. W. et al., 2011, J. Immunol. 186: 2871-2880 and Rekhter, M. et al., 2008, Bioch. Bioph. Res. Comm. 367: 642-648), and myocardial infarction (Maekawa, Y., et al., 2009 Circulation 120: 1401-1414). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and Ulcerative colitis, autoimmune uveitis, asthma, allergy, type I diabetes, and allograft rejection (Keogh, B. et al., 2011, Trends Pharmacol. Sci. 32: 435-442; Mann, D. L. 2011, Circ. Res. 108: 1133-1145; Horton, C. G. et al., 2010, Med. Inflamm. Pii. 498980; Goldstein, D. R. et al., 2005, J. Heart Lung Transpl. 24: 1721-1729; and Cario, E., 2010, Inflamm. Bowel Dis. 16: 1583-1597). Oncogenically active MyD88 mutations in diffuse large B cell lymphomas have been identified that are sensitive to IRAK4 inhibition (Ngo, V N et al., 2011, Nature 470: 115-121). Whole genome sequencing also identified mutations in MyD88 associated with chronic lymphatic leukemia suggesting that IRAK4 inhibitors may also have utility in treating leukemias (Puente, X. S. et al., 2011, Nature 475: 101-105).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; autoinflammatory diseases including CAPS, TRAPS, FMF, adult onset stills; systemic onset juvenile idiopathic arthritis; stroke; GVHD; smoldering multiple myeloma; recurrent pericarditis; osteoarthritis; emphysema (Dinarello, C. A., 2011, Eur. J. Immunol. 41: 1203-1217 and Couillin, I. et al., 2009. J. Immunol. 183: 8195-8202). In a mouse model of Alzheimer's disease, blockade of IL-1 receptor improved cognitive defects, attenuated tau pathology and reduced oligomeric forms of amyloid-β (Kitazawa, M. et al., 2011, J. Immunol. 187: 6539-6549). IL-1 has also been shown to be a critical link to adaptive immunity, driving differentiation of the TH17 effector T cell subset (Chung, Y., Chang, S. H. et al., 2009, Immunity 30: 576-587). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M., et al., 2011, Trends Immunol. 32: 603-61).

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heterocyclic-substituted pyridyl compounds found to be effective inhibitors of protein kinases including IRAK-4.

SUMMARY OF THE INVENTION

Modulators of kinase activity which may generally be described as heterocyclic-substituted pyridyl compounds found are provided herein.

The invention is directed to compounds of Formula I that which are useful as inhibitors of IRAK-4, and are useful for the treatment of proliferative diseases, allergic diseases, autoimmune diseases and inflammatory diseases, or stereoisomers, tautomers, pharmaceutically acceptable slats, solvates or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

A preferred embodiment is a method for treating inflammatory and autoimmune diseases wherein the treatment of inflammatory diseases is even more preferred. Particular, inflammatory and autoimmune diseases include, but are not limited to, Crohn's, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

An alternate preferred embodiment is a method for treating metabolic diseases, including type 2 diabetes and atherosclerosis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE EMBODIMENTS OF THE INVENTION

Provided herein is at least one chemical entity chosen from compounds of formula (I):

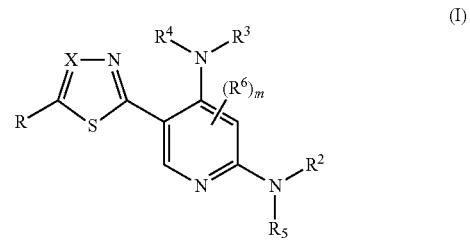

or a stereoisomer or pharmaceutically-acceptable salt thereof, wherein

X is N or C—$R^7$;

R is $R^1$, halogen, cyano, nitro, —O—$R^1$, —C(=O)—$R^1$, —C(=O)O—$R^1$, —C(=O)$NR^{11}$—$R^1$, —S(=O)$_2$—$R^1$, —$NR^{11}$C(=O)—$R^1$, —$NR^{11}$C(=O)$NR^{11}$—$R^1$, —$NR^{11}$C(=O)O—$R^1$, —$NR^{11}$S(=O)$_2$—$R^1$, or —$NR^{11}$—$R^1$;

$R^1$ is $C_{1-6}$ alkyl substituted with 0-4 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocycle containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^2$ is $C_{6-10}$ aryl substituted with 0-4 $R^{2a}$, a 5-10 membered heterocycle containing 1-4 heteroatoms selected from N, O, and S, substituted with 0-4 $R^{2a}$, a 5-10 membered heteroaryl containing 1-4 heteroatoms selected from N, O, and S, substituted with 0-4 $R^{2a}$;

$R^{2a}$ at each occurrence is independently selected from hydrogen, =O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)Rb$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-2 $R^a$;

$R^3$ is $C_{1-6}$ alkyl substituted with 0-3 $R^{3a}$, $C_{1-6}$ haloalkyl, $C_{2-6}$ alkenyl substituted with 0-3 $R^{3a}$, $C_{2-6}$ alkynyl substituted with 0-3 $R^{3a}$, $C_{3-10}$ cycloalkyl substituted with 0-3 $R^{3a}$, $C_{6-10}$ aryl substituted with 0-3 $R^{3a}$, a 5-10 membered heterocycle containing 1-4 heteroatoms selected from N, O, and S, substituted with 0-3 $R^{3a}$, or a 5-10 membered heteroaryl containing 1-4 heteroatoms selected from N, O, and S, substituted with 0-3 $R^{3a}$;

$R^{3a}$ is hydrogen, =O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-1 Ra, or —$(CH_2)_r$-5-7 membered heterocycle or heteroaryl, each comprising carbon atoms and 1-4 heteroatoms selected from N, O, and $S(O)_p$ substituted with 0-1 $R^a$;

$R^4$ and $R^5$ are independently selected from hydrogen, $C_{1-4}$ alkyl substituted with 0-1 $R^f$, $(CH_2)$-phenyl substituted with 0-3 $R^d$, and a —$(CH_2)$-5-7 membered heterocycle comprising carbon atoms and 1-4 heteroatoms selected from N, O, and $S(O)_p$;

$R^6$ and $R^7$ are independently at each occurrence is selected from hydrogen, =O, F, Cl, Br, $OCF_3$, CN, $NO_2$, —$(CH_2)_rOR^b$, —$(CH_2)_rSR^b$, —$(CH_2)_rC(O)Rb$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$haloalkyl, —$(CH_2)_r$-3-14 membered carbocycle substituted with 0-3 $R^a$, or —$(CH_2)_r$-5-7 membered heterocycle or heteroaryl, each comprising carbon atoms and 1-4 heteroatoms selected from N, O, and $S(O)_p$ substituted with 0-3 $R^a$, provided $R^6$ and $R^7$ are not both hydrogen;

$R^{11}$ at each occurrence is independently $R^e$, $C_{1-4}$ alkyl substituted with 0-1 $R^f$, $CH_2$-phenyl substituted with 0-3 $R^d$, or —$(CH_2)$-5-7 membered heterocycle or heteroaryl, each comprising carbon atoms and 1-4 heteroatoms selected from N, O, and $S(O)_p$ substituted with 0-3 $R^d$;

alternatively, $R^{11}$ and along with another $R^{11}$, $R^1$, or $R^2$ on the same nitrogen atom may join to form an optionally substituted azetidinyl, pyrrolidinyl, piperidinyl, morpholinyl, or 4-($C_{1-6}$ alkyl)piperazinyl;

$R^a$ is $R^d$, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-1 $R^f$, $C_{1-6}$ haloalkyl, —$(CH_2)_r$-3-14 membered carbocycle, or —$(CH_2)_r$-5-7 membered heterocycle comprising carbon atoms and 1-4 heteroatoms selected from N, O, and $S(O)_p$; alternatively two $R^a$ on adjacent or the same carbon atom form a cyclic acetal of the formula —O—$(CH_2)_6$—O—, or —O—$CF_2$—O—, wherein n is selected from 1 or 2;

$R^b$ is $R^e$, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-3 $R^d$;

$R^c$ is $C_{1-6}$ alkyl substituted with 0-1 $R^f$, $C_{3-6}$ cycloalkyl, or $(CH_2)_r$-phenyl substituted with 0-3 $R^f$;

$R^d$ is hydrogen, F, Cl, Br, $OCF_3$, $CF_3$, CN, $NO_2$, —$OR^e$, —$(CH_2)_rC(O)R^e$, —$NR^eR^e$, —$NR^eC(O)OR^e$, $C_{1-6}$ alkyl, or $(CH_2)_r$-phenyl substituted with 0-3 $R^f$;

$R^e$ is selected from hydrogen, $C_{1-6}$ alkyl, $C_{3-6}$ cycloalkyl, and $(CH_2)_r$-phenyl substituted with 0-3 $R^f$;

$R^f$ is hydrogen, halo, $NH_2$, OH, or O($C_{1-6}$alkyl);

p is 0, 1, or 2;

r is 0, 1, 2, 3, or 4; and m is 0, 1, or 2.

In another embodiment, there is provided a compound of formula I, or a stereoisomer or pharmaceutically-acceptable salt thereof, wherein $R^2$ is phenyl, pyridyl, pyrimidinyl, naphthyl, benzothiazolyl, pyrazolopyridinyl, benzoisothiazolyl, triazolopyridinyl, imidazopyridinyl, benzooxazolyl, triazolopyridinyl, imidazopyridinyl, pyridopyrazinyl, quinazolinyl, pyridopyrazinyl, benzooxadiazolyl, benzothiadiazolyl, benzoimidazolyl, triazolopyridinyl, imdazopyridazinyl, pyridopyrazinyl, naphthyridinyl, quinoxalinyl, phthalazinyl, quinolinyl, indolyl, benzothiazolyl, benzodioxolyl, benzothienyl, isoquinolinyl, benzopyranyl, indolizinyl, benzofuranyl, chromonyl, coumarinyl, benzopyranyl, cinnolinyl, pyrrolopyridyl, furopyridyl, isoindolyl, or quinazolinyl, each group substituted by 1-4 groups selected from $R^{2a}$.

In another embodiment, there is provided a compound of formula I, wherein m is 0.

In another embodiment, there is provided a compound of formula I, wherein both $R^4$ and $R^5$ are hydrogen.

In another embodiment, there is provided a compound of formula

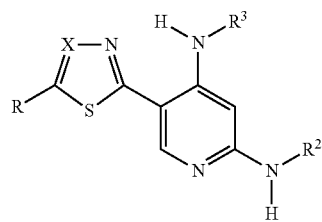

or a stereoisomer or pharmaceutically acceptable salt thereof, wherein:

R is —C(=O)—$R^1$, —C(=O)O—$R^1$ or —C(=O)$NR^{11}$—$R^1$;

$R^1$ is $C_{1-6}$ alkyl substituted with 0-4 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, $NR^bS(O)_pR^c$, —$S(O)R^c$, —$S(O)_2R^c$, $C_{1-6}$ alkyl substituted with 0-2 $R^a$, $C_{1-6}$ haloalkyl, —$(CH_2)_r$-3-14 membered carbocycle substituted with 0-3 Ra, or —$(CH_2)_r$-5-7 membered heterocycle or heteroaryl, each comprising carbon atoms and 1-4 heteroatoms selected from N, O, and $S(O)_p$ substituted with 0-3 $R^a$;

$R^2$ is phenyl, pyridyl, pyrimidinyl, naphthyl, benzothiazolyl, pyrazolopyridinyl, benzoisothiazolyl, triazolopyridinyl, imidazopyridinyl, benzooxazolyl, triazolopyridinyl, imidazopyridinyl, pyridopyrazinyl, quinazolinyl, pyridopyrazinyl, benzooxadiazolyl, benzothiadiazolyl, benzoimidazolyl, triazolopyridinyl, imdazopyridazinyl, pyridopyrazinyl, naphthyridinyl, quinoxalinyl, phthalazinyl, quinolinyl, indolyl, benzothiazolyl, benzodioxolyl, benzothienyl, isoquinolinyl, benzopyranyl, indolizinyl, benzofuranyl, chromonyl, coumarinyl, benzopyranyl, cinnolinyl, pyrrolopyridyl, furopyridyl, isoindolyl, or quinazolinyl each group substituted by 1-4 groups selected from $R^{2a}$;

$R^{2a}$ is hydrogen, =O, F, Cl, Br, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, $C_{1-6}$haloalkyl, —$(CH_2)_r$-3-14 membered carbocycle substituted with 0-1 $R^a$, or —$(CH_2)_r$-5-7 membered heterocycle or heteroaryl, each comprising carbon atoms and 1-4 heteroatoms selected from N, O, and $S(O)_p$ substituted with 0-1 $R^a$;

R³ is C₁₋₆ alkyl substituted with 0-3 $R^{3a}$, or a C₃₋₇cycloalkyl, phenyl, tetrahydropyranyl, tetrahydrofuranyl, or oxetane ring, each ring optionally substituted with 0-3 $R^{3a}$;

$R^{3a}$ is hydrogen, =O, F, Cl, Br, OCF₃, CN, NO₂, —(CH₂)ᵣOR$^b$, —(CH₂)ᵣSR$^b$, —(CH₂)ᵣC(O)R$^b$, —(CH₂)ᵣC(O)OR$^b$, —(CH₂)ᵣOC(O)R$^b$, —(CH₂)ᵣNR¹¹R¹¹, —(CH₂)ᵣC(O)NR¹¹R¹¹, —(CH₂)ᵣNR$^b$C(O)R$^c$, —(CH₂)ᵣNR$^b$C(O)OR$^c$, —NR$^b$C(O)NR¹¹R¹¹, —S(O)ₚNR¹¹R¹¹, —NR$^b$S(O)ₚR$^c$, —S(O)R$^c$, —S(O)₂R$^c$, C₁₋₆ alkyl substituted with 0-2 $R^a$, C₁₋₆ haloalkyl, —(CH₂)ᵣ-3-14 membered carbocycle substituted with 0-1 $R^a$, or —(CH₂)ᵣ-5-7 membered heterocycle comprising carbon atoms and 1-4 heteroatoms selected from N, O, and S(O)ₚ substituted with 0-1 $R^a$;

R⁷ is F, Cl, Br, OCF₃, CN, NO₂, —OR$^e$, —(CH₂)ᵣC(O)R$^b$, —NR$^e$R$^e$, or —NR$^e$C(O)OR$^c$ C₁₋₆ alkyl substituted with 0-2 $R^d$, C₁₋₆ haloalkyl, C₃₋₆ cycloalkyl substituted with 0-2 $R^d$, or (CH₂)ᵣ-phenyl substituted with 0-3 $R^d$;

R¹¹ at each occurrence is independently hydrogen, C₁₋₄ alkyl substituted with 0-1 $R^f$, CH₂-phenyl substituted with 0-3 $R^d$, or —(CH₂)-5-7 membered heterocycle comprising carbon atoms and 1-4 heteroatoms selected from N, O, and S(O)ₚ substituted with 0-3 $R^d$;

$R^a$ is hydrogen, Cl, Br, OCF₃, CF₃, CHF₂, CN, NO₂, —(CH₂)ᵣOR$^b$, —(CH₂)ᵣSR$^b$, —(CH₂)ᵣC(O)R$^b$, —(CH₂)ᵣC(O)OR$^b$, —(CH₂)ᵣOC(O)R$^b$, —(CH₂)ᵣNR¹¹R¹¹, —(CH₂)ᵣC(O)NR¹¹R¹¹, —(CH₂)ᵣNR$^b$C(O)R$^c$, —(CH₂)ᵣNR$^b$C(O)OR$^c$, —NR$^b$C(O)NR¹¹R¹¹, —S(O)ₚNR¹¹R¹¹, —NR$^b$S(O)ₚR$^c$, —S(O)R$^c$, —S(O)₂R$^c$, C₁₋₆ alkyl, C₁₋₆ haloalkyl, —(CH₂)ᵣ-3-14 membered carbocycle, or —(CH₂)ᵣ-5-7 membered heterocycle comprising carbon atoms and 1-4 heteroatoms selected from N, O, and S(O)ₚ, alternatively two $R^a$ on adjacent or the same carbon atom form a cyclic acetal of the formula —O—(CH₂)ₙ—O—, or —O—CF₂—O—, wherein n is selected from 1 or 2;

$R^b$ is hydrogen, C₁₋₆ alkyl substituted with 0-2 $R^d$, C₁₋₆ haloalkyl, C₃₋₆ cycloalkyl substituted with 0-2 $R^d$, or (CH₂)ᵣ-phenyl substituted with 0-3 $R^d$;

$R^c$ is C₁₋₆ alkyl, C₃₋₆ cycloalkyl, or (CH₂)ᵣ-phenyl substituted with 0-3 $R^f$;

$R^d$ is hydrogen, F, Cl, Br, OCF₃, CF₃, CN, NO₂, —OR$^e$, —(CH₂)ᵣC(O)R$^e$, —NR$^e$R$^e$, —NR$^e$C(O)OR$^c$, C₁₋₆ alkyl, or (CH₂)ᵣ-phenyl substituted with 0-3 $R^f$;

$R^e$ is hydrogen, C₁₋₆ alkyl, C₃₋₆ cycloalkyl, or (CH₂)ᵣ-phenyl substituted with 0-3 $R^f$;

$R^f$ is hydrogen, F, Cl, Br, NH₂, OH, or O(C₁₋₆alkyl);

r is 0, 1, 2, 3, or 4; and p is 0, 1, or 2.

In another embodiment, there is provided a compound of formula I, or a stereoisomer or pharmaceutically acceptable salt thereof, wherein R² is selected from

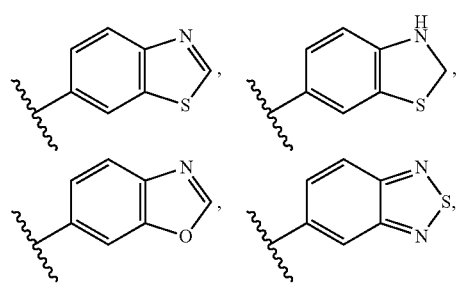

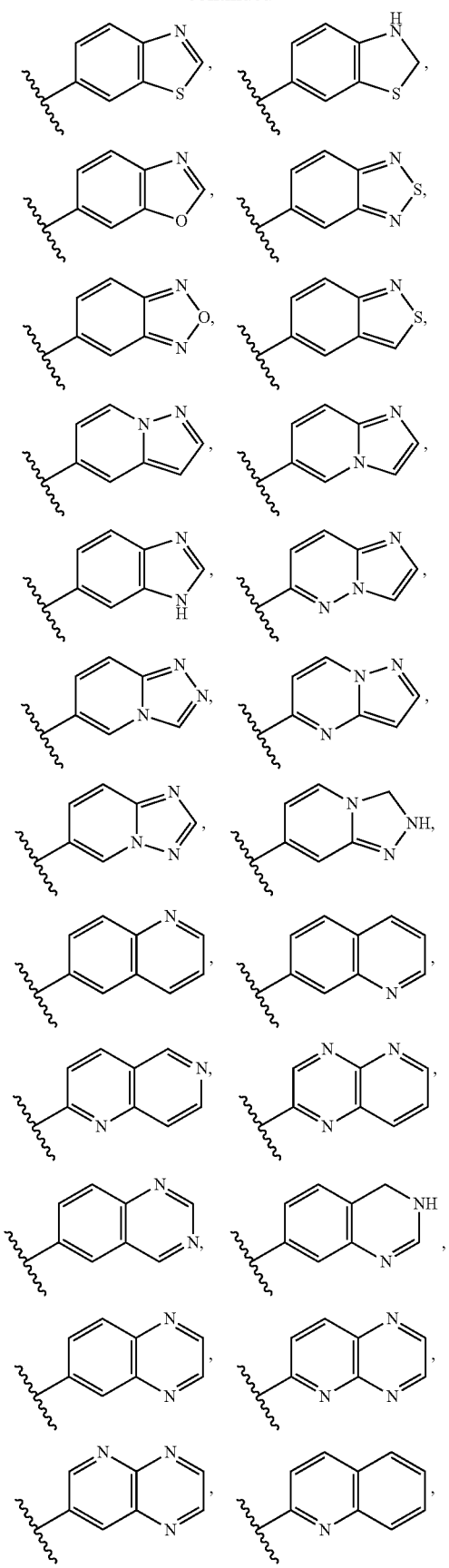

-continued

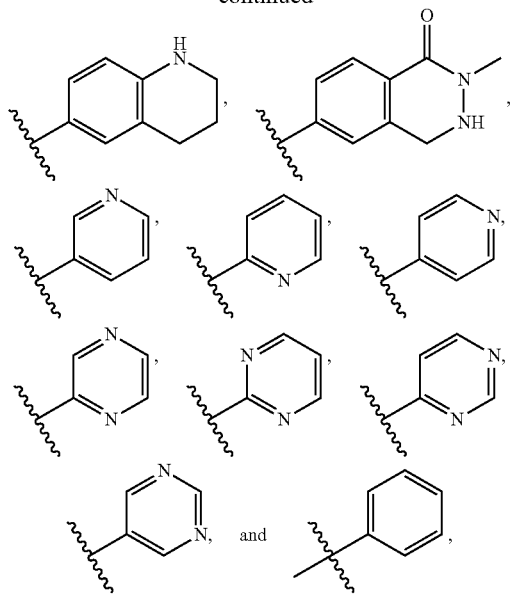

each group substituted by 0-4 $R^{2a}$.

In an even more preferred embodiment there is provided a compound of formula I, or a stereoisomer or pharmaceutically acceptable salt thereof, wherein $R^{2a}$ is selected from hydrogen, =O, $C_{1-6}$alkyl, F, Cl, Br, —O$C1$-6alkyl, pyridyl, morpholinyl, oxazolyl, C(O)O C1-6alkyl, C(O)NHC1-6alkyl, CN, C1-6haloalkyl, $NH_2$, —$NHC_{1-6}$alkyl, N($C_{1-6}$ alkyl), OH, and a 5-6 membered heterocycle having 1-3 ring atoms selected from O, N or S.

In a more preferred embodiment compounds of formula I are provided, or a stereoisomer or pharmaceutically acceptable salt thereof, wherein $R^{2a}$ is independently selected from 1-4 groups at each occurrence from fluoro, chloro, =O, —OH, OMe, hydrogen, $CO_2Et$, CONHMe, CN, $CF_3$, $NH_2$, OH, CN, $CONH_2$, pyridyl, morpholinyl, and oxazolyl.

In yet another more preferred embodiment compounds of formula I are provided, or a stereoisomer or pharmaceutically acceptable salt thereof, wherein $R_2$ is selected from:

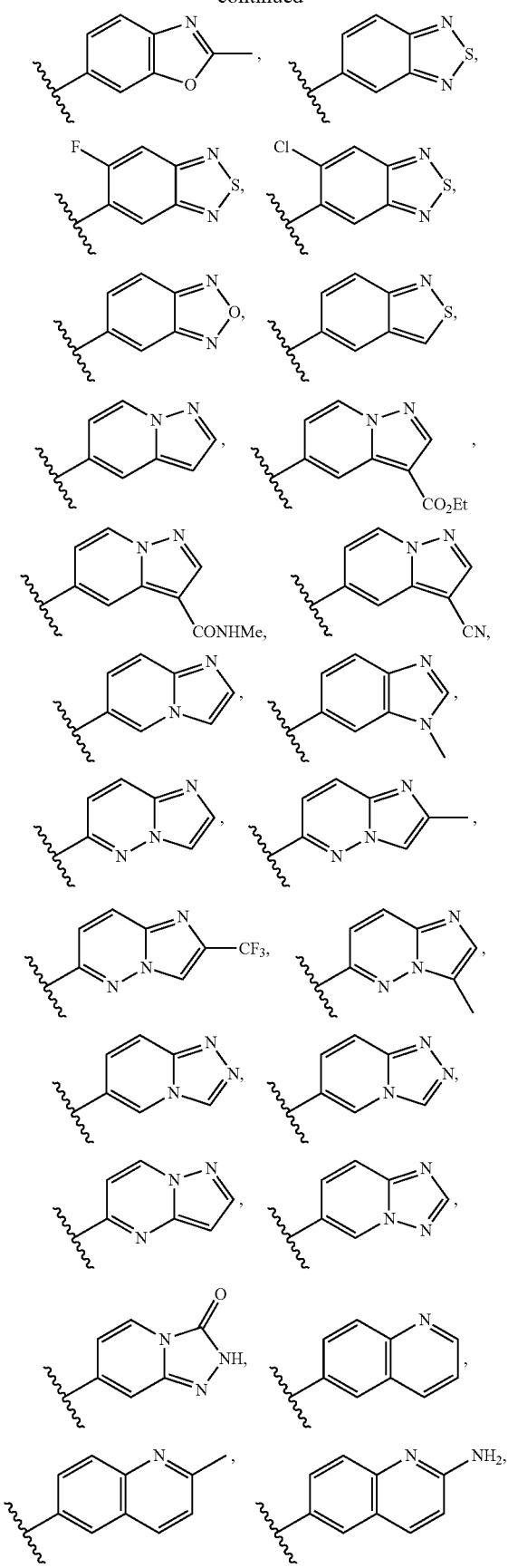

-continued

[Chemical structures shown]

-continued

[Chemical structures shown]

In another embodiment, there is provided a compound of formula I, or a stereoisomer or pharmaceutically acceptable salt thereof, wherein $R^2$ is selected from

[Chemical structures shown]

In another embodiment, there is provided a compound of formula I, or a stereoisomer or pharmaceutically acceptable salt thereof, wherein $R^2$ is selected from

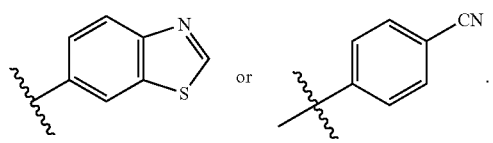 [SMILES: *c1ccc2ncsc2c1 ; *c1ccc(C#N)cc1]

In a further embodiment, there is provided a compound of formula I, or a stereoisomer or pharmaceutically acceptable salt thereof, wherein R is selected from —C(O)NH$_2$, —C(O)OC$_{1-6}$alkyl, —C(O)NH(C$_{1-6}$alkyl), —C(O)N(C$_{1-6}$alkyl)$_2$,

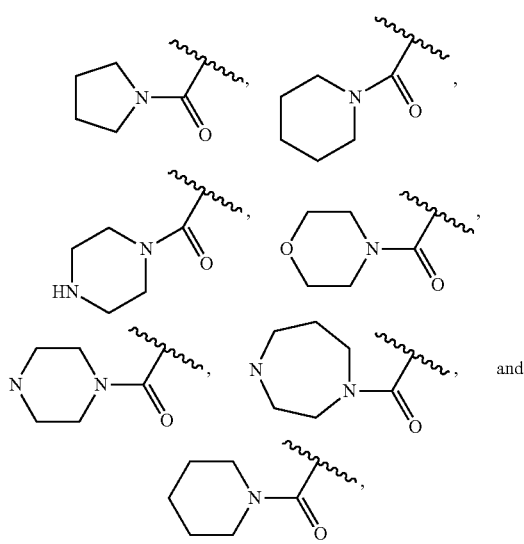

each group substituted by 0-3 R$^{1a}$.

In a further preferred embodiment, there is provided a compound of formula I, or a stereoisomer or pharmaceutically acceptable salt thereof, wherein R$^{1a}$ at each occurrence is independently selected from hydrogen, F, Cl, Br, C$_{1-6}$alkyl, C$_{1-6}$haloalkyl, —(CH$_2$)$_n$OH, —(CH$_2$)$_n$NH$_2$, —(CH$_2$)$_n$CN, C(O)NH$_2$, —NHC$_{1-6}$alkyl, —N(C$_{1-6}$alkyl)$_2$, —NHC(O)C$_{1-6}$alkyl, =O, acyl, NH$_2$, H, NHC(O)$_2$C$_{1-6}$alkyl, OC$_{1-6}$alkyl, C(O)phenyl, —(CH$_2$)$_n$morpholinyl, —(CH$_2$)$_n$phenyl, —(C$_2$)$_n$benzodioxo, —(CH$_2$)$_n$pyrrolidinyl, —(CH$_2$)$_n$pyrimidinyl, —(CH$_2$)$_n$pyridyl, —(CH$_2$)$_n$piperidinyl, —(CH$_2$)$_n$diazapanyl, each group optionally further substituted by 1-3 groups selected from C$_{1-6}$alkyl, halo, hal°C$_{1-6}$alkyl, C$_{3-7}$cycloalkyl, tetrahydrofuranyl, —NH(acyl), NH$_2$, —NHC$_{1-6}$alkyl, —N(C$_{1-6}$alkyl)$_2$, —OC$_{1-6}$alkyl, acyl, CN, OH, piperidinyl, pyridyl, morpholinyl, pyrrolidinyl, and pyrimidinyl, wherein n is selected from 0, 1, 2, 3, and 4.

In a more preferred embodiment compounds of formula I are provided, or a stereoisomer or pharmaceutically acceptable salt thereof, in which R$^{1a}$ is selected from the following:

-continued

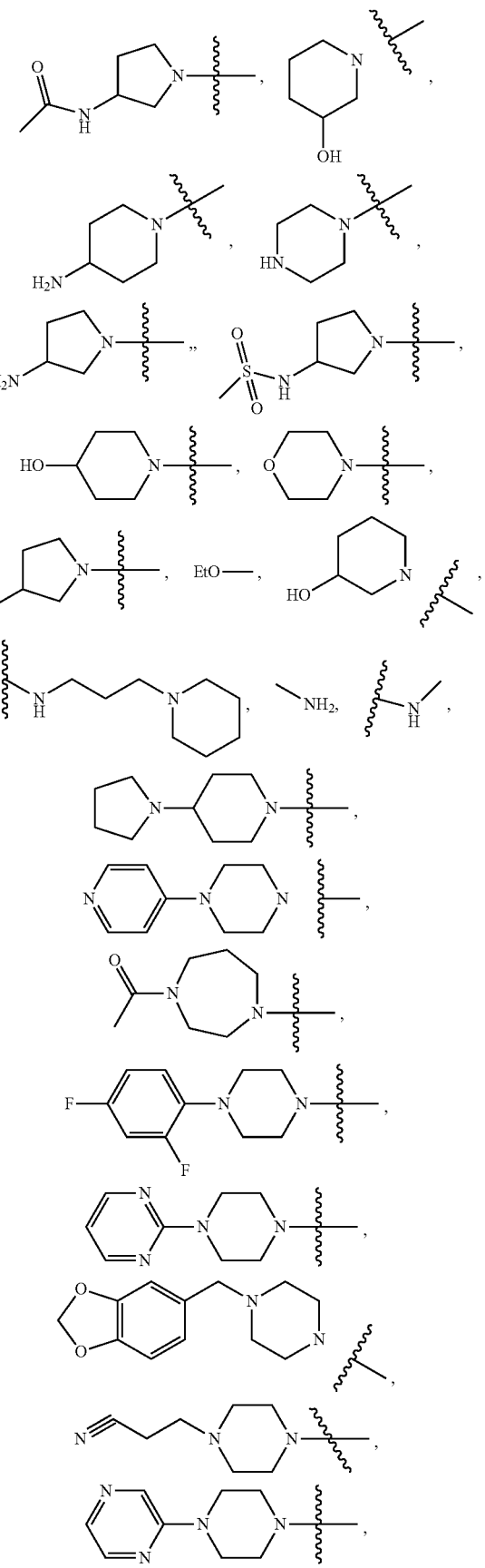

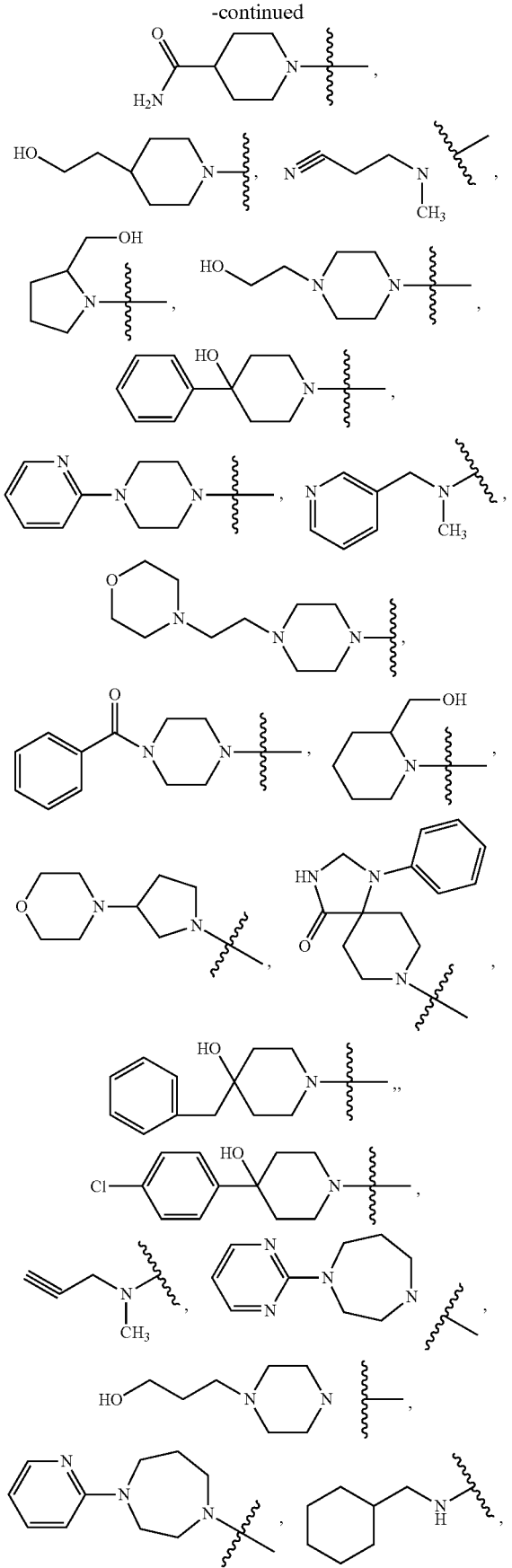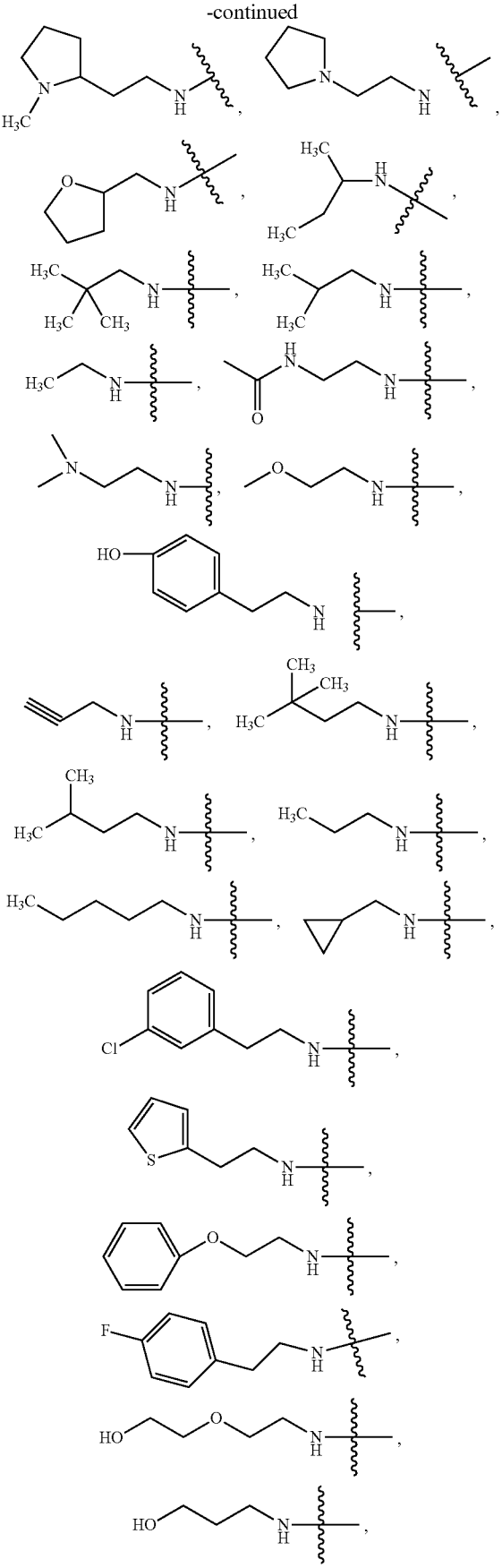

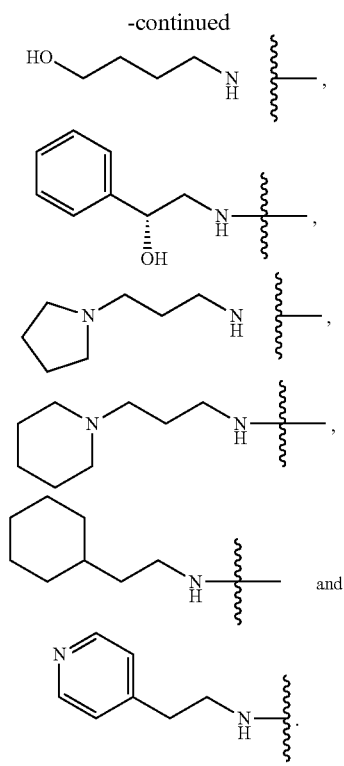

In another embodiment, compounds of formula I are provided, or a stereoisomer or pharmaceutically acceptable salt thereof, wherein X is $CR^7$; and $R^7$ is hydrogen or $C_{1-6}$alkyl.

In another embodiment, compounds of formula I are provided, or a stereoisomer or pharmaceutically acceptable salt thereof, wherein X is N.

In yet another embodiment compounds of formula I are provided, or a stereoisomer or pharmaceutically acceptable salt thereof, wherein $R^3$ is $C_{1-6}$ alkyl substituted with 0-3 $R^{3a}$ or phenyl optionally substituted with 0-3 $R^{3a}$.

In another preferred embodiment, compounds of formula I are provided, or a stereoisomer or pharmaceutically acceptable salt thereof, wherein $R^3$ is selected from $C_{1-6}$ alkyl ($R^3$ is preferably isopropyl).

In another embodiment, there is provided a pharmaceutical composition comprising one or more compounds of formula I and a pharmaceutically acceptable carrier or diluent.

The present invention is also directed to pharmaceutical compositions useful in treating diseases associated with kinase modulation, including modulation (especially inhibition) of IRAK-4, comprising compounds of formula (I), or pharmaceutically-acceptable salts thereof, and pharmaceutically-acceptable carriers or diluents.

The invention further relates to methods of treating diseases associated with the kinase modulation, including the modulation of IRAK-4, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases (or use of the compounds of the present invention or stereoisomers, tautomers, pharmaceutically acceptable salts, solvates, or prodrugs thereof, for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of formula I, wherein the disease is Crohn's, ulcerative colitis, asthma, graft versus host disease, allograft rejection, chronic obstructive pulmonary disease; Graves' disease, rheumatoid arthritis, systemic lupus erythematosis, psoriasis; CAPS, TRAPS, FMF, adult onset stills, systemic onset juvenile idiopathic arthritis, multiple sclerosis, neuropathic pain, gout, and gouty arthritis.

The present invention also provides a method of treating a metabolic disease (or use of the compounds of the present invention or stereoisomers, tautomers, pharmaceutically acceptable salts, solvates, or prodrugs thereof, for the manufacture of a medicament for the treatment of these diseases) wherein the disease is selected from type 2 diabetes and atherosclerosis.

In addition, the present invention also provides a method of treating a condition (or use of the compounds of the present invention or stereoisomers, tautomers, pharmaceutically acceptable salts, solvates, or prodrugs thereof, for the manufacture of a medicament for the treatment of these conditions) comprising administering to a patient in need of such treatment a therapeutically-effective amount of a compound of formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method for treating a rheumatoid arthritis (or use of the compounds of the present invention or stereoisomers, tautomers, pharmaceutically acceptable salts, solvates, or prodrugs thereof, for the manufacture of a medicament for the treatment of rheumatoid arthritis), comprising administering to a patient in need of such treatment a therapeutically-effective amount of a compound of formula I.

The present invention also provides a method of treating a TLR/IL-1 mediated disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of formula I The present invention also provides a method of treating a TLR/IL-1 mediated disease (or use of the compounds of the present invention or stereoisomers, tautomers, pharmaceutically acceptable salts, solvates, or prodrugs thereof, for the manufacture of a medicament for the treatment of these diseases), comprising administering to a patient in need of such treatment a therapeutically-effective amount of a compound of formula I, wherein the TLR/IL-1 mediated disease is a disease modulated by a kinase selected from IRAK-4.

The present invention also provides a method of treating diseases, comprising administering to a patient in need of such treatment a therapeutically-effective amount of a compound of formula I, or pharmaceutically acceptable salt thereof, in combination with other therapeutic agents.

The present invention also provides the compounds of the present invention or stereoisomers, tautomers, pharmaceutically acceptable salts, solvates, or prodrugs thereof, for use in therapy.

In another embodiment, compounds of formula I are selected from exemplified compounds or combinations of exemplified compounds or other embodiments herein.

In another embodiment, the present invention is directed to a pharmaceutical composition comprising a compound of formula (I) and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of formula (I) and one or more active ingredients.

In another embodiment, the present invention is directed to a method for modulation of CCR-1 receptor activity comprising administering to a patient in need thereof a therapeutically effective amount of a pharmaceutical composition comprised of a compound of formula (I) and one or more active ingredients.

In another embodiment are compounds having an $IC_{50}$<1000 nM in the IRAK-4 assay described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

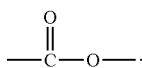

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

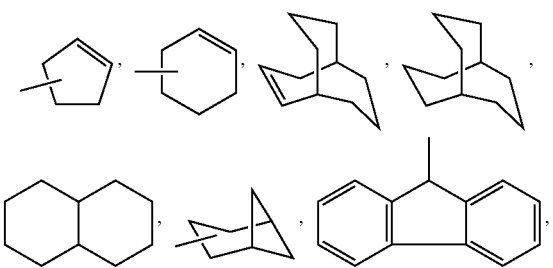

-continued and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

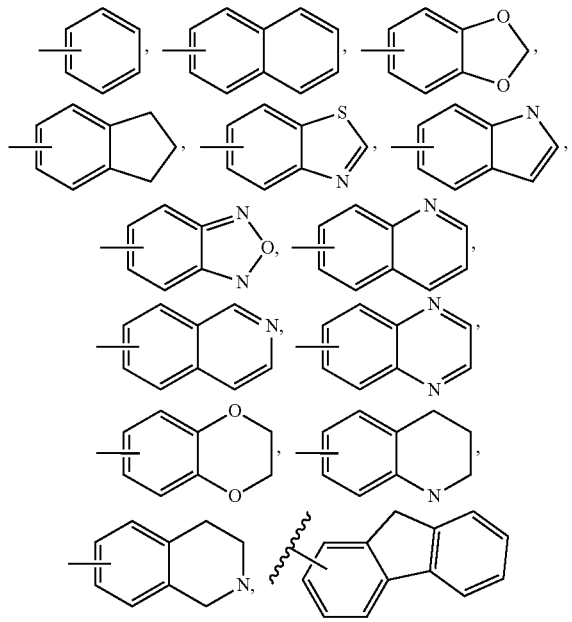

(fluorenyl) and the like, which optionally may be substituted at any available carbon or nitrogen atom. A preferred aryl group is optionally-substituted phenyl.

The terms "heterocycloalkyl", "heterocycle", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

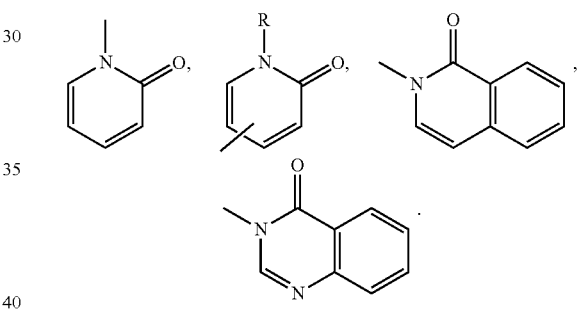

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula (I), preferred heteroaryl groups include

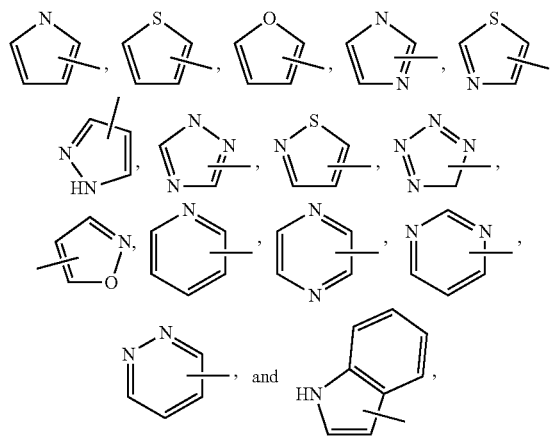

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers, It should further be understood that solvates (e.g., hydrates) of the compounds of Formula (I) are also with the scope of the present invention. Methods of solvation are generally known in the art.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's and ulcerative colitis, asthma, graft versus host disease, allograft rejection, chronic obstructive pulmonary disease; autoimmune diseases such as Graves' disease, rheumatoid arthritis, systemic lupus erythematosis, psoriasis; autoinflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by mediation of IRAK-4 enzyme levels.

Biological Assays

IRAK4 Inhibition Assay:

The assays were performed in U-bottom 384-well plates. The final assay volume was 30 μL prepared from 15 μL additions of enzyme and substrates (fluoresceinated peptide and ATP) and test compounds in assay buffer (20 mM HEPES pH 7.2, 10 mM $MgCl_2$, 0.015% Brij35 and 4 mM DTT). The reaction was initiated by the combination of IRAK4 with substrates and test compounds. The reaction was incubated at room temperature for 60 min. and terminated by adding 45 μL of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 μM; FL-IPTSPITTTYFFFKKK peptide 1.5 μM; IRAK4, 0.6 nM; and DMSO, 1.6%.

| IRAK4 Inhibition Data | |
|---|---|
| Example No. | IRAK4 $IC_{50}$ (μM) |
| 1 | 0.0253 |
| 3 | 0.0025 |
| 6 | 0.0028 |
| 7 | 0.0032 |
| 8 | 0.0033 |
| 19 | 0.0032 |
| 23 | 0.9607 |
| 25 | 0.0027 |
| 27 | 0.0018 |
| 31 | 0.7638 |
| 48 | 0.5759 |
| 56 | 0.795 |
| 59 | 0.024 |
| 81 | 0.026 |
| 82 | 0.0031 |
| 106 | 0.875 |
| 108 | 0.0027 |
| 115 | 0.0229 |
| 128 | 0.0264 |
| 129 | 0.0254 |
| 130 | 0.0221 |
| 143 | 0.6759 |
| 148 | 0.5642 |
| 152 | 0.0245 |
| 161 | 0.023 |
| 176 | 0.6158 |
| 177 | 0.8128 |

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Triazole derivatives of general formula (I) can be prepared according to the method outlined in Scheme 1. Displacement of the C4 chloride of ethyl 4,6-dichloronicotinate (1) with an appropriately substituted amine can provide the C4 amino product (1.1) which can be further reacted with another amine in the presence of a catalyst, such as Pd, or under high temperatures to provide the bis-amino substituted pyridine (1.2). Hydrolysis of the ester with a suitable hydroxide source, such as KOH, can pr ovide the carboxylic acid 1.3 which can be reacted with a suitable reagent, such as ethyl 2-amino-2-hydrazonoacetate, to afford the heterocycle precursor 1.4. Cyclization under thermal control can afford the general C5 triazole shown in Scheme 1.

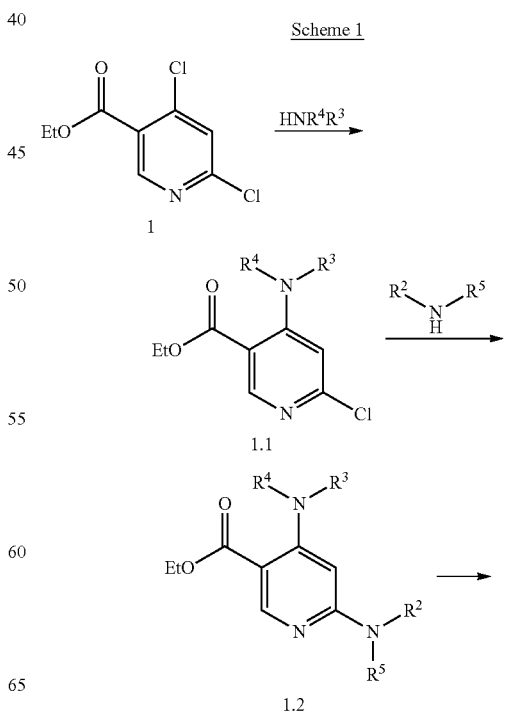

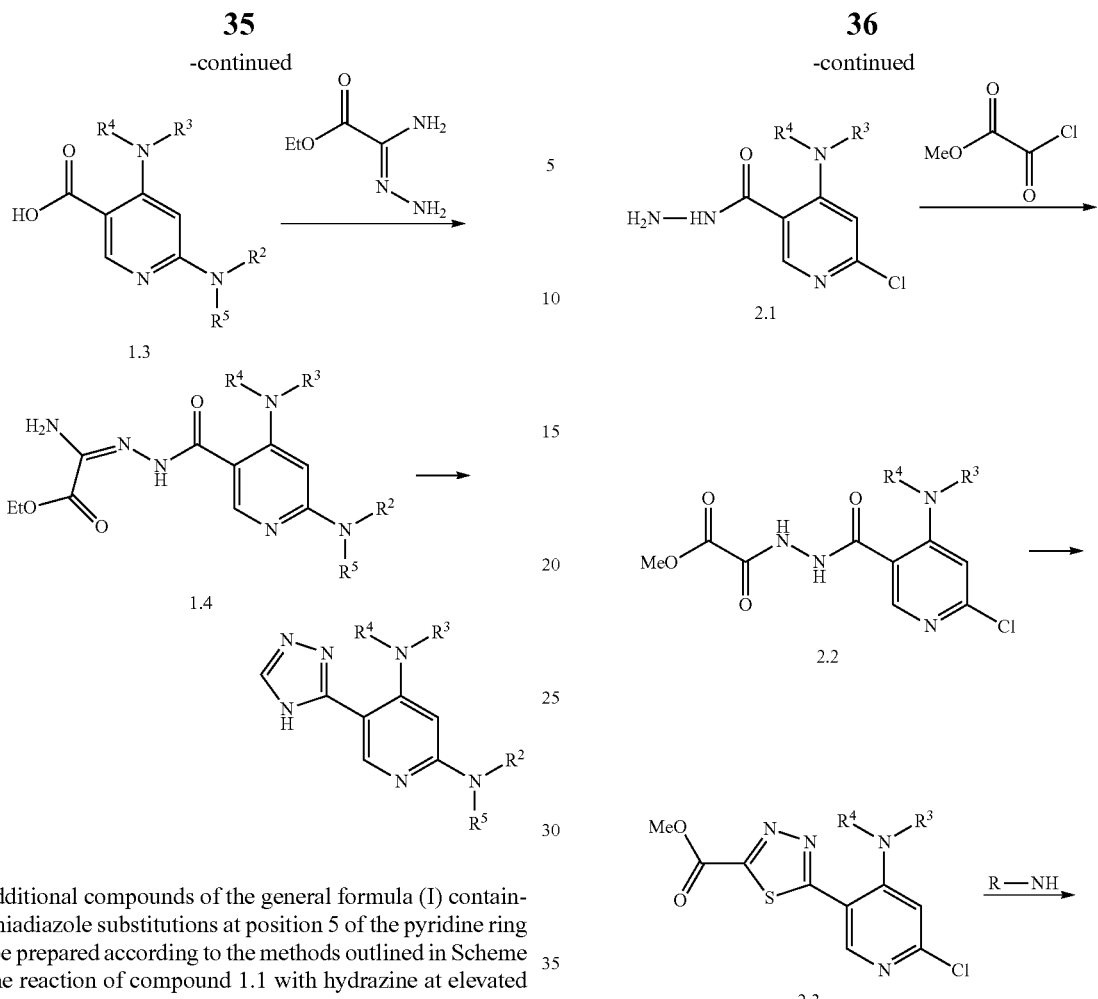

Additional compounds of the general formula (I) containing thiadiazole substitutions at position 5 of the pyridine ring can be prepared according to the methods outlined in Scheme 2. The reaction of compound 1.1 with hydrazine at elevated temperatures in an appropriate solvent, such as ethanol, can provide compound 2.1. Further reaction with methyl 2-chloro-2-oxoacetate in the presence of a base followed by cyclization can provide compound 2.3. Hydrolysis of the ester under standard conditions followed by amide bond formation can provide compound 2.4. Alternatively, 2.4 can be prepared directly from 2.3 by direct reaction with an amine at elevated temperatures. Incorporation of the C2 amine fragment under metal catalyzed conditions or elevated temperatures can provide the thiadiazole derivatives of the general formula (I). Additional functional group manipulations can be performed at various regions of the molecule. For example, compounds of the formula 2.5 can be reacted with a hydroxide source, such as KOH, to provide the carboxylic acid 2.6. This can then be further reacted with a variety of reagents, such as an amine, to provide intermediates, such as 2.7, which can be reacted further with amines at position 2 to afford compounds of the general formula (I).

Scheme 2

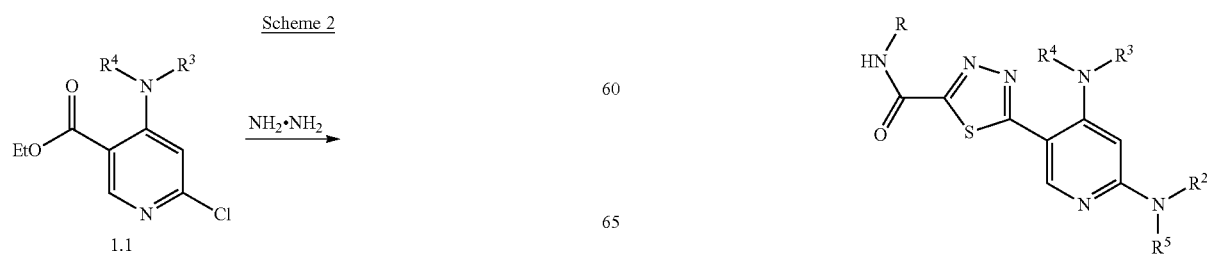

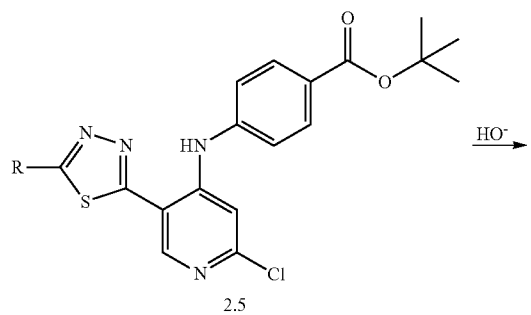

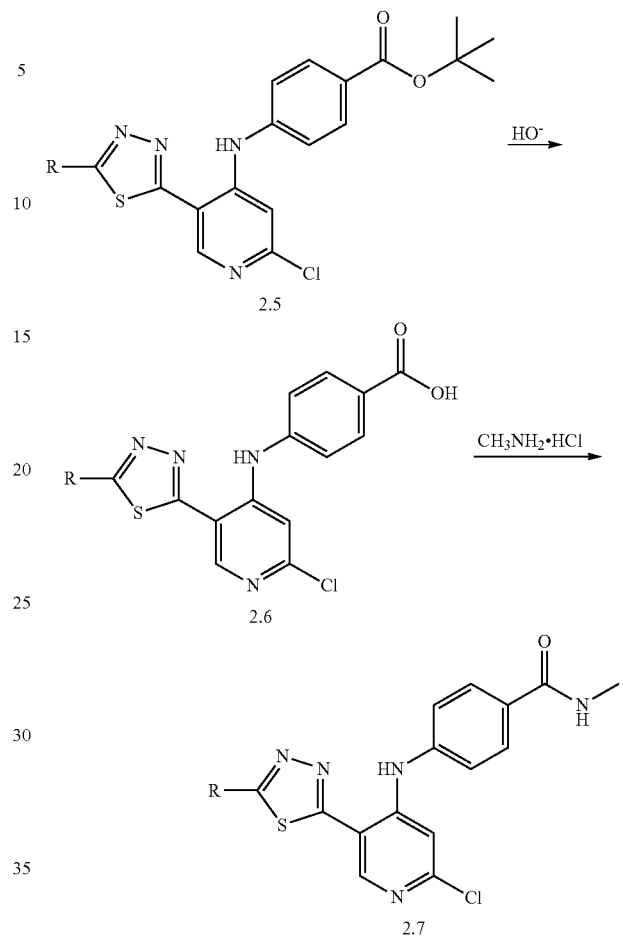

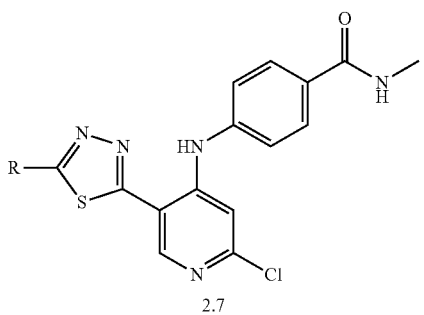

Thiazole derived analogs can be prepared according to the general methods outlined in Scheme 3. Reaction of compound 3.1, the hydrolysis product of compound 1.1, can be reacted with a halogenating reagent, such as oxalyl chloride followed by quenching with an amine source, such as ammonia, to provide intermediates of the formula 3.2. Dehydration of the amide can provide nitrile 3.3 which can be further reacted with an amine to provide intermediates of the formula 3.4. Conversion of the nitrile to a thioamide (3.5) followed by condensation with a halo ketone can provide thiazole substituted compounds of the formula 3.6. Further hydrolysis of 3.6 can provide the acid 3.7 which, in turn can be reacted under a variety of functional group transforming conditions, such as the conversion to an amine 3.8, to provide additional compounds of the general formula I.

Scheme 3

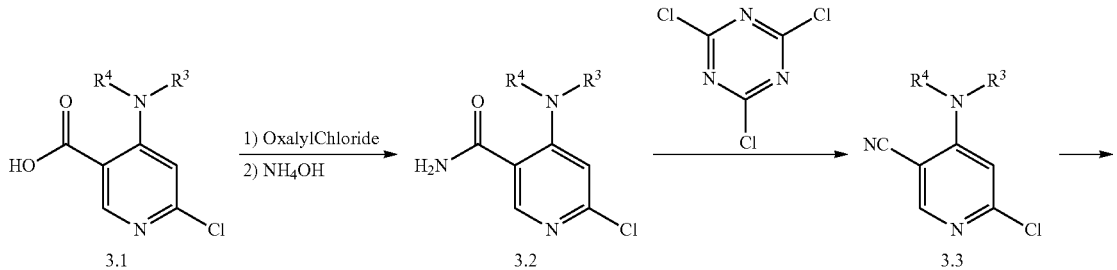

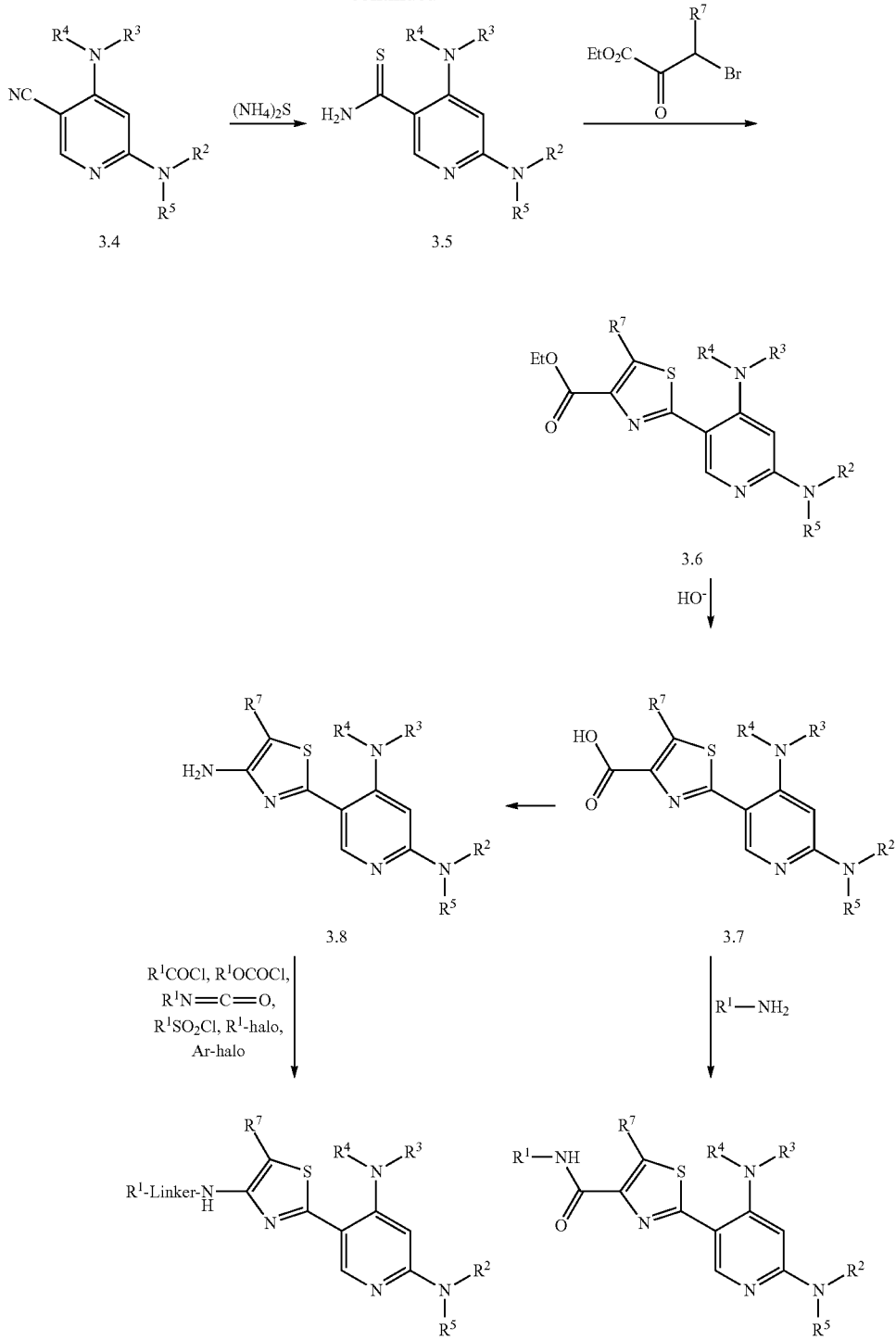

Similarly, oxazole compounds of the general formula I can be prepared according to the general procedures outlined in Scheme 4. Treatment of compound 3.1 with a chlorinating reagent can provide compounds such as 4.1 which can then be reacted with a variety of substituted amino ketones then cyclized to the desired oxazole intermediate 4.2. Reaction at C2 with an amine using previously stated conditions can provide the intermediate 4.3. Intermediates 4.3 and 4.2 can both be manipulated to provide compounds of the general formula I according to the methods outlined below. First, 4.3 can be hydrolyzed and coupled with amines to form amide analogs of formula I. Alternatively, the acid 4.4 can be converted to the amine 4.5 under Curtius reaction conditions, and then further functionalized to amide, carbamates, sulfonamides, ureas, alkyl and aryl amines to name a few. Additionally, intermediate 4.2 can first undergo hydrolysis and functional group manipulation at the oxazole as just described then coupled with an amine at C2.

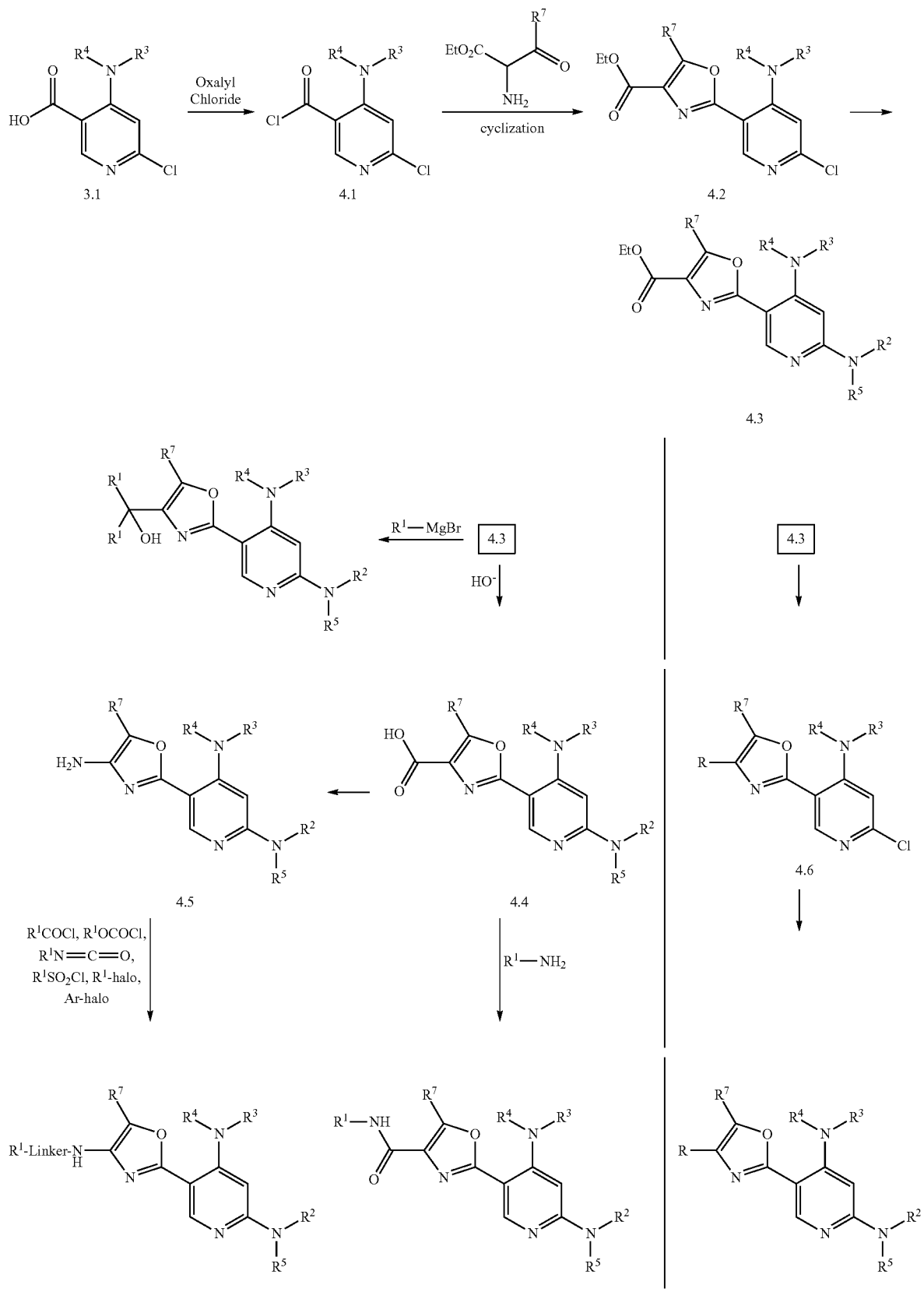
Scheme 4

Reaction of hydrazide 5.1 with carbon disulfide followed by alkylation can provide the intermediate 5.3. Oxidation with a reagent such as MCPBA, can provide the sulfone 5.4 which can be reacted preferentially at the oxadiazole to give intermediates such as 5.5. Further reaction with an amine in the presence of a catalyst, such as Pd, or at elevated temperatures, can provide compounds of the general formula I. Alternatively, the reaction of 5.1 with a carboxylic acid with a coupling reagent such as HATU can provide the acyl hydrazide 5.6 which can be cyclized to 5.7 and further reacted on to compounds of the general formula I in the presence of an amine. It is understood to one skilled in the art that the R groups may be functionalized, for example as a protected amine or alcohol, in such a manner that further manipulations are allowable in the context of these general Schemes. Additional functional groups that can also be considered for these types of manipulations are: nitriles, halides, esters, alkenes, alkynes and nitro groups.

Scheme 5

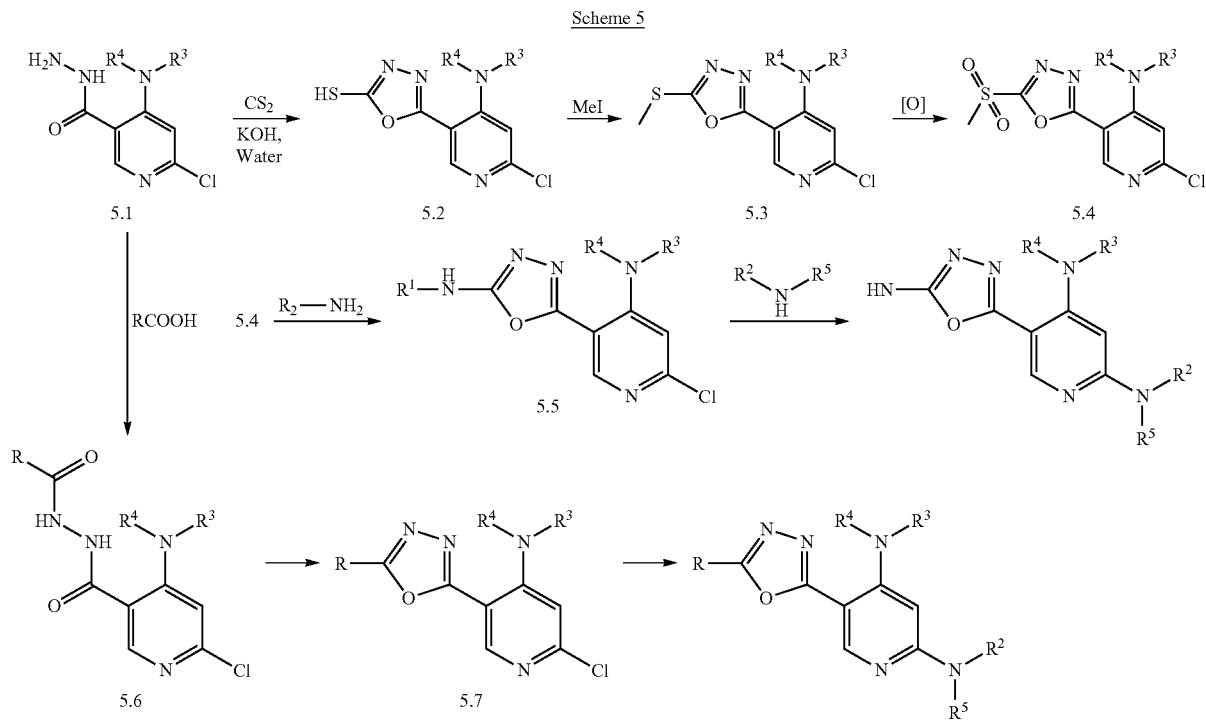

Reaction of hydrazide 5.1 with a carbonylating reagent, such as CDI, can provide compounds of the general formula 6.1. Reaction of 6.1 with various amines can provide the ring opened compounds 6.2 which can be cyclized to form intermediates such as 6.3. Displacement of the C2 chloride with an amine using a metal catalyst or elevated temperature can afford additional compounds of the general formula I.

Scheme 6

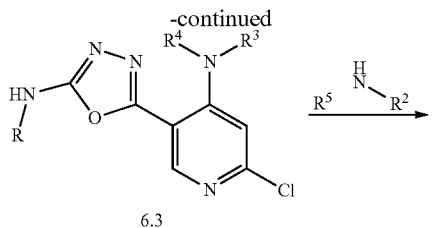

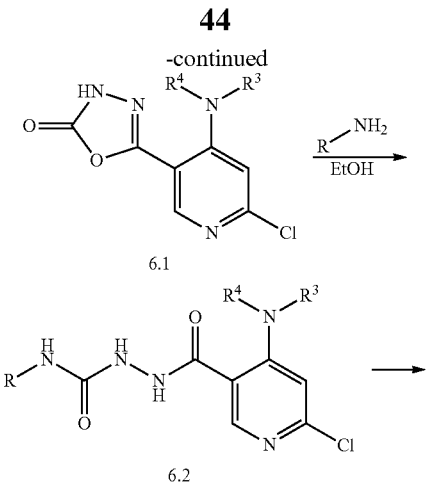

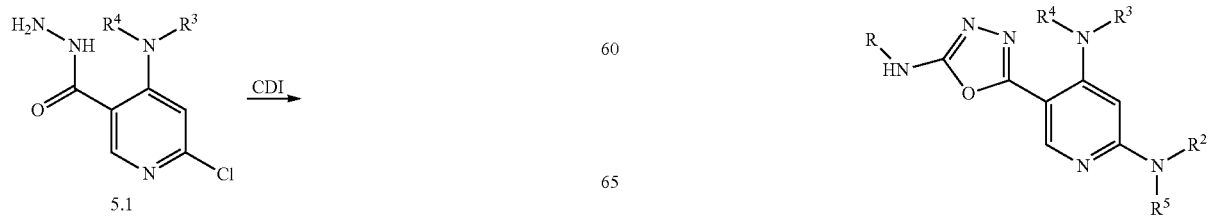

Additional analogs can be prepared according to the method outlined in Scheme 7. Ester 1.7 can be reacted with hydrazine to provide the substituted pyridine hydrazide 7.1. Reaction of 7.1 with various orthoformates in the presence of acid can provide compounds of the general formula I.

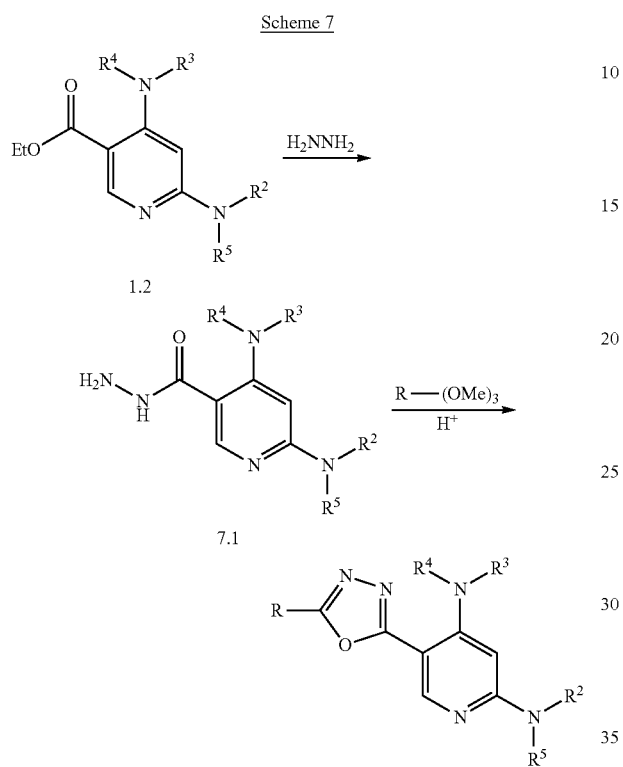

Additional heterocycles can be prepared according to the methods outlined in Schemes 8 and 9. First, compound 4.1 can be reacted with ethyl-2-amino oxamate in the presence of a base, such as TEA, to afford intermediate 8.1 which can be cyclized to intermediate 8.2 by heating at high temperature in a suitable solvent such as DMF. Amidolysis of the pendant ester can afford 8.3 which can be further elaborated upon reaction with an amine at C2 to afford compound of the general formula I.

In Scheme 9, compound 1.1 can be reduced to alcohol 9.1 using an appropriate hydride source, such as DIBAL, then oxidized to the aldehyde under standard conditions (COCl)$_2$, DMSO to furnish 9.2. Intermediate 9.2 can be converted to the oxazole upon reaction with Tosmic and a base such as K$_2$CO$_3$. Reaction with an amine at C2 can furnish additional compounds of the general formula I.

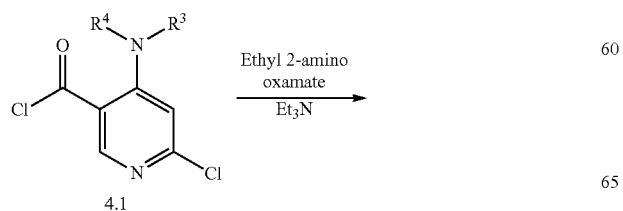

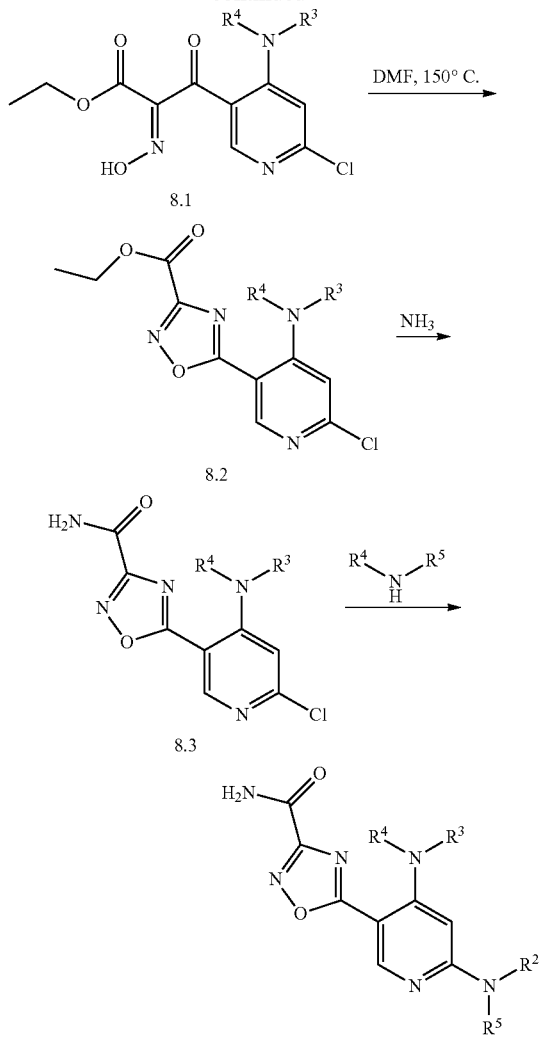

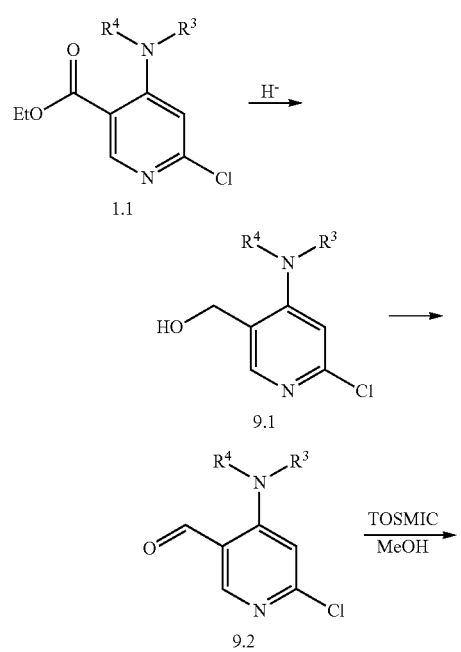

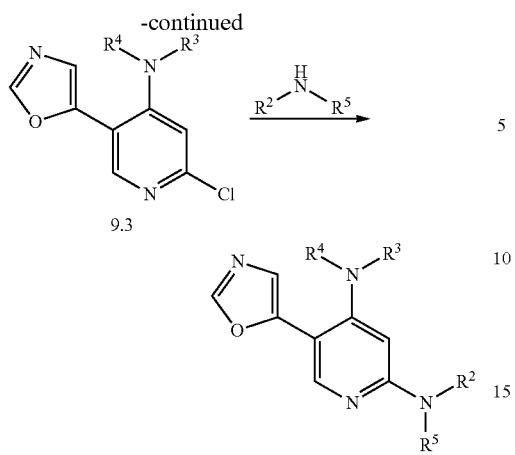

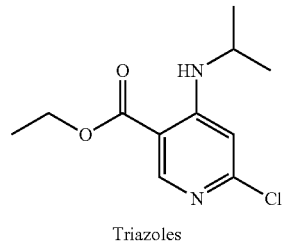

Triazoles

EXAMPLES

Preparation of compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, Phenomenex Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

NaHCO$_3$ (aq)—saturated aqueous sodium bicarbonate
brine—saturated aqueous sodium chloride
DCM—dichloromethane
DIEA—N,N-diisopropylethylamine
DMAP—4-(N,N-dimethylamino)pyridine
DMF—N,N-dimethylformamide
DMSO—dimethyl sulfoxide
EDC—N-(3-dimethylaminopropyl)-N'-ethylcarbodiimide hydrochloride
EtOAc—ethyl acetate
HOAT—1-hydroxy-7-azabenzotriazole
HOBT—1-hydroxybenzotriazole hydrate
rt—ambient room temperature (generally about 20-25° C.)
TEA—triethylamine
TFA—trifluoroacetic acid
THF—tetrahydrofuran Synthesis of ethyl 6-chloro-4-(isopropylamino)nicotinate (2): A stirred solution of ethyl 4,6-dichloronicotinate (1) (10 g, 43.4 mmol), isopropyl amine (8 mL) and DIPEA (8 mL) in DMA (50 mL) were heated at 120° C. in a sealed tube for 3 h. The reaction mixture was concentrated to dryness to remove excess of DMA from the reaction mass. The crude material obtained was purified by column chromatography through silica gel and EtOAC:pet. Ether as eluent to obtain the title compound (2). LC/MS: Acquity BEH C18 2.1×50 mm, 1.8 micron; Solvent A=0.1% TFA in water; Solvent B=0.1% TFA in ACN; gradient 0-100% B over 2 min; retention time: 0.90 min; LCMS (ES-API), m/z 243.7 (M+H).

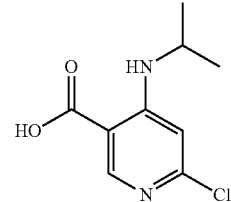

Synthesis of 6-chloro-4-(isopropylamino)nicotinic acid (3): Ethyl 6-chloro-4-(cyclobutylamino)nicotinate (2) (3 g, 12.3 mmol) in ethanol (20 mL) and water (10 mL) was stirred at rt. LiOH (61.7 mmol, 5 equiv.) was added and the reaction mixture was stirred at room temperature for 4 h. The solvent was concentrated under reduced pressure. Diluted with EtOAc and added water. The aqueous layer was collected and acidified to pH 3-4 using solid citric acid. Solid material precipitated out. Filtered the solid material and dried under vacuum to furnish the title compound (3). $^1$H NMR: 400 MHz, DMSO-d$_6$: δ 1.20 (d, J=6.40 Hz, 6H), 3.80-3.88 (m, 1H), 6.80 (s, 1H), 8.20 (d, J=7.60 Hz, 1H), 8.51 (s, 1H), 13.33 (bs, 1H).

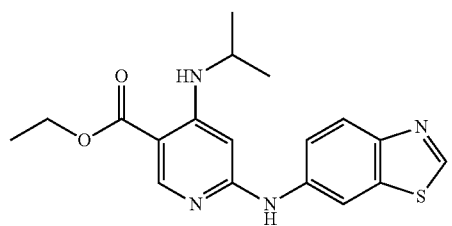 [SMILES: CCOC(=O)c1cnc(Nc2ccc3ncsc3c2)cc1NC(C)C]

Synthesis of ethyl 6-(benzo[d]thiazol-6-ylamino)-4-(isopropylamino)nicotinate (3): To a solution of ethyl 6-chloro-4-(isopropylamino)nicotinate (2) (5 g, 20.66 mmol) in dioxane (30 mL):H$_2$O (5 mL), 6-amino benzothiazole (20.66 mmol, 1 equiv.), xanthphos (8.2 mmol, 0.4 equiv.) and Na$_2$CO$_3$ (82.6 mmol, 4 equiv.) were added and degassed for 10 min. To the reaction mixture Pd$_2$(dba)$_3$ (8.2 mmol, 0.4 equiv.) was added and degassed again for 10 min. It was then heated at 115° C., overnight. The reaction was cooled and filtered through small pad of celite. The filtrate obtained was concentrated to provide crude material. The crude material was purified by column chromatography through silica gel and EtOAC:pet. Ether as eluent to afford ethyl 6-(benzo[d]thiazol-6-ylamino)-4-(isopropylamino)nicotinate (3). LC/MS: Acquity BEH C18 2.1×50 mm, 1.8 micron; Solvent A=0.1% TFA in water; Solvent B=0.1% TFA in ACN; gradient 0-100% B over 2 min; retention time: 0.78 min; LCMS (ES-API), m/z 357.8 (M+H).

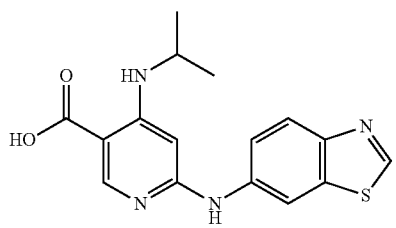 [SMILES: CC(C)Nc1cc(Nc2ccc3ncsc3c2)ncc1C(=O)O]

Synthesis of 6-(benzo[d]thiazol-6-ylamino)-4-(isopropylamino)nicotinic acid (4): Ethyl 6-(benzo[d]thiazol-6-ylamino)-4-(isopropylamino)nicotinate (3) (1 g, 2.8 mmol) in ethanol (20 mL) and water (5 mL) was stirred at rt then added LiOH (14 mmol, 5 equiv.). The reaction mixture was stirred at room temperature for 4 h, the then heated at 70° C. for 1 h. The solvent was concentrated under reduced pressure, diluted with EtOAc and added water. The aqueous layer was collected and acidified to pH 3-4 using solid citric acid. Solid material precipitated out. Filtered the solid material and dried under vacuum to furnish the title compound (4). LC/MS: Acquity BEH C18 2.1×50 mm, 1.8 micron; Solvent A=0.1% TFA in water; Solvent B=0.1% TFA in ACN; gradient 0-100% B over 2 min; retention time: 0.65 min; LCMS (ES-API), m/z 329.8 (M+H).

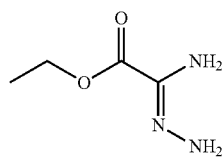

Synthesis of ethyl 2-amino-2-hydrazonoacetate (6): Ethyl 2-amino-2-thioxoacetate (5) (5 g, 37.5 mmol) was dissolved in ethanol and cooled to 0° C. Hydrazine in THF (1M, 37.5 mmol) was added dropwise and stirred at ambient temperature for 1 h. The reaction mixture was concentrated, white flakes of ethyl 2-amino-2-hydrazonoacetate were obtained.

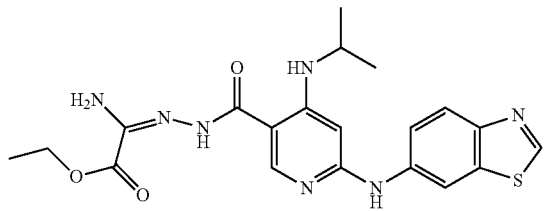 [SMILES: CCOC(=O)/C(N)=N\NC(=O)c1cnc(Nc2ccc3ncsc3c2)cc1NC(C)C]

Synthesis of ethyl 2-amino-2-(2-(6-(benzo[d]thiazol-6-ylamino)-4-(isopropylamino)nicotinoyl)hydrazono)acetate (7): To a stirred solution of 6-(benzo[d]thiazol-6-ylamino)-4-(isopropylamino)nicotinic acid (4) (500 mg, 3.8 mmol) and ethyl 2-amino-2-hydrazonoacetate (6) (3.8 mmol, 1 equiv.) in DMF (10 mL), HATU (7.63 mmol, 2 equiv.) and DIPEA (15.2 mmol, 4 equiv.) were added and stirred for 4 h. The reaction mixture was concentrated under reduced pressure to remove excess of DMF. The residue obtained was partitioned between water and EtOAc. The organic layer was separated, dried over Na$_2$SO$_4$, filtered and concentrated. The crude material obtained was purified by column chromatography through silica gel and MeOH:CHCl$_3$ as eluent to afford the title compound.

Example 1

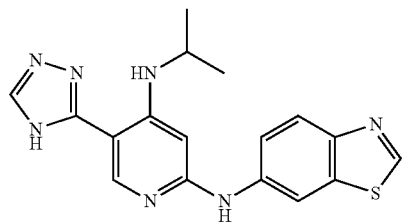 [SMILES: CC(C)Nc1cc(Nc2ccc3ncsc3c2)ncc1-c1nnc[nH]1]

Ethyl 2-amino-2-(2-(6-(benzo[d]thiazol-6-ylamino)-4-(isopropylamino)nicotinoyl)hydrazono)acetate (7) (300 mg, 0.679 mmol) was taken in a sealed tube and heated at 180° C. for 1 h. The reaction mass was dissolved in methanol then concentrated. The crude material obtained was purified by flash column chromatography through silica gel and MeOH:CHCl$_3$ as eluting agents. The material was further purified by prep HPLC to obtain N2-(benzo[d]thiazol-6-yl)-N4-isopropyl-5-(4H-1,2,4-triazol-3-yl)pyridine-2,4-diamine. $^1$H NMR: 400 MHz, CD$_3$OD: δ 1.32 (d, J=4.00 Hz, 6H), 1.43 (t, J=6.80 Hz, 3H), 3.72-3.74 (m, 1H), 4.41 (q, J=6.80 Hz, 2H), 6.17 (s, 1H), 7.48 (dd, J=2.40, 8.8 Hz, 1H), 7.93 (d, J=8.80 Hz, 1H), 8.33 (s, 1H), 8.61 (s, 1H), 9.02 (s, 1H). LC/MS: Ascentis Express C18, 5×2.1 mm-2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 3 min; retention time: 1.789 min; LCMS (ES-API), m/z 422.0 (M−H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.569 min; Purity: 99%.

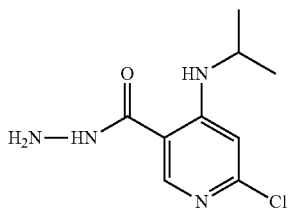

Thiadiazoles

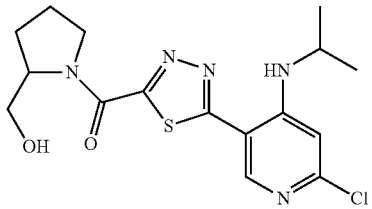 [SMILES: CC(C)Nc1cc(Cl)ncc1-c1nnc(C(=O)N2CCCC2CO)s1]

DCM as eluent afford methyl 5-(6-chloro-4-(isopropylamino)pyridin-3-yl)-1,3,4-thiadiazole-2-carboxylate.

Synthesis of 6-chloro-4-(isopropylamino)nicotinohydrazide (10): To a stirred solution of ethyl 6-chloro-4-(isopropylamino)nicotinate (2) (3 g, 12.39 mmol) in ethanol (10 mL), hydrazine hydrate (3 mL) was added and refluxed at 80° C. for 3 h. The reaction mixture was cooled and concentrated to obtain crude compound. The residue obtained was triturated with diethyl ether and hexane and filtered to get solid, 6-chloro-4-(isopropylamino)nicotinohydrazide (10). LC/MS: Acquity BEH C18 2.1×50 mm, 1.8 micron; Solvent A=0.1% TFA in water; Solvent B=0.1% TFA in ACN; gradient 0-100% B over 2 min; retention time: 0.58 min; LCMS (ES-API), m/z 229.6 (M+H).

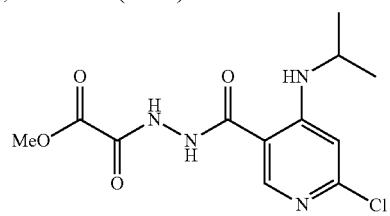

Synthesis of methyl 2-(2-(6-chloro-4-(isopropylamino)nicotinoyl)hydrazinyl)-2-oxoacetate (11): To a stirred solution of 6-chloro-4-(isopropylamino)nicotinohydrazide (10) (200 mg, 0.35 mmol) in DCM (10 mL), Et$_3$N (3.1 mmol, 3 equiv) was added and cooled to 0° C. Methyl 2-chloro-2-oxoacetate (0.42 mmol, 1.2 equiv) was added dropwise and stirred for 6 h at room temperature. The reaction mixture was quenched with aq. NaHCO$_3$ solution and extracted in DCM. The organic layer was separated, dried over Na$_2$SO$_4$, filtered and concentrated. The crude material was purified by column chromatography through silica gel and MeOH:DCM as eluent to afford methyl 2-(2-(6-chloro-4-(isopropylamino)nicotinoyl)hydrazinyl)-2-oxoacetate.

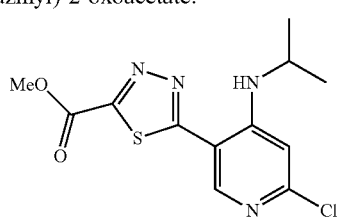

Synthesis of methyl 5-(6-chloro-4-(isopropylamino)pyridin-3-yl)-1,3,4-thiadiazole-2-carboxylate (12): To a stirred solution of methyl 2-(2-(6-chloro-4-(isopropylamino)nicotinoyl)hydrazinyl)-2-oxoacetate (11) (1 g, 3.1 mmol) in THF (30 mL), Lawesson's reagent (6.3 mmol, 2 equiv) was added and heated to reflux for 3 h. The reaction mixture was diluted with EtOAc and washed twice with 10% NaHCO$_3$ solution. The organic layer was collected, dried over Na$_2$SO$_4$, filtered and concentrated. The crude material obtained was purified by column chromatography through silica gel and MeOH:

Synthesis of (5-(6-chloro-4-(isopropylamino)pyridin-3-yl)-1,3,4-thiadiazol-2-yl)(3-(hydroxymethyl)pyrrolidin-1-yl)methanone (13): To a stirred solution of methyl 5-(6-chloro-4-(isopropylamino)pyridin-3-yl)-1,3,4-thiadiazole-2-carboxylate (12) (60 mg, 0.1 mmol) in MeOH (2 mL), (S)-Prolinol (0.9 mmol, 5 equiv) was added and refluxed at 80° C. for 1 h. The reaction mixture was cooled and concentrated. The crude material obtained was purified by column chromatography through silica gel and MeOH:DCM as eluent to isolate the desired product, (5-(6-chloro-4-(isopropylamino)pyridin-3-yl)-1,3,4-thiadiazol-2-yl)(3-(hydroxymethyl)pyrrolidin-1-yl)methanone (). LCMS: XBridge Phe 8, 4.6×30 mm, 3.5 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.585 min; LCMS (ES-API), m/z 379.8 (M−H).

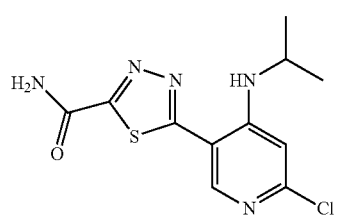 [SMILES: CC(C)Nc1cc(Cl)ncc1-c1nnc(C(N)=O)s1]

Synthesis of 5-(6-chloro-4-(isopropylamino)pyridin-3-yl)-1,3,4-thiadiazole-2-carboxamide (14): A solution of methyl 5-(6-chloro-4-(isopropylamino)pyridin-3-yl)-1,3,4-thiadiazole-2-carboxylate (12) (200 mg, 0.64 mmol) in MeOH (10 mL) was cooled to −10° C. and NH$_3$(g) was purged through the reaction mixture for 5 min. The reaction was heated for 4 h at 80° C., cooled to 0° C. and concentrated to afford the desired compound, 5-(6-chloro-4-(isopropylamino)pyridin-3-yl)-1,3,4-thiadiazole-2-carboxamide. The material was used directly in the next step without purification.

Example 2

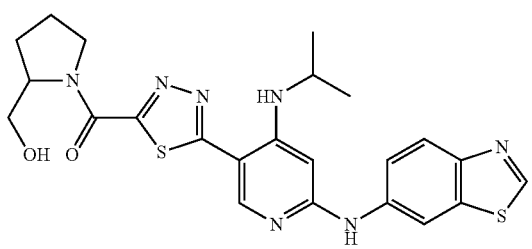 [SMILES: CC(C)Nc1cc(Nc2ccc3ncsc3c2)ncc1-c1nnc(C(=O)N2CCCC2CO)s1]

Synthesis of (5-(6-(benzo[d]thiazol-6-ylamino)-4-(isopropylamino)pyridin-3-yl)-1,3,4-thiadiazol-2-yl)(2-(hydroxymethyl)pyrrolidin-1-yl)methanone. To a solution of (5-(6-chloro-4-(isopropylamino)pyridin-3-yl)-1,3,4-thiadiazol-2-yl)(3-(hydroxymethyl)pyrrolidin-1-yl)methanone (27a) (50 mg, 0.15 mmol) in dioxane (5 mL):$H_2O$ (1 mL), 6-amino benzothiazole (0.18 mmol, 1.2 equiv.), xanthphos (0.07 mmol, 0.5 equiv.) and $Na_2CO_3$ (0.7 mmol, 3 equiv.) were added and degassed for 10 min. To the reaction mixture $Pd_2(dba)_3$ (0.07 mmol, 0.5 equiv.) was added and degassed again for 10 min then heated at 115° C., overnight. The reaction mixture was cooled and filtered through small pad of celite. The filtrate was concentrated and the crude material was purified by column chromatography through silica gel and MeOH:$CHCl_3$ as eluent. The material was further purified by prep HPLC to afford the title compound. $^1$H NMR: 400 MHz, $CD_3OD$: δ 1.38 (d, J=6.40 Hz, 1H), 2.01-2.03 (m, 4H), 3.71-3.85 (m, 4H), 3.87-4.23 (m, 2H), 6.22 (s, 1H), 7.57 (dd, J=2.00, 8.80 Hz, 1H), 8.15 (d, J=8.80 Hz, 1H), 8.22 (m, 1H), 8.35 (bs, 1H), 9.28 (s, 1H). LC/MS: Purospher@star RP-18, 4×55 mm, 3 μm; Solvent A=10% ACN: 90% $H_2O$: 20 mM $NH_4OAc$; Solvent B=90% ACN: 10% $H_2O$: 20 mM $NH_4COOAc$; gradient 0-100% B over 1.5 min (3.2 min run time); retention time: 1.809 min; LCMS (ES-API), m/z 496.2 (M+H). HPLC: Sunfire C18 (150×4.6 mm), 3.5 micron; Solvent A=5% ACN: 95% $H_2O$: 0.05% TFA pH=2.5; Solvent B=95% ACN: 5% $H_2O$: 0.05% TFA pH=2.5; gradient 0-100% B over 15 min (23 min run time); Flow rate: 1.0 μL/min; Retention time: 6.317 min; Purity: 96.7%.

Synthesis of Examples 3-18: The method outlined above for Example 2 was used to prepared Examples 3-18, using appropriate amines Example 16 was prepared from compound 14 using the procedures outlined above.

TABLE 1

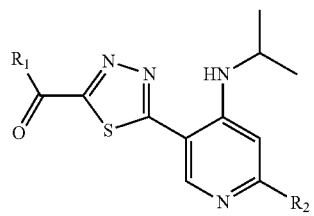

| Example No. | $R_1$ | $R_2$ |
|---|---|---|
| 2 | 2-(hydroxymethyl)pyrrolidin-1-yl | benzo[d]thiazol-6-ylamino |
| 3 | (S)-3-hydroxypyrrolidin-1-yl | benzo[c][1,2,5]thiadiazol-5-ylamino |
| 4 | (R)-3-hydroxypyrrolidin-1-yl | benzo[c][1,2,5]thiadiazol-5-ylamino |
| 5 | 3-hydroxypyrrolidin-1-yl | benzo[d]thiazol-6-ylamino |
| 6 | 3-hydroxypyrrolidin-1-yl (Dia 1) | benzo[d]thiazol-6-ylamino |
| 7 | 3-hydroxypyrrolidin-1-yl (Dia 2) | benzo[d]thiazol-6-ylamino |
| 8 | 3-acetamidopyrrolidin-1-yl (Ent 2) | benzo[d]thiazol-6-ylamino |
| 9 | 3-hydroxypiperidin-1-yl | benzo[d]thiazol-6-ylamino |
| 10 | 4-aminopiperidin-1-yl | benzo[d]thiazol-6-ylamino |
| 11 | piperazin-1-yl | 4-cyanophenylamino |
| 12 | 3-aminopyrrolidin-1-yl (Ent 2) | benzo[d]thiazol-6-ylamino |

TABLE 1-continued

| Example No. | R₁ | R₂ |
|---|---|---|
| 13 | (3-acetamidopyrrolidin-1-yl), Racemic | benzothiazol-6-ylamino |
| 14 | (3-aminopyrrolidin-1-yl), Racemic | benzothiazol-6-ylamino |
| 15 | (3-methylsulfonamidopyrrolidin-1-yl) | benzothiazol-6-ylamino |
| 16 | NH₂ | benzothiazol-6-ylamino |
| 17 | 4-hydroxypiperidin-1-yl | 4-cyanophenylamino |
| 18 | morpholin-4-yl | 4-cyanophenylamino |

Example 3

(R)-(5-(6-(Benzo[c][1,2,5]thiadiazol-5-ylamino)-4-(isopropylamino)pyridin-3-yl)-1,3,4-thiadiazol-2-yl)(3-hydroxypyrrolidin-1-yl)methanone

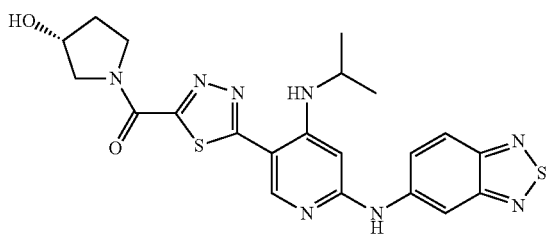 [SMILES: CC(C)Nc1cc(Nc2ccc3nsnc3c2)ncc1-c1nnc(C(=O)N2CC[C@@H](O)C2)s1]

$^1$H NMR: 400 MHz, DMSO-d$_6$: δ 1.34 (d, J=6.40 Hz, 6H), 1.87-1.99 (m, 2H), 3.59-3.70 (m, 2H), 3.77-3.81 (m, 1H), 3.98-4.00 (m, 1H), 4.05-4.20 (m, 1H), 4.35-4.42 (m, 1H), 5.07 (s, 1H), 7.61 (dd, J=2.00, −78.20 Hz, 1H), 7.97 (d, J=9.20 Hz, 1H), 8.46 (d, J=7.20 Hz, 1H), 8.63 (s, 1H), 8.77 (d, J=1.60 Hz, 1H), 9.76 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.91 min; LCMS (ES-API), m/z 483.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.869 min; Purity: 98.5%.

Example 4

(S)-(5-(6-(Benzo[c][1,2,5]thiadiazol-5-ylamino)-4-(isopropylamino)pyridin-3-yl)-1,3,4-thiadiazol-2-yl)(3-hydroxypyrrolidin-1-yl)methanone

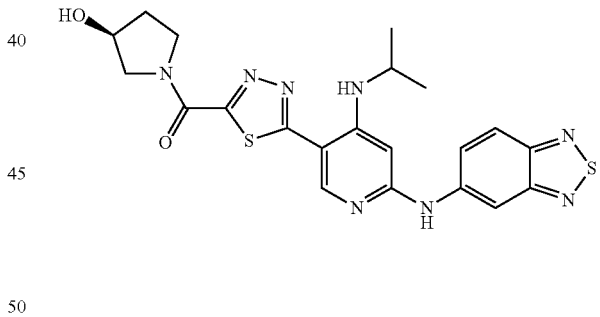

$^1$H NMR: 400 MHz, DMSO-d$_6$: δ 1.35 (d, J=6.00 Hz, 6H), 1.95-1.98 (m, 2H), 3.18 (d, J=5.20 Hz, 3H), 3.60-4.42 (m, 7H), 5.10 (bs, 1H), 6.32 (s, 1H), 7.61 (dd, J=2.40, −76.60 Hz, 1H), 7.98 (d, J=9.60 Hz, 1H), 8.47 (d, J=6.80 Hz, 1H), 8.64 (s, 1H), 8.79 (d, J=2.00 Hz, 1H), 9.78 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.91 min; LCMS (ES-API), m/z 483.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.86 min; Purity: 95.4%.

Example 5

(5-(6-(Benzo[d]thiazol-6-ylamino)-4-(isopropylamino)pyridin-3-yl)-1,3,4-thiadiazol-2-yl)(3-hydroxypyrrolidin-1-yl)methanone

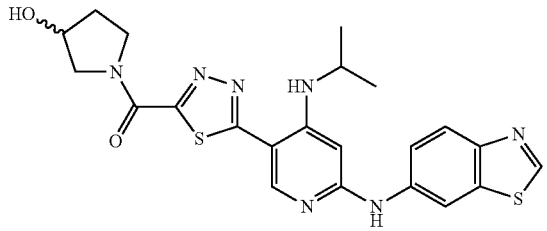 [SMILES: CC(C)Nc1cc(Nc2ccc3ncsc3c2)ncc1-c1nnc(C(=O)N2CCC(O)C2)s1]

$^1$H NMR: 400 MHz, DMSO-$d_6$: δ 1.33 (d, J=6.40 Hz, 6H), 1.87-1.99 (m, 2H), 3.54-3.79 (m, 3H), 4.00-4.02 (m, 1H), 4.20-4.42 (m, 2H), 5.07 (d, J=3.20 Hz, 1H), 6.20 (s, 1H), 7.60 (dd, J=2.40, 9.00 Hz, 1H), 7.98 (d, J=8.80 Hz, 1H), 8.40 (d, J=7.20 Hz, 1H), 8.52 (s, 1H), 8.69 (d, J=2.00 Hz, 1H), 9.18 (s, 1H), 9.49 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.515 min; LCMS (ES-API), m/z 482.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.619 min; Purity: 97.1%.

Example 6

(5-(6-(Benzo[d]thiazol-6-ylamino)-4-(isopropylamino)pyridin-3-yl)-1,3,4-thiadiazol-2-yl)(3-hydroxypyrrolidin-1-yl)methanone

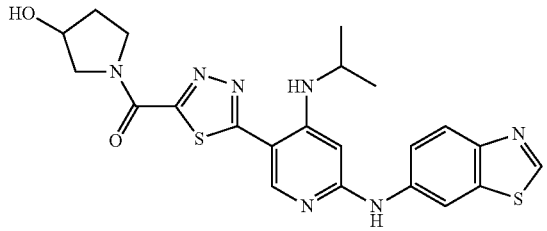 [SMILES: CC(C)Nc1cc(Nc2ccc3ncsc3c2)ncc1-c1nnc(C(=O)N2CCC(O)C2)s1]

$^1$H NMR: 400 MHz, DMSO-$d_6$: δ 1.32 (d, J=6.00 Hz, 6H), 1.86-1.97 (m, 2H), 3.50-3.78 (m, 3H), 4.00-4.01 (m, 2H), 4.01-4.41 (m, 1H), 5.06 (d, J=3.60 Hz, 1H), 6.19 (s, 1H), 7.59 (dd, J=2.00, 8.80 Hz, 1H), 7.97 (d, J=9.20 Hz, 1H), 8.39 (d, J=6.80 Hz, 1H), 8.51 (s, 1H), 8.67 (d, J=2.00 Hz, 1H), 9.17 (s, 1H), 9.40 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.510 min; LCMS (ES-API), m/z 482.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μL/min; Retention time: 11.92 min; Purity: 98.9%.

Example 7

(5-(6-(Benzo[d]thiazol-6-ylamino)-4-(isopropylamino)pyridin-3-yl)-1,3,4-thiadiazol-2-yl)(3-hydroxypyrrolidin-1-yl)methanone

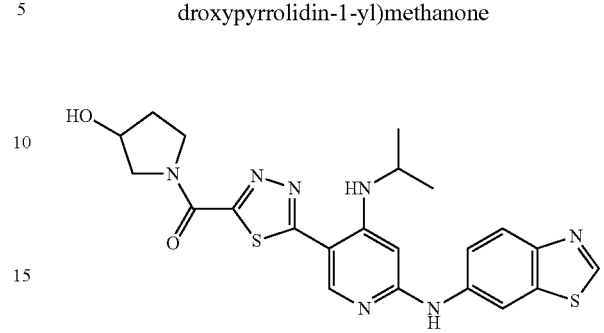

$^1$H NMR: 400 MHz, DMSO-$d_6$: δ 1.32 (d, J=6.40 Hz, 6H), 1.94-1.97 (m, 2H), 3.50-3.78 (m, 3H), 3.97-4.04 (m, 2H), 4.19-4.41 (m, 1H), 5.06 (d, J=3.20 Hz, 1H), 6.19 (s, 1H), 7.59 (dd, J=2.00, 8.80 Hz, 1H), 7.97 (d, J=8.80 Hz, 1H), 8.39 (d, J=7.20 Hz, 1H), 8.51 (s, 1H), 8.67 (d, J=2.00 Hz, 1H), 9.17 (s, 1H), 9.48 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.510 min; LCMS (ES-API), m/z 482.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μL/min; Retention time: 11.43 min; Purity: 95.1%.

Example 8

N-(1-(5-(6-(Benzo[d]thiazol-6-ylamino)-4-(isopropylamino)pyridin-3-yl)-1,3,4-thiadiazole-2-carbonyl)pyrrolidin-3-yl)acetamide

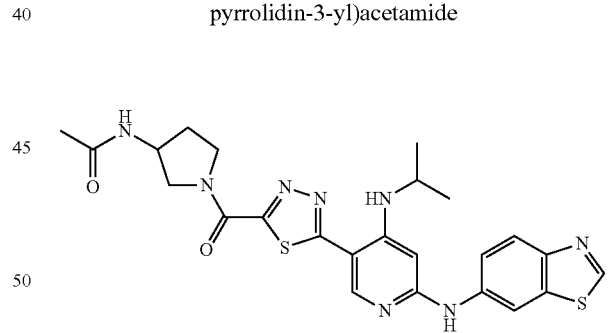

$^1$H NMR: 400 MHz, CD$_3$OD: δ 1.37-1.38 (m, 6H), 1.94-2.01 (m, 4H), 2.15-2.23 (m, 2H), 3.78-3.94 (m, 2H), 4.11-4.15 (m, 1H), 4.25-4.36 (m, 2H), 4.45-4.51 (m, 1H), 6.17 (s, 1H), 7.55 (dd, J=2.00, 8.80 Hz, 1H), 7.98 (d, J=8.80 Hz, 1H), 8.43 (d, J=1.20 Hz, 1H), 8.50 (d, J=1.60 Hz, 1H), 9.09 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.773 min; LCMS (ES-API), m/z 523.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.936 min; Purity: 95.5%.

Example 9

(5-(6-(Benzo[d]thiazol-6-ylamino)-4-(isopropylamino)pyridin-3-yl)-1,3,4-thiadiazol-2-yl)(3-hydroxypiperidin-1-yl)methanone

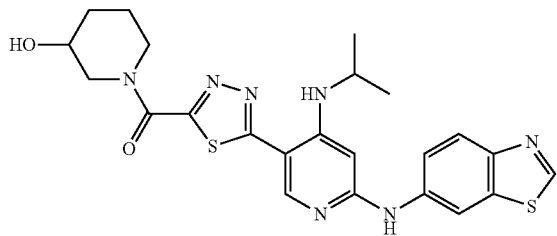 [SMILES: CC(C)Nc1cc(Nc2ccc3ncsc3c2)ncc1-c1nnc(C(=O)N2CCCC(O)C2)s1]

$^1$H NMR: 400 MHz, CD$_3$OD: δ 1.38 (d, J=6.40 Hz, 6H), 1.63-1.72 (m, 2H), 1.93-2.06 (m, 2H), 3.60-3.87 (m, 5H), 4.18-4.21 (m, 1H), 4.39-4.42 (m, 1H), 6.19 (s, 1H), 7.56 (dd, J=2.00, 8.80 Hz, 1H), 7.98 (d, J=8.80 Hz, 1H), 8.42 (s, 1H), 8.49 (s, 1H), 9.09 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.57 min; LCMS (ES-API), m/z 496.0 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.131 min; Purity: 95%.

Example 10

(4-Aminopiperidin-1-yl)(5-(6-(benzo[d]thiazol-6-ylamino)-4-(isopropylamino)pyridin-3-yl)-1,3,4-thiadiazol-2-yl)methanone

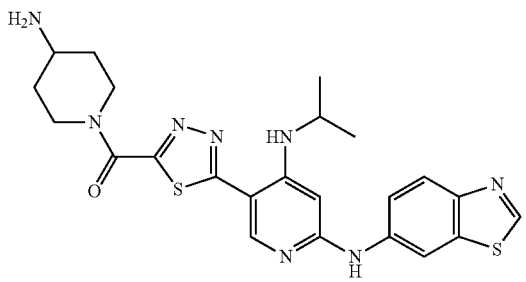 [SMILES: CC(C)Nc1cc(Nc2ccc3ncsc3c2)ncc1-c1nnc(C(=O)N2CCC(N)CC2)s1]

$^1$H NMR: 400 MHz, CD$_3$OD: δ 1.39 (d, J=6.40 Hz, 6H), 1.67-1.69 (m, 1H), 1.78-1.80 (m, 1H), 2.14-2.22 (m, 2H), 3.06-3.02 (m, 1H), 3.33-3.34 (1H, merged with water peak), 3.50-3.54 (m, 1H), 3.88-3.91 (m, 1H), 4.73-4.86 (1H, merged with CD$_3$OD peak), 5.25-5.28 (m, 1H), 6.25 (s, 1H), 7.58 (dd, J=1.60, 8.80 Hz, 1H), 8.16 (d, J=1.60 Hz, 1H), 8.22 (d, J=8.80 Hz, 1H), 8.32 (s, 1H), 9.34 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.455 min; LCMS (ES-API), m/z 495.0 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.621 min; Purity: 90.7%.

Example 11

4-((4-(Isopropylamino)-5-(5-(piperazine-1-carbonyl)-1,3,4-thiadiazol-2-yl)pyridin-2-yl)amino)benzonitrile

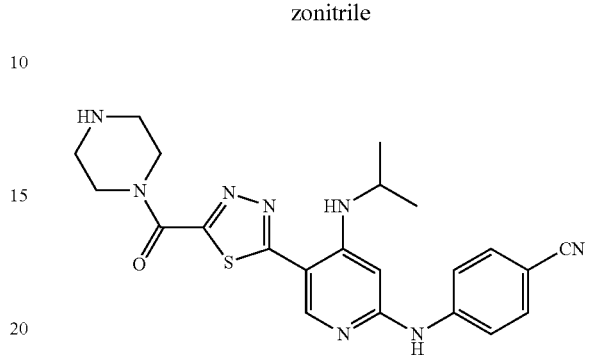

$^1$H NMR: 400 MHz, DMSO-d$_6$: δ 1.31 (d, J=6.00 Hz, 6H), 3.27-3.39 (m, 4H), 3.74-3.79 (m, 1H), 3.90 (bs, 2H), 4.41 (bs, 1H), 6.26 (s, 1H), 7.69-7.71 (m, 2H), 7.86-7.88 (m, 2H), 8.40-8.42 (m, 1H), 8.54 (s, 1H), 9.09 (bs, 1H), 9.81 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.725 min; LCMS (ES-API), m/z 449.0 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.055 min; Purity: 91.9%.

Example 12

(3-Aminopyrrolidin-1-yl)(5-(6-(benzo[d]thiazol-6-ylamino)-4-(isopropylamino)pyridin-3-yl)-1,3,4-thiadiazol-2-yl)methanone

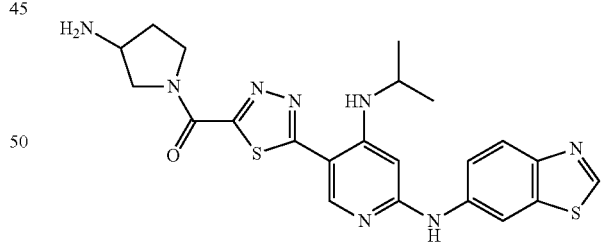

$^1$H NMR: 400 MHz, CD$_3$OD: δ 1.36-1.38 (m, 6H), 2.19-2.31 (m, 1H), 3.64-3.75 (m, 2H), 3.81-3.97 (m, 3H), 4.22-4.35 (m, 2H), 6.18 (s, 1H), 6.68-6.70 (m, 1H), 7.14-7.16 (m, 1H), 7.58 (dd, J=2.00, 26.80 Hz, 1H), 7.98 (d, J=8.80 Hz, 1H), 8.42 (s, 1H), 8.48 (d, J=2.00 Hz, 1H), 9.08 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.656 min; LCMS (ES-API), m/z 479.0 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient

Example 13

N-(1-(5-(6-(Benzo[d]thiazol-6-ylamino)-4-(isopropylamino)pyridin-3-yl)-1,3,4-thiadiazole-2-carbonyl)pyrrolidin-3-yl)acetamide

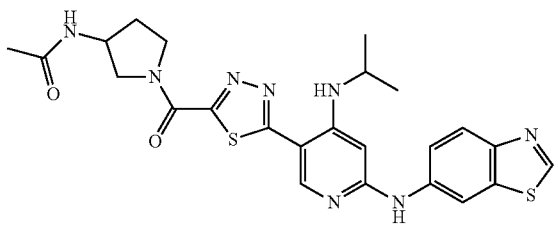 [SMILES: CC(=O)NC1CCN(C(=O)c2nnc(-c3cnc(Nc4ccc5ncsc5c4)cc3NC(C)C)s2)C1]

¹H NMR: 400 MHz, CD₃OD: δ 1.37 (d, J=6.40 Hz, 6H), 1.97-2.03 (m, 2H), 2.08-2.34 (m, 2H), 3.62-3.65 (m, 1H), 3.78-3.94 (m, 3H), 4.10-4.14 (m, 1H), 4.25-4.34 (m, 2H), 4.50-4.57 (m, 2H), 6.18 (s, 1H), 7.55 (dd, J=2.00, 8.80 Hz, 1H), 7.98 (d, J=8.80 Hz, 1H), 8.42 (s, 1H), 8.48 (bs, 1H), 8.61 (d, J=7.20 Hz, 1H), 9.08 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.503 min; LCMS (ES-API), m/z 523.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.657 min; Purity: 98.3%.

Example 14

(3-Aminopyrrolidin-1-yl)(5-(6-(benzo[d]thiazol-6-ylamino)-4-(isopropylamino)pyridin-3-yl)-1,3,4-thiadiazol-2-yl)methanone

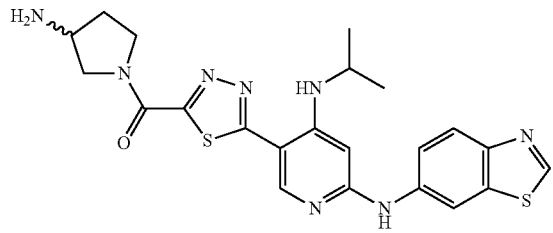 [SMILES: CC(C)Nc1cc(Nc2ccc3ncsc3c2)ncc1-c1nnc(C(=O)N2CCC(N)C2)s1]

¹H NMR: 400 MHz, CD₃OD: δ 1.37 (d, J=6.00 Hz, 6H), 1.82-1.97 (m, 2H), 2.18-2.24 (m, 1H), 3.65-3.74 (m, 2H), 3.80-3.94 (m, 3H), 4.21-4.30 (m, 2H), 6.17 (s, 1H), 7.55 (dd, J=2.00, 8.80 Hz, 1H), 7.98 (d, J=8.80 Hz, 1H), 8.42 (s, 1H), 8.48 (d, J=2.00 Hz, 1H), 9.08 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.458 min; LCMS (ES-API), m/z 481.2 (M+H). HPLC: Eclipse XDB C18 (150×4 6 mm) 5 micron; Solvent A=20 mM NH₄OAc in water; Solvent B=ACN; Flow rate=1.0 mL/min; Retention time: 7.946 min; Purity: 90.5%.

Example 15

N-(1-(5-(6-(Benzo[d]thiazol-6-ylamino)-4-(isopropylamino)pyridin-3-yl)-1,3,4-thiadiazole-2-carbonyl)pyrrolidin-3-yl)methanesulfonamide

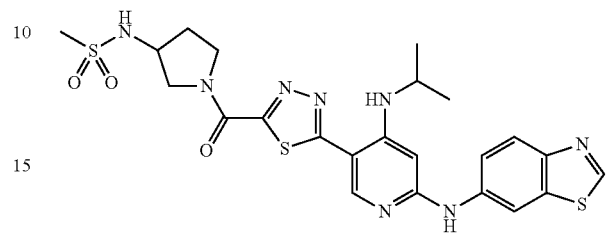

¹H NMR: 400 MHz, CD₃OD: δ 1.37-1.38 (m, 6H), 2.00-2.41 (m, 4H), 3.04-3.04 (m, 3H), 3.60-4.40 (m, 4H), 4.57 (s, 4H), 6.18 (s, 1H), 7.55 (dd, J=2.00, 8.80 Hz, 1H), 7.98 (d, J=8.80 Hz, 1H), 8.43 (s, 1H), 8.48 (d, J=2.00 Hz, 1H), 9.08 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.576 min; LCMS (ES-API), m/z 559.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 6.104 min; Purity: 90.7%.

Example 16

5-(6-(Benzo[d]thiazol-6-ylamino)-4-(isopropylamino)pyridin-3-yl)-1,3,4-thiadiazole-2-carboxamide

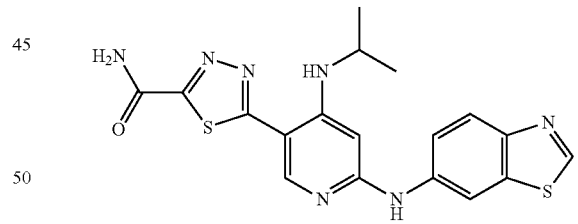

¹H NMR: 400 MHz, DMSO-d₆: δ 1.32 (d, J=6.00 Hz, 6H), 1.77 (s, 2H), 3.72-3.80 (m, 1H), 6.20 (s, 1H), 7.60 (dd, J=2.40, 8.80 Hz, 1H), 7.97-7.99 (m, 1H), 8.13 (s, 1H), 8.43 (d, J=7.20 Hz, 1H), 8.52-8.55 (m, 2H), 8.69 (d, J=2.00 Hz, 1H), 9.18 (s, 1H), 9.51 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.539 min; LCMS (ES-API), m/z 412.2 (M+H). HPLC: XBridge (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 6.653 min; Purity: 94.9%.

Example 17

4-((5-(5-(4-Hydroxypiperidine-1-carbonyl)-1,3,4-thiadiazol-2-yl)-4-(isopropylamino)pyridin-2-yl)amino)benzonitrile

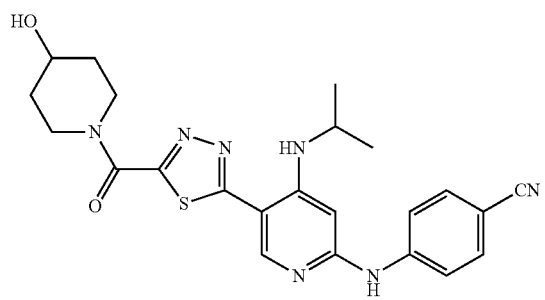 [SMILES: CC(C)Nc1cc(Nc2ccc(C#N)cc2)ncc1-c1nnc(C(=O)N2CCC(O)CC2)s1]

$^1$H NMR: 400 MHz, CD$_3$OD: δ 1.40 (d, J=6.40 Hz, 6H), 1.62-1.70 (m, 2H), 2.00-2.04 (m, 2H), 3.48-3.53 (m, 1H), 3.84-3.90 (m, 2H), 4.00-4.03 (m, 1H), 4.19-4.22 (m, 1H), 4.80-4.90 (m, 1H), 6.23 (s, 1H), 7.57 (dd, J=2.40, 8.60 Hz, 1H), 8.20 (d, J=1.60 Hz, 1H), 8.31 (s, 1H), 9.30 (s, 1H). LC/MS: XBridge Phe 8, 4.6×30 mm, 3.5 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.529 min; LCMS (ES-API), m/z 496.0 (M+H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 6.815 min; Purity: 98.5%.

Example 18

4-((4-(Isopropylamino)-5-(5-(morpholine-4-carbonyl)-1,3,4-thiadiazol-2-yl)pyridin-2-yl)amino)benzonitrile

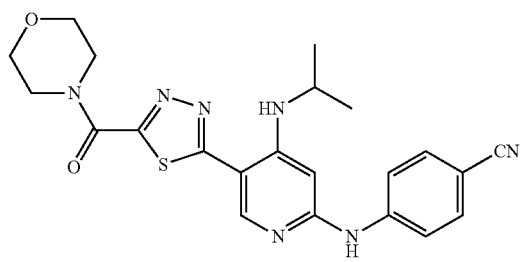 [SMILES: CC(C)Nc1cc(Nc2ccc(C#N)cc2)ncc1-c1nnc(C(=O)N2CCOCC2)s1]

$^1$H NMR: 400 MHz, CDCl$_3$: δ 1.33 (d, J=6.40 Hz, 6H), 3.66-3.71 (m, 1H), 3.81-3.84 (m, 6H), 4.40-4.42 (m, 2H), 6.10 (s, 1H), 6.71 (s, 1H), 7.43 (dd, J=2.00, 8.80 Hz, 1H), 8.09-8.12 (m, 2H), 8.40 (s, 1H), 8.56 (d, J=6.40 Hz, 1H), 8.92 (s, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.612 min; LCMS (ES-API), m/z 482.2 (M+H). HPLC: Eclipse XDB C18 (150×4.6 mm) 5 micron; Solvent A=20 mM NH$_4$OAc in water; Solvent B=ACN; Flow rate=1.0 mL/min; Retention time: 10.488 min; Purity: 96%.

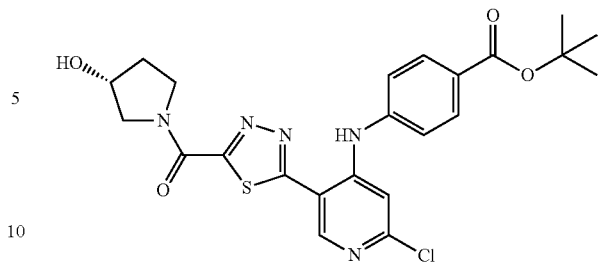

Synthesis of (R)-tert-butyl 4-((2-chloro-5-(5-(3-hydroxypyaolidine-1-carbonyl)-1,3,4-thiadiazol-2-yl)pyridin-4-yl)amino)benzoate (14): Prepared according to the methods outlined in Example 2 from ethyl 4,6-dichloronicotinate (1) and tert-butyl 4-aminobenzoate. LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 2.113 min; LCMS (ES-API), m/z 502.0 (M+H).

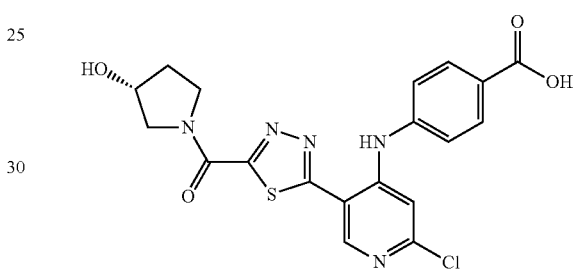

Synthesis of (R)-4-((2-chloro-5-(5-(3-hydroxypyrrolidine-1-carbonyl)-1,3,4-thiadiazol-2-yl)pyridin-4-yl)amino)benzoic acid (15): Followed the same procedure as mentioned in the synthesis of compound no. 2. LC/MS: Acquity BEH C18 2.1×50 mm, 1.8 micron; Solvent A=0.1% TFA in water; Solvent B=0.1% TFA in ACN; gradient 0-100% B over 2 min; retention time: 0.74 min; LCMS (ES-API), m/z 446.39 (M+H).

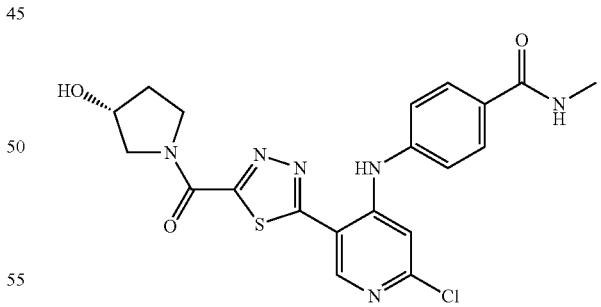

Synthesis of (R)-4-((2-chloro-5-(5-(3-hydroxypyrrolidine-1-carbonyl)-1,3,4-thiadiazol-2-yl)pyridin-4-yl)amino)-N-methylbenzamide (16): To a stirred solution of (R)-4-((2-chloro-5-(5-(3-hydroxypyrrolidine-1-carbonyl)-1,3,4-thiadiazol-2-yl)pyridin-4-yl)amino)benzoic acid (15) (150 mg, 0.336 mmol) in DMF (10 mL), DIPEA (1.682 mmol, 5 equiv.), methanamine HCl (3.36 mmol, 10 equiv.) and HATU (0.673 mmol, 2 equiv.) were added at room temperature. The reaction mixture was allowed to stir overnight at ambient temperature. The reaction mixture was evaporated to remove excess of DMF. The residue obtained was then diluted with water and extracted using EtOAc. The organic layer was dried over Na$_2$SO$_4$, filtered and evaporated to get crude compound. The crude compound was purified by column chromatography through silica gel and MeOH:DCM as eluent to isolate the desired compound, (R)-4-((2-chloro-5-(5-(3-hydroxypyrrolidine-1-carbonyl)-1,3,4-thiadiazol-2-yl)pyridin-4-yl)amino)-N-methylbenzamide (16). LC/MS: Acquity BEH C18 2.1×50 mm, 1.8 micron; Solvent A=0.1% TFA in water; Solvent B=0.1% TFA in ACN; gradient 0-100% B over 2 min; retention time: 0.71 min; LCMS (ES-API), m/z 459.63 (M+H).

Example 19

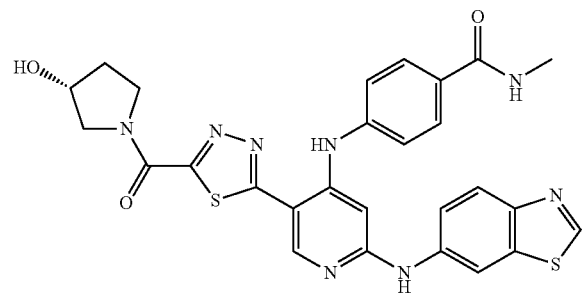 [SMILES: CNC(=O)c1ccc(Nc2cc(Nc3ccc4ncsc4c3)ncc2-c2nnc(C(=O)N3CC[C@@H](O)C3)s2)cc1]

Synthesis of (R)-4-((2-(benzo[d]thiazol-6-ylamino)-5-(5-(3-hydroxypyrrolidine-1-carbonyl)-1,3,4-thiadiazol-2-yl)pyridin-4-yl)amino)-N-methylbenzamide: Prepared according to the methods outlined in Example 2. $^1$H NMR: 400 MHz, CD$_3$OD: δ 1.95 (s, 2H), 2.96 (s, 3H), 3.53-3.54 (m, 1H), 3.74-3.75 (m, 1H), 3.83-3.85 (m, 1H), 3.93 (t, J=6.40 Hz, 1H), 4.15-4.24 (m, 1H), 6.80 (s, 1H), 7.48 (d, J=8.40 Hz, 2H), 7.55 (dd, J=2.00, 8.80 Hz, 1H), 7.91-7.98 (m, 3H), 8.56 (d, J=2.00 Hz, 1H), 8.62 (s, 1H), 9.09 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.71 min; LCMS (ES-API), m/z 573.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.148 min; Purity: 96.3%.

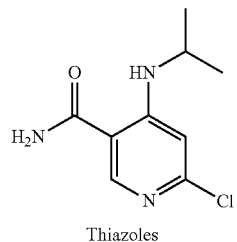

Thiazoles

Synthesis of 6-chloro-4-(isopropylamino)nicotinamide (17): 6-chloro-4-(isopropylamino)nicotinic acid (9) (3 g, 14 mmol) was dissolved in DCM (15 mL) and cooled to 0° C. Oxalyl chloride (2 equiv.) was added, followed by addition of 2 drops of DMF. The reaction mixture was stirred at room temperature for 2 h. The reaction mixture was concentrated to remove excess of oxalyl chloride and redissolved in DCM (15 mL) and cooled to 0° C. Aqueous NH$_3$ solution was added dropwise to the reaction mixture and stirred at room temperature for 3 h. The reaction mixture was diluted using DCM and washed with aq. NaHCO$_3$ solution. The organic layer was separately collected, dried over Na$_2$SO$_4$, filtered and concentrated to obtain the desired compound, 6-chloro-4-(isopropylamino)nicotinamide. LC/MS: Acquity BEH C18 2.1×50 mm, 1.8 micron; Solvent A=0.1% TFA in water; Solvent B=0.1% TFA in ACN; gradient 0-100% B over 2 min; retention time: 0.58 min; LCMS (ES-API), m/z 214.7 (M+H).

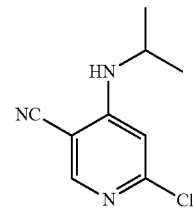

Synthesis of 6-chloro-4-(isopropylamino)nicotinonitrile (18): To a stirred solution of 6-chloro-4-(isopropylamino)nicotinamide (17) (2.5 g, 11.7 mmol) in DMF (10 mL), cyanuric chloride (11.7 mmol, 1 equiv.) was added at 0° C. and stirred for 2 h. The reaction mixture was quenched with ice-cool water and extracted twice using EtOAc. The organic layer was collected, dried over Na$_2$SO$_4$, filtered and concentrated. The crude material was purified by column chromatography, silica gel (60-120 mesh) and EtOAc:pet Ether as eluent to furnish 6-chloro-4-(isopropylamino)nicotinonitrile. $^1$H NMR: 400 MHz, CDCl$_3$: δ 1.32 (d, J=6.40 Hz, 6H), 3.69-3.79 (m, 1H), 4.91 (bs, 1H), 6.57 (s, 1H), 8.23 (s, 1H).

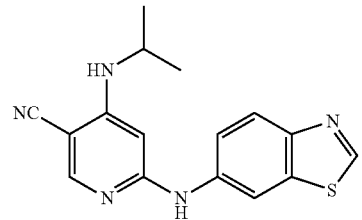 [SMILES: CC(C)Nc1cc(Nc2ccc3ncsc3c2)ncc1C#N]

Synthesis of 6-(benzo[d]thiazol-6-ylamino)-4-(isopropylamino)nicotinonitrile (19): To a solution of 6-chloro-4-(isopropylamino)nicotinonitrile (18) (1 g, 5.1 mmol) in dioxane (40 mL):H$_2$O (4 mL), 6-amino benzothiazole (5.1 mmol, 1 equiv.), xanthphos (2.0 mmol, 0.4 equiv.) and Na$_2$CO$_3$ (20.5 mmol, 4 equiv.) were added and degassed for 10 min. To the reaction mixture Pd$_2$(dba)$_3$ (2.0 mmol, 0.4 equiv.) was added and degassed again for 10 min. It was then heated at 115° C. for overnight. The reaction mixture was cooled and filtered through small pad of celite. The filtrate obtained was concentrated and the crude material was purified by column chromatography through silica gel and MeOH:CHCl$_3$ as eluent to afford 6-(benzo[d]thiazol-6-ylamino)-4-(isopropylamino)nicotinonitrile.

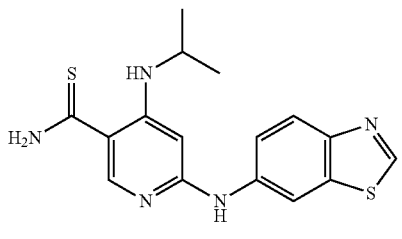 [SMILES: CC(C)Nc1cc(Nc2ccc3ncsc3c2)ncc1C(N)=S]

Synthesis of 6-(benzo[d]thiazol-6-ylamino)-4-(isopropylamino)pyridine-3-carbothioamide (20): To a stirred solution of 6-(benzo[d]thiazol-6-ylamino)-4-(isopropylamino)nicotinonitrile (19) (30 mg, 0.09 mmol) in MeOH (2 mL), ammonium thiosulfide (5 mL) was added. The reaction mixture was heated at 60° C. in a pressure tube overnight. The reaction mixture was then evaporated to remove excess of solvent. The crude material was purified by column chromatography through silica gel and MeOH:CHCl$_3$ as eluent to afford 6-(benzo[d]thiazol-6-ylamino)-4-(isopropylamino)pyridine-3-carbothioamide.

Example 20

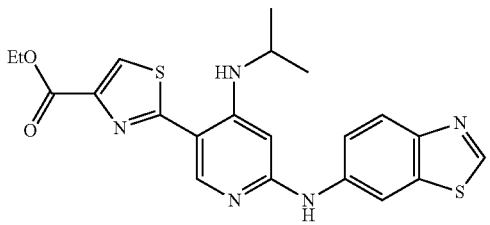 [SMILES: CCOC(=O)c1csc(-c2cnc(Nc3ccc4ncsc4c3)cc2NC(C)C)n1]

Synthesis of ethyl 2-(6-(benzo[d]thiazol-6-ylamino)-4-(isopropylamino)pyridin-3-yl)thiazole-4-carboxylate: 6-(benzo[d]thiazol-6-ylamino)-4-(isopropylamino)pyridine-3-carbothioamide (20) (30 mg, 0.08 mmol) and ethyl bromopyruvate (0.17 mmol, 2 equiv.) were taken in DMF (5 mL) and heated at 100° C. for 3 h. The reaction mixture was then concentrated under reduced pressure to remove excess of DMF. The residue was diluted with EtOAc and washed with water. The aqueous layer was extracted with EtOAc twice. The organic layers were collected, dried over Na$_2$SO$_4$, filtered and concentrated. The crude material obtained was purified by column chromatography through silica gel and MeOH:CHCl$_3$ as eluent to afford ethyl 2-(6-(benzo[d]thiazol-6-ylamino)-4-(isopropylamino)pyridin-3-yl)thiazole-4-carboxylate. $^1$H NMR: 400 MHz, CD$_3$OD: δ 1.34 (d, J=20.00 Hz, 6H), 1.43 (t, J=7.20 Hz, 3H), 3.75-3.77 (m, 1H), 4.41 (q, J=7.20 Hz, 2H), 6.16 (s, 1H), 7.54 (dd, J=2.00, 8.8 Hz, 1H), 7.97 (d, J=8.80 Hz, 1H), 8.21 (s, 1H), 8.43 (s, 1H), 9.07 (s, 1H). LC/MS: Ascentis Express C18, 5×2.1 mm-2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 3 min; retention time: 2.131 min; LCMS (ES-API), m/z 440.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 7.409 min; Purity: 98%.

Example 21

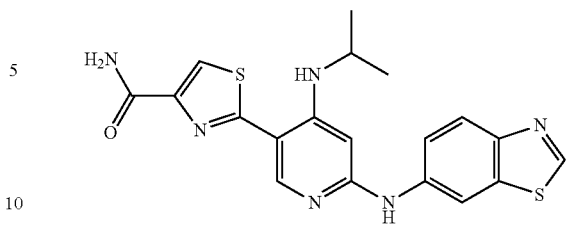

Synthesis of 2-(6-(benzo[d]thiazol-6-ylamino)-4-(isopropylamino)pyridin-3-yl)thiazole-4-carboxamide: The ethyl 2-(6-(benzo[d]thiazol-6-ylamino)-4-(isopropylamino)pyridin-3-yl)thiazole-4-carboxylate (Example 20) (200 mg, 0.455 mmol) was taken in a sealed tube, to it methanol (2 mL) was added, followed by addition of methanolic ammonia (10 mL). The reaction mixture was heated at 80° C. for 3 h. The reaction mixture was concentrated. The crude material was purified by column chromatography through silica gel and MeOH:CHCl$_3$ as eluent. The material obtained was further purified on preparative TLC to obtain 2-(6-(benzo[d]thiazol-6-ylamino)-4-(isopropylamino)pyridin-3-yl)thiazole-4-carboxamide. $^1$H NMR: 400 MHz, DMSO-d$_6$: δ 1.33 (d, J=6.40 Hz, 6H), 3.64-3.72 (m, 1H), 6.15 (s, 1H), 7.58 (dd, J=2.00, 8.80 Hz, 1H), 7.63 (bs, 1H), 7.69 (bs, 1H), 7.95 (d, J=8.80 Hz, 1H), 8.14 (s, 1H), 8.32 (s, 1H), 8.35 (d, J=6.80 Hz, 1H), 8.49 (s, 1H), 8.72 (d, J=2.00 Hz, 1H), 9.15 (s, 1H), 9.35 (s, 1H). LC/MS: Ascentis Express C18, 5×2.1 mm-2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 3 min; retention time: 1.933 min; LCMS (ES-API), m/z 411.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 5.137 min; Purity: 99.8%.

Example 22

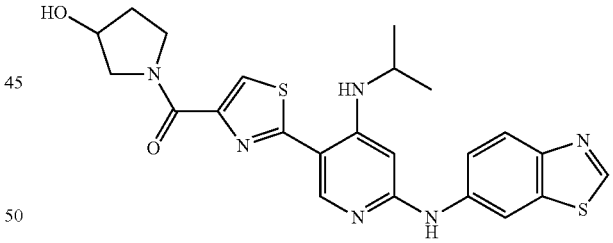

Synthesis of (2-(6-(benzo[d]thiazol-6-ylamino)-4-(isopropylamino)pyridin-3-yl)thiazol-4-yl)(3-hydroxypyrrolidin-1-yl)methanone: The ethyl 2-(6-(benzo[d]thiazol-6-ylamino)-4-(isopropylamino)pyridin-3-yl)thiazole-4-carboxylate (Example 20) (100 mg, 0.228 mmol) was dissolved in methanol (10 mL) and to it pyrrolidin-3-ol (0.455 mmol, 2 equiv) was added and heated at 80° C. for 2 h. The reaction mixture was concentrated, the crude obtained was purified on preparative TLC to obtain (2-(6-(benzo[d]thiazol-6-ylamino)-4-(isopropylamino)pyridin-3-yl)thiazol-4-yl)(3-hydroxypyrrolidin-1-yl)methanone. $^1$H NMR: 400 MHz, DMSO-d$_6$: δ 1.24 (d, J=4.00 Hz, 6H), 1.85-1.86 (m, 3H), 3.46-3.50 (m, 1H), 3.56-3.57 (m, 1H), 3.72-3.73 (m, 1H), 3.90-3.91 (m, 1H), 4.35 (bs, 1H), 5.00-5.01 (m, 1H), 6.18 (s, 1H), 7.58 (dd, J=2.00, 9.00 Hz, 1H), 7.95-7.97 (m, 1H), 8.13-8.13 (m, 1H), 8.14-8.18 (m, 1H), 8.52-8.52 (m, 1H), 8.72-8.72 (m, 1H), 9.16 (s, 1H), 9.37 (s, 1H). LC/MS: Ascentis Express C18, 5×2.1 mm-2.7 μm; Solvent A=2% ACN: 98% H₂O: 10 mM NH₄COOH; Solvent B=98% ACN: 2% H₂O: 10 mM NH₄COOH; gradient 0-100% B over 3 min; retention time: 1.883 min; LCMS (ES-API), m/z 481.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.062 min; Purity: 92.2%.

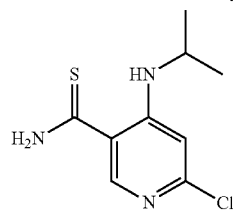

Synthesis of 6-chloro-4-(isopropylamino)pyridine-3-carbothioamide (21): Followed the same procedure as mentioned in the synthesis of Example 20.

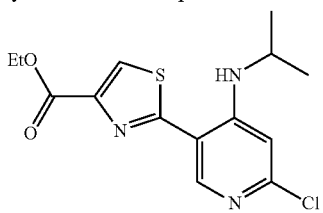

Synthesis of ethyl 2-(6-chloro-4-(isopropylamino)pyridin-3-yl)thiazole-4-carboxylate (22a): Followed the same procedure as mentioned in the synthesis of Example 20.

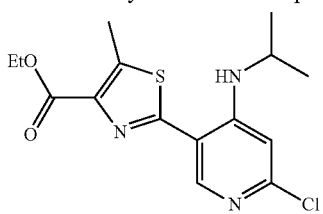

Synthesis of ethyl 2-(6-chloro-4-(isopropylamino)pyridin-3-yl)-5-methylthiazole-4-carboxylate (22b): Followed the same procedure as mentioned in the synthesis of Example 20, instead of ethyl bromo pyruvate (2 equiv.), methyl ethyl bromo pyruvate (2 equiv.) was used.

Example 23

Ethyl 2-(6-(benzo[d]thiazol-6-ylamino)-4-(isopropylamino)pyridin-3-yl)-5-methylthiazole-4-carboxylate

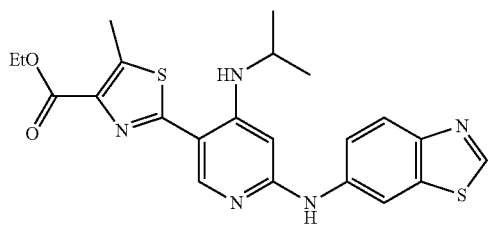 [SMILES: CCOC(=O)c1nc(-c2cnc(Nc3ccc4ncsc4c3)cc2NC(C)C)sc1C]

¹H NMR: 400 MHz, DMSO-d₆: δ 1.31-1.37 (m, 6H), 1.41-1.46 (m, 3H), 2.80 (s, 1H), 3.76-3.79 (m, 1H), 4.35 (q, J=7.20 Hz, 2H), 6.15 (s, 1H), 7.53 (dd, J=2.00, 8.80 Hz, 1H), 7.97 (d, J=8.80 Hz, 1H), 8.31 (s, 1H), 8.41 (d, J=2.00 Hz, 1H), 9.07 (s, 1H). LC/MS: ZORBAX SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 2.249 min; LCMS (ES-API), m/z 454.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 7.622 min; Purity: 88.2%.

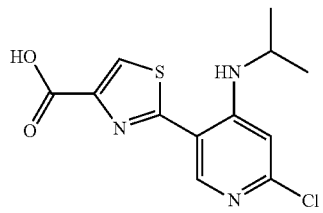 [SMILES: CC(C)Nc1cc(Cl)ncc1-c1nc(C(=O)O)cs1]

Synthesis of 2-(6-chloro-4-(isopropylamino)pyridin-3-yl)thiazole-4-carboxylic acid (23a): Followed the same procedure as mentioned in the synthesis of compound no. 9.

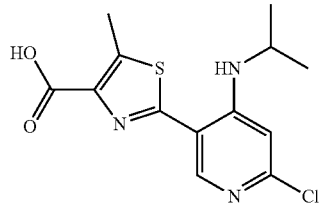 [SMILES: Cc1sc(-c2cnc(Cl)cc2NC(C)C)nc1C(=O)O]

2-(6-chloro-4-(isopropylamino)pyridin-3-yl)-5-methylthiazole-4-carboxylic acid (23b): Followed the same procedure as mentioned in the synthesis of compound no. 9.

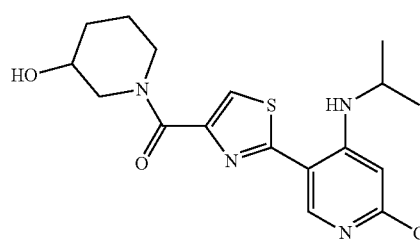

Synthesis of (2-(6-chloro-4-(isopropylamino)pyridin-3-yl)thiazol-4-yl)(3-hydroxypiperidin-1-yl)methanone (24a): The 2-(6-chloro-4-(isopropylamino)pyridin-3-yl)thiazole-4- carboxylic acid (23a) (100 mg, 0.336 mmol) was dissolved in DMF (5 mL), piperidin-3-ol (1.679 mmol) was added and stirred at room temperature. Added DIPEA (1.343 mmol), followed by addition of HATU (1.008 mmol) and stirred for 3 h. The reaction mixture was concentrated under reduced pressure to remove excess of DMF. The residue obtained was partitioned between water and EtOAc. The organic layer was separated, dried over $Na_2SO_4$, filtered and concentrated. The crude material obtained was purified by column chromatography through silica gel and $MeOH:CHCl_3$ as eluent to afford the title compound, (2-(6-chloro-4-(isopropylamino)pyridin-3-yl)thiazol-4-yl)(3-hydroxypiperidin-1-yl)methanone.

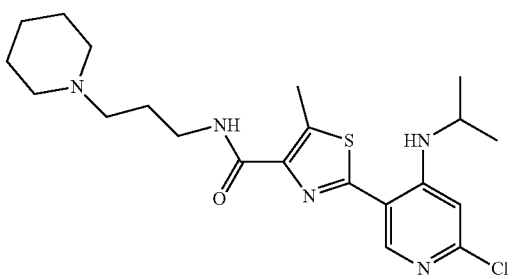 [SMILES: Cc1sc(-c2cnc(Cl)cc2NC(C)C)nc1C(=O)NCCCN1CCCCC1]

Synthesis of 2-(6-chloro-4-(isopropylamino)pyridin-3-yl)-5-methyl-N-(3-(piperidin-1-yl)propyl)thiazole-4-carboxamide (24b): Followed the same procedure as mentioned in the synthesis of compound no. 24a, instead of piperidin-3-ol, 3-(piperidin-1-yl)propan-1-amine was used.

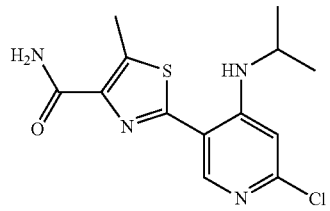 [SMILES: Cc1sc(-c2cnc(Cl)cc2NC(C)C)nc1C(N)=O]

Synthesis of 2-(6-chloro-4-(isopropylamino)pyridin-3-yl) 5-methylthiazole-4-carboxamide (24c): Followed the same procedure as mentioned in the synthesis of compound no. 24a, instead of piperidin-3-ol, ammonium chloride was used.

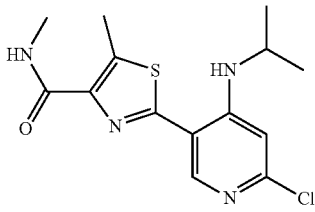 [SMILES: CNC(=O)c1nc(-c2cnc(Cl)cc2NC(C)C)sc1C]

Synthesis of 2-(6-chloro-4-(isopropylamino)pyridin-3-yl) 5-methylthiazole-4-methyl carboxamide (24d): Followed the same procedure as mentioned in the synthesis of compound no. 24a, instead of piperidin-3-ol, methyl amine was used.

TABLE 2

| Example No. | R | $R_1$ |
|---|---|---|
| 24 | H | 3-hydroxypiperidin-1-yl |
| 25 | $CH_3$ | 3-(piperidin-1-yl)propylamino |
| 26 | $CH_3$ | $NH_2$ |

Synthesis of (2-(6-(benzo[d]thiazol-6-ylamino)-4-(isopropylamino)pyridin-3-yl)thiazol-4-yl)(3-hydroxypiperidin-1-yl)methanone (Example 24): (2-(6-chloro-4-(isopropylamino)pyridin-3-yl)thiazol-4-yl)(3-hydroxypiperidin-1-yl)methanone (24a) (100 mg, 0.263 mmol) was dissolved in 1,4-Dioxane (10 mL):$H_2O$ (2 mL), to it benzo[d]thiazol-6-amine (0.263 mmol), $Na_2CO_3$ (1.05 mmol) and xanthphos (0.105 mmol) were added and degassed for 10 min. $Pd_2(dba)_3$ (0.105 mmol) was added and degassed once again for 15 min and heated at 115° C., overnight. The reaction mass was filtered through celite and concentrated to remove solvent. The crude material obtained was purified by column chromatography through silica gel and $MeOH:CHCl_3$ as eluent. The material obtained was further purified by prep. HPLC to obtain the title compound, (2-(6-(benzo[d]thiazol-6-ylamino)-4-(isopropylamino)pyridin-3-yl)thiazol-4-yl)(3-hydroxypiperidin-1-yl)methanone. $^1$H NMR: 400 MHz, $CD_3OD$: δ 0.87-0.94 (m, 1H), 1.31-1.36 (m, 6H), 1.62-0.00 (m, 2H), 1.92-2.03 (m, 2H), 3.42-3.43 (m, 1H), 3.75-3.98 (m, 4H), 6.16 (s, 1H), 7.54 (dd, J=2.00, 8.80 Hz, 1H), 7.79 (bs, 1H), 7.91 (s, 1H), 7.97 (d, J=8.80 Hz, 1H), 8.43 (d, J=2.40 Hz, 1H), 8.45 (s, 1H), 9.07 (s, 1H). LC/MS: Ascentis Express C18, 5×2.1 mm-2.7 μm; Solvent A=2% ACN: 98% $H_2O$: 10 mM $NH_4COOH$; Solvent B=98% ACN: 2% $H_2O$: 10 mM $NH_4COOH$; gradient 0-100% B over 3 min; retention time: 1.754 min; LCMS (ES-API), m/z 495.2 (M+H). HPLC: Sunfire C18 (150×4.6 mm), 3.5 micron; Solvent A=5% ACN: 95% $H_2O$: 0.05% TFA pH=2.5; Solvent B=95% ACN: 5% $H_2O$: 0.05% TFA pH=2.5; gradient 0-100% B over 15 min (23 min run time); Flow rate: 1.0 μL/min; Retention time: 5.431 min; Purity: 96.29%.

Synthesis of 2-(6-(benzo[d]thiazol-6-ylamino)-4-(isopropylamino)pyridin-3-yl)-5-methyl-N-(3-(piperidin-1-yl)propyl)thiazole-4-carboxamide (Example 25): Followed the same procedure as mentioned in the synthesis of Example 24. $^1$H NMR: 400 MHz, DMSO-$d_6$: δ 1.33 (d, J=6.40 Hz, 6H), 1.50-1.91 (m, 8H), 2.20-2.34 (m, 2H), 2.545 (2H, merged with DMSO-$d_6$ peak), 2.75 (s, 3H), 3.00-3.15 (m, 4H), 3.64-3.69 (m, 1H), 6.14 (s, 1H), 7.58 (dd, J=2.40, 9.00 Hz, 1H), 7.95 (d, J=9.20 Hz, 1H), 8.19 (d, J=5.60 Hz, 1H), 8.37 (s, 1H), 8.71 (d, J=2.00 Hz, 1H), 9.15 (s, 1H), 9.34 (s, 1H). LC/MS: Ascentis Express C18, 5×2.1 mm-2.7 µm; Solvent A=2% ACN: 98% H₂O: 10 mM NH₄COOH; Solvent B=98% ACN: 2% H₂O: 10 mM NH₄COOH; gradient 0-100% B over 3 min; retention time: 1.766 min; LCMS (ES-API), m/z 550.2 (M+H). HPLC: XBridge Phenyl (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 10.867 min; Purity: 96.2%.

Synthesis of 2-(6-(benzo[d]thiazol-6-ylamino)-4-(isopropylamino)pyridin-3-yl)-5-methylthiazole-4-carboxamide (Example 26): Followed the same procedure as mentioned in the synthesis of Example 24. ¹H NMR: 400 MHz, CDCl₃: δ 1.28-1.34 (m, 6H), 2.01-2.11 (m, 2H), 2.84 (s, 3H), 3.62-3.67 (m, 1H), 5.54-5.57 (m, 1H), 6.08 (bs, 1H), 6.69 (bs, 1H), 7.42 (dd, J=2.00, 8.80 Hz, 1H), 8.06-8.09 (m, 2H), 8.29 (bs, 2H), 8.90 (s, 1H). LC/MS: Ascentis Express C18, 5×2.1 mm-2.7 µm; Solvent A=2% ACN: 98% H₂O: 10 mM NH₄COOH; Solvent B=98% ACN: 2% H₂O: 10 mM NH₄COOH; gradient 0-100% B over 3 min; retention time: 1.846 min; LCMS (ES-API), m/z 423.0 (M−H). HPLC: XBridge (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 6.399 min; Purity: 73.5%.

Synthesis of 2-(6-(benzo[d]thiazol-6-ylamino)-4-(isopropylamino)pyridin-3-yl)thiazole-4-carboxylic acid (25a) and 2-(6-(benzo[d]thiazol-6-ylamino)-4-(isopropylamino)pyridin-3-yl)-5-methylthiazole-4-carboxylic acid (25b): Followed the same procedure as mentioned in the synthesis of compound no. 9.

Example 27

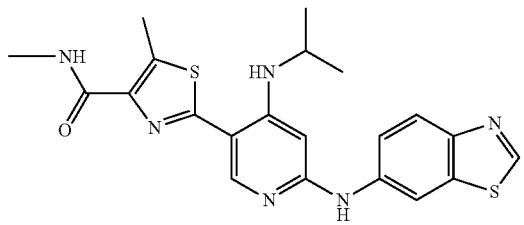 [SMILES: CNC(=O)c1nc(-c2cnc(Nc3ccc4ncsc4c3)cc2NC(C)C)sc1C]

Synthesis of 2-(6-(benzo[d]thiazol-6-ylamino)-4-(isopropylamino)pyridin-3-yl)-N,5-dimethylthiazole-4-carboxamide (Example 27). 2-(6-(Benzo[d]thiazol-6-ylamino)-4-(isopropylamino)pyridin-3-yl)-5-methylthiazole-4-carboxylic acid (25b) was dissolved in DMF (10 mL), to it methanamine (1 equiv.) was added followed by the addition of HATU (1.5 equiv.) and DIPEA (4 equiv.) and stirred for 3 h at room temperature. The reaction mixture was concentrated to remove DMF under reduced pressure. The crude material obtained was purified by flash column chromatography using silica gel and MeOH:CHCl₃ as eluent. The material obtained was triturated with diethyl ether and hexane to afford ethyl 2-(6-(benzo[d]thiazol-6-ylamino)-4-(isopropylamino)pyridin-3-yl)-5-methylthiazole-4-carboxylate. ¹H NMR: 400 MHz, DMSO-d₆: δ 1.32 (d, J=6.40 Hz, 6H), 2.73 (s, 3H), 2.81 (d, J=4.40 Hz, 3H), 3.64-3.69 (m, 1H), 6.13 (s, 1H), 7.58 (dd, J=2.00, 8.80 Hz, 1H), 7.95 (d, J=8.80 Hz, 1H), 8.13 (d, J=4.80 Hz, 1H), 8.20 (d, J=7.20 Hz, 1H), 8.37 (s, 1H), 8.71 (d, J=2.00 Hz, 1H), 9.15 (s, 1H), 9.33 (s, 1H). LC/MS: ZORBAX SB C18, 4.6×50 mm, 5 µm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.606 min; LCMS (ES-API), m/z 439.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 6.323 min; Purity: 96.3%.

Synthesis of Examples 28-85: Followed the same procedure as mentioned in the synthesis of compound Example 27.

TABLE 3

| Example No. | R₁ |
|---|---|
| 28 | pyrrolidin-1-yl-piperidin-1-yl |
| 29 | 4-(pyridin-4-yl)piperazin-1-yl |
| 30 | 4-acetyl-1,4-diazepan-1-yl |
| 31 | 4-(2,4-difluorophenyl)piperazin-1-yl |
| 32 | 4-(pyrimidin-2-yl)piperazin-1-yl |
| 33 | 4-(benzo[d][1,3]dioxol-5-ylmethyl)piperazin-1-yl |
| 34 | 4-(2-cyanoethyl)piperazin-1-yl |
| 35 | 4-(pyrazin-2-yl)piperazin-1-yl |

TABLE 3-continued
| Example No. | R₁ |
|---|---|
| 36 | 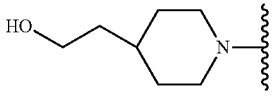 |
| 37 | 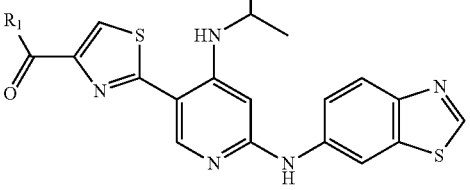 |
| 38 | 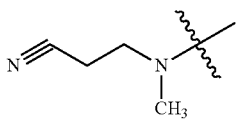 |
| 39 | 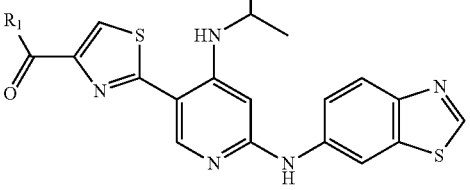 |
| 40 | 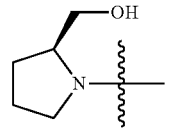 [SMILES: *N1CCC[C@H]1CO] |
| 41 | 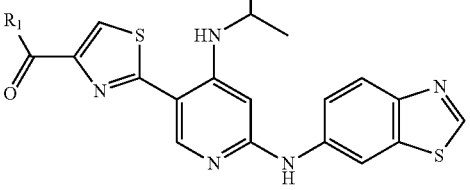 |
| 42 | 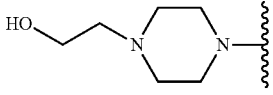 |
| 43 | 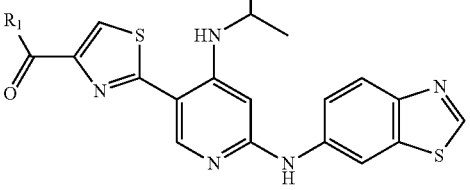 |
| 44 | 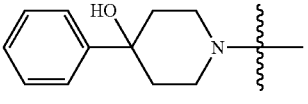 |
| 45 | 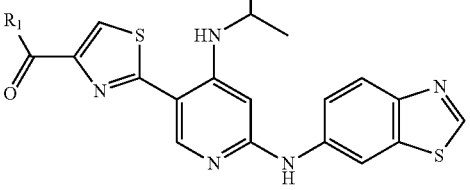 |
| 46 | 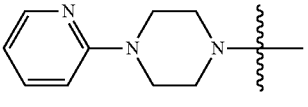 |
| 47 | 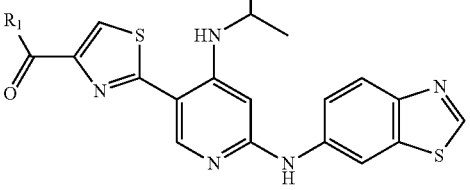 |
| 48 | 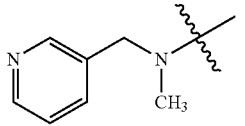 [SMILES: *N(C)Cc1cccnc1] |
| 49 | 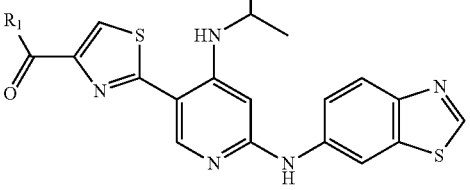 |
| 50 | 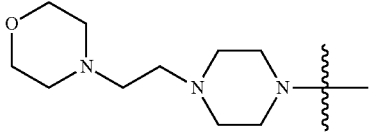 [SMILES: *N1CCN(CCN2CCOCC2)CC1] |
| 51 | 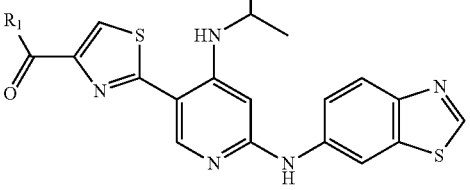 |
| 52 | 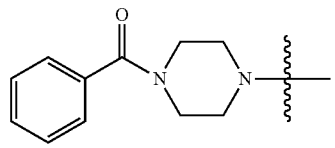 [SMILES: *N1CCN(C(=O)c2ccccc2)CC1] |
| 53 | 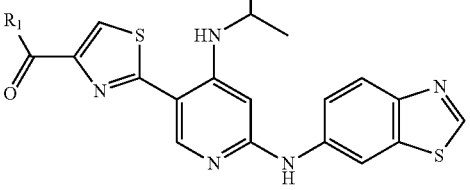 |
| 54 | 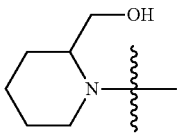 [SMILES: *N1CCCCC1CO] |

TABLE 3-continued
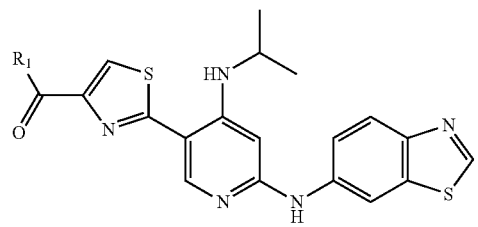
| Example No. | R₁ |
|---|---|
| 55 | 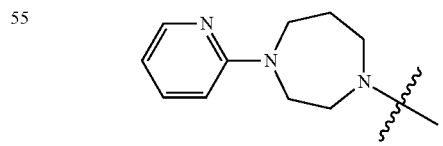 |
| 56 | 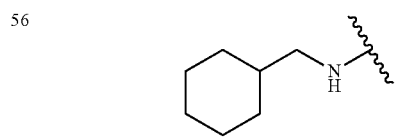 |
| 57 | 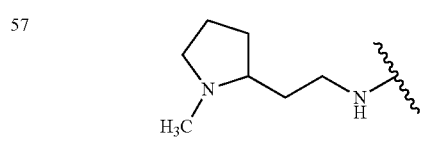 |
| 58 | 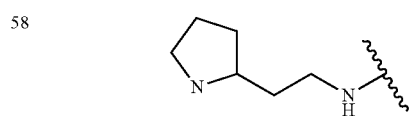 |
| 59 | 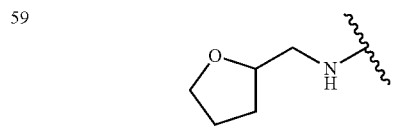 |
| 60 | 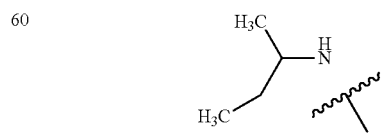 |
| 61 | 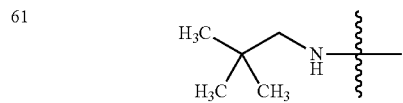 |
| 62 | 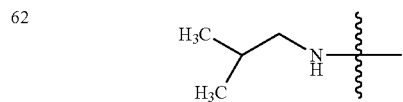 |
| 63 | 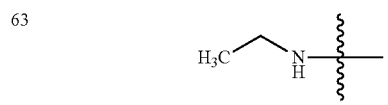 |
| 64 | 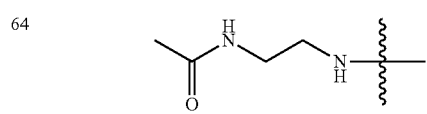 |
TABLE 3-continued
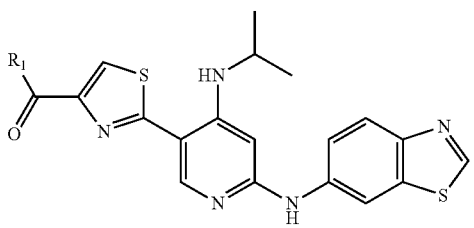
| Example No. | R₁ |
|---|---|
| 65 | 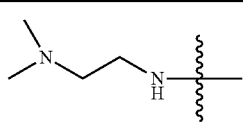 |
| 66 | 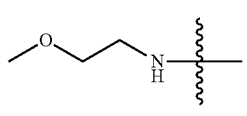 [SMILES: *NCCOC] |
| 67 | 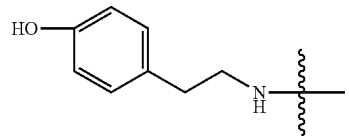 [SMILES: *NCCc1ccc(O)cc1] |
| 68 | 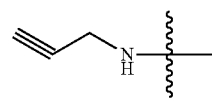 |
| 69 | 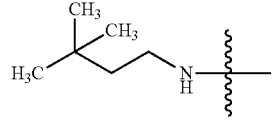 [SMILES: *NCCC(C)(C)C] |
| 70 | 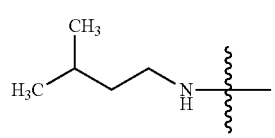 [SMILES: *NCCC(C)C] |
| 71 | 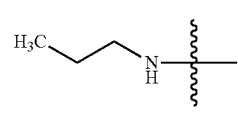 [SMILES: *NCCC] |
| 72 | 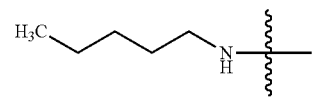 |
| 73 | 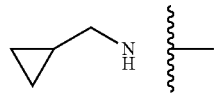 |
| 74 | 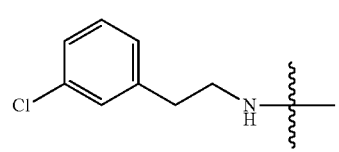 [SMILES: *NCCc1cccc(Cl)c1] |

TABLE 3-continued

[Structure: R₁-C(=O)- attached to thiazole-pyridine core with isopropylamino and benzothiazol-6-ylamino substituents]

| Example No. | R₁ |
|---|---|
| 75 | thiophen-2-yl-ethyl-NH- |
| 76 | phenoxy-ethyl-NH- |
| 77 | 4-fluorophenyl-ethyl-NH- |
| 78 | HO-CH₂CH₂-O-CH₂CH₂-NH- |
| 79 | HO-(CH₂)₃-NH- |
| 80 | HO-(CH₂)₄-NH- |
| 81 | phenyl-CH(OH)-CH₂-NH- |
| 82 | pyrrolidin-1-yl-(CH₂)₃-NH- |
| 83 | piperidin-1-yl-(CH₂)₃-NH- |
| 84 | cyclohexyl-CH₂CH₂-NH- |
| 85 | pyridin-4-yl-ethyl-NH- |

Example 28

(2-(6-(Benzo[d]thiazol-6-ylamino)-4-(isopropylamino)pyridin-3-yl)thiazol-4-yl)(4-(pyrrolidin-1-yl)piperidin-1-yl)methanone $^1$H NMR: 400 MHz, DMSO-d$_6$: δ 1.28-1.30 (m, 6H), 1.42-1.44 (m, 2H), 1.65-1.75 (m, 4H), 1.85-1.99 (m, 5H), 2.33-2.34 (m, 1H), 2.52 (1H, merged with DMSO-d$_6$ peak), 3.04 (bs, 1H), 3.68-3.76 (m, 1H), 3.98-4.28 (m, 2H), 6.16 (s, 1H), 7.58 (dd, J=2.00, 9.00 Hz, 1H), 7.92-7.97 (m, 2H), 8.36 (d, J=7.20 Hz, 1H), 8.52 (s, 1H), 8.72 (d, J=2.40 Hz, 1H), 9.16 (s, 1H), 9.36 (s, 1H). Mol. wt.: 547.74. LC/MS: Retention time: 1.895 min. Purity: 99.7%.

Example 29

(2-(6-(Benzo[d]thiazol-6-ylamino)-4-(isopropylamino)pyridin-3-yl)thiazol-4-yl)(4-((1Z,3E)-1-(methyleneamino)penta-1,3-dien-3-yl)piperazin-1-yl)methanone $^1$H NMR: 400 MHz, DMSO-d$_6$: δ 1.24-1.28 (m, 6H), 3.46 (bs, 4H), 3.69-3.74 (m, 1H), 3.82 (bs, 4H), 6.17 (s, 1H), 6.86 (d, J=6.00 Hz, 2H), 7.59 (dd, J=2.40, 9.00 Hz, 1H), 7.96 (d, J=8.80 Hz, 1H), 8.04 (s, 1H), 8.20 (d, J=5.20 Hz, 2H), 8.31 (d, J=6.80 Hz, 1H), 8.54 (s, 1H), 8.72 (d, J=2.00 Hz, 1H), 9.16 (s, 1H), 9.38 (s, 1H). Mol. wt.: 556.71. LC/MS: Retention time: 1.956 min. Purity: 99.4%.

Example 30

1-(4-(2-(6-(Benzo[d]thiazol-6-ylamino)-4-(isopropylamino)pyridin-3-yl)thiazole-4-carbonyl)-1,4-diazepan-1-yl)ethanone $^1$H NMR: 400 MHz, DMSO-d$_6$: δ 1.27-1.29 (m, 6H), 1.62-1.91 (m, 3H), 2.01-2.08 (m, 2H), 3.50-3.80 (m, 9H), 6.16 (s, 1H), 7.57-7.60 (m, 1H), 7.93-7.98 (m, 2H), 8.18-8.27 (m, 1H), 8.51 (s, 1H), 8.72 (s, 1H), 9.16 (s, 1H), 9.36 (s, 1H). Mol. wt.: 535.68. LC/MS: Retention time: 1.93 min. Purity: 97%.

Example 31

(2-(6-(Benzo[d]thiazol-6-ylamino)-4-(isopropylamino)pyridin-3-yl)thiazol-4-yl)(4-(2,4-difluorophenyl)piperazin-1-yl)methanone $^1$H NMR: 400 MHz, DMSO-d$_6$: δ 1.29 (d, J=6.40 Hz, 6H), 3.04 (s, 4H), 3.70-3.75 (m, 1H), 3.83-3.84 (m, 4H), 6.17 (s, 1H), 7.01-7.13 (m, 2H), 7.21-7.27 (m, 1H), 7.58 (dd, J=2.00, 8.80 Hz, 1H), 7.96 (d, J=8.80 Hz, 1H), 8.03 (s, 1H), 8.35 (bs, 1H), 8.52 (s, 1H), 8.71 (s, 1H), 9.16 (s, 1H), 9.39 (s, 1H). Mol. wt.: 591.7. LC/MS: Retention time: 2.962 min. Purity: 99.5%.

Example 32

(2-(6-(Benzo[d]thiazol-6-ylamino)-4-(isopropylamino)pyridin-3-yl)thiazol-4-yl)(4-(pyrimidin-2-yl)piperazin-1-yl)methanone $^1$H NMR: 400 MHz, DMSO-d$_6$: δ 1.24-1.28 (m, 6H), 3.71-3.84 (m, 9H), 6.17 (s, 1H), 6.69 (t, J=4.80 Hz, 1H), 7.59 (dd, J=2.40, 8.80 Hz, 1H), 7.96 (d, J=8.80 Hz, 1H), 8.03 (s, 1H), 8.31 (d, J=7.20 Hz, 1H), 8.41 (d, J=4.80 Hz, 2H), 8.53 (s, 1H), 8.72 (d, J=2.00 Hz, 1H), 9.16 (s, 1H), 9.37 (s, 1H). Mol. wt.: 557.69. LC/MS: Retention time: 2.483 min. Purity: 96%.

Example 33

(4-(Benzo[d][1,3]dioxol-5-ylmethyl)piperazin-1-yl)(2-(6-(benzo[d]thiazol-6-ylamino)-4-(isopropylamino)pyridin-3-yl)thiazol-4-yl)methanone $^1$H NMR: 400 MHz, DMSO-d$_6$: δ 1.28-1.30 (m, 6H), 2.41-2.43 (m, 4H), 3.45 (s, 2H), 3.62-3.64 (m, 4H), 3.65-3.75 (m, 1H), 6.00 (s, 2H), 6.16 (s, 1H), 6.76-6.78 (m, 1H), 6.85-6.89 (m, 2H), 7.58 (dd, J=2.00, 9.00 Hz, 1H), 7.95-7.97 (m, 2H), 8.31 (dd, J=7.20, Hz, 1H), 8.52 (s, 1H), 8.72 (dd, J=2.00, Hz, 1H), 9.16 (s, 1H), 9.37 (s, 1H). Mol. wt.: 613.75. LC/MS: Retention time: 2.748 min. Purity: 98.8%.

Example 34

3-(4-(2-(6-(Benzo[d]thiazol-6-ylamino)-4-(isopropylamino)pyridin-3-yl)thiazole-4-carbonyl)piperazin-1-yl)propanenitrile $^1$H NMR: 400 MHz, DMSO-d$_6$: δ 1.30 (d, J=6.40 Hz, 6H), 2.63-2.73 (m, 4H), 3.67-3.73 (m, 5H), 6.17 (s, 1H), 7.58 (dd, J=2.00, 8.80 Hz, 1H), 7.95-7.98 (m, 2H), 8.32-8.34 (m, 1H), 8.52 (s, 1H), 8.72 (d, J=2.00 Hz, 1H), 9.16 (s, 1H), 9.38 (s, 1H). Mol. wt.: 532.68. LC/MS: Retention time: 2.146 min. Purity: 98.5%.

Example 35

(2-(6-(Benzo[d]thiazol-6-ylamino)-4-(isopropylamino)pyridin-3-yl)thiazol-4-yl)(4-(pyrazin-2-yl)piperazin-1-yl)methanone $^1$H NMR: 400 MHz, DMSO-d$_6$: δ 1.28 (d, J=6.00 Hz, 6H), 3.69-3.72 (m, 5H), 3.82 (bs, 4H), 6.17 (s, 1H), 7.59 (dd, J=2.00, 8.80 Hz, 1H), 7.89 (d, J=2.80 Hz, 1H), 7.96 (d, J=8.80 Hz, 1H), 8.04 (s, 1H), 8.12-8.13 (m, 1H), 8.31 (d, J=7.20 Hz, 1H), 8.36 (d, J=1.20 Hz, 1H), 8.54 (s, 1H), 8.72 (d, J=2.00 Hz, 1H), 9.16 (s, 1H), 9.37 (s, 1H). Mol. wt.: 557.69. LC/MS: Retention time: 2.277 min. Purity: 95.4%.

Example 36

1-(2-(6-(Benzo[d]thiazol-6-ylamino)-4-(isopropylamino)pyridin-3-yl)thiazole-4-carbonyl)piperidine-4-carboxamide $^1$H NMR: 400 MHz, DMSO-d$_6$: δ 1.29 (d, J=6.40 Hz, 1H), 1.50-1.58 (m, 2H), 1.78-1.80 (m, 2H), 2.40-2.46 (m, 1H), 2.88 (bs, 1H), 3.18 (bs, 1H), 3.69-3.74 (m, 1H), 4.07 (bs, 1H), 4.44 (bs, 1H), 6.17 (s, 1H), 6.80 (bs, 1H), 7.30 (bs, 1H), 7.58 (dd, J=2.00, 8.80 Hz, 1H), 7.94-7.97 (m, 2H), 8.36 (d, J=6.80 Hz, 1H), 8.52 (s, 1H), 8.72 (d, J=2.00 Hz, 1H), 9.16 (s, 1H), 9.37 (s, 1H). Mol. wt.: 521.66. LC/MS: Retention time: 1.831 min. Purity: 99.1%.

Example 37

(2-(6-(Benzo[d]thiazol-6-ylamino)-4-(isopropylamino)pyridin-3-yl)thiazol-4-yl)(4-(2-hydroxyethyl)piperidin-1-yl)methanone $^1$H NMR: 400 MHz, DMSO-d$_6$: δ 1.05-1.14 (m, 2H), 1.29 (d, J=6.40 Hz, 6H), 1.37-1.42 (m, 2H), 1.65-1.72 (m, 3H), 2.67-3.10 (m, 3H), 3.44-3.49 (m, 2H), 3.70-3.75 (m, 1H), 4.01-4.10 (m, 1H), 4.38 (t, J=5.20 Hz, 1H), 4.45 (bs, 1H), 6.16 (s, 1H), 7.58 (dd, J=2.00, 8.80 Hz, 1H), 7.90 (s, 1H), 7.96 (d, J=8.80 Hz, 1H), 8.37 (d, J=7.20 Hz, 1H), 8.51 (s, 1H), 8.72 (d, J=2.00 Hz, 1H), 9.16 (s, 1H), 9.36 (s, 1H). Mol. wt.: 522.69. LC/MS: Retention time: 2.059 min. Purity: 95.4%.

Example 38

2-(6-(Benzo[d]thiazol-6-ylamino)-4-(isopropylamino)pyridin-3-yl)-N-(2-cyanoethyl)-N-methylthiazole-4-carboxamide $^1$H NMR: 400 MHz, DMSO-d$_6$: δ 1.28 (d, J=6.00 Hz, 6H), 2.85-2.91 (m, 2H), 3.71-3.90 (m, 3H), 6.16 (s, 1H), 7.57 (dd, J=2.40, 8.80 Hz, 1H), 7.95-8.05 (m, 2H), 8.43-8.51 (m, 2H), 8.69 (s, 1H), 9.17 (s, 1H), 9.40 (s, 1H). Mol. wt.: 477.61. LC/MS: Retention time: 2.166 min. Purity: 99.5%.

Example 39

(S)-(2-(6-(Benzo[d]thiazol-6-ylamino)-4-(isopropylamino)pyridin-3-yl)thiazol-4-yl)(2-(hydroxymethyl)pyrrolidin-1-yl)methanone $^1$H NMR: 400 MHz, DMSO-d$_6$: δ 1.24-1.29 (m, 6H), 1.81-2.03 (m, 4H), 3.17 (bs, 1H), 3.50-3.64 (m, 2H), 3.71-3.85 (m, 2H), 4.22 (bs, 1H), 4.81 (bs, 1H), 6.17 (s, 1H), 7.58 (dd, J=2.40, 9.00 Hz, 1H), 7.96 (d, J=9.20 Hz, 1H), 8.11 (s, 1H), 8.30-8.32 (m, 1H), 8.51 (s, 1H), 8.71 (d, J=2.00 Hz, 1H), 0.00 (s, 1H), 9.37 (s, 1H). Mol. wt.: 494.63. LC/MS: Retention time: 2.109 min. Purity: 98.1%.

Example 40

(2-(6-(Benzo[d]thiazol-6-ylamino)-4-(isopropylamino)pyridin-3-yl)thiazol-4-yl)(4-(2-hydroxyethyl)piperazin-1-yl)methanone $^1$H NMR: 400 MHz, DMSO-d$_6$: δ 1.30 (d, J=6.00 Hz, 6H), 2.42-2.51 (m, 3H), 3.51-3.55 (m, 2H), 3.64-3.75 (m, 5H), 4.44-4.45 (m, 1H), 6.16 (s, 1H), 7.58 (dd, J=2.00, 9.00 Hz, 1H), 7.95-7.97 (m, 2H), 8.33 (d, J=7.20 Hz, 1H), 8.52 (s, 1H), 8.72 (d, J=2.00 Hz, 1H), 9.16 (s, 1H), 9.36 (s, 1H). Mol. wt.: 523.67. LC/MS: Retention time: 1.849 min. Purity: 98.1%.

Example 41

(2-(6-(Benzo[d]thiazol-6-ylamino)-4-(isopropylamino)pyridin-3-yl)thiazol-4-yl)(4-hydroxy-4-phenylpiperidin-1-yl)methanone $^1$H NMR: 400 MHz, DMSO-d$_6$: δ 1.25-1.26 (m, 6H), 1.69-1.74 (m, 2H), 1.91-1.96 (m, 2H), 3.31 (1H, merged with water peak), 3.59 (bs, 1H), 3.68-3.73 (m, 1H), 4.01 (bs, 1H), 4.47 (bs, 1H), 5.23 (s, 1H), 6.16 (s, 1H), 7.22-7.26 (m, 1H), 7.32-7.36 (m, 2H), 7.50-7.52 (m, 2H), 7.58 (dd, J=2.40, 8.80 Hz, 1H), 7.95-7.98 (m, 2H), 8.38 (dd, J=7.20, Hz, 1H), 8.51 (s, 1H), 8.71 (d, J=2.00 Hz, 1H), 9.16 (s, 1H), 9.37 (s, 1H). Mol. wt.: 570.73. LC/MS: Retention time: 2.477 min. Purity: 98.2%.

Example 42

(2-(6-(Benzo[d]thiazol-6-ylamino)-4-(isopropylamino)pyridin-3-yl)thiazol-4-yl)(4-(pyridin-2-yl)piperazin-1-yl)methanone $^1$H NMR: 400 MHz, DMSO-d$_6$: δ 1.27 (d, J=6.40 Hz, 6H), 3.60 (bs, 4H), 3.69-3.74 (m, 1H), 3.78-3.80 (m, 4H), 6.17 (s, 1H), 6.69 (dd, J=4.80, 6.60 Hz, 1H), 6.87 (d, J=8.80 Hz, 1H), 7.56-7.60 (m, 2H), 7.96 (d, J=9.20 Hz, 1H), 8.03 (s, 1H), 8.15 (dd, J=1.20, 4.80 Hz, 1H), 8.34 (d, J=6.80 Hz, 1H), 8.53 (s, 1H), 8.72 (d, J=2.00 Hz, 1H), 0.00 (s, 1H), 9.38 (s, 1H). Mol. wt.: 556.71. LC/MS: Retention time: 1.55 min. Purity: 96%.

Example 43

2-(6-(Benzo[d]thiazol-6-ylamino)-4-(isopropylamino)pyridin-3-yl)-N-methyl-N-(pyridin-3-ylmethyl)thiazole-4-carboxamide $^1$H NMR: 400 MHz, DMSO-d$_6$: δ 1.21 (d, J=6.40 Hz, 6H), 2.94-3.15 (m, 3H), 3.66-3.71 (m, 1H), 4.76-4.92 (m, 2H), 6.15 (s, 1H), 7.40-7.41 (m, 1H), 7.57 (dd, J=2.00, 8.80 Hz, 1H), 7.76 (bs, 1H), 7.96 (d, J=8.80 Hz, 1H), 8.04-8.08 (m, 1H), 8.41-8.60 (m, 3H), 8.70 (d, J=1.60 Hz, 1H), 9.16 (s, 1H), 9.37 (s, 1H). Mol. wt.: 515.65. LC/MS: Retention time: 2.197 min. Purity: 99.9%.

Example 44

(2-(6-(Benzo[d]thiazol-6-ylamino)-4-(isopropylamino)pyridin-3-yl)thiazol-4-yl)(4-(2-morpholinoethyl)piperazin-1-yl)methanone $^1$H NMR: 400 MHz, DMSO-d$_6$: δ 1.30 (d, J=6.00 Hz, 6H), 2.50 (4H, merged with DMSO-d$_6$ peak), 2.99 (bs, 2H), 3.30 (5H, merged with water peak), 3.57-3.75 (m, 9H), 6.17 (s, 1H), 7.59 (dd, J=2.00, 8.80 Hz, 1H), 7.95-7.97 (m, 2H), 8.33 (d, J=7.20 Hz, 1H), 8.52 (s, 1H), 8.72 (d, J=2.40 Hz, 1H), 9.16 (s, 1H), 9.37 (s, 1H). Mol. wt.: 592.78. LC/MS: Retention time: 2.008 min. Purity: 96%.

Example 45

(2-(6-(Benzo[d]thiazol-6-ylamino)-4-(isopropylamino)pyridin-3-yl)thiazol-4-yl)(4-benzoylpiperazin-1-yl)methanone $^1$H NMR: 400 MHz, DMSO-d$_6$: δ 1.24-1.29 (m, 6H), 3.71-3.78 (m, 9H), 6.16 (s, 1H), 7.46-7.48 (m, 5H), 7.58 (dd, J=2.40, 9.00 Hz, 1H), 7.96 (d, J=8.80 Hz, 1H), 8.04 (s, 1H), 8.24 (bs, 1H), 8.51 (s, 1H), 8.71 (d, J=1.20 Hz, 1H), 9.16 (s, 1H), 9.38 (s, 1H). Mol. wt.: 583.73. LC/MS: Retention time: 2.352 min. Purity: 97.6%.

Example 46

(2-(6-(Benzo[d]thiazol-6-ylamino)-4-(isopropylamino)pyridin-3-yl)thiazol-4-yl)(2-(hydroxymethyl)piperidin-1-yl)methanone $^1$H NMR: 400 MHz, DMSO-d$_6$: δ 1.28-1.30 (m, 6H), 1.31-1.43 (m, 5H), 2.75-3.15 (m, 1H), 3.41-3.59 (m, 2H), 3.68-3.76 (m, 1H), 4.06-4.34 (m, 1H), 4.73-4.78 (m, 1H), 6.16 (s, 1H), 7.58 (dd, J=2.00, 8.80 Hz, 1H), 7.83 (bs, 1H), 7.96 (d, J=8.80 Hz, 1H), 8.43 (bs, 1H), 8.51 (s, 1H), 8.72 (d, J=2.00 Hz, 1H), 0.00 (s, 1H), 9.35 (s, 1H). Mol. wt.: 508.66. LC/MS: Retention time: 2.196 min. Purity: 95.2%.

Example 47

(2-(6-(Benzo[d]thiazol-6-ylamino)-4-(isopropylamino)pyridin-3-yl)thiazol-4-yl)(3-morpholinopyrrolidin-1-yl)methanone $^1$H NMR: 400 MHz, DMSO-d$_6$: δ 1.24-1.31 (m, 6H), 1.71-1.91 (m, 1H), 2.10-2.20 (m, 1H), 2.50-0.00 (m, 5H), 2.80-2.90 (m, 1H), 3.45-3.62 (m, 5H), 3.70-3.85 (m, 2H), 4.08-4.10 (m, 1H), 6.17 (s, 1H), 6.51 (s, 2H), 7.58 (dd, J=2.00, 8.80 Hz, 1H), 7.96 (d, J=8.80 Hz, 1H), 8.12 (d, J=14.80 Hz, 1H), 8.17-8.30 (m, 1H), 8.52 (d, J=2.00 Hz, 1H), 8.72 (d, J=2.40 Hz, 1H), 9.16 (s, 1H), 9.36 (s, 1H). Mol. wt.: 549.71. LC/MS: Retention time: 2.124 min. Purity: 96.8%.

Example 48

8-(2-(6-(Benzo[d]thiazol-6-ylamino)-4-(isopropylamino)pyridin-3-yl)thiazole-4-carbonyl)-1-phenyl-1,3,8-triazaspiro[4.5]decan-4-one $^1$H NMR: 400 MHz, DMSO-d$_6$: δ 1.25 (d, J=6.00 Hz, 6H), 1.79 (bs, 2H), 2.38-2.41 (m, 1H), 2.50 (1H, merged with DMSO-d$_6$ peak), 3.59 (bs, 1H), 3.66-3.74 (m, 1H), 3.96 (s, 1H), 4.23 (bs, 1H), 4.42 (bs, 1H), 4.63 (s, 2H), 6.16 (s, 1H), 6.78-6.82 (m, 3H), 7.24-7.28 (m, 2H), 7.58 (dd, J=2.40, 9.00 Hz, 1H), 7.96 (d, J=8.80 Hz, 1H), 8.07 (s, 1H), 8.32 (d, J=7.20 Hz, 1H), 8.52 (s, 1H), 8.72 (d, J=2.40 Hz, 1H), 8.83 (s, 1H), 9.16 (s, 1H), 9.37 (s, 1H). Mol. wt.: 624.78. LC/MS: Retention time: 2.485 min. Purity: 98.3%.

Example 49

(2-(6-(Benzo[d]thiazol-6-ylamino)-4-(isopropylamino)pyridin-3-yl)thiazol-4-yl)(4-benzyl-4-hydroxypiperidin-1-yl)methanone $^1$H NMR: 400 MHz, DMSO-d$_6$: δ 1.27 (d, J=6.00 Hz, 6H), 1.40-1.51 (m, 4H), 2.73 (s, 2H), 3.15 (s, 1H), 3.44-3.41 (m, 1H), 3.69-3.74 (m, 1H), 3.89-3.91 (m, 1H), 4.21-4.25 (m, 1H), 4.55 (s, 1H), 6.16 (s, 1H), 7.18-7.29 (m, 5H), 7.58 (dd, J=2.00, 8.80 Hz, 1H), 7.91 (s, 1H), 7.96 (d, J=8.80 Hz, 1H), 8.32 (d, J=7.20 Hz, 1H), 8.50 (s, 1H), 8.71 (d, J=2.00 Hz, 1H), 9.16 (s, 1H), 9.36 (s, 1H). Mol. wt.: 584.76. LC/MS: Retention time: 2.578 min. Purity: 97.9%.

Example 50

(R)-(2-(6-(benzo[d]thiazol-6-ylamino)-4-(isopropylamino)pyridin-3-yl)thiazol-4-yl)(2-(hydroxymethyl)pyrrolidin-1-yl)methanone $^1$H NMR: 400 MHz, DMSO-d$_6$: δ 1.27-1.29 (m, 6H), 1.81-2.03 (m, 4H), 3.18 (s, 1H), 3.50-3.64 (m, 2H), 3.71-3.85 (m, 3H), 4.22 (bs, 1H), 4.81 (bs, 1H), 6.17 (s, 1H), 7.58 (dd, J=2.40, 8.80 Hz, 1H), 7.96 (d, J=8.80 Hz, 1H), 8.11 (s, 1H), 8.20-8.32 (m, 1H), 8.51 (s, 1H), 8.71 (d, J=1.60 Hz, 1H), 9.16 (s, 1H), 9.38 (s, 1H). Mol. wt.: 494.63. LC/MS: Retention time: 2.141 min. Purity: 99.7%.

Example 51

(2-(6-(Benzo[d]thiazol-6-ylamino)-4-(isopropylamino)pyridin-3-yl)thiazol-4-yl)(4-(4-chlorophenyl)-4-hydroxypiperidin-1-yl)methanone $^1$H NMR: 400 MHz, DMSO-d$_6$: δ 1.25-1.26 (m, 6H), 1.67-1.74 (m, 2H), 1.92-2.00 (m, 2H), 3.18-3.26 (m, 2H), 3.70-3.78 (m, 2H), 3.98-3.99 (m, 1H), 4.43-4.48 (m, 1H), 5.32-5.34 (m, 1H), 6.18 (s, 1H), 7.39-7.41 (m, 2H), 7.52-7.57 (m, 3H), 8.04-8.08 (m, 2H), 8.43 (s, 1H), 8.51 (bs, 1H), 8.71 (bs, 1H), 9.27 (s, 1H), 9.66 (bs, 1H). Mol. wt.: 605.17. LC/MS: Retention time: 2.695 min. Purity: 99.1%.

Example 52

2-(6-(Benzo[d]thiazol-6-ylamino)-4-(isopropylamino)pyridin-3-yl)-N-methyl-N-(prop-2-yn-1-yl)thiazole-4-carboxamide $^1$H NMR: 400 MHz, DMSO-d$_6$: δ 1.29 (d, J=6.40 Hz, 6H), 2.50 (1H, merged with DMSO-d$_6$ peak), 3.09-3.23 (m, 3H), 3.68-3.76 (m, 1H), 4.35-4.49 (m, 2H), 6.17 (s, 1H), 7.58 (dd, J=2.40, 8.80 Hz, 1H), 7.96 (d, J=8.80 Hz, 1H), 8.05-8.42 (m, 2H), 8.53 (s, 1H), 8.72 (d, J=2.00 Hz, 1H), 9.16 (s, 1H), 9.37 (s, 1H). Mol. wt.: 462.59. LC/MS: Retention time: 2.419 min. Purity: 96.2%.

Example 53

(2-(6-(Benzo[d]thiazol-6-ylamino)-4-(isopropylamino)pyridin-3-yl)thiazol-4-yl)(4-(pyrimidin-2-yl)-1,4-diazepan-1-yl)methanone $^1$H NMR: 400 MHz, DMSO-d$_6$: δ 1.21-1.29 (m, 6H), 1.80-1.81 (m, 1H), 1.91-1.92 (m, 1H), 3.63-3.73 (m, 3H), 3.82-3.95 (m, 6H), 6.15-6.17 (m, 1H), 6.51-6.64 (m, 1H), 7.57-7.59 (m, 1H), 7.65-7.88 (m, 1H), 7.96 (d, J=9.20 Hz, 1H), 8.16-8.38 (m, 3H), 8.50-8.51 (m, 1H), 8.71 (s, 1H), 9.16 (s, 1H), 9.37 (s, 1H). Mol. wt.: 571.72. LC/MS: Retention time: 2.466 min. Purity: 97.4%.

Example 54

(2-(6-(Benzo[d]thiazol-6-ylamino)-4-(isopropylamino)pyridin-3-yl)thiazol-4-yl)(4-(3-hydroxypropyl)piperazin-1-yl)methanone $^1$H NMR: 400 MHz, DMSO-d$_6$: δ 1.30 (d, J=6.00 Hz, 6H), 1.58-1.63 (m, 2H), 2.33-2.42 (m, 6H), 3.43-3.46 (m, 2H), 3.62-3.65 (m, 4H), 3.70-3.75 (m, 1H), 6.16 (s, 1H), 7.58 (dd, J=2.00, 8.80 Hz, 1H), 7.96 (t, J=4.40 Hz, 2H), 8.33 (d, J=7.20 Hz, 1H), 8.52 (s, 1H), 8.72 (d, J=2.40 Hz, 1H), 9.16 (s, 1H), 9.36 (s, 1H). Mol. wt.: 537.7. LC/MS: Retention time: 1.935 min. Purity: 99.1%.

Example 55

(2-(6-(Benzo[d]thiazol-6-ylamino)-4-(isopropylamino)pyridin-3-yl)thiazol-4-yl)(4-(pyridin-2-yl)-1,4-diazepan-1-yl)methanone $^1$H NMR: 400 MHz, DMSO-d$_6$: δ 1.22-1.30 (m, 6H), 1.80-1.82 (m, 1H), 1.91-1.96 (m, 1H), 2.50 (1H, merged with DMSO-d$_6$ peak), 3.44-3.47 (m, 1H), 3.57-3.61 (m, 2H), 3.70-3.76 (m, 3H), 3.83 (bs, 3H), 6.16-6.17 (m, 1H), 6.51-6.74 (m, 2H), 7.45-7.60 (m, 2H), 7.89-7.97 (m, 2H), 8.09-8.19 (m, 1H), 8.31 (d, J=6.80 Hz, 1H), 8.51 (bs, 1H), 8.72 (bs, 1H), 9.16 (s, 1H), 9.37 (bs, 1H). Mol. wt.: 570.73. LC/MS: Retention time: 2.62 min. Purity: 99.4%.

Example 56

2-(6-(Benzo[d]thiazol-6-ylamino)-4-(isopropylamino)pyridin-3-yl)-N-(cyclohexylmethyl)thiazole-4-carboxamide $^1$H NMR: 400 MHz, DMSO-d$_6$: δ 0.94-0.97 (m, 2H), 1.16-1.24 (m, 3H), 1.33 (d, J=6.40 Hz, 6H), 1.64-1.76 (m, 6H), 3.16 (t, J=6.40 Hz, 2H), 3.66-3.71 (m, 1H), 6.15 (s, 1H), 7.58 (dd, J=2.40, 8.80 Hz, 1H), 7.96 (d, J=9.20 Hz, 1H), 8.11 (s, 1H), 8.22 (t, J=6.00 Hz, 1H), 8.33 (d, J=6.40 Hz, 1H), 8.49 (s, 1H), 8.71 (d, J=2.00 Hz, 1H), 9.16 (s, 1H), 9.37 (s, 1H). Mol. wt.: 506.69. LC/MS: Retention time: 3.040 min. Purity: 97.2%.

Example 57

2-(6-(Benzo[d]thiazol-6-ylamino)-4-(isopropylamino)pyridin-3-yl)-N-(2-(1-methylpyrrolidin-2-yl)ethyl)thiazole-4-carboxamide $^1$H NMR: 400 MHz, DMSO-d$_6$: δ 1.34 (d, J=6.40 Hz, 6H), 1.42-1.49 (m, 2H), 1.60-1.65 (m, 2H), 1.99-2.12 (m, 2H), 2.20-2.23 (m, 3H), 2.52 (2H, merged with DMSO-d$_6$ peak), 2.98 (bs, 2H), 3.66-3.71 (m, 1H), 6.15 (s, 1H), 7.58 (dd, J=2.00, 9.00 Hz, 1H), 7.96 (d, J=8.80 Hz, 1H), 8.11 (s, 1H), 8.31-8.33 (m, 2H), 8.49 (s, 1H), 8.72 (d, J=2.40 Hz, 1H), 9.15 (s, 1H), 9.36 (s, 1H). Mol. wt.: 521.7. LC/MS: Retention time: 2.202 min. Purity: 95.4%.

Example 58

2-(6-(Benzo[d]thiazol-6-ylamino)-4-(isopropylamino)pyridin-3-yl)-N-(2-(pyrrolidin-1-yl)ethyl)thiazole-4-carboxamide $^1$H NMR: 400 MHz, DMSO-d$_6$: δ 1.33 (d, J=6.00 Hz, 6H), 1.71 (bs, 4H), 2.50 (4H, merged with DMSO-d$_6$ peak), 2.55-2.64 (m, 2H), 3.43-3.47 (m, 2H), 3.69-3.71 (m, 1H), 6.16 (s, 1H), 7.58 (dd, J=2.00, 9.00 Hz, 1H), 7.95-7.99 (m, 2H), 8.15 (s, 1H), 8.28 (s, 1H), 8.50 (s, 1H), 8.72 (d, J=2.00 Hz, 1H), 9.16 (s, 1H), 9.37 (s, 1H). Mol. wt.: 507.67. LC/MS: Retention time: 2.386 min. Purity: 96.9%.

Example 59

2-(6-(Benzo[d]thiazol-6-ylamino)-4-(isopropylamino)pyridin-3-yl)-N-((tetrahydrofuran-2-yl)methyl)thiazole-4-carboxamide $^1$H NMR: 400 MHz, DMSO-$d_6$: δ 1.34 (d, J=6.00 Hz, 6H), 1.57-1.62 (m, 1H), 1.82-1.96 (m, 3H), 3.35 (2H, merged with water peak), 3.40-3.44 (m, 1H), 3.64-3.71 (m, 2H), 3.77-3.80 (m, 1H), 3.97-3.99 (m, 1H), 6.16 (s, 1H), 7.58 (dd, J=2.00, 8.80 Hz, 1H), 7.96 (d, J=8.80 Hz, 1H), 8.03 (t, J=6.00 Hz, 1H), 8.16 (s, 1H), 8.29 (d, J=7.20 Hz, 1H), 8.50 (s, 1H), 8.72 (d, J=2.00 Hz, 1H), 9.16 (s, 1H), 9.37 (s, 1H). Mol. wt.: 494.63. LC/MS: Retention time: 2.399 min. Purity: 97.7%.

Example 60

2-(6-(Benzo[d]thiazol-6-ylamino)-4-(isopropylamino)pyridin-3-yl)-N-(sec-butyl)thiazole-4-carboxamide $^1$H NMR: 400 MHz, DMSO-$d_6$: δ 0.90 (t, J=7.20 Hz, 3H), 1.18 (d, J=6.80 Hz, 3H), 1.29-1.34 (m, 6H), 1.51-1.59 (m, 2H), 3.67-3.72 (m, 1H), 3.88-3.93 (m, 1H), 6.15 (s, 1H), 7.58 (dd, J=2.00, 8.80 Hz, 1H), 7.94-7.98 (m, 2H), 8.13 (s, 1H), 8.44-8.52 (m, 2H), 8.68 (bs, 1H), 9.18 (s, 1H), 9.42 (bs, 1H). Mol. wt.: 466.62. LC/MS: Retention time: 2.644 min. Purity: 99.6%.

Example 61

2-(6-(Benzo[d]thiazol-6-ylamino)-4-(isopropylamino)pyridin-3-yl)-N-neopentylthiazole-4-carboxamide $^1$H NMR: 400 MHz, DMSO-$d_6$: δ 0.82 (s, 2H), 0.93 (s, 9H), 1.32 (d, J=6.00 Hz, 6H), 3.15-3.18 (m, 2H), 3.71-3.74 (m, 1H), 6.17 (s, 1H), 7.57 (dd, J=2.00, 8.80 Hz, 1H), 8.00 (d, J=8.80 Hz, 1H), 8.14-8.19 (m, 2H), 8.46-8.50 (m, 2H), 8.61 (bs, 1H), 9.21 (s, 1H), 9.56 (bs, 1H). Mol. wt.: 480.65. LC/MS: Retention time: 2.832 min. Purity: 95%.

Example 62

2-(6-(Benzo[d]thiazol-6-ylamino)-4-(isopropylamino)pyridin-3-yl)-N-isobutylthiazole-4-carboxamide $^1$H NMR: 400 MHz, DMSO-$d_6$: δ 0.92 (d, J=6.80 Hz, 6H), 1.33 (d, J=6.40 Hz, 6H), 1.83-1.88 (m, 1H), 3.14 (t, J=6.40 Hz, 2H), 3.66-3.71 (m, 1H), 6.16 (s, 1H), 7.58 (dd, J=2.40, 9.00 Hz, 1H), 7.96 (d, J=8.80 Hz, 1H), 8.12 (s, 1H), 8.26 (t, J=6.00 Hz, 1H), 8.33 (d, J=6.80 Hz, 1H), 8.49 (s, 1H), 8.71 (d, J=2.00 Hz, 1H), 9.16 (s, 1H), 9.37 (s, 1H). Mol. wt.: 466.62. LC/MS: Retention time: 2.645 min. Purity: 96.3%.

Example 63

2-(6-(Benzo[d]thiazol-6-ylamino)-4-(isopropylamino)pyridin-3-yl)-N-ethylthiazole-4-carboxamide $^1$H NMR: 400 MHz, DMSO-$d_6$: δ 1.16 (t, J=7.20 Hz, 3H), 1.34 (d, J=6.40 Hz, 6H), 3.35 (2H, merged with water peak), 3.66-3.71 (m, 1H), 6.15 (s, 1H), 7.58 (dd, J=2.00, 9.00 Hz, 1H), 7.96 (d, J=8.80 Hz, 1H), 8.11 (s, 1H), 8.24-8.26 (m, 1H), 8.39 (d, J=6.80 Hz, 1H), 8.49 (s, 1H), 8.72 (d, J=2.00 Hz, 1H), 9.15 (s, 1H), 9.36 (s, 1H). Mol. wt.: 438.57. LC/MS: Retention time: 2.298 min. Purity: 98.1%.

Example 64

N-(2-Acetamidoethyl)-2-(6-(benzo[d]thiazol-6-ylamino)-4-(isopropylamino)pyridin-3-yl)thiazole-4-carboxamide $^1$H NMR: 400 MHz, DMSO-$d_6$: δ 1.35 (d, J=6.40 Hz, 6H), 1.82 (s, 3H), 3.22-3.38 (m, 4H), 3.67-3.72 (m, 1H), 6.16 (s, 1H), 7.58 (dd, J=2.00, 9.00 Hz, 1H), 7.96 (d, J=8.80 Hz, 1H), 8.04-8.05 (m, 1H), 8.14 (s, 1H), 8.32-8.36 (m, 2H), 8.49 (s, 1H), 8.72 (d, J=2.00 Hz, 1H), 9.16 (s, 1H), 9.36 (s, 1H). Mol. wt.: 495.62. LC/MS: Retention time: 1.834 min. Purity: 99.6%.

Example 65

2-(6-(Benzo[d]thiazol-6-ylamino)-4-(isopropylamino)pyridin-3-yl)-N-(2-(dimethylamino)ethyl)thiazole-4-carboxamide $^1$H NMR: 400 MHz, DMSO-$d_6$: δ 1.34 (d, J=6.00 Hz, 6H), 2.24 (bs, 6H), 2.52 (2H, merged with DMSO-$d_6$ peak), 3.41-3.46 (m, 2H), 3.68-3.73 (m, 1H), 6.16 (s, 1H), 7.59 (dd, J=2.40, 8.80 Hz, 1H), 7.91-7.97 (m, 2H), 8.15 (s, 1H), 8.25 (d, J=6.80 Hz, 1H), 8.50 (s, 1H), 8.71 (d, J=2.00 Hz, 1H), 9.16 (s, 1H), 9.37 (s, 1H). Mol. wt.: 481.64. LC/MS: Retention time: 2.269 min. Purity: 95.9%.

Example 66

2-(6-(Benzo[d]thiazol-6-ylamino)-4-(isopropylamino)pyridin-3-yl)-N-(2-methoxyethyl)thiazole-4-carboxamide $^1$H NMR: 400 MHz, DMSO-$d_6$: δ 1.34 (d, J=6.40 Hz, 6H), 3.29 (3H, merged with water peak), 3.48-3.50 (m, 4H), 3.67-3.70 (m, 1H), 6.16 (s, 1H), 7.58 (dd, J=2.00, 8.80 Hz, 1H), 7.96 (d, J=8.80 Hz, 1H), 8.04-8.07 (m, 1H), 8.15 (s, 1H), 8.32 (d, J=6.80 Hz, 1H), 8.50 (s, 1H), 8.72 (d, J=2.00 Hz, 1H), 9.16 (s, 1H), 9.37 (s, 1H). Mol. wt.: 468.6. LC/MS: Retention time: 2.243 min. Purity: 96.6%.

Example 67

2-(6-(Benzo[d]thiazol-6-ylamino)-4-(isopropylamino)pyridin-3-yl)-N-(4-hydroxyphenethyl)thiazole-4-carboxamide $^1$H NMR: 400 MHz, DMSO-$d_6$: δ 1.29 (d, J=6.40 Hz, 6H), 2.73-2.77 (m, 2H), 3.47-3.51 (m, 2H), 3.66-3.71 (m, 1H), 6.15 (s, 1H), 6.67-6.70 (m, 2H), 7.04 (d, J=8.40 Hz, 2H), 7.58 (dd, J=2.40, 8.80 Hz, 1H), 7.96 (d, J=8.80 Hz, 1H), 8.12 (s, 1H), 8.20-8.23 (m, 1H), 8.28 (d, J=6.80 Hz, 1H), 8.49 (s, 1H), 8.71 (d, J=2.00 Hz, 1H), 9.16 (d, J=2.00 Hz, 1H), 9.36 (s, 1H). Mol. wt.: 530.66. LC/MS: Retention time: 2.284 min. Purity: 98.7%.

Example 68

2-(6-(Benzo[d]thiazol-6-ylamino)-4-(isopropylamino)pyridin-3-yl)-N-(prop-2-yn-1-yl)thiazole-4-carboxamide $^1$H NMR: 400 MHz, DMSO-$d_6$: δ 1.34 (d, J=6.40 Hz, 6H), 3.15 (t, J=2.40 Hz, 1H), 3.66-3.71 (m, 1H), 4.09 (dd, J=2.40, 5.60 Hz, 2H), 6.16 (s, 1H), 7.58 (dd, J=2.00, 8.80 Hz, 1H), 7.96 (d, J=8.80 Hz, 1H), 8.19 (s, 1H), 8.35 (d, J=6.80 Hz, 1H), 8.50 (s, 1H), 8.70-8.72 (m, 2H), 9.16 (s, 1H), 9.36 (s, 1H). Mol. wt.: 448.56. LC/MS: Retention time: 2.291 min. Purity: 98.1%.

Example 69

2-(6-(Benzo[d]thiazol-6-ylamino)-4-(isopropylamino)pyridin-3-yl)-N-(3,3-dimethylbutyl)thiazole-4-carboxamide $^1$H NMR: 400 MHz, DMSO-d$_6$: δ 0.94 (s, 9H), 1.34 (d, J=6.40 Hz, 6H), 1.47-1.51 (m, 2H), 3.66-3.71 (m, 1H), 6.15 (s, 1H), 7.58 (dd, J=2.00, 8.80 Hz, 1H), 7.96 (d, J=8.80 Hz, 1H), 8.10 (s, 1H), 8.20 (t, J=6.00 Hz, 1H), 8.34 (d, J=7.20 Hz, 1H), 8.49 (s, 1H), 8.72 (d, J=2.00 Hz, 1H), 9.15 (s, 1H), 9.36 (s, 1H). Mol. wt.: 494.68. LC/MS: Retention time: 2.866 min. Purity: 95.1%.

Example 70

2-(6-(Benzo[d]thiazol-6-ylamino)-4-(isopropylamino)pyridin-3-yl)-N-isopentylthiazole-4-carboxamide $^1$H NMR: 400 MHz, DMSO-d$_6$: δ 0.91 (d, J=6.40 Hz, 6H), 1.33 (d, J=6.40 Hz, 6H), 1.42-1.48 (m, 2H), 1.65-1.68 (m, 1H), 3.35 (2H, merged with water peak), 3.66-3.71 (m, 1H), 6.15 (s, 1H), 7.58 (dd, J=2.00, 8.80 Hz, 1H), 7.96 (d, J=8.80 Hz, 1H), 8.11 (s, 1H), 8.20-8.22 (m, 1H), 8.37 (bs, 1H), 8.49 (s, 1H), 8.70 (bs, 1H), 9.16 (s, 1H), 9.38 (bs, 1H). Mol. wt.: 480.65. LC/MS: Retention time: 2.826 min. Purity: 96.7%.

Example 71

2-(6-(Benzo[d]thiazol-6-ylamino)-4-(isopropylamino)pyridin-3-yl)-N-propylthiazole-4-carboxamide $^1$H NMR: 400 MHz, DMSO-d$_6$: δ 0.92 (t, J=7.20 Hz, 3H), 1.33 (d, J=6.40 Hz, 6H), 1.54-1.59 (m, 2H), 3.24-3.29 (m, 2H), 3.66-3.71 (m, 1H), 6.15 (s, 1H), 7.58 (dd, J=2.40, 8.80 Hz, 1H), 7.96 (d, J=8.80 Hz, 1H), 8.11 (s, 1H), 8.25-8.26 (m, 1H), 8.35-8.37 (m, 1H), 8.36 (d, J=6.80 Hz, 1H), 8.49 (s, 1H), 8.72 (d, J=2.00 Hz, 1H), 9.15 (s, 1H), 9.36 (s, 1H). Mol. wt.: 452.6. LC/MS: Retention time: 2.49 min. Purity: 99.4%.

Example 72

2-(6-(Benzo[d]thiazol-6-ylamino)-4-(isopropylamino)pyridin-3-yl)-N-pentylthiazole-4-carboxamide $^1$H NMR: 400 MHz, DMSO-d$_6$: δ 0.87-0.90 (m, 3H), 1.30-1.34 (m, 6H), 1.53-1.57 (m, 2H), 3.29 (4H, merged with water peak), 3.68-3.73 (m, 1H), 6.16 (s, 1H), 7.57 (dd, J=2.00, 8.80 Hz, 1H), 8.01 (dd, J=8.80, Hz, 1H), 8.16 (s, 1H), 8.25-8.29 (m, 1H), 8.45 (s, 1H), 8.60 (bs, 1H), 9.22 (s, 1H), 9.54 (bs, 1H). Mol. wt.: 480.65. LC/MS: Retention time: 2.864 min. Purity: 98.3%.

Example 73

2-(6-(Benzo[d]thiazol-6-ylamino)-4-(isopropylamino)pyridin-3-yl)-N-(cyclopropylmethyl)thiazole-4-carboxamide $^1$H NMR: 400 MHz, DMSO-d$_6$: δ 0.25-0.29 (m, 2H), 0.43-0.48 (m, 2H), 1.05-1.08 (m, 1H), 1.35 (d, J=6.00 Hz, 6H), 3.19 (t, J=6.40 Hz, 2H), 3.67-3.72 (m, 1H), 6.16 (s, 1H), 7.59 (dd, J=2.00, 8.80 Hz, 1H), 7.96 (d, J=8.80 Hz, 1H), 8.13 (s, 1H), 8.23 (t, J=6.00 Hz, 1H), 8.37 (d, J=6.80 Hz, 1H), 8.50 (s, 1H), 8.72 (d, J=2.00 Hz, 1H), 9.16 (s, 1H), 9.37 (s, 1H). Mol. wt.: 464.61. LC/MS: Retention time: 2.531 min. Purity: 99.5%.

Example 74

2-(6-(Benzo[d]thiazol-6-ylamino)-4-(isopropylamino)pyridin-3-yl)-N-(3-chlorophenethyl)thiazole-4-carboxamide $^1$H NMR: 400 MHz, DMSO-d$_6$: δ 1.24-1.28 (m, 6H), 2.90 (t, J=7.20 Hz, 2H), 3.55-3.66 (m, 3H), 6.14 (s, 1H), 7.21-7.35 (m, 4H), 7.58 (dd, J=2.00, 8.80 Hz, 1H), 7.95 (d, J=8.80 Hz, 1H), 8.12 (s, 1H), 8.25-8.32 (m, 2H), 8.49 (s, 1H), 8.71 (d, J=2.00 Hz, 1H), 9.15 (s, 1H), 9.36 (s, 1H). Mol. wt.: 549.11. LC/MS: Retention time: 2.917 min. Purity: 99.5%.

Example 75

2-(6-(Benzo[d]thiazol-6-ylamino)-4-(isopropylamino)pyridin-3-yl)-N-(2-(thiophen-2-yl)ethyl)thiazole-4-carboxamide $^1$H NMR: 400 MHz, DMSO-d$_6$: δ 1.30 (d, J=6.40 Hz, 6H), 3.10 (t, J=6.80 Hz, 2H), 3.56-3.61 (m, 2H), 3.67-3.68 (m, 1H), 6.15 (s, 1H), 6.93-6.97 (m, 2H), 7.34 (dd, J=1.20, 5.00 Hz, 1H), 7.58 (dd, J=2.40, 8.80 Hz, 1H), 7.98 (d, J=8.80 Hz, 1H), 8.16 (s, 1H), 8.38-8.41 (m, 2H), 8.47 (s, 1H), 8.67 (bs, 1H), 9.18 (s, 1H), 9.42 (bs, 1H). Mol. wt.: 520.69. LC/MS: Retention time: 2.689 min. Purity: 94.5%.

Example 76

2-(6-(Benzo[d]thiazol-6-ylamino)-4-(isopropylamino)pyridin-3-yl)-N-(2-phenoxyethyl)thiazole-4-carboxamide $^1$H NMR: 400 MHz, DMSO-d$_6$: δ 1.27-1.31 (m, 6H), 3.65-3.72 (m, 3H), 4.15 (t, J=5.60 Hz, 2H), 6.14 (s, 1H), 6.93-6.97 (m, 3H), 7.28-7.32 (m, 2H), 7.58 (dd, J=2.40, 9.00 Hz, 1H), 7.96 (d, J=8.80 Hz, 1H), 8.19 (s, 1H), 8.36-8.38 (m, 2H), 8.49 (s, 1H), 8.70 (bs, 1H), 9.16 (s, 1H), 9.38 (bs, 1H). Mol. wt.: 530.66. LC/MS: Retention time: 2.742 min. Purity: 97.8%.

Example 77

2-(6-(Benzo[d]thiazol-6-ylamino)-4-(isopropylamino)pyridin-3-yl)-N-(4-fluorophenethyl)thiazole-4-carboxamide $^1$H NMR: 400 MHz, DMSO-d$_6$: δ 1.24-1.27 (m, 6H), 2.87 (t, J=7.20 Hz, 2H), 3.52-3.58 (m, 2H), 3.63-3.68 (m, 1H), 6.14 (s, 1H), 7.10-7.14 (m, 2H), 7.27-7.31 (m, 2H), 7.58 (dd, J=2.00, 9.00 Hz, 1H), 7.95 (d, J=8.80 Hz, 1H), 8.12 (s, 1H), 8.24-8.29 (m, 2H), 8.49 (s, 1H), 8.71 (d, J=2.40 Hz, 1H), 9.15 (s, 1H), 9.36 (s, 1H). Mol. wt.: 532.66. LC/MS: Retention time: 2.76 min. Purity: 98.9%.

Example 78

2-(6-(Benzo[d]thiazol-6-ylamino)-4-(isopropylamino)pyridin-3-yl)-N-(2-(2-hydroxyethoxy)ethyl)thiazole-4-carboxamide $^1$H NMR: 400 MHz, DMSO-d$_6$: δ 1.33 (d, J=6.00 Hz, 6H), 3.45-3.52 (m, 6H), 3.57-3.59 (m, 2H), 3.66-3.70 (m, 1H), 4.59-4.61 (m, 1H), 6.15 (s, 1H), 7.58 (dd, J=2.00, 8.80 Hz, 1H), 7.82 (d, J=−100.40 Hz, 1H), 8.12-8.15 (m, 2H), 8.33 (d, J=6.80 Hz, 1H), 8.50 (s, 1H), 8.71 (d, J=2.00 Hz, 1H), 9.16 (s, 1H), 9.37 (s, 1H). Mol. wt.: 498.62. LC/MS: Retention time: 1.888 min. Purity: 99.5%.

Example 79

2-(6-(Benzo[d]thiazol-6-ylamino)-4-(isopropylamino)pyridin-3-yl)-N-(3-hydroxypropyl)thiazole-4-carboxamide $^1$H NMR: 400 MHz, DMSO-$d_6$: δ 1.34 (d, J=6.40 Hz, 6H), 1.69-1.72 (m, 2H), 3.35 (2H, merged with water peak), 3.49-3.52 (m, 2H), 3.68-3.69 (m, 1H), 4.55 (s, 1H), 6.15 (s, 1H), 7.58 (dd, J=2.40, 8.80 Hz, 1H), 7.96 (d, J=8.80 Hz, 1H), 8.12 (s, 1H), 8.25 (t, J=6.00 Hz, 1H), 8.33 (d, J=6.80 Hz, 1H), 8.49 (s, 1H), 8.71 (d, J=2.40 Hz, 1H), 9.16 (s, 1H), 9.37 (s, 1H). Mol. wt.: 468.6. LC/MS: Retention time: 1.916 min. Purity: 99.6%.

Example 80

2-(6-(Benzo[d]thiazol-6-ylamino)-4-(isopropylamino)pyridin-3-yl)-N-(4-hydroxybutyl)thiazole-4-carboxamide $^1$H NMR: 400 MHz, DMSO-$d_6$: δ 1.33 (d, J=6.40 Hz, 6H), 1.47-1.52 (m, 2H), 1.55-1.60 (m, 2H), 3.41-3.45 (m, 2H), 3.66-3.71 (m, 1H), 4.40 (t, J=4.80 Hz, 1H), 6.15 (s, 1H), 7.58 (dd, J=2.00, 8.80 Hz, 1H), 7.96 (d, J=8.80 Hz, 1H), 8.11 (s, 1H), 8.24 (t, J=5.60 Hz, 1H), 8.35 (d, J=6.80 Hz, 1H), 8.49 (s, 1H), 8.72 (d, J=2.00 Hz, 1H), 9.16 (s, 1H), 9.36 (s, 1H). Mol. wt.: 482.62. LC/MS: Retention time: 1.961 min. Purity: 99.6%.

Example 81

(R)-2-(6-(Benzo[d]thiazol-6-ylamino)-4-(isopropylamino)pyridin-3-yl)-N-(2-hydroxy-2-phenylethyl)thiazole-4-carboxamide $^1$H NMR: 400 MHz, DMSO-$d_6$: δ 1.31-1.35 (m, 6H), 3.38-3.43 (m, 1H), 3.60-3.72 (m, 2H), 4.80-4.81 (m, 1H), 5.67 (d, J=4.40 Hz, 1H), 6.16 (s, 1H), 7.24-7.28 (m, 1H), 7.33-7.37 (m, 2H), 7.40-7.42 (m, 2H), 7.58 (dd, J=2.00, 9.00 Hz, 1H), 7.95-7.99 (m, 2H), 8.16 (s, 1H), 8.25 (d, J=6.80 Hz, 1H), 8.50 (s, 1H), 8.71 (d, J=2.00 Hz, 1H), 9.16 (s, 1H), 9.38 (s, 1H). Mol. wt.: 530.66. LC/MS: Retention time: 2.392 min. Purity: 99.1%.

Example 82

2-(6-(Benzo[d]thiazol-6-ylamino)-4-(isopropylamino)pyridin-3-yl)-N-(3-(pyrrolidin-1-yl)propyl)thiazole-4-carboxamide $^1$H NMR: 400 MHz, DMSO-$d_6$: δ 1.34 (d, J=6.40 Hz, 6H), 1.69-1.73 (m, 6H), 2.50 (4H, merged with DMSO-$d_6$ peak), 3.35 (4H, merged with water peak), 3.66-3.71 (m, 1H), 6.15 (s, 1H), 7.58 (dd, J=2.00, 9.00 Hz, 1H), 7.96 (d, J=8.80 Hz, 1H), 8.11 (s, 1H), 8.32-8.34 (m, 2H), 8.49 (s, 1H), 8.72 (d, J=2.00 Hz, 1H), 9.16 (s, 1H), 9.36 (s, 1H). Mol. wt.: 521.7. LC/MS: Retention time: 2.24 min. Purity: 94.6%.

Example 83

2-(6-(Benzo[d]thiazol-6-ylamino)-4-(isopropylamino)pyridin-3-yl)-N-(3-(piperidin-1-yl)propyl)thiazole-4-carboxamide $^1$H NMR: 400 MHz, DMSO-$d_6$: δ 1.33-1.39 (m, 8H), 1.45-1.51 (m, 4H), 1.68-1.73 (m, 2H), 2.29-2.34 (m, 5H), 2.52 (2H, merged with DMSO-$d_6$ peak), 3.66-3.71 (m, 1H), 6.15 (s, 1H), 7.58 (dd, J=2.40, 9.00 Hz, 1H), 7.96 (d, J=8.80 Hz, 1H), 8.11 (s, 1H), 8.27 (t, J=5.60 Hz, 1H), 8.33 (d, J=6.80 Hz, 1H), 8.49 (s, 1H), 8.72 (d, J=2.40 Hz, 1H), 9.15 (s, 1H), 9.36 (s, 1H). Mol. wt.: 535.73. LC/MS: Retention time: 2.402 min. Purity: 96.7%.

Example 84

2-(6-(Benzo[d]thiazol-6-ylamino)-4-(isopropylamino)pyridin-3-yl)-N-(2-cyclohexylethyl)thiazole-4-carboxamide $^1$H NMR: 400 MHz, DMSO-$d_6$: δ 0.89-0.95 (m, 2H), 1.12-1.19 (m, 3H), 1.34 (d, J=6.00 Hz, 6H), 1.43-1.48 (m, 2H), 1.61-1.75 (m, 5H), 1.99-2.01 (m, 1H), 3.36 (2H, merged with water peak), 3.66-3.71 (m, 1H), 6.15 (s, 1H), 7.58 (dd, J=2.00, 9.00 Hz, 1H), 7.96 (d, J=8.80 Hz, 1H), 8.11 (s, 1H), 8.20 (t, J=6.00 Hz, 1H), 8.37 (bs, 1H), 8.49 (s, 1H), 8.71 (bs, 1H), 9.16 (s, 1H), 9.37 (bs, 1H). Mol. wt.: 520.7. LC/MS: Retention time: 3.236 min. Purity: 98.2%.

Example 85

2-(6-(Benzo[d]thiazol-6-ylamino)-4-(isopropylamino)pyridin-3-yl)-N-(2-(pyridin-4-yl)ethyl)thiazole-4-carboxamide $^1$H NMR: 400 MHz, DMSO-$d_6$: δ 1.26 (d, J=6.40 Hz, 6H), 2.92 (t, J=6.80 Hz, 2H), 3.59-3.66 (m, 3H), 6.14 (s, 1H), 7.30 (d, J=5.60 Hz, 1H), 7.58 (dd, J=2.40, 9.00 Hz, 1H), 7.96 (d, J=8.80 Hz, 1H), 8.13 (s, 1H), 8.25 (d, J=6.80 Hz, 1H), 8.36-8.39 (m, 1H), 8.47-8.49 (m, 3H), 8.71 (d, J=2.00 Hz, 1H), 9.16 (s, 1H), 9.36 (s, 1H). Mol. wt.: 515.65. LC/MS: Retention time: 2.13 min. Purity: 99.7%.

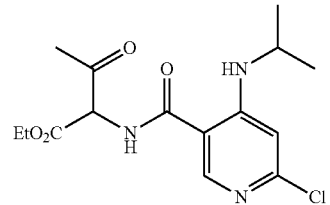

Oxazoles

Synthesis of ethyl 2-(6-chloro-4-(isopropylamino)nicotinamido)-3-oxobutanoate (27a): A stirred solution of 6-chloro-4-(isopropylamino)nicotinic acid (2) in DCM (15 mL) was cooled to 0° C., oxalyl chloride (2 equiv) was added, followed by addition of 2 drops of DMF. The reaction mixture was stirred at room temperature for 2 h. The reaction mixture was concentrated to remove excess of oxalyl chloride. The acyl chloride, generated in-situ was dissolved in THF and added dropwise to a cool, stirred solution of ethyl 2-amino-3-oxobutanoate (1.1 equiv.) and NMM (5 equiv.) in THF. The reaction temperature was slowly brought to room temperature and stirred overnight. The reaction mixture was diluted with EtOAc and washed with water, followed by brine solution. The EtOAc layer was collected, dried over $Na_2SO_4$, filtered and concentrated. The crude material obtained was purified by column chromatography through silica gel and EtOAc:Pet. Ether as eluent to afford the title compound, ethyl 2-(6-chloro-4-(isopropylamino)nicotinamido)-3-oxobutanoate.

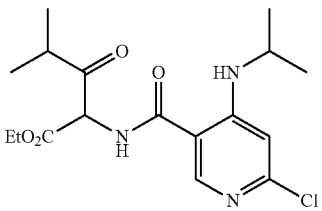 [SMILES: CCOC(=O)C(NC(=O)c1cnc(Cl)cc1NC(C)C)C(=O)C(C)C]

Synthesis of ethyl 2-(6-chloro-4-(isopropylamino)nicotinamido)-4-methyl-3-oxopentanoate (27b): Followed the same procedure as mentioned for the synthesis of compound no. 27a, using compound 26b, instead of compound, 26a.

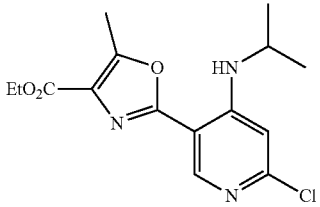 [SMILES: CCOC(=O)c1nc(-c2cnc(Cl)cc2NC(C)C)oc1C]

Synthesis of ethyl 2-(6-chloro-4-(isopropylamino)pyridin-3-yl)-5-methyloxazole-4-carboxylate (28a): To a stirred solution of ethyl 2-(6-chloro-4-(isopropylamino)nicotinamido)-3-oxobutanoate (27a) (200 mg, 0.58 mmol) in DCM (10 mL), triphenyl phosphine (2 equiv.), iodine (2 equiv.) and triethyl amine (3 equiv.) were added and stirred at room temperature for 4 h. The reaction mixture was diluted using DCM and washed with water. The organic layer was collected, dried over $Na_2SO_4$, filtered and concentrated. The crude material obtained was purified by column chromatography using silica gel and EtOAc:Pet. Ether as eluent to obtain the title compound, ethyl 2-(6-chloro-4-(isopropylamino)pyridin-3-yl)-5-methyloxazole-4-carboxylate. $^1$H NMR: 400 MHz, DMSO-$d_6$: δ 1.25 (d, J=6.40 Hz, 6H), 1.33 (t, J=7.20 Hz, 3H), 2.67 (s, 3H), 3.90-3.95 (m, 1H), 4.31 (q, J=7.20 Hz, 2H), 6.89 (s, 1H), 8.47 (d, J=7.60 Hz, 1H), 8.54 (s, 1H).

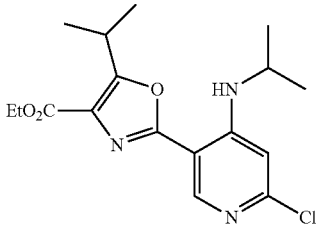 [SMILES: CCOC(=O)c1nc(-c2cnc(Cl)cc2NC(C)C)oc1C(C)C]

Synthesis of ethyl 2-(6-chloro-4-(isopropylamino)pyridin-3-yl)-5-isopropyloxazole-4-carboxylate (28b): Followed the same procedure as mentioned for the synthesis of compound no. 28a, using respective starting material, compound no. 27b.

Example 86

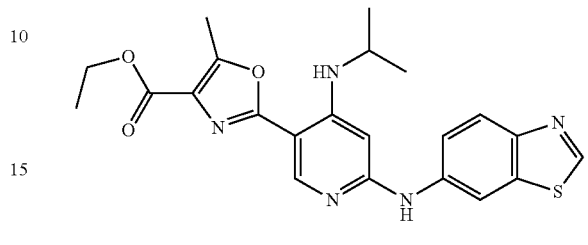

Synthesis of ethyl 2-(6-(benzo[d]thiazol-6-ylamino)-4-(isopropylamino)pyridin-3-yl)-5-methyloxazole-4-carboxylate: Ethyl 2-(6-chloro-4-(isopropylamino)pyridin-3-yl)-5-methyloxazole-4-carboxylate (28a) (50 mg, 0.15 mmol) was dissolved in 1,4-Dioxane (5 mL):$H_2O$ (1 mL), to it benzo[d]thiazol-6-amine (0.15 mmol), $Na_2CO_3$ (0.6 mmol) and xanthphos (0.06 mmol) were added and degassed for 10 min. $Pd_2(dba)_3$ (0.06 mmol) was added and degassed once again for 15 min and heated at 115° C., overnight. The reaction mass was filtered through a small pad of celite and concentrated the filtrate to remove solvent. The crude material obtained was purified by column chromatography through silica gel and MeOH:$CHCl_3$ as eluent. The material obtained was further purified by preparative TLC to obtain the title compound, ethyl 2-(6-(benzo[d]thiazol-6-ylamino)-4-(isopropylamino)pyridin-3-yl)-5-methyloxazole-4-carboxylate. $^1$H NMR: 400 MHz, DMSO-$d_6$: δ 1.28-1.35 (m, 9H), 2.66 (s, 3H), 3.71-3.72 (m, 1H), 4.30 (q, J=7.20 Hz, 2H), 6.16 (s, 1H), 7.59 (dd, J=2.40, 9.00 Hz, 1H), 7.96 (d, J=8.80 Hz, 1H), 8.10 (d, J=7.20 Hz, 1H), 8.53 (s, 1H), 8.66 (d, J=2.00 Hz, 1H), 9.16 (s, 1H), 9.36 (s, 1H). LC/MS: Ascentis Express C18, 5×2.1 mm, 2.7 μm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min; retention time: 2.127 min; LCMS (ES-API), m/z 438.2 (M+H). HPLC: Sunfire C18 (150×4.6 mm), 3.5 micron; Solvent A=5% ACN: 95% $H_2O$: 0.05% TFA pH=2.5; Solvent B=95% ACN: 5% $H_2O$: 0.05% TFA pH=2.5; gradient 0-100% B over 15 min (23 min run time); Flow rate: 1.0 μL/min; Retention time: 7.483 min; Purity: 99.7%.

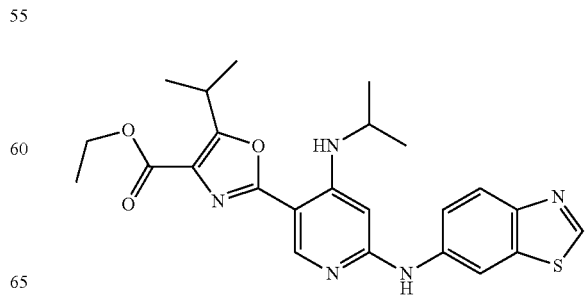

Synthesis of ethyl 2-(6-(benzo[d]thiazol-6-ylamino)-4-(isopropylamino)pyridin-3-yl)-5-isopropyloxazole-4-carboxylate (29): Followed the same procedure as mentioned for the synthesis of Example 86, using respective starting material, compound no. 28b.

TABLE 4

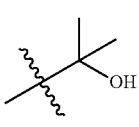 [SMILES: *C(C)(C)O]

| Example No. | R | R₁ |
|---|---|---|
| 87 | CH₃ | NH₂ |
| 88 | i-Pr | 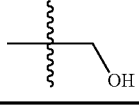 |
| 89 | i-Pr | (see structure) |

Example 87

Synthesis of 2-(6-(benzo[d]thiazol-6-ylamino)-4-(isopropylamino)pyridin-3-yl)-5-methyloxazole-4-carboxamide: A solution of ethyl 2-(6-(benzo[d]thiazol-6-ylamino)-4-(isopropylamino)pyridin-3-yl)-5-methyloxazole-4-carboxylate (Example 86) (30 mg, 0.06 mmol) in MeOH (4 mL) was cooled to 0° C., NH₃ (g) was purged for 5 min. The reaction mixture was heated at 80° C. in a closed condition for 48 h. The reaction mixture was cooled and transferred to rbf, concentrated to get solid material. The crude material obtained was purified by prep HPLC to furnish the desired compound, 2-(6-(benzo[d]thiazol-6-ylamino)-4-(isopropylamino)pyridin-3-yl)-5-methyloxazole-4-carboxamide. $^1$H NMR: 400 MHz, DMSO-$d_6$: δ 1.33 (d, J=6.40 Hz, 6H), 2.63 (s, 1H), 3.68-3.73 (m, 1H), 6.16 (s, 1H), 7.49 (bs, 1H), 7.59 (dd, J=2.40, 9.00 Hz, 1H), 7.75 (d, J=7.20 Hz, 1H), 7.96 (d, J=8.80 Hz, 1H), 8.52 (s, 1H), 8.66 (d, J=2.00 Hz, 1H), 9.14 (s, 1H), 9.32 (s, 1H). LC/MS: (Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.687 min; LCMS (ES-API), m/z 409.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 12 min (23 min run time); Flow rate: 1.0 μL/min; Retention time: 5.651 min; Purity: 99.9%.

Example 88

Synthesis of 2-(2-(6-(benzo[d]thiazol-6-ylamino)-4-(isopropylamino)pyridin-3-yl)-5-isopropyloxazol-4-yl)propan-2-ol: To a solution ethyl 2-(6-(benzo[d]thiazol-6-ylamino)-4-(isopropylamino)pyridin-3-yl)-5-methyloxazole-4-carboxylate (29) (150 mg, 0.34 mmol) in dry Tetrahydrofuran (10 mL) was added methyl magnesium bromide (2.132 mmol) (3.0 M in diethyl ether) at −78° C. Reaction mixture was allowed to warm up to 25° C. over 2 h. The reaction mixture was cooled to 0° C. and quenched by the addition of saturated aqueous NH₄Cl solution dropwise. Extracted with ethyl acetate, dried over Na₂SO₄, filtered and concentrated to get the crude product, which was purified by flash column using ethyl acetate/hexanes as eluent to furnish 2-(2-(6-(benzo[d]thiazol-6-ylamino)-4-(isopropylamino)pyridin-3-yl)-5-isopropyloxazol-4-yl)propan-2-ol. $^1$H NMR: 400 MHz, DMSO-$d_6$: δ 1.26-1.27 (m, 13H), 1.48 (s, 6H), 3.63-3.71 (m, 2H), 5.06 (s, 1H), 6.13 (s, 1H), 7.57 (dd, J=2.00, 8.80 Hz, 1H), 7.95 (d, J=8.80 Hz, 1H), 8.28 (d, J=6.80 Hz, 1H), 8.51 (s, 1H), 8.75 (d, J=2.00 Hz, 1H), 9.15 (s, 1H), 9.28 (s, 1H). LC/MS: ZORBAX SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.842 min; LCMS (ES-API), m/z 452.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 7.608 min; Purity: 97.8%.

Example 89

Synthesis of (2-(6-(benzo[d]thiazol-6-ylamino)-4-(isopropylamino)pyridin-3-yl)-5-isopropyloxazol-4-yl)methanol: To a solution of ethyl 2-(6-(benzo[d]thiazol-6-ylamino)-4-(isopropylamino)pyridin-3-yl)-5-methyloxazole-4-carboxylate (29) (150 mg, 0.34 mmol) in dry Tetrahydrofuran (10 mL) was added LAH (0.739 mmol) (4% in THF) at −10° C. The reaction mixture was stirred at 0° C. for 30 min, reaction temperature was then brought to room temperature and stirred for 30 min. The reaction mixture was cooled to 0° C. and quenched by using ice flakes (until the H₂ gas evolution ceased), followed by 1N NaOH solution, filtered through celite, precipitate was washed with ethyl acetate. The organic layers were combined, dried over Na₂SO₄, filtered and concentrated in vacuum to give crude compound. The crude material was purified by flash column chromatography using silica gel and ethyl acetate/hexane as eluent to provide (2-(6-(benzo[d]thiazol-6-ylamino)-4-(isopropylamino)pyridin-3-yl)-5-isopropyloxazol-4-yl)methanol. $^1$H NMR: 400 MHz, DMSO-$d_6$: δ 1.28-1.30 (m, 12H), 3.68-3.73 (m, 1H), 4.38-4.39 (m, 2H), 5.03-5.03 (m, 1H), 6.15 (s, 1H), 7.57 (dd, J=2.00, 8.80 Hz, 1H), 7.95 (d, J=8.80 Hz, 1H), 8.11 (d, J=6.80 Hz, 1H), 8.54 (s, 1H), 8.74 (d, J=1.60 Hz, 1H), 9.15 (s, 1H), 9.30 (s, 1H). LC/MS: ZORBAX SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.703 min; LCMS (ES-API), m/z 424.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 6.663 min; Purity: 99.2%.

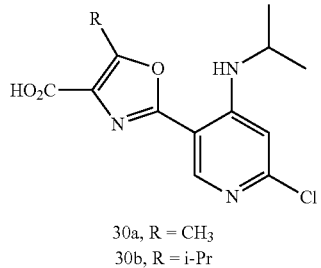

30a, R = CH₃
30b, R = i-Pr

Synthesis of 2-(6-chloro-4-(isopropylamino)pyridin-3-yl)-5-methyloxazole-4-carboxylic acid (30a) and 2-(6-chloro-4-(isopropylamino)pyridin-3-yl)-5-isopropyloxazole-4-carboxylic acid (30b): Followed the same procedure as mentioned in the synthesis of compound no. 9. LC/MS: Ascentis Express C18, 5×2.1 mm, 2.7 µm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.492 min; LCMS (ES-API), m/z 296.2 (M+H).

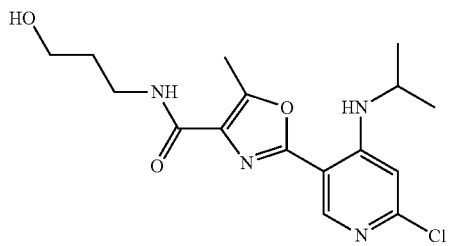

31

Synthesis of 2-(6-chloro-4-(isopropylamino)pyridin-3-yl)-N-(3-hydroxypropyl)-5-methyloxazole-4-carboxamide (31): 2-(6-chloro-4-(isopropylamino)pyridin-3-yl)-5-methyloxazole-4-carboxylic acid (30a) (100 mg, 0.338 mmol) was dissolved in DMF (5 mL). 3-aminopropan-1-ol (1.691 mmol, 5 equiv.) and DIPEA (1.353 mmol, 4 equiv.) were added to the reaction mixture and stirred at room temperature. HATU (1.014 mmol, 3 equiv.) was added to the reaction mixture and stirred for 3 h. The reaction mixture was concentrated under reduced pressure to remove excess of DMF. The residue obtained was partitioned between water and EtOAc. The organic layer was separated, dried over Na₂SO₄, filtered and concentrated. The crude material obtained was purified by flash column chromatography through silica gel and MeOH: CHCl₃ as eluent to afford the title compound, 2-(6-chloro-4-(isopropylamino)pyridin-3-yl)-N-(3-hydroxypropyl)-5-methyloxazole-4-carboxamide (31).

Example 90

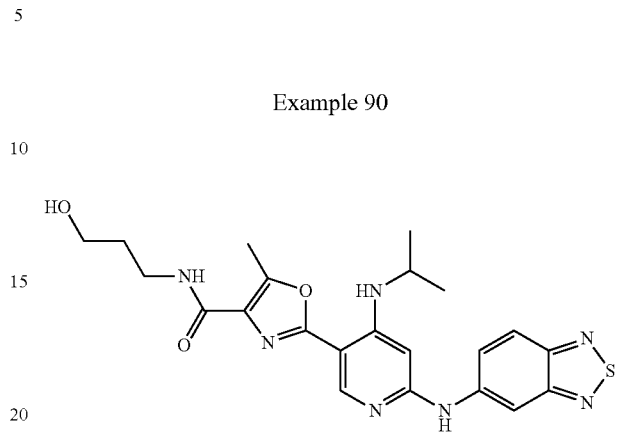

Synthesis of 2-(6-(benzo[c][1,2,5]thiadiazol-5-ylamino)-4-(isopropylamino)pyridin-3-yl)-N-(3-hydroxypropyl)-5-methyloxazole-4-carboxamide: To a stirred solution of (2-(6-chloro-4-(isopropylamino)pyridin-3-yl)-N-(3-hydroxypropyl)-5-methyloxazole-4-carboxamide (31) (100 mg, 0.283 mmol) in 1,4-Dioxane (10 mL), benzo[c][1,2,5]thiadiazol-5-amine (0.283 mmol, 1 equiv.), Na₂CO₃ (1.134 mmol, 4 equiv.) and Xanthphos (0.113 mmol, 0.4 equiv.) were added and degassed for 10 min. Pd₂(dba)₃ (0.113 mmol, 0.4 equiv.) was added and degassed once again for 10 min. Heated the reaction mixture at 115° C. for overnight. The reaction was cooled and filtered through small pad of celite. The filtrate obtained was concentrated to provide crude material. The crude material was purified by column chromatography through silica gel and MeOH:CHCl₃ as eluent to afford 2-(6-(benzo[c][1,2,5]thiadiazol-5-ylamino)-4-(isopropylamino)pyridin-3-yl)-N-(3-hydroxypropyl)-5-methyloxazole-4-carboxamide [Example 90]. ¹H NMR: 400 MHz, CD₃OD: δ 1.42 (d, J=6.40 Hz, 6H), 1.83-1.84 (m, 2H), 2.71 (s, 3H), 3.51 (t, J=1.20 Hz, 2H), 3.72 (t, J=7.20 Hz, 2H), 3.81-3.83 (m, 1H), 6.28 (s, 1H), 7.67 (dd, J=2.00, 9.40 Hz, 1H), 7.89 (dd, J=9.60, 9.20 Hz, 1H), 8.47 (s, 1H), 8.64 (s, 1H). LC/MS: Ascentis Express C18, 5×2.1 mm-2.7 µm; Solvent A=2% ACN: 98% H₂O: 10 mM NH₄COOH; Solvent B=98% ACN: 2% H₂O: 10 mM NH₄COOH; gradient 0-100% B over 3 min; retention time: 1.896 min; LCMS (ES-API), m/z 466.0 (M−H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 6.335 min; Purity: 98.7%.

Synthesis of Examples 91-105: The Examples in Table 5 were prepared according to the general method outlined for Example 90, using appropriate amines and their respective starting materials.

TABLE 5
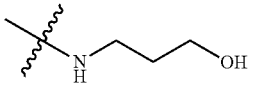 [SMILES: *NCCCO]
| Compound No. | R | R₁ | R₂ |
|---|---|---|---|
| 90 | CH₃ | 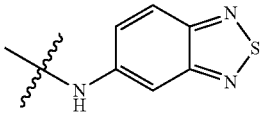 [SMILES: *Nc1ccc2nsnc2c1] | 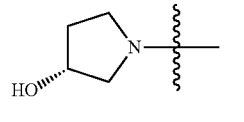 [SMILES: *N1CC[C@@H](O)C1] |
| 91 | CH₃ | 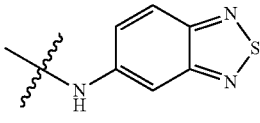 [SMILES: *Nc1ccc2nsnc2c1] | 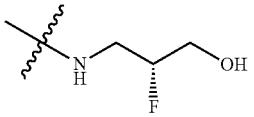 [SMILES: *NC[C@@H](F)CO] |
| 92 | CH₃ | 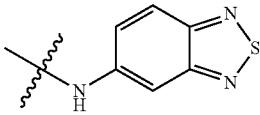 [SMILES: *Nc1ccc2nsnc2c1] | 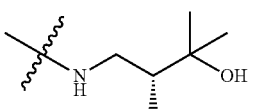 |
| 93 | CH₃ | 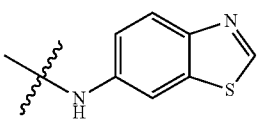 | 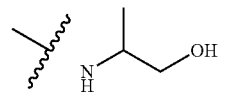 |
| 94 | CH₃ | 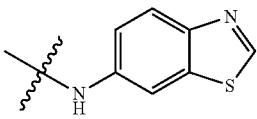 [SMILES: *Nc1ccc2ncsc2c1] | 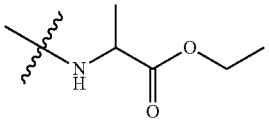 [SMILES: *NC(C)C(=O)OCC] |
| 95 | CH₃ | 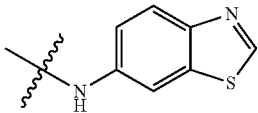 [SMILES: *Nc1ccc2ncsc2c1] | 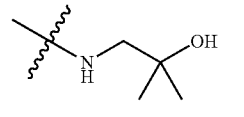 [SMILES: *NCC(C)(C)O] |
| 96 | CH₃ | 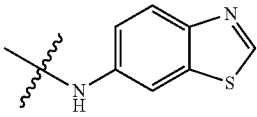 [SMILES: *Nc1ccc2ncsc2c1] | 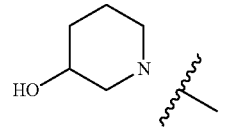 |
| 97 | CH₃ | 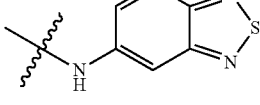 | 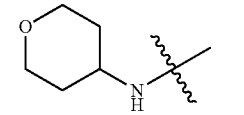 [SMILES: *NC1CCOCC1] |
| 98 | CH₃ | 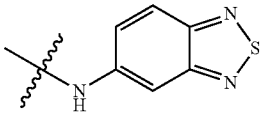 [SMILES: *Nc1ccc2nsnc2c1] | 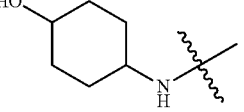 |
| 99 | CH₃ | 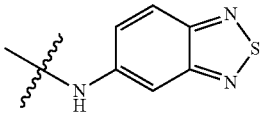 [SMILES: *Nc1ccc2nsnc2c1] | |

TABLE 5-continued

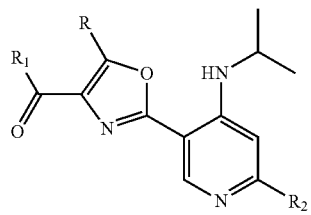

| Compound No. | R | $R_1$ | $R_2$ |
|---|---|---|---|
| 100 | $CH_3$ | -NH-CH₂CH₂-OH | -NH-(benzo[c][1,2,5]thiadiazol-5-yl) |
| 101 | $CH_3$ | -NH-CH₂CH₂CH₂-OH | -NH-(benzothiazol-6-yl) |
| 102 | $CH_3$ | (R)-3-hydroxypyrrolidin-1-yl | -NH-(benzothiazol-6-yl) |
| 103 | i-Pr | -C(CH₃)₂-C(O)NH₂ | -NH-(benzo[c][1,2,5]thiadiazol-5-yl) |
| 104 | i-Pr | -NH-CH₂CH₂CH₂-OH | -NH-(benzo[c][1,2,5]thiadiazol-5-yl) |
| 105 | $CH_3$ | -NH-CH₂CH₂-NH₂ | -NH-(benzothiazol-6-yl) |

Example 91

(R)-(2-(6-(Benzo[c][1,2,5]thiadiazol-5-ylamino)-4-(isopropylamino)pyridin-3-yl)-5-methyloxazol-4-yl)(3-hydroxypyrrolidin-1-yl)methanone $^1$H NMR: 400 MHz, CD$_3$OD: δ 1.37-1.37 (m, 7H), 2.09-2.10 (m, 2H), 2.69 (s, 3H), 3.68-3.70 (m, 3H), 4.05-4.07 (m, 1H), 4.15-4.17 (m, 1H), 4.50-4.51 (m, 1H), 6.29 (s, 1H), 7.68 (dd, J=2.00, 9.40 Hz, 1H), 7.88 (d, J=9.20 Hz, 1H), 8.00-8.02 (m, 1H), 4.49 (bs, 1H), 8.65 (s, 1H). LC/MS: Ascentis Express C18, 5×2.1 mm-2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 3 min; retention time: 1.853 min; LCMS (ES-API), m/z 478.0 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.104 min; Purity: 96.6%.

Example 92

2-(6-(Benzo[c][1,2,5]thiadiazol-5-ylamino)-4-(isopropylamino)pyridin-3-yl)-N-(2-fluoro-3-hydroxypropyl)-5-methyloxazole-4-carboxamide $^1$H NMR: 400 MHz, DMSO-d$_6$: δ 1.36 (d, J=6.40 Hz, 6H), 2.65 (s, 3H), 3.52-3.54 (m, 5H), 4.59-4.60 (m, 1H), 5.05 (t, J=5.60 Hz, 1H), 6.29 (s, 1H), 7.70 (dd, J=2.40, 9.40 Hz, 1H), 7.82 (d, J=7.20 Hz, 1H), 7.95 (d, J=9.20 Hz, 1H), 8.16 (t, J=6.00 Hz, 1H), 8.62 (s, 1H), 8.76 (s, 1H), 9.64 (s, 1H). LC/MS: Ascentis Express C18, 5×2.1 mm-2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 3 min; retention time: 1.920 min; LCMS (ES-API), m/z 486.2 (M+H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.057 min; Purity: 97.7%.

Example 93

2-(6-(Benzo[c][1,2,5]thiadiazol-5-ylamino)-4-(isopropylamino)pyridin-3-yl)-N-(2-fluoro-3-hydroxy-3-methylbutyl)-5-methyloxazole-4-carboxamide $^1$H NMR: 400 MHz, DMSO-$d_6$: δ 1.18 (s, 6H), 1.34 (d, J=6.40 Hz, 6H), 2.64 (s, 3H), 3.68-3.73 (m, 2H), 4.31-4.45 (m, 1H), 4.89 (s, 1H), 6.17 (s, 1H), 7.59 (dd, J=2.00, 9.00 Hz, 1H), 7.75 (d, J=7.60 Hz, 1H), 7.96 (d, J=8.80 Hz, 1H), 8.13 (t, J=5.60 Hz, 1H), 8.53 (s, 1H), 8.66 (d, J=2.00 Hz, 1H), 9.34 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.809 min; LCMS (ES-API), m/z 513.4 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.982 min; Purity: 95.2%.

Example 94

2-(6-(Benzo[d]thiazol-6-ylamino)-4-(isopropylamino)pyridin-3-yl)-N-(1-hydroxypropan-2-yl)-5-methyloxazole-4-carboxamide $^1$H NMR: 400 MHz, DMSO-$d_6$: δ 1.18 (s, 6H), 1.34 (d, J=6.40 Hz, 6H), 2.64 (s, 3H), 3.41-3.46 (m, 1H), 3.68-3.73 (m, 2H), 4.30-4.45 (m, 1H), 4.89 (s, 1H), 6.17 (s, 1H), 7.59 (dd, J=2.00, 8.80 Hz, 1H), 7.75 (d, J=7.20 Hz, 1H), 7.96 (d, J=8.80 Hz, 1H), 8.12 (t, J=5.60 Hz, 1H), 8.32 (s, 1H), 8.53 (s, 1H), 8.66 (d, J=2.00 Hz, 1H), 9.16 (s, 1H), 9.34 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.61 min; LCMS (ES-API), m/z 467.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.892 min; Purity: 92.1%.

Example 95

Ethyl 2-(2-(6-(benzo[d]thiazol-6-ylamino)-4-(isopropylamino)pyridin-3-yl)-5-methyloxazole-4-carboxamido)propanoate $^1$H NMR: 400 MHz, DMSO-$d_6$: δ 1.35-1.36 (m, 6H), 1.43-1.45 (m, 3H), 2.64 (s, 3H), 4.14-4.17 (m, 2H), 4.45-4.49 (m, 1H), 6.18 (s, 1H), 7.60 (dd, J=2.40, 8.80 Hz, 1H), 7.86 (d, J=6.40 Hz, 1H), 7.97 (d, J=8.80 Hz, 1H), 8.26 (d, J=7.60 Hz, 1H), 8.54 (s, 1H), 8.67 (d, J=2.40 Hz, 1H), 9.16 (s, 1H), 9.36 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.943 min; LCMS (ES-API), m/z 509.4 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.044 min; Purity: 93.2%.

Example 96

2-(6-(Benzo[d]thiazol-6-ylamino)-4-(isopropylamino)pyridin-3-yl)-N-(2-hydroxy-2-methylpropyl)-5-methyloxazole-4-carboxamide $^1$H NMR: 400 MHz, DMSO-$d_6$: δ 1.14 (s, 6H), 1.32 (d, J=6.40 Hz, 1H), 2.64 (s, 3H), 2.74 (d, J=4.80 Hz, 1H), 2.81 (d, J=4.80 Hz, 1H), 3.23 (3H, merged with water peak), 3.70-3.73 (m, 1H), 4.69 (s, 1H), 6.17 (s, 1H), 7.57-7.61 (m, 2H), 7.84 (d, J=6.80 Hz, 1H), 7.96 (d, J=8.40 Hz, 1H), 8.27 (s, 1H), 8.54 (s, 1H), 8.67 (d, J=2.40 Hz, 1H), 9.16 (s, 1H), 9.36 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.927 min; LCMS (ES-API), m/z 481.2 (M+H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.568 min; Purity: 92.8%.

Example 97

(2-(6-(Benzo[c][1,2,5]thiadiazol-5-ylamino)-4-(isopropylamino)pyridin-3-yl)-5-methyloxazol-4-yl)(3-hydroxypiperidin-1-yl)methanone $^1$H NMR: 400 MHz, DMSO-$d_6$: δ 1.31-1.32 (m, 6H), 1.46 (bs, 2H), 1.76-1.89 (m, 5H), 2.84 (2H, merged with water peak), 3.55 (bs, 1H), 3.74-3.75 (m, 1H), 4.15-4.18 (m, 2H), 4.81-4.96 (m, 1H), 6.29 (s, 1H), 7.70 (dd, J=2.00, 9.60 Hz, 1H), 7.81 (bs, 1H), 7.95 (d, J=9.60 Hz, 1H), 8.63 (s, 1H), 8.77 (d, J=1.60 Hz, 1H), 9.65 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.916 min; LCMS (ES-API), m/z 494.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.398 min; Purity: 97.4%.

Example 98

2-(6-(Benzo[c][1,2,5]thiadiazol-5-ylamino)-4-(isopropylamino)pyridin-3-yl)-5-methyl-N-(tetrahydro-2H-pyran-4-yl)oxazole-4-carboxamide $^1$H NMR: 400 MHz, DMSO-$d_6$: δ 1.37 (d, J=6.40 Hz, 6H), 1.62-1.68 (m, 2H), 1.79-1.81 (m, 2H), 2.65 (s, 3H), 3.39-3.45 (2H, merged with water peak), 3.72-3.75 (m, 1H), 3.87-3.90 (m, 2H), 3.99-4.00 (m, 1H), 6.28 (s, 1H), 7.70 (dd, J=1.60, 9.40 Hz, 1H), 7.85 (d, J=7.60 Hz, 1H), 7.94-7.97 (m, 2H), 8.62 (s, 1H), 8.77 (d, J=1.60 Hz, 1H), 9.64 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.924 min; LCMS (ES-API), m/z 494.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.082 min; Purity: 96.8%.

Example 99

2-(6-(Benzo[c][1,2,5]thiadiazol-5-ylamino)-4-(isopropylamino)pyridin-3-yl)-N-(4-hydroxycyclohexyl)-5-methyloxazole-4-carboxamide $^1$H NMR: 400 MHz, DMSO-$d_6$: δ 1.24-1.31 (m, 4H), 1.35 (d, J=6.40 Hz, 6H), 1.76-1.88 (m, 4H), 2.64 (s, 3H), 3.69-3.73 (m, 2H), 4.55-4.57 (m, 1H), 6.28 (s, 1H), 7.65-7.72 (m, 2H), 7.93-7.96 (m, 2H), 8.61 (s, 1H), 8.76 (d, J=1.60 Hz, 1H), 9.64 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.938 min; LCMS (ES-API), m/z 508.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.653 min; Purity: 95.5%.

Example 100

2-(6-(Benzo[c][1,2,5]thiadiazol-5-ylamino)-4-(isopropylamino)pyridin-3-yl)-N-(2-hydroxyethyl)-5-methyloxazole-4-carboxamide $^1$H NMR: 400 MHz, DMSO-$d_6$: δ 1.36 (d, J=6.40 Hz, 6H), 2.65 (s, 3H), 3.36 (2H, merged with water peak), 3.52-3.56 (m, 2H), 3.73-3.75 (m, 1H), 4.82 (t, J=5.20 Hz, 1H), 6.29 (s, 1H), 7.70 (dd, J=2.00, 9.60 Hz, 1H), 7.83-7.90 (m, 2H), 7.95 (d, J=9.20 Hz, 1H), 8.32 (s, 1H), 8.62 (s, 1H), 8.76 (d, J=2.00 Hz, 1H), 9.64 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.868 min; LCMS (ES-API), m/z 454.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.748 min; Purity: 98.4%.

Example 101

2-(6-(Benzo[d]thiazol-6-ylamino)-4-(isopropylamino)pyridin-3-yl)-N-(3-hydroxypropyl)-5-methyloxazole-4-carboxamide $^1$H NMR: 400 MHz, DMSO-$d_6$: δ 1.34 (d, J=6.40 Hz, 6H), 1.68-1.71 (m, 2H), 2.64 (s, 3H), 3.32-3.39 (m, 2H), 3.52-3.55 (m, 2H), 3.70-3.73 (m, 1H), 4.59-4.62 (m, 1H), 6.17 (s, 1H), 7.60 (dd, J=2.00, 8.80 Hz, 1H), 7.75 (d, J=6.80 Hz, 1H), 7.96 (d, J=8.80 Hz, 1H), 8.05 (s, 1H), 8.53 (s, 1H), 8.67 (d, J=2.00 Hz, 1H), 9.16 (s, 1H), 9.34 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.772 min; LCMS (ES-API), m/z 467.2 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.342 min; Purity: 91.4%.

Example 102

(R)-(2-(6-(Benzo[d]thiazol-6-ylamino)-4-(isopropylamino)pyridin-3-yl)-5-methyloxazol-4-yl)(3-hydroxypyrrolidin-1-yl)methanone $^1$H NMR: 400 MHz, DMSO-$d_6$: δ 1.24-1.31 (m, 6H), 1.81-1.95 (m, 2H), 2.62 (s, 3H), 3.41-4.10 (m, 6H), 4.32-4.35 (m, 1H), 7.59 (dd, J=2.00, 8.80 Hz, 1H), 7.85 (dd, J=7.20, 15.20 Hz, 1H), 7.96 (d, J=9.20 Hz, 1H), 8.32 (s, 1H), 8.54 (s, 1H), 8.67 (d, J=2.00 Hz, 1H), 9.16 (s, 1H), 9.35 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.728 min; LCMS (ES-API), m/z 479.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.704 min; Purity: 98.1%.

Example 103

2-(6-(Benzo[c][1,2,5]thiadiazol-5-ylamino)-4-(isopropylamino)pyridin-3-yl)-5-isopropyloxazole-4-carboxamide $^1$H NMR: 400 MHz, DMSO-$d_6$: δ 1.30-1.36 (m, 12H), 3.72-3.77 (m, 1H), 3.82-3.89 (m, 1H), 6.28 (s, 1H), 7.52 (bs, 1H), 7.62 (bs, 1H), 7.71 (dd, J=2.00, 9.60 Hz, 1H), 7.78 (d, J=7.20 Hz, 1H), 7.96 (d, J=9.60 Hz, 1H), 8.68 (s, 1H), 8.80 (d, J=1.60 Hz, 1H), 9.63 (s, 1H). LC/MS: Ascentis Express C18, 5×2.1 mm-2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 3 min; retention time: 2.051 min; LCMS (ES-API), m/z 436.2 (M−H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.876 min; Purity: 96.5%.

Example 104

2-(6-(Benzo[c][1,2,5]thiadiazol-5-ylamino)-4-(isopropylamino)pyridin-3-yl)-N-(3-hydroxypropyl)-5-isopropyloxazole-4-carboxamide $^1$H NMR: 400 MHz, DMSO-$d_6$: δ 1.30-1.36 (m, 12H), 1.67-1.73 (m, 2H), 3.31-3.41 (m, 3H), 3.51-3.55 (m, 2H), 3.71-3.76 (m, 1H), 3.81-3.88 (m, 1H), 4.59-4.62 (m, 1H), 6.28 (s, 1H), 7.70 (dd, J=2.40, 9.40 Hz, 1H), 7.78 (d, J=7.20 Hz, 1H), 7.95 (d, J=9.20 Hz, 1H), 8.07 (t, J=5.60 Hz, 1H), 8.32 (s, 1H), 8.68 (s, 1H), 8.79 (d, J=2.00 Hz, 1H), 9.64 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.938 min; LCMS (ES-API), m/z 496.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.134 min; Purity: 98.3%.

Example 105

Synthesis of N-(2-aminoethyl)-2-(6-(benzo[d]thiazol-6-ylamino)-4-(isopropylamino)pyridin-3-yl)-5-methyloxazole-4-carboxamide Step A: tert-butyl (2-(2-(6-(benzo[d]thiazol-6-ylamino)-4-(isopropylamino)pyridin-3-yl)-5-methyloxazole-4-carboxamido)ethyl)carbamate was prepared by following the same procedure as mentioned in the synthesis of compound no. 3, using tert-butyl (2-(2-(6-chloro-4-(isopropylamino)pyridin-3-yl)-5-methyloxazole-4-carboxamido)ethyl)carbamate as the starting material.

Step B: A solution of tert-butyl (2-(2-(6-(benzo[d]thiazol-6-ylamino)-4-(isopropylamino)pyridin-3-yl)-5-methyloxazole-4-carboxamido)ethyl)carbamate in DCM (5 mL) was treated with ether.HCl (5 mL) at 0° C. The reaction mixture was stirred at 0° C. for 30 min. The reaction temperature was raised to room temperature and stirred for 30 min. The reaction mixture was concentrated to dryness. The material obtained was purified by prep. HPLC to afford N-(2-aminoethyl)-2-(6-(benzo[d]thiazol-6-ylamino)-4-(isopropylamino)pyridin-3-yl)-5-methyloxazole-4-carboxamide $^1$H NMR: 400 MHz, DMSO-$d_6$: δ 1.35 (d, J=6.40 Hz, 6H), 2.64 (s, 3H), 2.70-2.80 (m, 2H), 3.70-3.74 (m, 1H), 6.17 (s, 1H), 7.60 (dd, J=2.00, 9.00 Hz, 1H), 7.79 (d, J=7.20 Hz, 1H), 7.96 (d, J=8.80 Hz, 1H), 8.02 (bs, 1H), 8.53 (s, 1H), 8.67 (d, J=2.00 Hz, 1H), 9.16 (s, 1H), 9.35 (s, 1H). LC/MS: Ascentis Express C18, 5×2.1 mm, 2.7 μm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min; retention time: 1.646 min; LCMS (ES-API), m/z 452.2 (M+H). HPLC: Sunfire C18 (150×4.6 mm), 3.5 micron; Solvent A=5% ACN: 95% $H_2O$: 0.05% TFA pH=2.5; Solvent B=95% ACN: 5% $H_2O$: 0.05% TFA pH=2.5; gradient 0-100% B over 30 min (36 min run time); Flow rate: 1.0 μL/min; Retention time: 8.956 min; Purity: 91.1%.

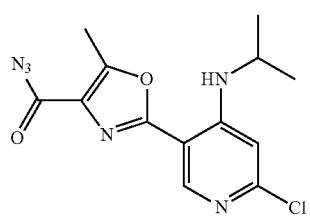 [SMILES: Cc1oc(-c2cnc(Cl)cc2NC(C)C)nc1C(=O)N=[N+]=[N-]]

Synthesis of 2-(6-chloro-4-(isopropylamino)pyridin-3-yl)-5-methyloxazole-4-carbonyl azide (33): 2-(6-chloro-4-(isopropylamino)pyridin-3-yl)-5-methyloxazole-4-carboxylic acid (30a) (750 mg, 2.54 mmol) and thionyl chloride (12.68 mmol) were refluxed at 100° C. for 20 h. Thionyl chloride was removed under reduced pressure. The resulting solid acid chloride was dissolved in acetone (15 mL) and cooled to 0° C. Sodium azide (7.61 mmol) dissolved in water (3 mL) was added to the reaction mixture at 0° C. and stirred for 30 min. The reaction temperature was raised to room temperature and stirred for 5 h. The reaction mixture was concentrated to remove the solvent. The compound precipitated in the aqueous layer was filtered and dried under vacuum to obtain the desired compound 2-(6-chloro-4-(isopropylamino)pyridin-3-yl)-5-methyloxazole-4-carbonyl azide. LC/MS: ZORBAX SB C18, 4.6×50 mm, 5 μm; Solvent A=10% MeOH: 90% $H_2O$: 0.1% TFA; Solvent B=90% MeOH: 10% $H_2O$: 0.1% TFA; gradient 0-100% B over 2 min (3 min run time); retention time: 2.363 min.

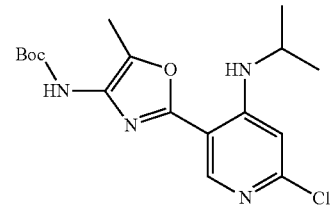 [SMILES: Cc1oc(-c2cnc(Cl)cc2NC(C)C)nc1NC(=O)OC(C)(C)C]

Synthesis of tert-butyl 2-(6-chloro-4-(isopropylamino)pyridin-3-yl)-5-methyloxazol-4-ylcarbamate (34): A solution of 2-(6-chloro-4-(isopropylamino)pyridin-3-yl)-5-methyloxazole-4-carbonyl azide (33) (500 mg, 1.559 mmol) in chloroform (15 mL) was refluxed for 10 h. t-Butanol (0.5 mL, 4.68 mmol) was added and once again refluxed for 10 h. The reaction mixture was concentrated and purified by flash column chromatography using silica gel and EtOAC:pet ether as eluting agents to afford tert-butyl 2-(6-chloro-4-(isopropylamino)pyridin-3-yl)-5-methyloxazol-4-ylcarbamate. LC/MS: Ascentis Express C18, 5×2.1 mm, 2.7 μm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min; retention time: 2.086 min; LCMS (ES-API), m/z 367.2 (M+H).

Example 106

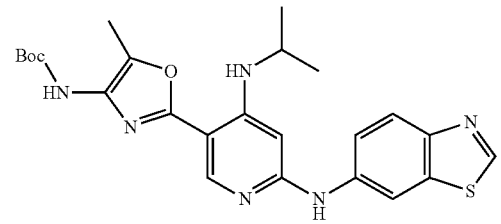 [SMILES: Cc1oc(-c2cnc(Nc3ccc4ncsc4c3)cc2NC(C)C)nc1NC(=O)OC(C)(C)C]

Synthesis of tert-butyl 2-(6-(benzo[d]thiazol-6-ylamino)-4-(isopropylamino)pyridin-3-yl)-5-methyloxazol-4-ylcarbamate: Followed the same procedure as mentioned in the synthesis of compound no. 3 using respective starting materials. $^1$H NMR: 400 MHz, DMSO-$d_6$: δ 1.28 (d, J=6.40 Hz, 6H), 1.46 (s, 9H), 2.28 (s, 3H), 3.67-3.72 (m, 1H), 6.14 (s, 1H), 7.58 (dd, J=2.00, 8.80 Hz, 1H), 7.91-7.96 (m, 2H), 8.47 (s, 1H), 8.67 (d, J=2.00 Hz, 1H), 8.88 (bs, 1H), 9.15 (s, 1H), 9.29 (s, 1H). LC/MS: Ascentis Express C18, 5×2.1 mm, 2.7 μm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min; retention time: 2.101 min; LCMS (ES-API), m/z 481.2 (M+H). HPLC: Sunfire C18 (150×4.6 mm), 3.5 micron; Solvent A=5% ACN: 95% $H_2O$: 0.05% TFA pH=2.5; Solvent B=95% ACN: 5% $H_2O$: 0.05% TFA pH=2.5; gradient 0-100% B over 15 min (23 min run time); Flow rate: 1.0 μL/min; Retention time: 7.712 min; Purity: 96.5%.

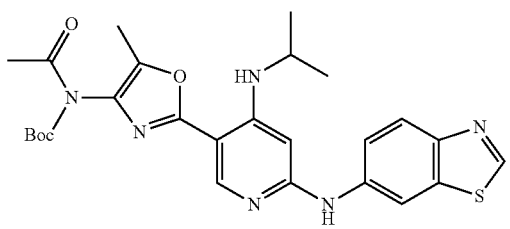 [SMILES: CC(=O)N(C(=O)OC(C)(C)C)c1nc(-c2cnc(Nc3ccc4ncsc4c3)cc2NC(C)C)oc1C]

Synthesis of tert-butyl acetyl(2-(6-(benzo[d]thiazol-6-ylamino)-4-(isopropylamino)pyridin-3-yl)-5-methyloxazol-4-yl)carbamate (35): A solution of tert-butyl 2-(6-(benzo[d]thiazol-6-ylamino)-4-(isopropylamino)pyridin-3-yl)-5-methyloxazol-4-ylcarbamate (Example 106) (20 mg, 0.042 mmol) in Tetrahydrofuran (5 mL) was cooled to 0° C. and treated with NaH (0.042 mmol). Stirred the reaction mixture at 0° C. for 10 min. Added Ac$_2$O (0.042 mmol) to the reaction mixture and stirred at 0° C. for 0.5 h. The reaction mixture was quenched with ice pieces and extracted with ethyl acetate. The organic layer was separated, dried over Na$_2$SO$_4$, filtered and concentrated to afford tert-butyl acetyl(2-(6-(benzo[d]thiazol-6-ylamino)-4-(isopropylamino)pyridin-3-yl)-5-methyloxazol-4-yl)carbamate. LC/MS: Acquity BEH C18 2.1×50 mm, 1.8 micron; Solvent A=0.1% TFA in water; Solvent B=0.1% TFA in ACN; gradient 0-100% B over 2 min; retention time: 0.90 min; LCMS (ES-API), m/z 523.6 (M+H).

Example 107

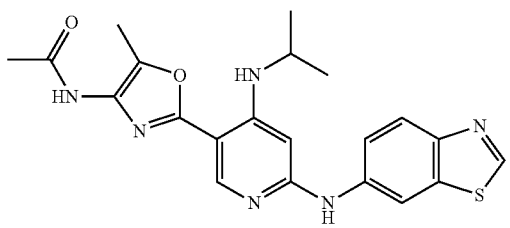 [SMILES: CC(=O)Nc1nc(-c2cnc(Nc3ccc4ncsc4c3)cc2NC(C)C)oc1C]

Synthesis of N-(2-(6-(benzo[d]thiazol-6-ylamino)-4-(isopropylamino)pyridin-3-yl)-5-methyloxazol-4-yl)acetamide: A solution of tert-butyl acetyl(2-(6-(benzo[d]thiazol-6-ylamino)-4-(isopropylamino)pyridin-3-yl)-5-methyloxazol-4-yl)carbamate (35) (30 mg, 0.057 mmol) in DCM (5 mL) was treated with TFA (0.230 mmol) and stirred at room temperature for 3 h. The reaction mixture was concentrated and azeotroped with chloroform three times to obtain gummy solid. The crude material obtained was purified by prep HPLC to furnish N-(2-(6-(benzo[d]thiazol-6-ylamino)-4-(isopropylamino)pyridin-3-yl)-5-methyloxazol-4-yl)acetamide. $^1$H NMR: 400 MHz, CD$_3$OD: δ 1.33 (d, J=6.40 Hz, 6H), 2.16 (s, 3H), 2.35 (s, 3H), 3.73-3.79 (m, 1H), 6.14 (s, 1H), 7.52 (dd, J=2.40, 8.80 Hz, 1H), 7.97 (d, J=8.80 Hz, 1H), 8.38 (d, J=2.00 Hz, 1H), 8.49 (s, 1H), 9.07 (s, 1H). LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.823 min; LCMS (ES-API), m/z 423.2 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 6.484 min; Purity: 95.1%.

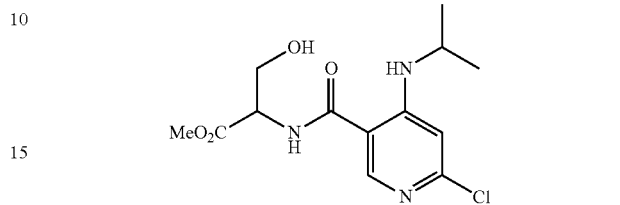

Synthesis of methyl 2-(6-chloro-4-(isopropylamino)nicotinamido)-3-hydroxypropanoate (36): To a stirred solution of 6-chloro-4-(isopropylamino)nicotinic acid (9) (1.3 g, 6.06 mmol) in DMF (25 mL), methyl 2-amino-3-hydroxypropanoate (12.11 mmol) and DIPEA (18.17 mmol) were added followed by the addition of HATU (30.3 mmol) to the reaction mixture and stirred at room temperature for 2 h. DMF was removed under reduced pressure. The residue obtained was diluted with EtOAC and washed with water and 10% NaHCO$_3$ solution. The organic layer was collected, dried over Na$_2$SO$_4$, filtered and concentrated. The crude material obtained was purified by flash chromatography using silica gel and EtOAC:pet ether as eluent to afford the title compound, methyl 2-(6-chloro-4-(isopropylamino)nicotinamido)-3-hydroxypropanoate. LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.312 min; LCMS (ES-API), m/z 316.0 (M+H).

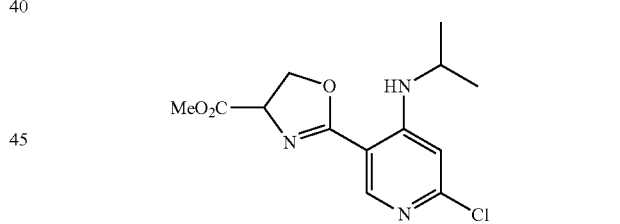

Synthesis of methyl 2-(6-chloro-4-(isopropylamino)pyridin-3-yl)-4,5-dihydrooxazole-4-carboxylate (37): To a stirred solution of methyl 2-(6-chloro-4-(isopropylamino)nicotinamido)-3-hydroxypropanoate (36) (100 mg, 0.317 mmol) in DCM (15 mL), DAST (0.317 mmol) was added at −78° C. and stirred for 4 h. K$_2$CO$_3$ (0.633 mmol) was added to the reaction mixture and stirred for 3 h. The reaction mixture was diluted with DCM and washed with water (twice) followed by brine solution. The organic layer was collected, dried over Na$_2$SO$_4$, filtered and concentrated. The crude material obtained was purified by flash chromatography using silica gel and EtOAC:pet ether as eluent to afford the title compound, methyl 2-(6-chloro-4-(isopropylamino)pyridin-3-yl)-4,5-dihydrooxazole-4-carboxylate. $^1$H NMR: 400 MHz, DMSO-d$_6$: δ 1.20-1.21 (m, 6H), 3.73 (s, 3H), 3.84-3.89 (m, 1H), 4.51-4.59 (m, 2H), 5.07-5.12 (m, 1H), 6.83 (s, 1H), 8.36 (s, 1H), 8.80 (d, J=7.60 Hz, 1H).

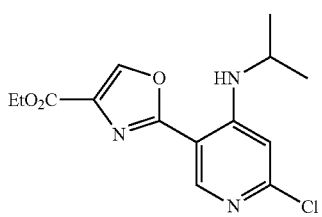

Synthesis of ethyl 2-(6-chloro-4-(isopropylamino)pyridin-3-yl)oxazole-4-carboxylate (38): To a stirred solution of methyl 2-(6-chloro-4-(isopropylamino)pyridin-3-yl)-4,5-dihydrooxazole-4-carboxylate (37) (100 mg, 0.336 mmol) in DCM (20 mL), DBU (1.008 mmol) and bromotrichloromethane (0.403 mmol) were added at 0° C. and stirred the reaction mixture for 2 h at 0° C. Reaction temperature was raised to room temperature and stirred the reaction for 10 min. The reaction mixture was diluted with DCM and washed with water, 10% NaHCO$_3$ solution and brine solution. The organic layer was collected, dried over Na$_2$SO$_4$, filtered and concentrated. The crude material obtained was purified by flash chromatography using silica gel and EtOAC:pet ether as eluent to afford the title compound, ethyl 2-(6-chloro-4-(isopropylamino)pyridin-3-yl)oxazole-4-carboxylate (38). $^1$H NMR: 400 MHz, DMSO-d$_6$: δ 1.24-1.27 (m, 6H), 3.87 (s, 3H), 3.92-3.97 (m, 1H), 6.92 (s, 1H), 8.36 (d, J=7.60 Hz, 1H), 8.60 (s, 1H), 9.00 (s, 1H).

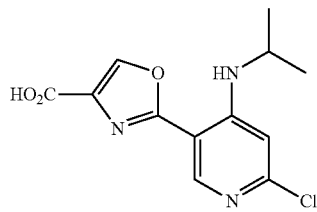 [SMILES: CC(C)Nc1cc(Cl)ncc1-c1nc(C(=O)O)co1]

Synthesis of 2-(6-chloro-4-(isopropylamino)pyridin-3-yl)oxazole-4-carboxylic acid (39): Followed the same procedure as mentioned in the synthesis of compound no. 9. LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.473 min; LCMS (ES-API), m/z 282.2 (M+H).

[2-(6-Chloro-4-(isopropylamino)pyridin-3-yl)-N-(3-(piperidin-1-yl)propyl)oxazole-4-carboxamide (40b)]: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.622 min; LCMS (ES-API), m/z 406.2 (M+H).

Synthesis of Examples 108-110: Followed the same procedure as mentioned for compound no. 13, using appropriate amines and their respective starting materials.

TABLE 6

![structure with R group]

| Example No. | R |
|---|---|
| 108 | NH$_2$ |
| 109 | ⸺NH⸺CH$_2$CH$_2$CH$_2$⸺N(piperidine) |
| 110 | ⸺NH⸺CH$_2$CH$_2$CH$_2$⸺N(pyrrolidine) |

Example 108

2-(6-(Benzo[d]thiazol-6-ylamino)-4-(isopropylamino)pyridin-3-yl)oxazole-4-carboxamide $^1$H NMR: 400 MHz, DMSO-d$_6$: δ 1.34 (d, J=6.40 Hz, 6H), 3.70-3.74 (m, 1H), 6.17 (s, 1H), 7.60 (dd, J=2.00, 8.80 Hz, 1H), 7.75 (bs, 1H), 7.83 (d, J=7.20 Hz, 1H), 7.96 (d, J=8.80 Hz, 1H), 8.56-8.56 (m, 2H), 8.67 (d, J=2.00 Hz, 1H), 9.16 (s, 1H), 9.35 (s, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.43 min; LCMS (ES-API), m/z 395.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 5.34 min; Purity: 96.8%.

Example 109

2-(6-(Benzo[d]thiazol-6-ylamino)-4-(isopropylamino)pyridin-3-yl)-N-(3-(piperidin-1-yl)propyl)oxazole-4-carboxamide $^1$H NMR: 400 MHz, DMSO-d$_6$: δ 1.31-1.40 (m, 6H), 1.61-1.72 (m, 3H), 1.81-1.85 (m, 2H), 1.92-1.97 (m, 2H), 2.84-2.92 (m, 2H), 3.07-3.12 (m, 2H), 3.34-3.49 (4H, merged with water peak), 3.71-3.78 (m, 1H), 6.20 (s, 1H), 7.59 (dd, J=2.00, 8.80 Hz, 1H), 8.01-8.03 (m, 1H), 8.45-8.56 (m, 2H), 8.66 (s, 1H), 8.97 (bs, 1H), 9.23 (s, 1H), 9.58 (bs, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.322 min; LCMS (ES-API), m/z 520.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 µL/min; Retention time: 9.410 min; Purity: 97.6%.

Example 110

2-(6-(Benzo[d]thiazol-6-ylamino)-4-(isopropylamino)pyridin-3-yl)-N-(3-(pyrrolidin-1-yl)propyl)oxazole-4-carboxamide $^1$H NMR: 400 MHz, DMSO-$d_6$: δ 1.35 (d, J=6.40 Hz, 6H), 1.68-1.76 (m, 6H), 1.85-1.89 (m, 4H), 2.42-2.47 (m, 6H), 3.69-3.74 (m, 1H), 6.17 (s, 1H), 7.60 (dd, J=2.00, 8.80 Hz, 1H), 7.84 (d, J=7.20 Hz, 1H), 7.96 (d, J=8.80 Hz, 1H), 8.22 (t, J=6.00 Hz, 1H), 8.56 (d, J=0.80 Hz, 1H), 8.67 (d, J=2.00 Hz, 1H), 9.16 (s, 1H), 9.37 (s, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.307 min; LCMS (ES-API), m/z 506.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 µL/min; Retention time: 9.117 min; Purity: 92.3%.

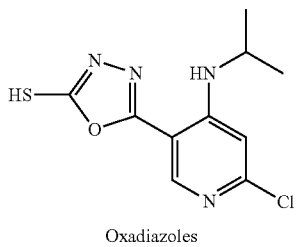 [SMILES: CC(C)Nc1cc(Cl)ncc1-c1nnc(S)o1]

Oxadiazoles

Synthesis of 5-(6-chloro-4-(isopropylamino)pyridin-3-yl)-1,3,4-oxadiazole-2-thiol (42): 6-chloro-4-(isopropylamino)nicotinohydrazide (10) (1.5 g, 8.7 mmol) was taken in EtOH (10 mL):H$_2$O (5 mL). Added KOH (13 mmol, 1.5 equiv.) followed by the addition of CS$_2$ (87 mmol, 10 equiv.) to the reaction mixture and heated at 90° C., overnight. The reaction mass was concentrated under reduced pressure to remove solvents from the reaction mixture. The crude material obtained was taken to next step as such without purification. LC/MS: Purospher@star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.27 min; LCMS (ES-API), m/z 269.0 (M–H).

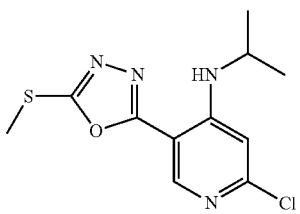 [SMILES: CSc1nnc(-c2cnc(Cl)cc2NC(C)C)o1]

Synthesis of 2-chloro-N-isopropyl-5-(5-(methylthio)-1,3,4-oxadiazol-2-yl)pyridin-4-amine (43): Methyl iodide (22 mmol, 2 equiv.) was added to a solution of 5-(6-chloro-4-(isopropylamino)pyridin-3-yl)-1,3,4-oxadiazole-2-thiol (42) (1.5 g, 5.5 mmol) in MeOH (10 mL). The reaction mixture was stirred overnight at room temperature. The reaction mass was concentrated under reduced pressure. The crude material obtained was purified by column chromatography through silica gel and MeOH:DCM as eluent to furnish the desired compound, 2-chloro-N-isopropyl-5-(5-(methylthio)-1,3,4-oxadiazol-2-yl)pyridin-4-amine (43). LC/MS: Purospher@star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.994 min; LCMS (ES-API), m/z 285.1 (M+H).

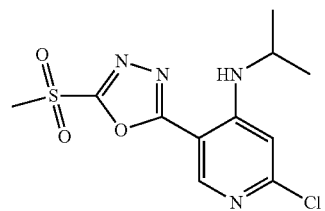 [SMILES: CC(C)Nc1cc(Cl)ncc1-c1nnc(S(C)(=O)=O)o1]

Synthesis of 2-chloro-N-isopropyl-5-(5-(methylsulfonyl)-1,3,4-oxadiazol-2-yl)pyridin-4-amine (44): m-CPBA (4 mmol, 3 equiv.) was added to a stirred solution of 2-chloro-N-isopropyl-5-(5-(methylthio)-1,3,4-oxadiazol-2-yl)pyridin-4-amine (43) (500 mg, 1.4 mmol) in DCM (5 mL). The reaction mixture was stirred overnight at room temperature. The reaction mass was diluted using DCM. The DCM layer was washed with saturated solution of NaHCO$_3$. Collected the DCM layer, dried over Na$_2$SO$_4$, filtered and concentrated. The crude material contained sulfone as well as sulfoxide compounds. The two compounds were separated by column chromatography through silica gel and MeOH:DCM as eluent. LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.805 min; LCMS (ES-API), m/z 316.8 (M+H).

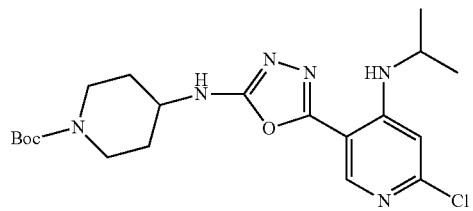 [SMILES: CC(C)Nc1cc(Cl)ncc1-c1nnc(NC2CCN(C(=O)OC(C)(C)C)CC2)o1]

Synthesis of tert-butyl 445-(6-chloro-4-(isopropylamino)pyridin-3-yl)-1,3,4-oxadiazol-2-yl)amino)piperidine-1-carboxylate (45): tert-butyl 4-aminopiperidine-1-carboxylate (8 mmol, 5 equiv.) was added to a stirred solution of 2-chloro-N-isopropyl-5-(5-(methylsulfonyl)-1,3,4-oxadiazol-2-yl)pyridin-4-amine (44) (500 mg, 1.7 mmol) in Dioxan (5 mL) and heated at 90° C. for 4 h. The reaction mass was concentrated under reduced pressure. The crude material obtained was purified by column chromatography through silica gel and MeOH:DCM as eluent to afford the desired compound, tert-butyl 4-((5-(6-chloro-4-(isopropylamino)pyridin-3-yl)-1,3,4-oxadiazol-2-yl)amino)piperidine-1-carboxylate. LC/MS: Purospher@star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 2.049 min; LCMS (ES-API), m/z 437.2 (M+H).

Example 111

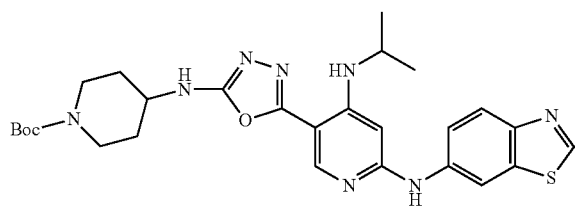 [SMILES: CC(C)Nc1cc(Nc2ccc3ncsc3c2)ncc1-c1nnc(NC2CCN(C(=O)OC(C)(C)C)CC2)o1]

Synthesis of tert-butyl 445-(6-(benzo[d]thiazol-6-ylamino)-4-(isopropylamino)pyridin-3-yl)-1,3,4-oxadiazol-2-yl)amino)piperidine-1-carboxylate: To a solution of tert-butyl 4-((5-(6-chloro-4-(isopropylamino)pyridin-3-yl)-1,3,4-oxadiazol-2-yl)amino)piperidine-1-carboxylate (45) (400 mg, 0.9 mmol) in dioxane (10 mL):H$_2$O (2 mL), 6-amino benzothiazole (1.3 mmol, 1.5 equiv.), xanthphos (0.4 mmol, 0.5 equiv.) and Na$_2$CO$_3$ (2.7 mmol, 3 equiv.) were added and degassed for 10 min. To the reaction mixture Pd$_2$(dba)$_3$ (0.4 mmol, 0.5 equiv.) was added and degassed again for 10 min. It was then heated at 110° C. for overnight. The reaction mass was cooled and filtered through small pad of celite. The filtrate obtained was concentrated to provide crude material. The crude material was purified by column chromatography through silica gel and MeOH:DCM as eluent. The material obtained was further purified by prep. HPLC to afford tert-butyl 4-((5-(6-(benzo[d]thiazol-6-ylamino)-4-(isopropylamino)pyridin-3-yl)-1,3,4-oxadiazol-2-yl)amino)piperidine-1-carboxylate. $^1$H NMR: 400 MHz, CD$_3$OD: δ 1.34 (d, J=6.00 Hz, 6H), 1.48 (s, 9H), 1.58-1.60 (m, 2H), 1.96-2.06 (m, 4H), 3.29-3.34 (2H, merged with the water peak), 3.61-3.64 (m, 1H), 3.78-3.82 (m, 1H), 4.00-4.04 (m, 2H), 6.16 (s, 1H), 7.53-7.58 (m, 2H), 7.97 (d, J=8.80 Hz, 1H), 8.37 (s, 1H), 8.43 (d, J=2.00 Hz, 1H), 9.08 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 2.028 min; LCMS (ES-API), m/z 551.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.276 min; Purity: 98.8%.

Synthesis of Examples 112-130: Prepared according to the general procedure outlined for Example 111, using their respective starting materials and appropriate amine.

TABLE 7

| Compound No. | R | R$_1$ |
|---|---|---|
| 111 | Boc-N-piperidine-NH | benzo[d]thiazol-6-ylamino |
| 112 | HO-propyl-NH | benzo[c][1,2,5]thiadiazol-5-ylamino |
| 113 | pyrrolidine-CH$_2$OH | benzo[d]thiazol-6-ylamino |
| 114 | 3-hydroxypyrrolidine | benzo[d]thiazol-6-ylamino |
| 115 | HO-CH$_2$-CHF-CH$_2$-NH | 4-cyanophenylamino |

TABLE 7-continued
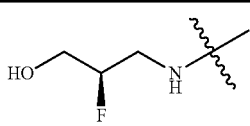
| Compound No. | R | R₁ |
|---|---|---|
| 116 | 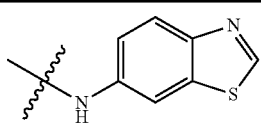 | 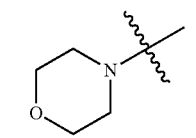 [SMILES: *N1CCOCC1] |
| 117 | 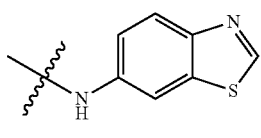 [SMILES: *Nc1ccc2ncsc2c1] | 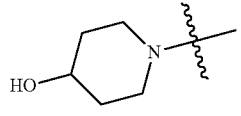 |
| 118 | 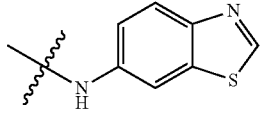 [SMILES: *Nc1ccc2ncsc2c1] | 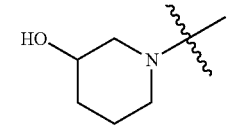 |
| 119 | 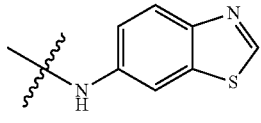 [SMILES: *Nc1ccc2ncsc2c1] | 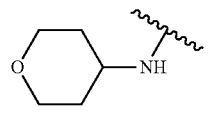 [SMILES: *NC1CCOCC1] |
| 120 | 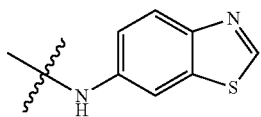 [SMILES: *Nc1ccc2ncsc2c1] | 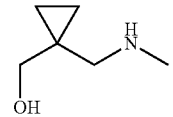 |
| 121 | 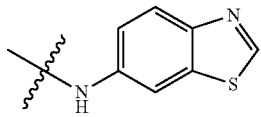 [SMILES: *Nc1ccc2ncsc2c1] | 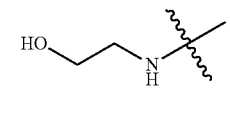 |
| 122 | 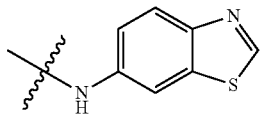 [SMILES: *Nc1ccc2ncsc2c1] | 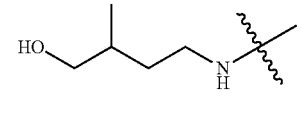 [SMILES: *NCCC(C)CO] |
| 123 | 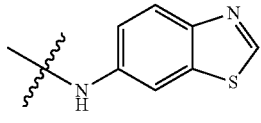 [SMILES: *Nc1ccc2ncsc2c1] | 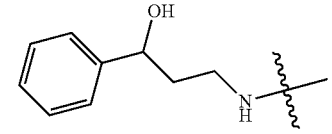 [SMILES: *NCCC(O)c1ccccc1] |
| 124 | 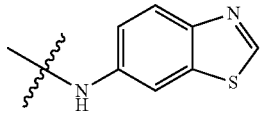 [SMILES: *Nc1ccc2ncsc2c1] | |

TABLE 7-continued

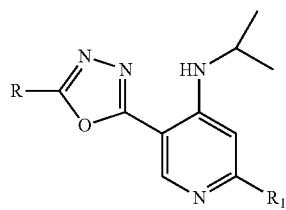

| Compound No. | R | R₁ |
|---|---|---|
| 125 | HO-cyclopentyl-CH₂CH₂-NH- | benzothiazol-6-yl-NH- |
| 126 | HO-CH(CH₃)-CH₂CH₂-NH- | benzothiazol-6-yl-NH- |
| 127 | HO-CH₂-cyclopentyl-CH₂-NH- | benzothiazol-6-yl-NH- |
| 128 | azetidin-3-yl-NH- | benzothiazol-6-yl-NH- |
| 129 | HO-CH₂CH₂-piperazin-1-yl- | benzothiazol-6-yl-NH- |
| 130 | morpholino-CH₂CH₂-piperazin-1-yl- | benzothiazol-6-yl-NH- |

Example 112

3-((5-(6-(Benzo[c][1,2,5]thiadiazol-5-ylamino)-4-(isopropylamino)pyridin-3-yl)-1,3,4-oxadiazol-2-yl)amino)propan-1-ol $^1$H NMR: 400 MHz, DMSO-$d_6$: δ 1.30 (d, J=6.40 Hz, 6H), 1.73-1.76 (m, 2H), 3.31 (1H, merged with water peak), 3.49-3.52 (m, 2H), 3.73-3.75 (m, 1H), 4.46-4.53 (m, 1H), 6.29 (s, 1H), 7.59 (d, J=7.20 Hz, 1H), 7.70 (dd, J=2.00, 9.40 Hz, 1H), 7.78 (bs, 1H), 7.95 (d, J=9.20 Hz, 1H), 8.32 (s, 1H), 8.38 (s, 1H), 8.77 (d, J=1.60 Hz, 1H), 9.64 (s, 1H). LC/MS: Purospher@star RP-18, 4×55 mm, 3 µm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.601 min; LCMS (ES-API), m/z 427.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 5.991 min; Purity: 93.1%.

Example 113

(1-(5-(6-(Benzo[d]thiazol-6-ylamino)-4-(isopropylamino)pyridin-3-yl)-1,3,4-oxadiazol-2-yl)pyrrolidin-2-yl)methanol $^1$H NMR: 400 MHz, CD₃OD: δ 1.34 (d, J=6.40 Hz, 6H), 1.96-2.20 (m, 5H), 3.59-3.83 (m, 5H), 4.05-4.08 (m, 1H), 6.17 (s, 1H), 7.54 (dd, J=2.00, 8.80 Hz, 1H), 7.97 (d, J=8.80 Hz, 1H), 8.38 (s, 1H), 8.43 (d, J=2.00 Hz, 1H), 9.08 (s, 1H). LC/MS: Purospher@star RP-18, 4×55 mm, 3 µm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.628 min; LCMS (ES-API), m/z 452.2 (M+H). HPLC: XBridge Phenyl (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 6.722 min; Purity: 98.4%.

Example 114

1-(5-(6-(Benzo[d]thiazol-6-ylamino)-4-(isopropylamino)pyridin-3-yl)-1,3,4-oxadiazol-2-yl)pyrrolidin-3-ol $^1$H NMR: 400 MHz, CD$_3$OD: δ 1.34 (d, J=6.40 Hz, 6H), 2.12-2.26 (m, 2H), 3.55-3.58 (m, 1H), 3.71-3.81 (m, 5H), 4.59 (bs, 1H), 6.17 (s, 1H), 7.54 (dd, J=2.40, 8.80 Hz, 1H), 7.98 (d, J=8.80 Hz, 1H), 8.37 (s, 1H), 8.42 (d, J=2.40 Hz, 1H), 9.08 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.499 min; LCMS (ES-API), m/z 436.2 (M−H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.216 min; Purity: 98.1%.

Example 115

(R)-4-((5-(5-((2-Fluoro-3-hydroxypropyl)amino)-1,3,4-oxadiazol-2-yl)-4-(isopropylamino)pyridin-2-yl)amino)benzonitrile $^1$H NMR: 400 MHz, CD$_3$OD: δ 1.35 (d, J=6.40 Hz, 6H), 3.60-3.86 (m, 5H), 4.70-4.80 (m, 1H), 6.20 (s, 1H), 7.60 (d, J=11.20 Hz, 2H), 7.74 (d, J=8.80 Hz, 2H), 8.38 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.582 min; LCMS (ES-API), m/z 410.2 (M−H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.648 min; Purity: 96.6%.

Example 116

(R)-3-((5-(6-(Benzo[d]thiazol-6-ylamino)-4-(isopropylamino)pyridin-3-yl)-1,3,4-oxadiazol-2-yl)amino)-2-fluoropropan-1-ol $^1$H NMR: 400 MHz, CD$_3$OD: δ 1.31-1.35 (m, 6H), 3.60-3.84 (m, 5H), 4.68-4.70 (m, 1H), 6.17 (s, 1H), 7.52-7.59 (m, 2H), 7.97 (d, J=8.80 Hz, 1H), 8.35 (s, 1H), 8.42 (d, J=2.00 Hz, 1H), 9.08 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.482 min; LCMS (ES-API), m/z 442.2 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.274 min; Purity: 96.8%.

Example 117

N2-(Benzo[d]thiazol-6-yl)-N4-isopropyl-5-(5-morpholino-1,3,4-oxadiazol-2-yl)pyridine-2,4-diamine $^1$H NMR: 400 MHz, CD$_3$OD: δ 1.31-1.35 (m, 6H), 3.58-3.60 (m, 4H), 3.78-3.86 (m, 5H), 6.17 (s, 1H), 7.54 (dd, J=2.00, 8.80 Hz, 1H), 7.98 (d, J=8.80 Hz, 1H), 8.38 (s, 1H), 8.43 (d, J=2.00 Hz, 1H), 9.08 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.746 min; LCMS (ES-API), m/z 438.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.072 min; Purity: 96.8%.

Example 118

1-(5-(6-(Benzo[d]thiazol-6-ylamino)-4-(isopropylamino)pyridin-3-yl)-1,3,4-oxadiazol-2-yl)piperidin-4-ol $^1$H NMR: 400 MHz, CD$_3$OD: δ 1.31-1.34 (m, 6H), 1.61-1.70 (m, 2H), 1.99-2.03 (m, 2H), 3.39-3.42 (2H, merged with water peak), 3.77-3.82 (m, 1H), 3.88-3.94 (m, 3H), 6.16 (s, 1H), 7.52-7.58 (m, 2H), 7.96-7.98 (m, 1H), 8.37 (s, 1H), 8.42 (d, J=2.00 Hz, 1H), 9.07 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.731 min; LCMS (ES-API), m/z 452.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.801 min; Purity: 97.5%.

Example 119

1-(5-(6-(Benzo[d]thiazol-6-ylamino)-4-(isopropylamino)pyridin-3-yl)-1,3,4-oxadiazol-2-yl)piperidin-3-ol $^1$H NMR: 400 MHz, CD$_3$OD: δ 1.33-1.37 (m, 6H), 1.64-1.66 (m, 2H), 1.98-2.00 (m, 2H), 3.64-3.66 (m, 1H), 3.78-3.86 (m, 4H), 6.20 (s, 1H), 7.55 (dd, J=2.00, 8.80 Hz, 1H), 7.91 (s, 1H), 8.16-8.18 (m, 3H), 9.28 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.757 min; LCMS (ES-API), m/z 452.0 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.620 min; Purity: 89.2%.

Example 120

N2-(Benzo[d]thiazol-6-yl)-N4-isopropyl-5-(5-((tetrahydro-2H-pyran-4-yl)amino)-1,3,4-oxadiazol-2-yl)pyridine-2,4-diamine $^1$H NMR: 400 MHz, CD$_3$OD: δ 1.34 (d, J=6.40 Hz, 6H), 1.60-1.70 (m, 2H), 2.06-2.09 (m, 2H), 3.50-3.59 (m, 2H), 3.70-3.80 (m, 2H), 3.98-4.03 (m, 2H), 6.16 (s, 1H), 7.53 (dd, J=2.00, 9.00 Hz, 1H), 7.97 (d, J=8.80 Hz, 1H), 8.33 (s, 1H), 8.41 (d, J=2.00 Hz, 1H), 9.09 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH₄COOH; gradient 0-100% B over 1.5 min; retention time: 1.769 min; LCMS (ES-API), m/z 452.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 30 min (36 min run time); Flow rate: 1.0 μL/min; Retention time: 11.908 min; Purity: 94.05%.

Example 121

(1-(((5-(6-(Benzo[d]thiazol-6-ylamino)-4-(isopropylamino)pyridin-3-yl)-1,3,4-oxadiazol-2-yl)amino)methyl)cyclopropyl)methanol LCMS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.742 min; LCMS (ES-API), m/z 450.0 (M–H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.676 min; Purity: 93.2%.

Example 122

2-((5-(6-(Benzo[d]thiazol-6-ylamino)-4-(isopropylamino)pyridin-3-yl)-1,3,4-oxadiazol-2-yl)amino)ethanol $^1$H NMR: 400 MHz, CD₃OD: δ 1.31-1.35 (m, 6H), 3.45-3.51 (m, 3H), 3.75-3.81 (m, 3H), 6.16 (s, 1H), 7.53 (dd, J=2.40, 8.80 Hz, 1H), 7.97 (d, J=8.80 Hz, 1H), 8.34 (s, 1H), 8.42 (d, J=2.00 Hz, 1H), 9.08 (s, 1H). LC/MS: Ascentis Express C18, 5×2.1 mm, 2.7 μm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.657 min; LCMS (ES-API), m/z 412.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.389 min; Purity: 93.2%.

Example 123

4-((5-(6-(Benzo[d]thiazol-6-ylamino)-4-(isopropylamino)pyridin-3-yl)-1,3,4-oxadiazol-2-yl)amino)-2-methylbutan-1-ol $^1$H NMR: 400 MHz, DMSO-d₆: δ 0.89 (d, J=6.80 Hz, 3H), 1.28-1.36 (m, 7H), 1.59-1.74 (m, 2H), 3.25 (4H, merged with water peak), 3.69-3.74 (m, 1H), 4.46 (t, J=5.20 Hz, 1H), 6.16 (s, 1H), 7.53 (d, J=7.20 Hz, 1H), 7.58 (dd, J=2.40, 9.00 Hz, 1H), 7.73 (t, J=5.60 Hz, 1H), 7.95 (d, J=8.80 Hz, 1H), 8.29 (s, 1H), 8.68 (d, J=2.00 Hz, 1H), 9.15 (s, 1H), 9.31 (s, 1H). Mol. wt.: 453.57. LC/MS: Retention time: 1.987 min. Purity: 99.5%.

Example 124

3-(5-(6-(Benzo[d]thiazol-6-ylamino)-4-(isopropylamino)pyridin-3-yl)-1,3,4-oxadiazol-2-ylamino)-1-phenylpropan-1-ol $^1$H NMR: 400 MHz, DMSO-d₆: δ 1.28 (d, J=6.00 Hz, 6H), 1.90-1.92 (m, 2H), 3.69-3.73 (m, 1H), 4.66-4.70 (m, 1H), 5.31-5.32 (m, 1H), 6.16 (s, 1H), 7.22-7.26 (m, 1H), 7.32-7.38 (m, 4H), 7.52 (d, J=7.20 Hz, 1H), 7.59 (dd, J=2.40, 8.80 Hz, 1H), 7.76 (t, J=5.60 Hz, 1H), 7.95 (d, J=8.80 Hz, 1H), 8.28 (s, 1H), 8.68 (d, J=2.00 Hz, 1H), 9.15 (s, 1H), 9.32 (s, 1H). Mol. wt.: 501.61. LC/MS: Retention time: 2.288 min. Purity: 99.5%.

Example 125

1-(2-(5-(6-(Benzo[d]thiazol-6-ylamino)-4-(isopropylamino)pyridin-3-yl)-1,3,4-oxadiazol-2-ylamino)ethyl)cyclopentanol $^1$H NMR: 400 MHz, DMSO-d₆: δ 1.28 (d, J=6.40 Hz, 6H), 1.46-1.63 (m, 7H), 1.71-1.72 (m, 2H), 1.80-1.84 (m, 2H), 3.38 (2H, merged with water peak), 3.69-3.74 (m, 1H), 4.20 (s, 1H), 6.16 (s, 1H), 7.53 (d, J=6.80 Hz, 1H), 7.58 (dd, J=2.00, 8.80 Hz, 1H), 7.66 (t, J=5.60 Hz, 1H), 7.95 (d, J=8.80 Hz, 1H), 8.29 (s, 1H), 8.68 (d, J=2.00 Hz, 1H), 9.15 (s, 1H), 9.31 (s, 1H). Mol. wt.: 479.61. LC/MS: Retention time: 2.245 min. Purity: 96.5%.

Example 126

1-(2-(5-(6-(Benzo[d]thiazol-6-ylamino)-4-(isopropylamino)pyridin-3-yl)-1,3,4-oxadiazol-2-ylamino)ethyl)cyclopentanol $^1$H NMR: 400 MHz, DMSO-d₆: δ 1.10 (d, J=6.40 Hz, 3H), 1.24-1.29 (m, 6H), 1.60-1.68 (m, 2H), 1.98-2.03 (m, 2H), 3.70-3.74 (m, 2H), 4.52 (d, J=4.80 Hz, 1H), 6.16 (s, 1H), 7.52 (d, J=7.20 Hz, 1H), 7.58 (dd, J=2.00, 9.00 Hz, 1H), 7.69 (t, J=5.60 Hz, 1H), 7.95 (d, J=8.80 Hz, 1H), 8.29 (s, 1H), 8.68 (d, J=2.00 Hz, 1H), 9.15 (s, 1H), 9.32 (s, 1H). Mol. wt.: 439.54. LC/MS: Retention time: 1.986 min. Purity: 99.8%.

Example 127

(1-((5-(6-(Benzo[d]thiazol-6-ylamino)-4-(isopropylamino)pyridin-3-yl)-1,3,4-oxadiazol-2-ylamino)methyl)cyclopentyl)methanol $^1$H NMR: 400 MHz, DMSO-d₆: δ 1.24-1.29 (m, 6H), 1.41-1.43 (m, 4H), 1.56-1.58 (m, 4H), 1.98-2.01 (m, 2H), 3.23 (4H, merged with water peak), 3.69-3.74 (m, 1H), 4.71 (t, J=5.60 Hz, 1H), 5.33 (t, J=4.80 Hz, 1H), 6.17 (s, 1H), 7.49 (d, J=Hz, 1H), 7.59 (dd, J=2.00, 8.80 Hz, 1H), 7.71 (t, J=6.00 Hz, 1H), 7.95 (d, J=8.80 Hz, 1H), 8.30 (s, 1H), 8.67 (d, J=2.00 Hz, 1H), 9.15 (s, 1H), 9.32 (s, 1H). Mol. wt.: 479.61. LC/MS: Retention time: 2.364 min. Purity: 99.6%.

Example 128

5-(5-(Azetidin-3-ylamino)-1,3,4-oxadiazol-2-yl)-N2-(benzo[d]thiazol-6-yl)-N4-isopropylpyridine-2,4-diamine $^1$H NMR: 400 MHz, DMSO-d₆: δ 1.18-1.21 (m, 3H), 1.24-1.28 (m, 6H), 3.67-3.82 (m, 1H), 4.02-4.20 (m, 4H), 4.57-4.62 (m, 1H), 6.27 (s, 1H), 7.49-7.56 (m, 1H), 8.12-8.14 (m, 1H), 8.17-8.18 (m, 1H), 8.25-8.32 (m, 1H), 8.94-8.96 (m, 1H), 9.19 (bs, 2H), 9.37-9.40 (m, 1H), 10.40 (bs, 1H). Mol. wt.: 422.52. LC/MS: Retention time: 1.504 min. Purity: 95%.

Example 129

2-(4-(5-(6-(Benzo[d]thiazol-6-ylamino)-4-(isopropylamino)pyridin-3-yl)-1,3,4-oxadiazol-2-yl)piperazin-1-yl)ethanol $^1$H NMR: 400 MHz, DMSO-d$_6$: δ 1.28 (d, J=6.40 Hz, 6H), 2.46 (2H, merged with DMSO-d$_6$ peak), 2.56 (4H, merged with DMSO-d$_6$ peak), 3.49-3.57 (m, 6H), 3.71-3.72 (m, 1H), 4.45 (t, J=5.20 Hz, 1H), 6.17 (s, 1H), 7.42 (d, J=6.80 Hz, 1H), 7.58 (dd, J=2.40, 9.00 Hz, 1H), 7.95 (d, J=8.80 Hz, 1H), 8.45 (s, 1H), 8.70 (d, J=2.00 Hz, 1H), 9.15 (s, 1H), 9.35 (s, 1H). Mol. wt.: 480.6. LC/MS: Retention time: 1.878 min. Purity: 98.3%.

Example 130

N2-(Benzo[d]thiazol-6-yl)-N4-isopropyl-5-(5-(4-(2-morpholinoethyl)piperazin-1-yl)-1,3,4-oxadiazol-2-yl)pyridine-2,4-diamine $^1$H NMR: 400 MHz, DMSO-d$_6$: δ 1.28 (d, J=6.40 Hz, 6H), 2.38-2.40 (m, 4H), 2.45 (4H, merged with DMSO-d$_6$ peak), 2.55 (4H, merged with DMSO-d$_6$ peak), 3.48-3.50 (m, 4H), 3.55-3.58 (m, 4H), 3.69-3.72 (m, 1H), 6.16 (s, 1H), 7.42 (d, J=7.20 Hz, 1H), 7.58 (dd, J=2.00, 8.80 Hz, 1H), 7.95 (d, J=8.80 Hz, 1H), 8.45 (s, 1H), 8.70 (d, J=2.40 Hz, 1H), 9.15 (s, 1H), 9.35 (s, 1H). Mol. wt.: 549.7. LC/MS: Retention time: 2.015 min. Purity: 95.2%.

Example 131

Synthesis of N2-(benzo[d]thiazol-6-yl)-N4-isopropyl-5-(5-(piperidin-4-ylamino)-1,3,4-oxadiazol-2-yl)pyridine-2,4-diamine: To a stirred solution of tert-butyl 4-((5-(6-(benzo[d]thiazol-6-ylamino)-4-(isopropylamino)pyridin-3-yl)-1,3,4-oxadiazol-2-yl)amino)piperidine-1-carboxylate (Example 111) (250 mg, 0.3 mmol) in DCM (10 mL), Ether.HCl (10 mL) was added at −10° C. Stirred the reaction mixture at 0° C. for 30 min. Reaction temperature was slowly brought to room temperature. The reaction mass was concentrated under reduced pressure to dryness. The material obtained was purified by prep. HPLC to afford the title compound, N$_2$-(benzo[d]thiazol-6-yl)-N4-isopropyl-5-(5-(piperidin-4-ylamino)-1,3,4-oxadiazol-2-yl)pyridine-2,4-diamine $^1$H NMR: 400 MHz, CD$_3$OD: δ 1.37 (d, J=6.40 Hz, 6H), 1.90-2.00 (m, 2H), 2.33-2.37 (m, 2H), 3.20-3.29 (m, 2H), 3.50-3.53 (m, 2H), 3.87-3.93 (m, 2H), 6.28 (s, 1H), 7.63 (dd, J=1.20, 8.40 Hz, 1H), 8.21-8.27 (m, 3H), 9.54 (bs, 1H). LC/MS: Purospher@star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.277 min; LCMS (ES-API), m/z 451.2 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 µL/min; Retention time: 8.965 min; Purity: 98.1%.

Example 132

N2-(Benzo[d]thiazol-6-yl)-N4-isopropyl-5-(5-((1-(methylsulfonyl)piperidin-4-yl)amino)-1,3,4-oxadiazol-2-yl)pyridine-2,4-diamine To a stirred solution of N2-(benzo[d]thiazol-6-yl)-N4-isopropyl-5-(5-(piperidin-4-ylamino)-1,3,4-oxadiazol-2-yl)pyridine-2,4-diamine (Example 131) (30 mg, 0.06 mmol) in DCM (4 mL): THF (4 mL), added DIPEA (0.09 mmol, 1.5 equiv.) and DMAP (0.006 mmol, 0.1 equiv.) and stirred for 5 min. Added mesyl chloride (0.5 mmol, 0.8 equiv.) dropwise at 0° C. Stirred the reaction mixture at 0° C. for 1 h, reaction temperature was brought to room temperature and stirred overnight. The reaction mixture was diluted with DCM. The DCM layer was washed with 10% NaHCO$_3$ solution followed by water. The DCM layer was collected, dried over Na$_2$SO$_4$, filtered and concentrated. The material obtained was purified by prep HPLC to afford the title compound, N2-(benzo[d]thiazol-6-yl)-N4-isopropyl-5-(5-((1-(methylsulfonyl)piperidin-4-yl)amino)-1,3,4-oxadiazol-2-yl)pyridine-2,4-diamine. $^1$H NMR: 400 MHz, CD$_3$OD: δ 1.34 (d, J=6.40 Hz, 6H), 1.66-1.75 (m, 2H), 2.10-2.14 (m, 2H), 3.027 (s, 3H), 3.30-3.36 (1H, merged with water peak), 3.56-3.60 (m, 1H), 3.78-3.82 (m, 1H), 4.00-4.05 (m, 2H), 6.17 (s, 1H), 7.53-7.57 (m, 1H), 7.98 (d, J=8.80 Hz, 1H), 8.38 (s, 1H), 8.43 (d, J=2.00 Hz, 1H), 9.08 (s, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.501 min; LCMS (ES-API), m/z 529.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 5.771 min; Purity: 99.7%.

Example 133

1-(4-((5-(6-(Benzo[d]thiazol-6-ylamino)-4-(isopropylamino)pyridin-3-yl)-1,3,4-oxadiazol-2-yl)amino)piperidin-1-yl)ethanone To a stirred solution of N2-(benzo[d]thiazol-6-yl)-N4-isopropyl-5-(5-(piperidin-4-ylamino)-1,3,4-oxadiazol-2-yl)pyridine-2,4-diamine (Example 131) (40 mg, 0.08 mmol) in DCM (5 mL): THF (5 mL), added DIPEA (0.08 mmol, 1.5 equiv.) and DMAP (0.008 mmol, 0.1 equiv.) and stirred for 5 min. Added acetyl chloride (0.8 mmol, 0.8 equiv.) dropwise at 0° C. Stirred the reaction mixture at 0° C. for 1 h, the reaction temperature was raised to room temperature and stirred overnight. The reaction mixture was diluted with DCM. The DCM layer was washed with 10% NaHCO$_3$ solution followed by water. The DCM layer was collected, dried over Na$_2$SO$_4$, filtered and concentrated. The material obtained was purified by prep HPLC to afford the title compound, 1-(4-((5-(6-(benzo[d]thiazol-6-ylamino)-4-(isopropylamino)pyridin-3-yl)-1,3,4-oxadiazol-2-yl)amino)piperidin-1-yl)ethanone. $^1$H NMR: 400 MHz, CD$_3$OD: δ 1.34 (d, J=6.40 Hz, 6H), 1.57-1.66 (m, 2H), 1.97 (s, 3H), 2.00-2.06 (m, 2H), 3.77-3.82 (m, 1H), 3.93-3.98 (m, 1H), 4.03-4.06 (m, 2H), 6.17 (s, 1H), 7.53-7.56 (m, 1H), 7.98 (d, J=8.80 Hz, 1H), 8.38 (s, 1H), 8.43 (d, J=2.00 Hz, 1H), 9.08 (s, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.514 min; LCMS (ES-API), m/z 493.2 (M+H). HPLC: Sunfire C18

(150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 5.396 min; Purity: 99.4%.

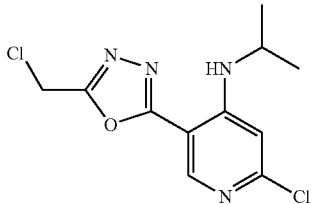 [SMILES: CC(C)Nc1cc(Cl)ncc1-c1nnc(CCl)o1]

Synthesis of 2-chloro-5-(5-(chloromethyl)-1,3,4-oxadiazol-2-yl)-N-isopropylpyridin-4-amine (46): To a stirred solution of 6-chloro-4-(isopropylamino)nicotinohydrazide (10) (500 mg, 2 mmol) in DCM (10 mL), Et₃N (6 mmol, 3 equiv.) and 2-chloroacetyl chloride (3 mmol, 1.5 equiv.) were added and stirred at room temperature for 4 h. Added tosyl chloride (3.2 mmol, 1.5 equiv.) was added at stirred overnight at room temperature. The reaction mixture was diluted with DCM. The DCM layer was washed with 10% NaHCO₃ solution followed by water. The organic layer was collected, dried over Na₂SO₄, filtered and concentrated. The crude material obtained was purified by column chromatography through silica gel and EtOAc:Pet. ether as eluent to afford the desired compound, 2-chloro-5-(5-(chloromethyl)-1,3,4-oxadiazol-2-yl)-N-isopropylpyridin-4-amine LC/MS: Acquity BEH C18 2.1×50 mm, 1.8 micron; Solvent A=0.1% TFA in water; Solvent B=0.1% TFA in ACN; gradient 0-100% B over 2 min; retention time: 0.95 min; LCMS (ES-API), m/z 287.6 (M+H).

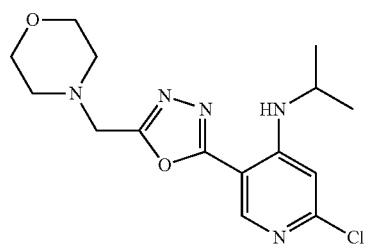 [SMILES: CC(C)Nc1cc(Cl)ncc1-c1nnc(CN2CCOCC2)o1]

Synthesis of 2-chloro-N-isopropyl-5-(5-(morpholinomethyl)-1,3,4-oxadiazol-2-yl)pyridin-4-amine (47): 2-chloro-5-(5-(chloromethyl)-1,3,4-oxadiazol-2-yl)-N-isopropylpyridin-4-amine (46) (60 mg, 0.2 mmol) was taken in a rbf, added morpholine (4 mL) to the rbf followed by the addition of potassium iodide (0.2 mmol), stirred the reaction mixture overnight at room temperature. The reaction mixture was concentrated under reduced pressure to remove excess of morpholine. The crude material obtained was taken to next step as such, without purification. LC/MS: Purospher@star RP-18, 4×55 mm, 3 µm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.608 min; LCMS (ES-API), m/z 338.2 (M+H).

Example 134

4-((4-(Isopropylamino)-5-(5-(morpholinomethyl)-1,3,4-oxadiazol-2-yl)pyridin-2-yl)amino)benzonitrile

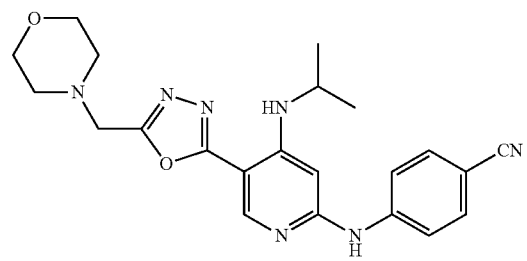 [SMILES: CC(C)Nc1cc(Nc2ccc(C#N)cc2)ncc1-c1nnc(CN2CCOCC2)o1]

To solution of 2-chloro-N-isopropyl-5-(5-(morpholinomethyl)-1,3,4-oxadiazol-2-yl)pyridin-4-amine (47) (100 mg, 0.2 mmol) in dioxane (5 mL):H₂O (1 mL), 4-cyano aniline (0.3 mmol, 1.1 equiv.), xanthphos (0.1 mmol, 0.5 equiv.) and Na₂CO₃ (0.8 mmol, 3 equiv.) were added and degassed for 10 min. To the reaction mixture Pd₂(dba)₃ (0.1 mmol, 0.5 equiv.) was added and degassed again for 10 min. It was then heated at 110° C. for overnight. The reaction mass was cooled and filtered through small pad of celite. The filtrate obtained was concentrated to provide crude material. The crude material was purified by column chromatography through silica gel and MeOH:DCM as eluent. The material obtained was repurified on preparative TLC to afford 4-((4-(isopropylamino)-5-(5-(morpholinomethyl)-1,3,4-oxadiazol-2-yl)pyridin-2-yl)amino)benzonitrile. ¹H NMR: 400 MHz, CD₃OD: δ 1.37 (d, J=6.40 Hz, 6H), 2.67 (t, J=4.8 Hz, 4H), 3.77 (t, J=4.4 Hz, 4H), 3.87 (q, J=6.4 Hz, 1H), 3.94 (s, 2H), 6.24 (s, 1H), 7.61-7.64 (m, 2H), 7.72 (d, J=6.4 Hz, 1H), 7.77-7.80 (m, 2H), 8.57 (s, 1H). LC/MS: XBridge Phe 8, 4.6×30 mm, 3.5 µm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.595 min; LCMS (ES-API), m/z 420.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 5.964 min; Purity: 95.1%.

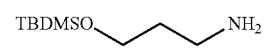

Synthesis of 3-((tert-butyldimethylsilyl)oxy)propan-1-amine (48): To a stirred solution of 3-aminopropan-1-ol (2 g, 20 mmol) in DCM (10 mL), imidazole (79 mmol, 3 equiv.) was added and stirred at room temperature for 10 min. Reaction mixture was cooled to 0° C., t-butyl dimethyl silyl chloride (30 mmol, 1.2 equiv.) was added in portions and stirred the reaction mixture overnight at room temperature. Diluted the reaction mixture using DCM, the DCM layer was washed with water. The organic layer was collected, dried over Na₂SO₄, filtered and concentrated. ELSD method LC/MS: Retention time: 1.5 min; (ES-API), m/z 189.7 (M+H).

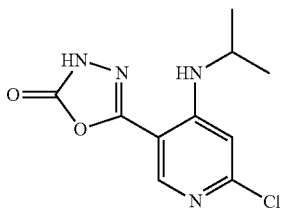 [SMILES: CC(C)Nc1cc(Cl)ncc1-c1n[nH]c(=O)o1]

Synthesis of 5-(6-chloro-4-(isopropylamino)pyridin-3-yl)-1,3,4-oxadiazol-2(3H)-one (49): 6-chloro-4-(isopropylamino)nicotinohydrazide (10) (800 mg, 3.5 mmol) was taken in DMF (4 mL). Added CDI (3.8 mmol, 1.1 equiv.) and stirred at room temperature for overnight. The reaction mass was concentrated under reduced pressure to remove excess of DMF. The residue was diluted using EtOAc, washed the EtOAc layer with water followed by brine solution. Collected the EtOAc layer, dried over $Na_2SO_4$, filtered and concentrated. The crude material obtained was taken to next step as such, without purification. LC/MS: Acquity BEH C18 2.1×50 mm, 1.8 micron; Solvent A=0.1% TFA in water; Solvent B=0.1% TFA in ACN; gradient 0-100% B over 2 min; retention time: 0.76 min; LCMS (ES-API), m/z 255.6 (M+H).

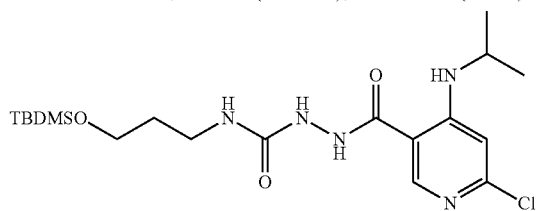

Synthesis of N-(3-((tert-butyldimethylsilyl)oxy)propyl)-2-(6-chloro-4-(isopropylamino)nicotinoyl)hydrazinecarboxamide (50): 5-(6-chloro-4-(isopropylamino)pyridin-3-yl)-1,3,4-oxadiazol-2(3H)-one (49) (1.2 g, 4 mmol) and 3-((tert-butyldimethylsilyl)oxy)propan-1-amine (48) (7 mmol, 1.5 equiv.) were dissolved in ethanol (5 mL). Refluxed the reaction mixture at 90° C., overnight. The reaction mass was concentrated under reduced pressure to remove excess of solvent. The crude material obtained was taken to next step as such, without purification. LC/MS: Acquity BEH C18 2.1×50 mm, 1.8 micron; Solvent A=0.1% TFA in water; Solvent B=0.1% TFA in ACN; gradient 0-100% B over 2 min; retention time: 1.02 min; LCMS (ES-API), m/z 444.9 (M+H).

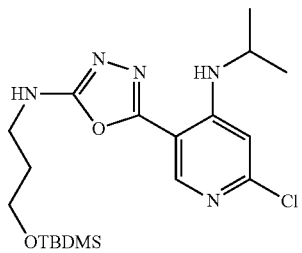 [SMILES: CC(C)Nc1cc(Cl)ncc1-c1nnc(NCCCO[Si](C)(C)C(C)(C)C)o1]

Synthesis of N-(3-((tert-butyldimethylsilyl)oxy)propyl)-5-(6-chloro-4-(isopropylamino)pyridin-3-yl)-1,3,4-oxadiazol-2-amine (51): N-(3-((tert-butyldimethylsilyl)oxy)propyl)-2-(6-chloro-4-(isopropylamino)nicotinoyl)hydrazinecarboxamide (50) (1 g, 2.2 mmol) in DCM (40 mL) was stirred at room temperature. Added triphenyl phosphine (6 mmol, 3 equiv.), $Et_3N$ (18 mol, 8 equiv.) and $CCl_4$ (6 mmol, 3 equiv.). The reaction mixture was heated at 50° C. for 3 h. Reaction mixture was diluted using DCM. The DCM layer was washed with water. The organic layer was collected, dried over $Na_2SO_4$, filtered and concentrated. The crude material was purified by column chromatography through silica gel and EtOAc:Pet. Ether as eluent to provide the desired compound, N-(3-((tert-butyldimethylsilyl)oxy)propyl)-5-(6-chloro-4-(isopropylamino)pyridin-3-yl)-1,3,4-oxadiazol-2-amine. LC/MS: Acquity BEH C18 2.1×50 mm, 1.8 micron; Solvent A=0.1% TFA in water; Solvent B=0.1% TFA in ACN; gradient 0-100% B over 2 min; retention time: 1.2 min; LCMS (ES-API), m/z 426.9 (M+H).

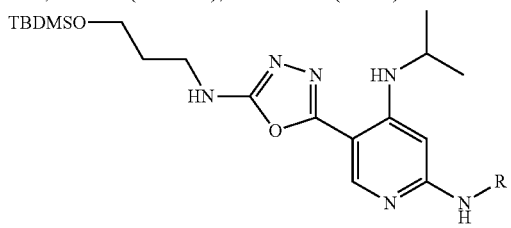

52a R = 4-cyano aniline
52b R = 6-amino Benzothiazole

Synthesis of 4-((5-(5-((3-((tert-butyldimethylsilyl)oxy)propyl)amino)-1,3,4-oxadiazol-2-yl)-4-(isopropylamino)pyridin-2-yl)amino)benzonitrile (52a) and N2-(benzo[d]thiazol-6-yl)-5-(5-((3-((tert-butyldimethylsilyl)oxy)propyl)amino)-1,3,4-oxadiazol-2-yl)-N4-isopropylpyridine-2,4-diamine (52b): Followed the same procedure as mentioned in the synthesis of Example 134 using their respective starting materials and appropriate amines LC/MS (Compound 52a): XBridge Phe 8, 4.6×30 mm, 3.5 µm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min (3.2 min run time); retention time: 1.922 min; LCMS (ES-API), m/z 506.0 (M−H).

LC/MS (Compound 52b): Purospher@star RP-18, 4×55 mm, 3 µm; Solvent A=10% ACN: 90% $H_2O$: 20 mM $NH_4OAc$; Solvent B=90% ACN: 10% $H_2O$: 20 mM $NH_4COOAc$; gradient 0-100% B over 1.5 min (3.2 min run time); retention time: 2.524 min; LCMS (ES-API), m/z 540.2 (M+H).

Example 135

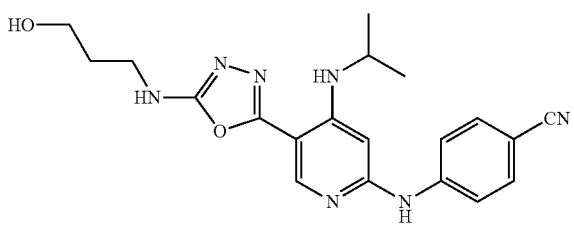 [SMILES: CC(C)Nc1cc(Nc2ccc(C#N)cc2)ncc1-c1nnc(NCCCO)o1]

Synthesis of 4-((5-(5-((3-hydroxypropyl)amino)-1,3,4-oxadiazol-2-yl)-4-(isopropylamino)pyridin-2-yl)amino)benzonitrile: N2-(benzo[d]thiazol-6-yl)-5-(5-((3-((tert-butyldimethylsilyl)oxy)propyl)amino)-1,3,4-oxadiazol-2-yl)-N4-isopropylpyridine-2,4-diamine (52a) (150 mg, 0.2 mmol) in THF (10 mL) was cooled to 0° C. Added TBAF (1M in THF) (2 equiv.) to the reaction mixture. Reaction mixture was warmed to room temperature and stirred for 1 h. Reaction mixture was quenched by using 10% $NaHCO_3$ solution. The aqueous layer was extracted with EtOAc (twice). The organic layers were collected together, dried over $Na_2SO_4$, filtered and concentrated. The crude material was purified by column chromatography through silica gel and MeOH:DCM as eluent. The material obtained was further purified by prep HPLC to provide the desired compound, 4-((5-(5-((3-hydroxypropyl)amino)-1,3,4-oxadiazol-2-yl)-4-(isopropylamino)pyridin-2-yl)amino)benzonitrile. ¹H NMR: 400 MHz, CD₃OD: δ 1.35 (d, J=6.40 Hz, 6H), 1.89-1.96 (m, 2H), 3.46 (t, J=6.80 Hz, 2H), 3.71 (t, J=6.00 Hz, 2H), 3.79-3.83 (m, 1H), 6.21 (s, 1H), 7.58-7.65 (m, 3H), 7.73-7.76 (m, 2H), 8.37 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.486 min; LCMS (ES-API), m/z 394.0 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.812 min; Purity: 99.4%.

Example 136

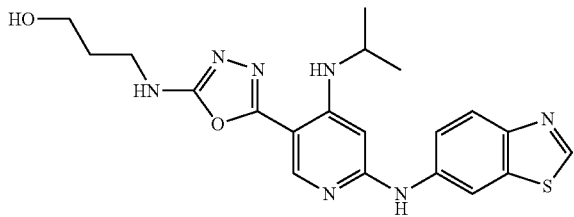 [SMILES: CC(C)Nc1cc(Nc2ccc3ncsc3c2)ncc1-c1nnc(NCCCO)o1]

Synthesis of 345-(6-(benzo[d]thiazol-6-ylamino)-4-(isopropylamino)pyridin-3-yl)-1,3,4-oxadiazol-2-yl)amino)propan-1-ol: Followed the same procedure as mentioned in the synthesis of Example 135. ¹H NMR: 400 MHz, CD₃OD: δ 1.34 (d, J=6.40 Hz, 6H), 1.88-1.94 (m, 2H), 3.46 (t, J=7.20 Hz, 2H), 3.71 (t, J=6.00 Hz, 2H), 3.78-3.82 (m, 1H), 6.16 (s, 1H), 7.54 (dd, J=2.00, 8.80 Hz, 1H), 7.60 (d, J=6.80 Hz, 1H), 7.97 (d, J=8.80 Hz, 1H), 8.34 (s, 1H), 8.42 (d, J=2.00 Hz, 1H), 9.08 (s, 1H). LC/MS: Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.443 min; LCMS (ES-API), m/z 424.2 (M–H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.157 min; Purity: 99.1%.

Synthesis of tert-butyl (2-((tert-butyldimethylsilyl)oxy)-1-(5-(6-chloro-4-(isopropylamino)pyridin-3-yl)-1,3,4-oxadiazol-2-yl)ethyl)carbamate (55)

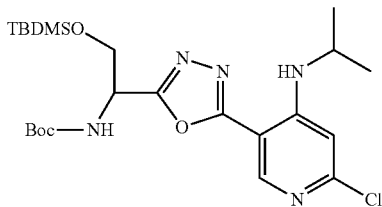 [SMILES: CC(C)Nc1cc(Cl)ncc1-c1nnc(C(CO[Si](C)(C)C(C)(C)C)NC(=O)OC(C)(C)C)o1]

Step 1: To a stirred solution of 2-((tert-butoxycarbonyl)amino)-3-hydroxypropanoic acid (500 mg, 2.4 mmol) and 6-chloro-4-(isopropylamino)nicotinohydrazide (10) (2.6 mmol, 1.1 equiv.) in DMF (10 mL), DIPEA (12 mmol, 5 equiv.) and HATU (2.6 mmol, 1.1 equiv.) were added and stirred overnight at room temperature. The reaction mass was concentrated under reduced pressure to remove excess of solvent present. Diluted the residue with EtOAc and washed water followed by brine solution. The organic layer was collected, dried over Na₂SO₄, filtered and concentrated to get tert-butyl (1-(2-(6-chloro-4-(isopropylamino)nicotinoyl)hydrazinyl)-3-hydroxy-1-oxopropan-2-yl)carbamate (53).

Step 2: tert-Butyl (1-(2-(6-chloro-4-(isopropylamino)nicotinoyl)hydrazinyl)-3-hydroxy-1-oxopropan-2-yl)carbamate (53) (1 g, 2 mmol) in DCM (10 mL), imidazole (7 mmol, 3 equiv.) was added and stirred at room temperature for 10 min. Reaction mixture was cooled to 0° C., t-butyl dimethyl silyl chloride (3.6 mmol, 1.5 equiv.) was added in portions and stirred the reaction mixture overnight at room temperature. Diluted the reaction mixture using DCM, the DCM layer was washed with water. The organic layer was collected, dried over Na₂SO₄, filtered and concentrated to get tert-butyl (3-((tert-butyldimethylsilyl)oxy)-1-(2-(6-chloro-4-(isopropylamino)nicotinoyl)hydrazinyl)-1-oxopropan-2-yl)carbamate (54). LC/MS: Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 2.319 min; LCMS (ES-API), m/z 530.2 (M+H).

Step 3: tert-Butyl (3-((tert-butyldimethylsilyl)oxy)-1-(2-(6-chloro-4-(isopropylamino)nicotinoyl)hydrazinyl)-1-oxopropan-2-yl)carbamate (54) (100 mg, 0.18 mmol) in DCM (5 mL) was stirred at room temperature. Added triphenyl phosphine (0.56 mmol, 3 equiv.), Et₃N (1.5 mol, 8 equiv.) and CCl₄ (0.56 mmol, 3 equiv.). The reaction mixture was heated at 50° C. for 3 h. Reaction mixture was diluted using DCM. The DCM layer was washed with water. The organic layer was collected, dried over Na₂SO₄, filtered and concentrated. The crude material was purified by column chromatography through silica gel and EtOAc:Pet. Ether as eluent to provide the desired compound, tert-butyl (2-((tert-butyldimethylsilyl)oxy)-1-(5-(6-chloro-4-(isopropylamino)pyridin-3-yl)-1,3,4-oxadiazol-2-yl)ethyl)carbamate (55). LC/MS: Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 2.567 min; LCMS (ES-API), m/z 512.3 (M+H).

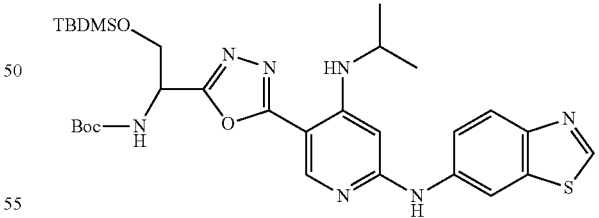

Synthesis of tert-butyl (1-(5-(6-(benzo[d]thiazol-6-ylamino)-4-(isopropylamino)pyridin-3-yl)-1,3,4-oxadiazol-2-yl)-2-((tert-butyldimethylsilyl)oxy)ethyl)carbamate (56): Followed the same procedure as mentioned in the synthesis of Example 134, using respective starting materials. LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.975 min; LCMS (ES-API), m/z 626.0 (M+H).

Example 137

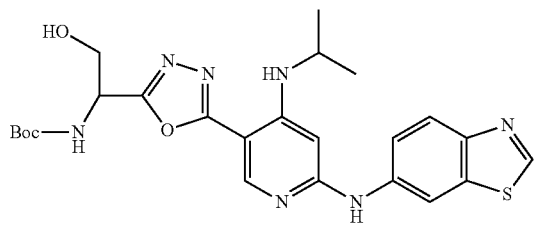 [SMILES: CC(C)Nc1cc(Nc2ccc3ncsc3c2)ncc1-c1nnc(C(CO)NC(=O)OC(C)(C)C)o1]

Synthesis of tert-butyl (1-(5-(6-(benzo[d]thiazol-6-ylamino)-4-(isopropylamino)pyridin-3-yl)-1,3,4-oxadiazol-2-yl)-2-hydroxyethyl)carbamate: Followed the same procedure as mentioned in the synthesis of Example 135. $^1$H NMR: 400 MHz, CD$_3$OD: δ 1.31-1.49 (m, 15H), 3.05 (bs, 1H), 3.79-3.86 (m, 1H), 3.98 (d, J=5.60 Hz, 2H), 5.06 (bs, 1H), 6.18 (s, 1H), 7.55 (dd, J=2.00, 8.80 Hz, 1H), 7.65 (d, J=7.20 Hz, 1H), 7.98 (d, J=8.80 Hz, 1H), 8.43 (d, J=2.00 Hz, 1H), 8.52 (s, 1H), 9.09 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.654 min; LCMS (ES-API), m/z 512.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.518 min; Purity: 92.3%.

Example 138

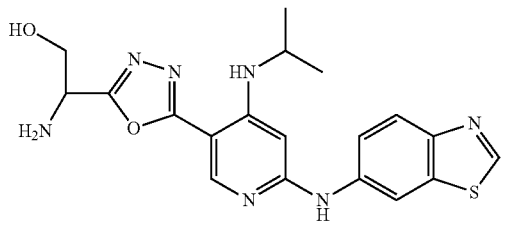 [SMILES: CC(C)Nc1cc(Nc2ccc3ncsc3c2)ncc1-c1nnc(C(N)CO)o1]

Synthesis of 2-amino-2-(5-(6-(benzo[d]thiazol-6-ylamino)-4-(isopropylamino)pyridin-3-yl)-1,3,4-oxadiazol-2-yl): tert-butyl (1-(5-(6-(benzo[d]thiazol-6-ylamino)-4-(isopropylamino)pyridin-3-yl)-1,3,4-oxadiazol-2-yl)-2-((tert-butyldimethylsilyl)oxy)ethyl)carbamate (56) (60 mg, 0.096 mmol) was dissolved in DCM (5 mL), cooled to 0° C. Added ether.HCl (5 mL) to the reaction mixture, stirred at 0° C. for 10 min. Gradually the reaction temperature was raised to room temperature and stirred for 30 min. The reaction mass was concentrated under reduced pressure. The crude material obtained was purified by prep. HPLC to afford the desired compound, 2-amino-2-(5-(6-(benzo[d]thiazol-6-ylamino)-4-(isopropylamino)pyridin-3-yl)-1,3,4-oxadiazol-2-yl)ethanol. $^1$H NMR: 400 MHz, CD$_3$OD: δ 1.39 (d, J=6.40 Hz, 6H), 3.88-3.94 (m, 1H), 4.15 (d, J=8.00 Hz, 2H), 4.97 (t, J=4.80 Hz, 1H), 6.27 (s, 1H), 7.58 (dd, J=2.40, 8.80 Hz, 1H), 8.17 (d, J=2.40 Hz, 1H), 8.23 (d, J=8.80 Hz, 1H), 8.39 (s, 1H), 9.35 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.359 min; LCMS (ES-API), m/z 412.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μL/min; Retention time: 8.639 min; Purity: 98.4%.

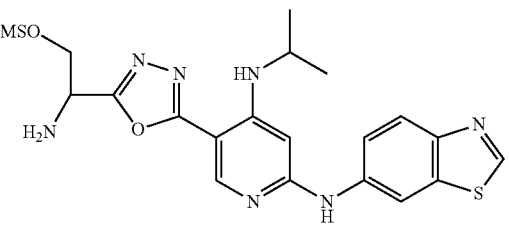

Synthesis of 5-(5-(1-amino-2-((tert-butyldimethylsilyl)oxy)ethyl)-1,3,4-oxadiazol-2-yl)-N2-(benzo[d]thiazol-6-yl)-N4-isopropylpyridine-2,4-diamine (57): tert-butyl (1-(5-(6-(benzo[d]thiazol-6-ylamino)-4-(isopropylamino)pyridin-3-yl)-1,3,4-oxadiazol-2-yl)-2-((tert-butyldimethylsilyl)oxy)ethyl)carbamate (56) (200 mg, 0.3 mmol) was dissolved in DCM (10 mL), cooled to −10° C. Added 2,6-lutidine (1.9 mmol, 6 equiv.) and stirred for 15 min. Added TBDMS-Triflate (1.6 mmol, 5 equiv.) in portions, dropwise to the reaction mixture and stirred at −10° C. for 30 min. Gradually, the reaction temperature was raised to room temperature and stirred for 30 min. Diluted the reaction mixture using DCM and quenched by addition of 5% citric acid solution. Extracted the reaction mixture in DCM. The organic layer was collected, dried over Na$_2$SO$_4$, filtered and concentrated. The crude material was purified by column chromatography through silica gel and MeOH:DCM as eluent to provide the desired compound, 5-(5-(1-amino-2-((tert-butyldimethylsilyl)oxy)ethyl)-1,3,4-oxadiazol-2-yl)-N2-(benzo[d]thiazol-6-yl)-N4-isopropylpyridine-2,4-diamine LC/MS: Acquity BEH C18 2.1×50 mm, 1.8 micron; Solvent A=0.1% TFA in water; Solvent B=0.1% TFA in ACN; gradient 0-100% B over 2 min; retention time: 0.79 min; LCMS (ES-API), m/z 526.9 (M+H).

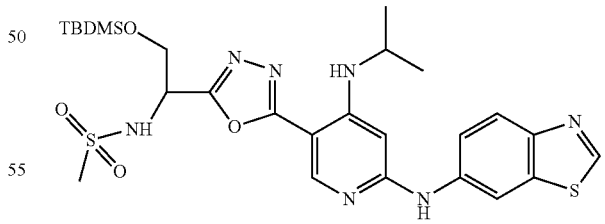

Synthesis of N-(1-(5-(6-(benzo[d]thiazol-6-ylamino)-4-(isopropylamino)pyridin-3-yl)-1,3,4-oxadiazol-2-yl)-2-((tert-butyldimethylsilyl)oxy)ethyl)methanesulfonamide (58): Followed the same procedure as mentioned in the synthesis of Example 132. LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.846 min; LCMS (ES-API), m/z 604.2 (M+H).

Example 139

Synthesis of N-(1-(5-(6-(benzo[d]thiazol-6-ylamino)-4-(isopropylamino)pyridin-3-yl)-1,3,4-oxadiazol-2-yl)-2-hydroxyethyl)methanesulfonamide: Followed the same procedure as mentioned in the synthesis of Example 135. $^1$H NMR: 400 MHz, CD$_3$OD: δ 1.36 (d, J=6.40 Hz, 6H), 3.06 (s, 3H), 3.79-3.86 (m, 1H), 4.03 (d, J=6.00 Hz, 1H), 4.97 (t, J=6.00 Hz, 2H), 6.19 (s, 1H), 7.56 (dd, J=2.40, 8.80 Hz, 1H), 7.99 (d, J=8.80 Hz, 1H), 8.45 (d, J=2.00 Hz, 1H), 8.55 (s, 1H), 9.09 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.490 min; LCMS (ES-API), m/z 490.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.484 min; Purity: 99.9%.

Example 140

Synthesis of N2-(benzo[d]thiazol-6-yl)-N4-isopropyl-5-(5-phenyl-1,3,4-oxadiazol-2-yl)pyridine-2,4-diamine Step 1: 6-Chloro-4-(isopropylamino)nicotinohydrazide (10) (500 mg, 2.1 mmol) and benzoic acid (2.1 mmol, 1 equiv.) were dissolved in DMF (10 mL). EDC.HCl (1.5 equiv.), DIPEA (3 equiv.) and HOBT (1.5 equiv.) were added to the reaction mixture and stirred at room temperature for 5 h. The reaction mass was concentrated under reduced pressure to remove excess of solvent present. Diluted the residue with EtOAc and washed water followed by brine solution. The organic layer was collected, dried over Na$_2$SO$_4$, filtered and concentrated to get N'-benzoyl-6-chloro-4-(isopropylamino)nicotinohydrazide.

Step 2: The crude material of N'-benzoyl-6-chloro-4-(isopropylamino)nicotinohydrazide was dissolved in DCM (15 mL). Tosyl chloride (1.5 equiv.) and triethyl amine (3 equiv.) were added to the reaction mixture and stirred overnight at room temperature. Reaction mixture was diluted using DCM. The DCM layer was washed with water. The organic layer was collected, dried over Na$_2$SO$_4$, filtered and concentrated. The crude material was purified by column chromatography through silica gel and MeOH:DCM as eluent to provide the desired compound, 2-chloro-N-isopropyl-5-(5-phenyl-1,3,4-oxadiazol-2-yl)pyridin-4-amine Step 3: To solution of 2-chloro-N-isopropyl-5-(5-phenyl-1,3,4-oxadiazol-2-yl)pyridin-4-amine (200 mg, 0.6 mmol) in dioxane (10 mL):H$_2$O (2 mL), 6-amino benzothiazole (0.63 mmol, 1 equiv.), xanthphos (0.2 mmol, 0.4 equiv.) and Na$_2$CO$_3$ (2.5 mmol, 4 equiv.) were added and degassed for 10 min. To the reaction mixture Pd$_2$(dba)$_3$ (0.2 mmol, 0.4 equiv.) was added and degassed again for 10 min. It was then heated at 110° C. for overnight. The reaction mass was cooled and filtered through small pad of celite. The filtrate obtained was concentrated to provide crude material. The crude material was purified by column chromatography through silica gel and MeOH:DCM as eluent. The material obtained was further purified by prep. HPLC to afford N2-(benzo[d]thiazol-6-yl)-N4-isopropyl-5-(5-phenyl-1,3,4-oxadiazol-2-yl)pyridine-2,4-diamine $^1$H NMR: 400 MHz, DMSO-d$_6$: δ 1.33 (d, J=6.40 Hz, 6H), 3.74-3.82 (m, 1H), 6.23 (s, 1H), 7.56-7.57 (m, 1H), 7.61-7.67 (m, 4H), 7.98 (d, J=8.80 Hz, 1H), 8.15-8.17 (m, 2H), 8.71 (d, J=2.00 Hz, 1H), 8.78 (s, 1H), 9.18 (s, 1H), 9.50 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 2.332 min; LCMS (ES-API), m/z 429.2 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 9.891 min; Purity: 94.5%.

Synthesis of Examples 141-148: Followed the same procedure as mentioned for the synthesis of Example 140, using appropriate starting materials.

TABLE 8

| Example No. | R | R$_1$ |
|---|---|---|
| 140 | phenyl | benzo[d]thiazol-6-ylamino |

TABLE 8-continued

[Structure: 1,3,4-oxadiazole substituted with R at position 2 and connected at position 5 to a pyridine bearing an isopropylamino (HN-iPr) group and R₁ substituent]

| Example No. | R | R₁ |
|---|---|---|
| 141 | 4-(aminosulfonyl)phenyl (H₂N-SO₂-C₆H₄-) | NH-benzothiazol-6-yl |
| 142 | cyclohexyl | NH-benzothiazol-6-yl |
| 143 | 2-fluoro-5-(N-tert-butylsulfamoyl)phenyl | NH-benzothiazol-6-yl |
| 144 | 4-fluoro-3-hydroxyphenyl | NH-benzothiazol-6-yl |
| 145 | 4-fluoro-3-(2-hydroxyethoxy)phenyl | NH-benzothiazol-6-yl |
| 146 | 3-fluoro-(N-cyclopropylsulfamoyl)phenyl | NH-benzothiazol-6-yl |
| 147 | 4-fluoro-3-sulfamoylphenyl | NH-benzothiazol-6-yl |
| 148 | 3-carbamoylphenyl | NH-benzothiazol-6-yl |

Example 141

4-(5-(6-(Benzo[d]thiazol-6-ylamino)-4-(isopropylamino)pyridin-3-yl)-1,3,4-oxadiazol-2-yl)benzenesulfonamide $^1$H NMR: 400 MHz, CD$_3$OD: δ 1.39 (d, J=6.40 Hz, 6H), 3.84-3.87 (m, 1H), 6.22 (s, 1H), 7.58 (dd, J=2.00, 9.00 Hz, 1H), 7.99-8.01 (m, 1H), 8.13-8.15 (m, 2H), 8.33-8.35 (m, 2H), 8.49 (d, J=2.00 Hz, 1H), 8.72 (s, 1H), 9.10 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.881 min; LCMS (ES-API), m/z 508.0 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 7.774 min; Purity: 99.5%.

Example 142

N2-(Benzo[d]thiazol-6-yl)-5-(5-cyclohexyl-1,3,4-oxadiazol-2-yl)-N4-isopropylpyridine-2,4-diamine $^1$H NMR: 400 MHz, DMSO-d$_6$: δ 1.30-1.31 (m, 6H), 1.36-1.48 (m, 2H), 1.57-1.70 (m, 3H), 1.76-1.80 (m, 2H), 2.06-2.09 (m, 2H), 3.01-3.07 (m, 1H), 3.72-3.77 (m, 1H), 6.20 (s, 1H), 7.54 (d, J=7.20 Hz, 1H), 7.60 (dd, J=2.80, 9.20 Hz, 1H), 7.96-7.99 (m, 1H), 8.52 (s, 1H), 8.69 (d, J=2.00 Hz, 1H), 9.18 (s, 1H), 9.43 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 2.273 min; LCMS (ES-API), m/z 435.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 8.135 min; Purity: 98.3%.

Example 143

5-(5-(6-(Benzo[d]thiazol-6-ylamino)-4-(isopropylamino)pyridin-3-yl)-1,3,4-oxadiazol-2-yl)-N-(tert-butyl)-2-fluorobenzenesulfonamide $^1$H NMR: 400 MHz, CD$_3$OD: δ 1.19 (s, 9H), 1.33 (d, J=6.40 Hz, 6H), 3.75-3.80 (m, 1H), 6.22 (s, 1H), 7.50 (d, J=7.20 Hz, 1H), 7.61 (dd, J=2.00, 9.20 Hz, 1H), 7.73 (t, J=9.20 Hz, 1H), 7.97-7.99 (m, 1H), 8.08 (s, 1H), 8.42-8.45 (m, 1H), 8.50-8.52 (m, 1H), 8.72 (d, J=2.00 Hz, 1H), 8.79 (d, J=Hz, 1H), 9.18 (s, 1H), 9.50 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 2.107 min; LCMS (ES-API), m/z 582.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 8.135 min; Purity: 95%.

Example 144

5-(5-(6-(Benzo[d]thiazol-6-ylamino)-4-(isopropylamino)pyridin-3-yl)-1,3,4-oxadiazol-2-yl)-2-fluorophenol $^1$H NMR: 400 MHz, DMSO-d$_6$: δ 1.32 (d, J=6.40 Hz, 6H), 3.76-3.81 (m, 1H), 6.23 (s, 1H), 7.40-7.44 (m, 1H), 7.59-7.61 (m, 2H), 7.71-7.73 (m, 2H), 8.02 (d, J=8.40 Hz, 1H), 8.62 (bs, 1H), 8.69 (s, 1H), 9.22 (s, 1H), 9.59 (bs, 1H), 10.52 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.973 min; LCMS (ES-API), m/z 461.0 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 7.283 min; Purity: 95.5%.

Example 145

2-(5-(5-(6-(Benzo[d]thiazol-6-ylamino)-4-(isopropylamino)pyridin-3-yl)-1,3,4-oxadiazol-2-yl)-2-fluorophenoxy)ethanol $^1$H NMR: 400 MHz, DMSO-d$_6$: δ 1.33 (d, J=6.40 Hz, 6H), 3.80-3.83 (m, 3H), 4.25-4.27 (m, 2H), 4.97-5.00 (m, 1H), 6.22 (s, 1H), 7.47-7.55 (m, 2H), 7.61-7.63 (m, 1H), 7.72-7.78 (m, 1H), 7.88-7.90 (m, 1H), 7.90-7.99 (m, 1H), 8.73 (d, J=2.40 Hz, 1H), 8.87 (s, 1H), 9.18 (s, 1H), 9.49 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.954 min; LCMS (ES-API), m/z 507.0 (M+H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 8.259 min; Purity: 97.6%.

Example 146

5-(5-(6-(Benzo[d]thiazol-6-ylamino)-4-(isopropylamino)pyridin-3-yl)-1,3,4-oxadiazol-2-yl)-N-cyclopropyl-2-fluorobenzenesulfonamide $^1$H NMR: 400 MHz, DMSO-d$_6$: δ 0.46-0.47 (m, 2H), 0.54-0.56 (m, 2H), 1.15-1.25 (m, 1H), 1.34 (d, J=6.40 Hz, 6H), 3.76-3.81 (m, 1H), 6.23 (s, 1H), 7.51 (d, J=6.80 Hz, 1H), 7.62 (dd, J=2.00, 9.00 Hz, 1H), 7.78 (t, J=8.80 Hz, 1H), 7.99 (d, J=8.80 Hz, 1H), 8.48-8.51 (m, 3H), 8.73 (d, J=1.60 Hz, 1H), 8.80 (s, 1H), 9.19 (s, 1H), 9.51 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.726 min; LCMS (ES-API), m/z 566.0 (M+H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 8.941 min; Purity: 96.9%.

Example 147

5-(5-(6-(Benzo[d]thiazol-6-ylamino)-4-(isopropylamino)pyridin-3-yl)-1,3,4-oxadiazol-2-yl)-2-fluorobenzenesulfonamide $^1$H NMR: 400 MHz, DMSO-d$_6$: δ 1.34 (d, J=6.40 Hz, 6H), 3.76-3.81 (m, 1H), 6.23 (s, 1H), 7.52 (d, J=7.20 Hz, 1H), 7.61-7.64 (m, 1H), 7.74 (t, J=9.20 Hz, 1H), 7.96-8.00 (m, 3H), 8.32 (s, 1H), 8.42-8.45 (m, 1H), 8.50-8.52 (m, 1H), 8.71 (d, J=2.00 Hz, 1H), 8.79 (s, 1H), 9.19 (s, 1H), 9.52 (s, 1H). LC/MS: ZORBAX SB C18, 4.6×50 mm, 5 µm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.576 min; LCMS (ES-API), m/z 526.0 (M+H). HPLC: Sunfire C18 (150×4 6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0µl/min; Retention time: 6.771 min; Purity: 94.1%.

Example 148

3-(5-(6-(Benzo[d]thiazol-6-ylamino)-4-(isopropylamino)pyridin-3-yl)-1,3,4-oxadiazol-2-yl)benzamide $^1$H NMR: 400 MHz, DMSO-d$_6$: δ 1.33-1.37 (m, 6H), 3.79-3.81 (m, 1H), 6.24 (s, 1H), 7.60-7.63 (m, 3H), 7.74 (t, J=7.60 Hz, 1H), 8.01 (d, J=8.80 Hz, 1H), 8.15 (d, J=8.00 Hz, 1H), 8.25 (s, 1H), 8.30 (d, J=7.60 Hz, 1H), 8.63-8.65 (m, 2H), 8.80 (s, 1H), 9.22 (s, 1H), 9.60 (s, 1H). LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.839 min; LCMS (ES-API), m/z 470.0 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µl/min; Retention time: 6.51 min; Purity: 91.1%.

TABLE 9

| Compound No. | R | R$_1$ | R$_2$ |
|---|---|---|---|
| 149 | isopropylamino | 4-fluorophenylamino | CH$_3$ |
| 150 | isopropylamino | 4-fluorophenylamino | H |

Step 1: To solution of ethyl 6-chloro-4-(isopropylamino)nicotinate (2) in dioxane (5 mL):H$_2$O (1 mL), 4-fluoro aniline (1 equiv.), xanthphos (0.4 equiv.) and Na$_2$CO$_3$ (4 equiv.) were added and degassed for 10 min. To the reaction mixture Pd$_2$(dba)$_3$ (0.4 equiv.) was added and degassed again for 10 min. It was then heated at 115° C., overnight. The reaction mass was cooled and filtered through small pad of celite. The filtrate obtained was concentrated to provide crude material. The crude material was purified by column chromatography through silica gel and MeOH:CHCl$_3$ as eluent to afford C-4 and C-6 substituted compound 61.

Step 2: To a stirred solution of 61 in ethanol (10 mL), hydrazine hydrate (3 mL) was added and refluxed at 80° C. for 3 h. The reaction mixture was cooled and concentrated to obtain crude compound. The residue obtained was washed with diethyl ether and hexane to get hydrazide derivative compound, 6-((4-fluorophenyl)amino)-4-(isopropylamino)nicotinohydrazide (62).

Step 3: A solution of 6-((4-fluorophenyl)amino)-4-(isopropylamino)nicotinohydrazide (91) (100 mg) and PTSA (10 mg) in trimethyl orthoacetate (5 mL) was heated at 100° C., overnight. The reaction mixture was concentrated, diluted with EtOAc. The organic layer was washed with sat. NaHCO$_3$ solution, water and brine solution. The organic layer was collected, dried over Na$_2$SO$_4$, filtered and concentrated. The crude material obtained was purified by prep. HPLC to afford N2-(4-fluorophenyl)-N4-isopropyl-5-(5-methyl-1,3,4-oxadiazol-2-yl)pyridine-2,4-diamine (Example 149).

$^1$H NMR: 400 MHz, DMSO-d$_6$: δ 1.29 (d, J=6.00 Hz, 6H), 2.57 (3H, merged with DMSO-d$_6$ peak), 3.69-3.82 (m, 1H), 6.08 (s, 1H), 6.96-7.21 (m, 2H), 7.60-7.63 (m, 3H), 8.39 (s, 1H), 9.20 (bs, 1H). LC/MS: XBridge Phe 8, 4.6×30 mm, 3.5 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.673 min; LCMS (ES-API), m/z 328.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 6.545 min; Purity: 91.05%.

Example 150

Synthesis of N2-(4-fluorophenyl)-N4-isopropyl-5-(1,3,4-oxadiazol-2-yl)pyridine-2,4-diamine: Followed the same procedure as mentioned in the synthesis of Example 149. Trimethyl orthoacetate was replaced by trimethyl orthoformate to get the desired compound. $^1$H NMR: 400 MHz, DMSO-d$_6$: δ 1.30 (d, J=6.40 Hz, 6H), 3.70-3.75 (m, 1H), 6.09 (s, 1H), 7.10-7.14 (m, 2H), 7.51-7.53 (m, 1H), 7.63-7.66 (m, 2H), 8.47 (s, 1H), 9.16 (s, 1H), 9.24 (s, 1H). LC/MS: XBridge Phe 8, 4.6×30 mm, 3.5 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.663 min; LCMS (ES-API), m/z 314.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 µL/min; Retention time: 6.44 min; Purity: 97.9%.

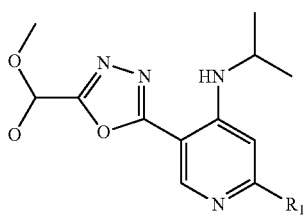

Synthesis of C-6 substituted methyl 5-(4-(isopropylamino)-pyridin-3-yl)-1,3,4-oxadiazole-2-carboxylate (65): Compounds of the general formula 64 were dissolved in DCM, added triethyl amine (3 equiv.) and cooled to 0° C. Added methyl oxalyl chloride (1.2 equiv.) to the reaction mixture dropwise, stirred the reaction mixture at room temperature for 6 h. Added tosyl chloride (2 equiv.) to the reaction mixture and stirred overnight at room temperature. The reaction mixture was quenched with sat. NaHCO$_3$ solution and extracted in DCM. The organic layer was collected, dried over Na$_2$SO$_4$, filtered and concentrated. The crude material obtained was purified by column chromatography, silica gel, MeOH:DCM as eluent to afford C-6 substituted methyl 5-(4-(isopropylamino)-pyridin-3-yl)-1,3,4-oxadiazole-2-carboxylate.

Example 151

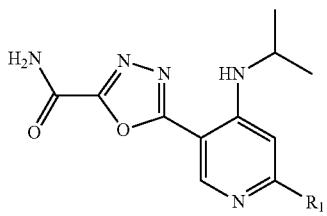

Synthesis of 5-(6-(benzo[d]thiazol-6-ylamino)-4-(isopropylamino)pyridin-3-yl)-1,3,4-oxadiazole-2-carboxamide: A solution of methyl 5-(6-(benzo[d]thiazol-6-ylamino)-4-(isopropylamino)pyridin-3-yl)-1,3,4-oxadiazole-2-carboxylate (derivative of 95) in MeOH (10 mL) was cooled to −10° C. and NH$_3$ (g) was purged through the reaction mixture for 5 min. Heated the reaction for 4 h in closed condition at 80° C. Cooled to 0° C. and transferred to rbf and concentrated. The crude material obtained was purified by prep. HPLC to afford the desired compound, 5-(6-(benzo[d]thiazol-6-ylamino)-4-(isopropylamino)pyridin-3-yl)-1,3,4-oxadiazole-2-carboxamide. $^1$H NMR: 400 MHz, CD$_3$OD: δ 1.36-1.38 (m, 6H), 3.82-3.86 (m, 1H), 6.19 (s, 1H), 7.57 (dd, J=2.00, 9.00 Hz, 1H), 7.68 (d, J=7.20 Hz, 1H), 7.99 (d, J=8.80 Hz, 1H), 8.48 (d, J=2.00 Hz, 1H), 8.66 (s, 1H), 9.10 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.465 min; LCMS (ES-API), m/z 396.2 (M+H). HPLC: XBridge (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.45 min; Purity: 95.2%.

Synthesis of Examples 152 and 153: Prepared according to the procedure outlined for the synthesis Example 151, using appropriate starting materials.

TABLE 10

| Example No. | R$_1$ |
|---|---|
| 151 | ![structure] |
| 152 | ![structure] |
| 153 | ![structure] |

Example 152

(S)-5-(6-(Benzo[d]thiazol-6-ylamino)-4-((1-hydroxy-3-phenylpropan-2-yl)amino)pyridin-3-yl)-1,3,4-oxadiazole-2-carboxamide $^1$H NMR: 400 MHz, CD$_3$OD: δ 2.90-2.95 (m, 1H), 3.02-3.07 (m, 1H), 3.66-3.74 (m, 2H), 3.85-3.87 (m, 1H), 6.19 (s, 1H), 7.14-7.26 (m, 5H), 7.53 (dd, J=2.40, 8.80 Hz, 1H), 7.98-8.02 (m, 1H), 8.36 (d, J=2.40 Hz, 1H), 8.62 (s, 1H), 9.12 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.682 min; LCMS (ES-API), m/z 488.4 (M+H). HPLC: XBridge Phenyl (150× 4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.579 min; Purity: 88.1%.

Example 153

5-(6-((3,3-Difluoro-1-methyl-2-oxoindolin-5-yl)amino)-4-(isopropylamino)pyridin-3-yl)-1,3,4-oxadiazole-2-carboxamide $^1$H NMR: 400 MHz, DMSO-d$_6$: δ 1.30 (d, J=6.40 Hz, 6H), 3.18 (s, 3H), 3.70-3.77 (m, 1H), 6.09 (s, 1H), 7.19 (d, J=8.40 Hz, 1H), 7.52 (bs, 1H), 7.68 (d, J=8.80 Hz, 1H), 8.14 (s, 1H), 8.26 (s, 1H), 8.58-8.61 (m, 2H), 9.47 (bs, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.75 min; LCMS (ES-API), m/z 444.2 (M+H). HPLC: XBridge Phenyl (150×4.6 mm), 3.5 micron;

Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 7.321 min; Purity: 98.4%.

TABLE 11

| Example No. | R₁ | R₂ |
|---|---|---|
| 154 | 6-aminobenzothiazole | CH(CH₃)—CH₂OH (structure shown) |
| 155 | 6-aminobenzothiazole | C(CH₃)₂—CH₂OH (structure shown) |
| 156 | 6-aminobenzothiazole | C(CH₃)₂—OH (structure shown) |

Example 154

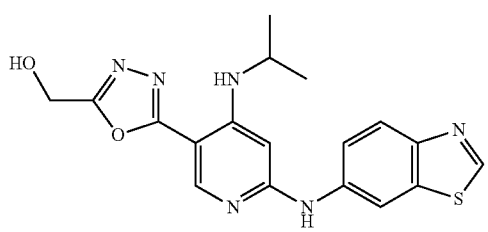 [SMILES: CC(C)Nc1cc(Nc2ccc3ncsc3c2)ncc1-c1nnc(CO)o1]

Synthesis of (5-(6-(benzo[d]thiazol-6-ylamino)-4-(isopropylamino)pyridin-3-yl)-1,3,4-oxadiazol-2-yl)methanol: A solution of methyl 5-(6-(benzo[d]thiazol-6-ylamino)-4-(isopropylamino)pyridin-3-yl)-1,3,4-oxadiazole-2-carboxylate (200 mg) in THF (10 mL):MeOH (10 mL) was cooled to 0° C. Added LiBH₄ (3 equiv.) in portions to the reaction mixture, stirred for 30 min at 0° C. Gradually the reaction temperature was raised to room temperature and stirred for 30 min. The reaction was quenched using ice pieces. The reaction mass was concentrated under reduced pressure. The residue obtained was diluted with EtOAc. The organic layer was washed with water. The organic layer was collected, dried over Na₂SO₄, filtered and concentrated. The crude material obtained was purified by prep HPLC to afford the desired compound, (5-(6-(benzo[d]thiazol-6-ylamino)-4-(isopropylamino)pyridin-3-yl)-1,3,4-oxadiazol-2-yl)methanol. ¹H NMR: 400 MHz, DMSO-d₆: δ 657.15 (d, J=524681.20 Hz, 6H), 3.71-3.79 (m, 1H), 4.71 (d, J=6.40 Hz, 2H), 5.93 (t, J=6.40 Hz, 1H), 6.21 (s, 1H), 7.36-7.38 (m, 1H), 7.52 (d, J=7.20 Hz, 1H), 7.61 (dd, J=2.00, 8.80 Hz, 1H), 7.97 (d, J=8.80 Hz, 1H), 8.49 (s, 1H), 8.65 (d, J=2.00 Hz, 1H), 9.17 (s, 1H), 9.44 (s, 1H). LC/MS: XBridge Phe 8, 4.6×30 mm, 3.5 µm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.454 min; LCMS (ES-API), m/z 383.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 5.528 min; Purity: 85.66%.

Example 155

Synthesis of 2-(5-(6-(benzo[d]thiazol-6-ylamino)-4-(isopropylamino)pyridin-3-yl)-1,3,4-oxadiazol-2-yl)ethanol: Followed the same procedure as mentioned in the synthesis of Example 154, using appropriate starting materials. ¹H NMR: 400 MHz, CD₃OD: δ 1.36 (d, J=6.40 Hz, 6H), 3.17 (t, J=6.40 Hz, 2H), 3.79-3.85 (m, 1H), 4.03 (t, J=6.40 Hz, 2H), 6.18 (s, 1H), 7.56 (dd, J=2.40, 8.80 Hz, 1H), 7.99 (d, J=8.80 Hz, 1H), 8.45 (d, J=2.00 Hz, 1H), 8.52 (s, 1H), 9.09 (s, 1H). LC/MS: Ascentis Express C18, 5×2.1 mm, 2.7 µm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.641 min; LCMS (ES-API), m/z 396.9 (M−H). HPLC: XBridge (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 µL/min; Retention time: 6.196 min; Purity: 97%.

Example 156

Synthesis of 2-(5-(6-(benzo[d]thiazol-6-ylamino)-4-(isopropylamino)pyridin-3-yl)-1,3,4-oxadiazol-2-yl)propan-2-ol: To a solution methyl 5-(6-(benzo[d]thiazol-6-ylamino)-4-(isopropylamino)pyridin-3-yl)-1,3,4-oxadiazole-2-carboxylate (150 mg) in dry Tetrahydrofuran (10 mL) was added methyl magnesium bromide (3 equiv.) (3.0 M in diethyl ether) at −78° C. Reaction mixture was allowed to warm up to 25° C. over 2 h. The reaction mixture was cooled to 0° C. and quenched by the addition of saturated aqueous NH₄Cl solution dropwise. Extracted with ethyl acetate, dried over Na₂SO₄, filtered and concentrated to get the crude product, which was purified by flash column using ethyl acetate/hexanes as eluent to furnish 2-(5-(6-(benzo[d]thiazol-6-ylamino)-4-(isopropylamino)pyridin-3-yl)-1,3,4-oxadiazol-2-yl)propan-2-ol. ¹H NMR: 400 MHz, DMSO-d₆: δ 1.30 (d, J=6.40 Hz, 6H), 1.61 (s, 6H), 3.71-3.79 (m, 1H), 5.89 (s, 1H), 6.20 (s, 1H), 7.51 (d, J=6.80 Hz, 1H), 7.60 (dd, J=2.00, 8.80 Hz, 1H), 7.97 (d, J=8.80 Hz, 1H), 8.54 (s, 1H), 8.68 (d, J=2.40 Hz, 1H), 9.17 (s, 1H), 9.45 (s, 1H). LC/MS: Ascentis Express C18, 5×2.1 mm, 2.7 µm; Solvent A=2% ACN: 98% H₂O: 10 mM NH₄COOH; Solvent B=98% ACN: 2% H₂O: 10 mM NH₄COOH; gradient 0-100% B over 1.5 min; retention time: 1.788 min; LCMS (ES-API), m/z 409.2 (M−H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 30 min (36 min run time); Flow rate: 1.0 µL/min; Retention time: 11.704 min; Purity: 98.6%.

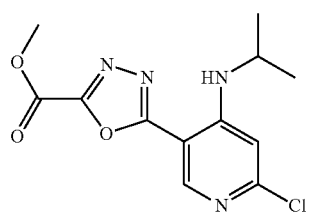 [SMILES: COC(=O)c1nnc(-c2cnc(Cl)cc2NC(C)C)o1]

Synthesis of methyl 5-(6-chloro-4-(isopropylamino)pyridin-3-yl)-1,3,4-oxadiazole-2-carboxylate (66): Followed the same procedure as mentioned in the synthesis of compound no 65. LC/MS: Purospher@star RP-18, 4×55 mm, 3 μm; Solvent A=10% ACN: 90% $H_2O$: 20 mM $NH_4OAc$; Solvent B=90% ACN: 10% $H_2O$: 20 mM $NH_4COOAc$; gradient 0-100% B over 1.5 min (3.2 min run time); retention time: 1.821 min; LCMS (ES-API), m/z 297.2 (M+H).

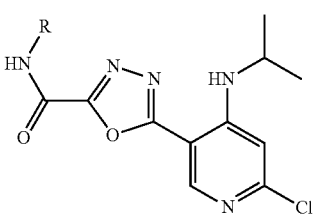

Synthesis of (5-(6-chloro-4-(isopropylamino)pyridin-3-yl)-1,3,4-oxadiazol-2-yl)(morpholino)methanone (67): A solution of methyl 5-(6-chloro-4-(isopropylamino)pyridin-3-yl)-1,3,4-oxadiazole-2-carboxylate (66) (150 mg, 0.51 mmol) in morpholine (1 mL) and MeOH (1 mL) was heated at 80° C. for 2 h. The reaction mass was concentrated under reduced pressure. The crude material obtained was triturated with diethyl ether and filtered to get the desired compound, (5-(6-chloro-4-(isopropylamino)pyridin-3-yl)-1,3,4-oxadiazol-2-yl)(morpholino)methanone. LC/MS: Acquity BEH C18 2.1×50 mm, 1.8 micron; Solvent A=0.1% TFA in water; Solvent B=0.1% TFA in ACN; gradient 0-100% B over 2 min; retention time: 0.88 min; LCMS (ES-API), m/z 352.7 (M+H).

TABLE 12

TABLE 12-continued

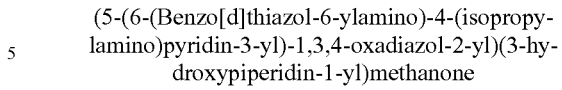

| Example No. | R | R₁ |
|---|---|---|
| 167 | 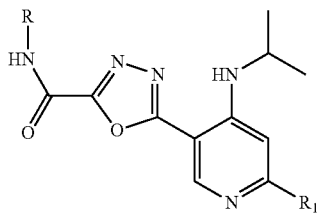 | |

Example 157

Synthesis of (5-(6-(benzo[d]thiazol-6-ylamino)-4-(isopropylamino)pyridin-3-yl)-1,3,4-oxadiazol-2-yl)(morpholino)methanone: To solution of (5-(6-chloro-4-(isopropylamino)pyridin-3-yl)-1,3,4-oxadiazol-2-yl)(morpholino)methanone in dioxane (5 mL):H₂O (1 mL), 6-amino benzothiazole (1.2 equiv.), xanthphos (0.5 equiv.) and Na₂CO₃ (3 equiv.) were added and degassed for 10 min. To the reaction mixture Pd₂(dba)₃ (0.5 equiv.) was added and degassed again for 10 min. It was then heated at 115° C., overnight. The reaction mass was cooled and filtered through small pad of celite. The filtrate obtained was concentrated to provide crude material. The crude material was purified by column chromatography through silica gel (230-400 mesh) and MeOH:CHCl₃ as eluent. It was further purified by prep HPLC to afford the title compound. ¹H NMR: 400 MHz, CD₃OD: δ 1.31-1.38 (m, 6H), 3.81-3.86 (m, 7H), 4.19-4.22 (m, 2H), 6.19 (s, 1H), 7.57 (dd, J=2.00, 8.60 Hz, 1H), 7.66-7.68 (m, 1H), 7.99 (d, J=8.80 Hz, 1H), 8.48 (d, J=2.00 Hz, 1H), 8.63 (s, 1H), 9.10 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.604 min; LCMS (ES-API), m/z 463.8 (M−H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 6.224 min; Purity: 98.3%.

Synthesis of Examples 158-167: Followed the same method as mentioned for Example 157, using appropriate amines Example 158

(5-(6-(Benzo[d]thiazol-6-ylamino)-4-(isopropylamino)pyridin-3-yl)-1,3,4-oxadiazol-2-yl)(3-hydroxypiperidin-1-yl)methanone ¹H NMR: 400 MHz, CD₃OD: δ 1.37 (d, J=6.40 Hz, 6H), 1.63-1.73 (m, 2H), 1.97-2.06 (m, 2H), 3.74-3.87 (m, 4H), 4.15-4.16 (m, 1H), 6.19 (s, 1H), 7.56 (dd, J=2.00, 7.20 Hz, 1H), 7.67 (d, J=7.20 Hz, 1H), 7.98 (d, J=8.80 Hz, 1H), 8.48 (s, 1H), 8.62 (s, 1H), 9.09 (s, 1H). LC/MS: ZORBAX SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.48 min; LCMS (ES-API), m/z 480.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.95 min; Purity: 98.8%.

Example 159

4-((4-(Isopropylamino)-5-(5-(piperazine-1-carbonyl)-1,3,4-oxadiazol-2-yl)pyridin-2-yl)amino)benzonitrile ¹H NMR: 400 MHz, DMSO-d₆: δ 1.32 (d, J=6.40 Hz, 6H), 3.23-3.32 (m, 4H), 3.76-3.81 (m, 1H), 3.89 (m, 2H), 4.22 (m, 2H), 6.29 (s, 1H), 7.55-7.57 (m, 1H), 7.70-7.72 (m, 2H), 7.88-7.90 (m, 2H), 8.55 (s, 1H), 8.81 (bs, 1H), 9.81 (s, 1H). LC/MS: Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.552 min; LCMS (ES-API), m/z 431.2 (M−H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.062 min; Purity: 96.8%.

Example 160

4-((5-(5-(4-Hydroxypiperidine-1-carbonyl)-1,3,4-oxadiazol-2-yl)-4-(isopropylamino)pyridin-2-yl)amino)benzonitrile ¹H NMR: 400 MHz, DMSO-d₆: δ 1.32 (d, J=6.40 Hz, 6H), 1.43-1.51 (m, 2H), 1.84-1.86 (m, 2H), 3.37-3.43 (m, 1H), 3.58-3.64 (m, 1H), 3.76-3.85 (m, 2H), 3.98-4.04 (m, 1H), 4.12-4.18 (m, 1H), 4.86 (d, J=4.00 Hz, 1H), 6.27 (s, 1H), 7.57 (d, J=6.80 Hz, 1H), 7.70-7.72 (m, 2H), 7.87-7.89 (m, 2H), 8.53 (s, 1H), 9.76 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.552 min; LCMS (ES-API), m/z 448.0 (M+H). HPLC: XBridge (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 7.235 min; Purity: 99.6%.

Example 161

(4-Aminopiperidin-1-yl)(5-(6-(benzo[d]thiazol-6-ylamino)-4-(isopropylamino)pyridin-3-yl)-1,3,4-oxadiazol-2-yl)methanone $^1$H NMR: 400 MHz, CD$_3$OD: δ 1.37 (d, J=6.00 Hz, 6H), 1.62-1.76 (m, 2H), 2.14-2.20 (m, 2H), 3.04-3.10 (m, 1H), 3.33-3.51 (4H, merged with water peak), 3.83-3.86 (m, 1H), 6.20 (s, 1H), 7.57 (dd, J=2.00, 8.80 Hz, 1H), 8.00 (d, J=8.80 Hz, 1H), 8.47 (d, J=2.00 Hz, 1H), 8.63 (s, 1H), 9.11 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.434 min; LCMS (ES-API), m/z 479.0 (M+H). HPLC: XBridge Phenyl (150× 4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 5.613 min; Purity: 99.4%.

Example 162

(5-(6-(Benzo[d]thiazol-6-ylamino)-4-(isopropylamino)pyridin-3-yl)-1,3,4-oxadiazol-2-yl)(4-hydroxypiperidin-1-yl)methanone $^1$H NMR: 400 MHz, CD$_3$OD: δ 1.36-1.38 (m, 6H), 1.62-1.68 (m, 2H), 2.00-2.03 (m, 2H), 3.49-3.55 (m, 1H), 3.75-3.86 (m, 2H), 3.96-4.01 (m, 1H), 4.18-4.24 (m, 1H), 4.41-4.47 (m, 1H), 6.19 (s, 1H), 7.56 (dd, J=2.40, 8.80 Hz, 1H), 7.67 (d, J=7.20 Hz, 1H), 7.98 (d, J=8.80 Hz, 1H), 8.48 (d, J=2.00 Hz, 1H), 8.62 (s, 1H), 9.09 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.494 min; LCMS (ES-API), m/z 480.0 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.723 min; Purity: 97.5%.

Example 163

5-(6-((4-Cyanophenyl)amino)-4-(isopropylamino)pyridin-3-yl)-N-(2-hydroxyethyl)-1,3,4-oxadiazole-2-carboxamide $^1$H NMR: 400 MHz, CD$_3$OD: δ 1.37-1.39 (m, 6H), 3.50-3.60 (m, 1H), 3.75-3.84 (m, 4H), 6.24 (s, 1H), 7.62-7.64 (m, 2H), 7.80-7.82 (m, 2H), 7.92 (s, 1H), 8.70 (s, 1H). LC/MS: Purospher@star RP-18, 4×55 mm, 3 μm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 1.58 min; LCMS (ES-API), m/z 406.2 (M−H). HPLC: Purospher RP18 (4.6× 150 mm), 3 micron; Solvent A=20 mM NH4COOAc; Solvent=ACN; Flow rate: 1.0 mL/min; Retention time: 8.905 min; Purity: 95.7%.

Example 164

5-(6-((4-Cyanophenyl)amino)-4-(isopropylamino)pyridin-3-yl)-N-(2-fluoro-3-hydroxypropyl)-1,3,4-oxadiazole-2-carboxamide $^1$H NMR: 400 MHz, DMSO-d$_6$: δ 1.32 (d, J=6.40 Hz, 6H), 3.50-3.68 (m, 4H), 3.70-3.80 (m, 1H), 4.61-4.77 (m, 1H), 5.05 (t, J=5.60 Hz, 1H), 6.26 (s, 1H), 7.49 (d, J=7.20 Hz, 1H), 7.69-7.71 (m, 2H), 7.86-7.89 (m, 2H), 8.66 (s, 1H), 9.40 (t, J=6.00 Hz, 1H), 9.77 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.389 min; LCMS (ES-API), m/z 440.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.446 min; Purity: 95.2%.

Example 165

4-((5-(5-(4-Aminopiperidine-1-carbonyl)-1,3,4-oxadiazol-2-yl)-4-(isopropylamino)pyridin-2-yl)amino)benzonitrile $^1$H NMR: 400 MHz, DMSO-d$_6$: δ 1.32 (d, J=6.40 Hz, 6H), 1.42-1.58 (m, 2H), 1.97-2.04 (m, 2H), 3.01-3.07 (m, 1H), 3.31-3.38 (2H, merged with water peak), 3.74-3.82 (m, 1H), 4.42-4.52 (m, 2H), 6.28 (s, 1H), 7.05 (bs, 2H), 7.54-7.56 (m, 1H), 7.69-7.71 (m, 2H), 7.87-7.89 (m, 2H), 8.52 (s, 1H), 9.80 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.289 min; LCMS (ES-API), m/z 447.2 (M+H). HPLC: XBridge Phenyl (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.118 min; Purity: 99.2%.

Example 166

5-(6-((4-Cyanophenyl)amino)-4-(isopropylamino)pyridin-3-yl)-N-(3-hydroxypropyl)-1,3,4-oxadiazole-2-carboxamide $^1$H NMR: 400 MHz, DMSO-d$_6$: δ 1.32 (d, J=6.00 Hz, 6H), 1.69-1.76 (m, 2H), 3.31-3.40 (2H, merged with water peak), 3.47-3.52 (m, 2H), 3.73-3.79 (m, 1H), 4.53-4.55 (m, 1H), 6.26 (s, 1H), 7.50 (d, J=7.20 Hz, 1H), 7.69-7.71 (m, 2H), 7.86-7.89 (m, 2H), 8.65 (s, 1H), 9.15-9.20 (m, 1H), 9.77 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.733 min; LCMS (ES-API), m/z 420.0 (M−H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.282 min; Purity: 97.2%.

Example 167

5-(6-(Benzo[d]thiazol-6-ylamino)-4-(isopropylamino)pyridin-3-yl)-N-methyl-1,3,4-oxadiazole-2-carboxamide $^1$H NMR: 400 MHz, CD$_3$OD: δ 1.36 (d, J=6.40 Hz, 6H), 3.00 (s, 3H), 3.79-3.87 (m, 1H), 6.19 (s, 1H), 7.56 (dd, J=2.40, 8.80 Hz, 1H), 7.66-7.67 (m, 1H), 7.99 (d, J=8.80 Hz, 1H), 8.47 (d, J=2.40 Hz, 1H), 8.65 (s, 1H), 9.09 (s, 1H). LC/MS:

XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.515 min; LCMS (ES-API), m/z 410.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 5.921 min; Purity: 97.3%.

Example 168

4-((5-(5-(4-Acetylpiperazine-1-carbonyl)-1,3,4-oxadiazol-2-yl)-4-(isopropylamino)pyridin-2-yl)amino)benzonitrile Prepared following similar procedures as mentioned for the synthesis of Example 157. ¹H NMR: 400 MHz, DMSO-d₆: δ 1.32 (d, J=6.40 Hz, 6H), 2.06 (s, 3H), 3.59-3.81 (m, 7H), 3.94-4.02 (m, 2H), 6.28 (s, 1H), 7.55-7.57 (m, 1H), 7.69-7.71 (m, 2H), 7.86-7.89 (m, 2H), 8.54 (s, 1H), 9.79 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.576 min; LCMS (ES-API), m/z 473.0 (M–H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 6.646 min; Purity: 97.9%.

Example 169

N-(1-(5-(6-(Benzo[d]thiazol-6-ylamino)-4-(isopropylamino)pyridin-3-yl)-1,3,4-oxadiazole-2-carbonyl)piperidin-4-yl)acetamide Prepared following similar procedures as mentioned for the synthesis of Example 157. ¹H NMR: 400 MHz, CD₃OD: δ 1.37 (d, J=6.40 Hz, 6H), 1.53-1.65 (m, 2H), 1.97 (s, 3H), 2.08-2.20 (m, 2H), 3.14-3.21 (m, 1H), 3.48-3.54 (m, 1H), 3.82-3.86 (m, 1H), 4.04-4.05 (m, 1H), 4.56-4.59 (m, 1H), 4.74-4.86 (1H, merged with CD₃OD peak), 6.19 (s, 1H), 7.57 (dd, J=2.40, 8.80 Hz, 1H), 7.99 (d, J=8.80 Hz, 1H), 8.48 (d, J=2.00 Hz, 1H), 8.62 (s, 1H), 9.10 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.487 min; LCMS (ES-API), m/z 521.0 (M+H). HPLC: XBridge Phenyl (150×4 6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 6.617 min; Purity: 91.6%.

Example 170

N-(1-(5-(6-(Benzo[d]thiazol-6-ylamino)-4-(isopropylamino)pyridin-3-yl)-1,3,4-oxadiazole-2-carbonyl)piperidin-4-yl)methanesulfonamide Prepared following similar procedures as mentioned for the synthesis of Example 157. ¹H NMR: 400 MHz, DMSO-d₆: δ 1.32 (d, J=6.40 Hz, 6H), 1.43-1.59 (m, 2H), 1.95-2.02 (m, 2H), 2.98 (s, 3H), 3.13-3.19 (m, 1H), 3.42-3.56 (m, 2H), 3.74-3.82 (m, 1H), 4.29-4.33 (m, 1H), 4.40-4.43 (m, 1H), 6.22 (s, 1H), 7.25 (d, J=7.20 Hz, 1H), 7.51 (d, J=6.80 Hz, 1H), 7.62 (dd, J=2.00, 8.80 Hz, 1H), 7.98-8.00 (m, 1H), 8.53 (s, 1H), 8.66 (d, J=2.00 Hz, 1H), 9.19 (s, 1H), 9.52 (s, 1H). LC/MS: XBridge Phe 8, 4.6×30 mm, 3.5 μm; Solvent A=2% ACN: 98% H₂O: 10 mM NH₄COOH; Solvent B=98% ACN: 2% H₂O: 10 mM NH₄COOH; gradient 0-100% B over 1.5 min (3.2 min run time); retention time: 1.557 min; LCMS (ES-API), m/z 557.0 (M+H). HPLC: XBridge Phenyl (150× 4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μL/min; Retention time: 7.261 min; Purity: 98.07%.

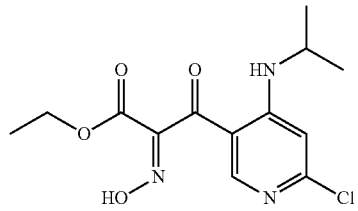 [SMILES: CCOC(=O)/C(=N\O)C(=O)c1cnc(Cl)cc1NC(C)C]

Synthesis of ethyl 2-(6-chloro-4-(isopropylamino)nicotinamido)-2-(hydroxyimino)acetate (69): A stirred solution of 6-chloro-4-(isopropylamino)nicotinic acid (2) in DCM (15 mL) was cooled to 0° C., oxalyl chloride (2 equiv) was added, followed by addition of 2 drops of DMF. The reaction mixture was stirred at room temperature for 2 h. The reaction mixture was concentrated to remove excess of oxalyl chloride. The acyl chloride, generated in-situ was dissolved in DCM and added dropwise to a cool stirred solution of ethyl 2-amino oxamate (1.5 equiv.) and Et₃N (5 equiv.) in DCM. The reaction temperature was slowly brought to room temperature and stirred for 2 h. The reaction mixture was diluted with DCM and washed with water, followed by brine solution. The DCM layer was collected, dried over Na₂SO₄, filtered and concentrated. The crude material of ethyl 2-(6-chloro-4-(isopropylamino)nicotinamido)-2-(hydroxyimino)acetate obtained was taken to next step as such without purification.

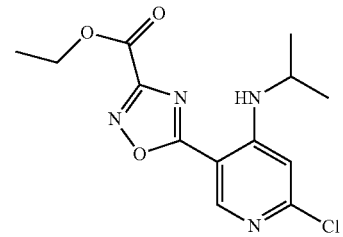 [SMILES: CCOC(=O)c1noc(-c2cnc(Cl)cc2NC(C)C)n1]

Synthesis of ethyl 5-(6-chloro-4-(isopropylamino)pyridin-3-yl)-1,2,4-oxadiazole-3-carboxylate (69): A solution of 2-(6-chloro-4-(isopropylamino)nicotinamido)-2-(hydroxyimino)acetate (68) (800 mg) in DMF (15 mL) was heated at 150° C. for 3 h. The reaction mixture was concentrated. The crude material obtained was purified by column chromatography through silica gel and MeOH:DCM to afford ethyl 5-(6-chloro-4-(isopropylamino)pyridin-3-yl)-1,2,4-oxadiazole-3-carboxylate.

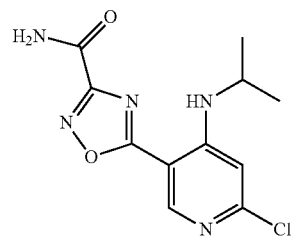 [SMILES: CC(C)Nc1cc(Cl)ncc1-c1nc(C(N)=O)no1]

Synthesis of 5-(6-chloro-4-(isopropylamino)pyridin-3-yl)-1,2,4-oxadiazole-3-carboxamide (70): Followed the same procedure as mentioned in the synthesis of Example 87.

Example 171

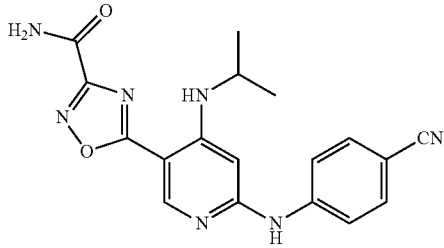 [SMILES: CC(C)Nc1cc(Nc2ccc(C#N)cc2)ncc1-c1nc(C(N)=O)no1]

Synthesis of 5-(6-((4-cyanophenyl)amino)-4-(isopropylamino)pyridin-3-yl)-1,2,4-oxadiazole-3-carboxamide: A solution of 5-(6-chloro-4-(isopropylamino)pyridin-3-yl)-1,2,4-oxadiazole-3-carboxamide (70) (200 mg, 0.7 mmol) in NMP (2 mL) was treated with dioxan.HCl (4 mL) and heated in a closed condition at 150° C. for overnight. The reaction mixture was diluted with EtOAc and was quenched with ice cool water. The EtOAc layer was then washed with sat-.NaHCO$_3$ solution. The organic layer was collected, dried over Na$_2$SO$_4$, filtered and concentrated. The crude material obtained was purified by prep HPLC to afford 5-(6-((4-cyanophenyl)amino)-4-(isopropylamino)pyridin-3-yl)-1,2,4-oxadiazole-3-carboxamide. $^1$H NMR: 400 MHz, CD$_3$OD: δ 1.42 (d, J=6.80 Hz, 6H), 3.89-3.95 (m, 1H), 6.33 (s, 1H), 7.64-7.66 (m, 2H), 7.76-7.78 (m, 2H), 8.71 (s, 1H). LC/MS: XBridge Phe 8, 4.6×30 mm, 3.5 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min (3.2 min run time); retention time: 1.543 min; LCMS (ES-API), m/z 364.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μL/min; Retention time: 6.744 min; Purity: 98.4%.

Example 172

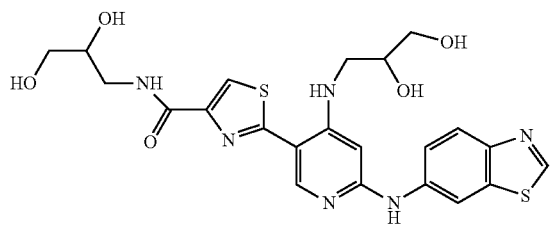 [SMILES: O=C(NCC(O)CO)c1csc(-c2cnc(Nc3ccc4ncsc4c3)cc2NCC(O)CO)n1]

Synthesis of 2-(6-(benzo[d]thiazol-6-ylamino)-4-(2,3-dihydroxypropylamino)pyridin-3-yl)-N-(2,3-dihydroxypropyl)thiazole-4-carboxamide: Example 172 was prepared in a similar fashion as Example 24 using appropriate substitutions.

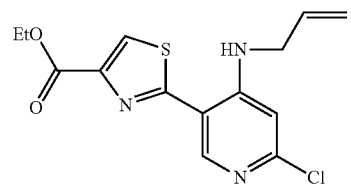 [SMILES: C=CCNc1cc(Cl)ncc1-c1nc(C(=O)OCC)cs1]

$^1$H NMR [ethyl 2-(4-(allylamino)-6-chloropyridin-3-yl)thiazole-4-carboxylate (71)]: 400 MHz, DMSO-d$_6$: δ 1.34 (t, J=7.20 Hz, 3H), 4.02-4.05 (m, 2H), 4.35 (q, J=6.80 Hz, 2H), 5.28 (dd, J=1.20, 10.60 Hz, 1H), 5.45 (dd, J=1.20, 17.40 Hz, 1H), 5.98-6.07 (m, 1H), 6.86 (s, 1H), 8.61 (d, J=4.80 Hz, 1H), 9.31-9.33 (m, 1H).

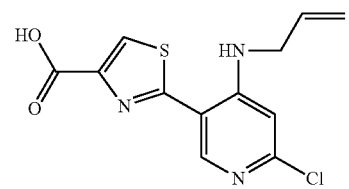 [SMILES: C=CCNc1cc(Cl)ncc1-c1nc(C(=O)O)cs1]

LC/MS [2-(4-(allylamino)-6-chloropyridin-3-yl)thiazole-4-carboxylic acid (72)]: Acquity BEH C18 2.1×50 mm, 1.8 micron; Solvent A=0.1% TFA in water; Solvent B=0.1% TFA in ACN; gradient 0-100% B over 2 min; retention time: 0.72 min; LCMS (ES-API), m/z 296.3 (M+H).

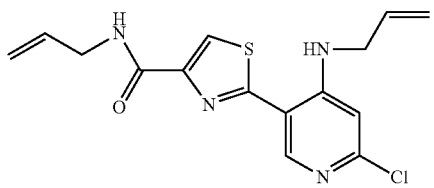 [SMILES: C=CCNC(=O)c1csc(-c2cnc(Cl)cc2NCC=C)n1]

LC/MS [N-allyl-2-(4-(allylamino)-6-chloropyridin-3-yl)thiazole-4-carboxamide (73)]: Acquity BEH C18 2.1×50 mm, 1.8 micron; Solvent A=0.1% TFA in water; Solvent B=0.1% TFA in ACN; gradient 0-100% B over 2 min; retention time: 0.83 min; LCMS (ES-API), m/z 335.4 (M+H).

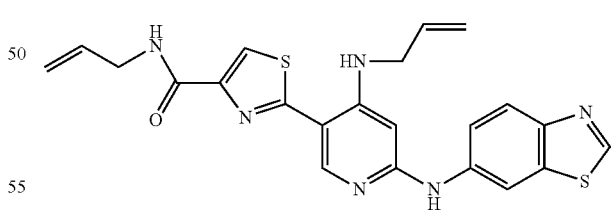

LC/MS [N-allyl-2-(4-(allylamino)-6-(benzo[d]thiazol-6-ylamino)pyridin-3-yl)thiazole-4-carboxamide (74)]: Acquity BEH C18 2.1×50 mm, 1.8 micron; Solvent A=0.1% TFA in water; Solvent B=0.1% TFA in ACN; gradient 0-100% B over 2 min; retention time: 0.74 min; LCMS (ES-API), m/z 449.3 (M+H).

To a stirred solution of N-allyl-2-(4-(allylamino)-6-(benzo[d]thiazol-6-ylamino)pyridin-3-yl)thiazole-4-carboxamide (74) (90 mg, 0.201 mmol) in mixed solvents acetone (7 mL) and water (2 mL) was added Osmium Tetraoxide (6.37 mmol, 0.032 equiv.) at −78° C. After being stirred for 10 min, N-methyl morpholine oxide (NMO) (1.204 mmol, 6 equiv.) was added to the reaction mixture in two portions at 30 min interval. The reaction mixture was quenched with a pinch of NaHSO$_3$, and concentrated to give crude material. The crude material obtained was purified by prep HPLC to furnish the title compound 2-(6-(benzo[d]thiazol-6-ylamino)-4-((2,3-dihydroxypropyl)amino)pyridin-3-yl)-N-(2,3-dihydroxypropyl)thiazole-4-carboxamide. $^1$H NMR: 400 MHz, DMSO-d$_6$: δ 3.25 (2H, merged with water peak), 3.85 (3H, merged with water peak), 3.44-3.53 (m, 3H), 3.66-3.68 (m, 1H), 3.89-3.92 (m, 1H), 4.67 (s, 1H), 4.91-5.01 (m, 2H), 5.45 (s, 1H), 6.14 (s, 1H), 7.59 (dd, J=2.00, 8.80 Hz, 1H), 7.96 (d, J=8.80 Hz, 1H), 8.09-8.16 (m, 2H), 8.51 (s, 1H), 8.70 (d, J=2.40 Hz, 1H), 8.99-9.03 (m, 1H), 9.16 (s, 1H), 9.37 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.205 min; LCMS (ES-API), m/z 517.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μL/min; Retention time: 8.085 min; Purity: 96.2%.

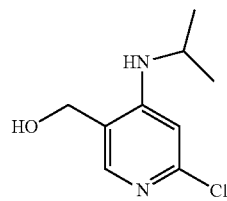

Synthesis of (6-chloro-4-(isopropylamino)pyridin-3-yl)methanol (75): To a stirred solution of ethyl 6-chloro-4-(isopropylamino)nicotinate (2) (1 g, 4.12 mmol) in dry DCM (30 mL), DIBAL-H (8.24 mmol, 2 equiv.) (1.0 M in DCM) was added dropwise at −78° C. The reaction mixture was stirred at −78° C. for 2 h, gradually, the reaction was allowed to warm up to −10° C. over 1 h. The reaction mixture was quenched with saturated solution of sodium potassium tarterate and allowed to stir at room temperature. The reaction mixture was filtered through a small pad of celite. The filtrate was washed with brine solution, dried over Na$_2$SO$_4$, filtered and concentrated to give crude alcohol. The crude material obtained was purified by flash column chromatography through silica gel and MeOH:CHCl$_3$ as eluent to afford (6-chloro-4-(isopropylamino)pyridin-3-yl)methanol. LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 0.806 min; LCMS (ES-API), m/z 201.0 (M+H).

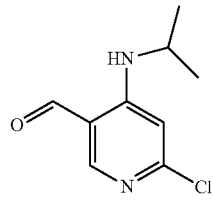

Synthesis of 6-chloro-4-(isopropylamino)nicotinaldehyde (76): To a stirred solution of DMSO (13.43 mmol, 3.5 equiv.) in dry DCM (30 mL), oxalyl chloride (11.51 mmol, 3 equiv.) was added at −78° C. After being stirred for 20 min, (6-chloro-4-(isopropylamino)pyridin-3-yl)methanol (75) (770 mg, 3.84 mmol) was added to the above reaction mixture at −78° C. and stirred for 2 h. The reaction mixture was allowed to warm up to −20° C. and added Et$_3$N (19.19 mmol, 5 equiv.) dropwise over a period of 5 mins. The reaction mixture was allowed to warm up to 0° C. over 30 mins and quenched with ice-flakes followed by 10% NaHCO$_3$ solution. The organic layer was separated, aqueous layer was extracted with DCM (twice). The organic layers were collected together, dried over Na$_2$SO$_4$, filtered and concentrated to give crude aldehyde. The crude material obtained was purified by column chromatography through silica gel and EtOAc:pet ether as eluent provided the desired compound, 6-chloro-4-(isopropylamino)nicotinaldehyde. LC/MS: Acquity BEH C18 2.1×50 mm, 1.8 micron; Solvent A=0.1% TFA in water; Solvent B=0.1% TFA in ACN; gradient 0-100% B over 2 min; retention time: 0.76 min; LCMS (ES-API), m/z 199.26 (M+H).

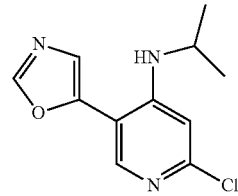 [SMILES: CC(C)Nc1cc(Cl)ncc1-c1cnco1]

Synthesis of 2-chloro-N-isopropyl-5-(oxazol-5-yl)pyridin-4-amine (77): To a stirred solution of 6-chloro-4-(isopropylamino)nicotinaldehyde (76) (200 mg, 1.007 mmol) in MeOH (10 mL) was added TOSMIC (1.208 mmol, 1.2 equiv.) and K$_2$CO$_3$ (2.014 mmol, 2 equiv.) and refluxed for 4 h. The reaction mixture was concentrated under reduced pressure. The residue obtained was dissolved in DCM and washed with water. The organic layer dried over Na$_2$SO$_4$, filtered and concentrated to give crude oxazole compound. The crude material was purified by preparative TLC (eluted with 40% EtOAC:pet ether) to afford 2-chloro-N-isopropyl-5-(oxazol-5-yl)pyridin-4-amine $^1$H NMR: 400 MHz, DMSO-d$_6$: δ 1.19 (d, J=6.40 Hz, 6H), 3.80-3.85 (m, 1H), 5.98 (d, J=8.00 Hz, 1H), 6.76 (s, 1H), 7.52 (s, 1H), 8.09 (s, 1H), 8.50 (s, 1H).

Example 173

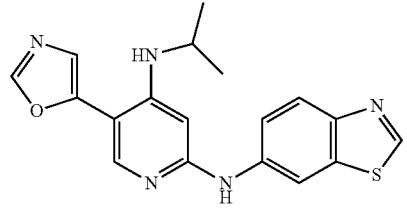 [SMILES: CC(C)Nc1cc(Nc2ccc3ncsc3c2)ncc1-c1cnco1]

Synthesis of N2-(benzo[d]thiazol-6-yl)-N4-isopropyl-5-(oxazol-5-yl)pyridine-2,4-diamine. Followed the procedure as mentioned in the synthesis of compound 3. $^1$H NMR: 400 MHz, DMSO-d$_6$: δ 1.25 (d, J=6.40 Hz, 6H), 3.63-3.70 (m, 1H), 5.39 (d, J=7.60 Hz, 1H), 6.16 (s, 1H), 7.36 (s, 1H), 7.58 (dd, J=2.40, 8.80 Hz, 1H), 7.94 (d, J=8.80 Hz, 1H), 8.07 (s, 1H), 8.42 (s, 1H), 8.72 (d, J=2.00 Hz, 1H), 9.14 (s, 1H), 9.23 (s, 1H) LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.379 min; LCMS (ES-API), m/z 352.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 30 min (36 min run time); Flow rate: 1.0 μL/min; Retention time: 5.518 min; Purity: 99.4%.

Example 174

(2S,3S)-3-((2-(Benzo[d]thiazol-6-ylamino)-5-(1H-1,2,4-triazol-5-yl)pyridin-4-yl)amino)-3-phenylpropane-1,2-diol

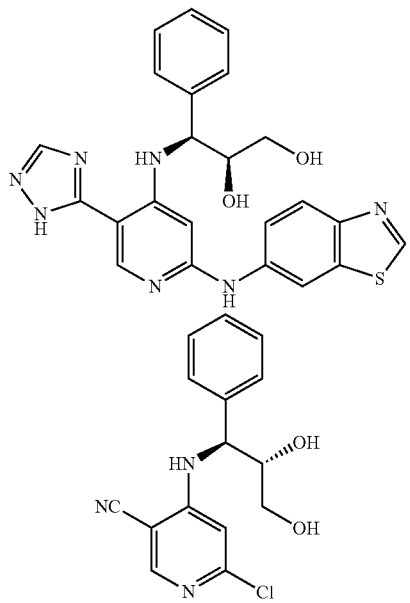

Step 1: A mixture of 4,6-dichloronicotinonitrile (760 mg, 4.39 mmol), (2S,3S)-3-amino-3-phenylpropane-1,2-diol (780 mg, 4.66 mmol) (Pico, Anna; Moyano, Albert ARKIVOC (Gainesville, Fla., United States) (2007), (4), 132-156) and DIPEA (921 µL, 5.27 mmol) in DMA (4393 µL) was stirred at 50° C. for 2.5 hours after which LCMS indicated ~98% reaction completion. The vessel was cooled to room temperature and the dark solution was partitioned between ethyl acetate and water. The organic portion was washed with water and the combined aqueous layers were extracted with ethyl acetate. The organics were combined, dried over anhydrous sodium sulfate, filtered and concentrated. The mixture was dissolved in 2 mL of DCM and purified on a 40 G ISCO column using 5-100% EA/Heptane. Following concentration, the regioisomers were collected as isolates 01 and 02.

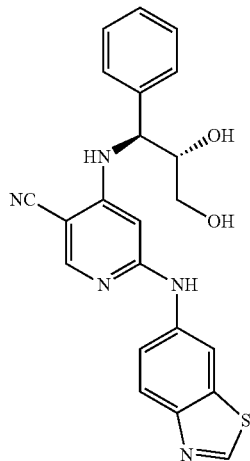 [SMILES: N#Cc1cnc(Nc2ccc3ncsc3c2)cc1N[C@@H](c1ccccc1)[C@H](O)CO]

Step 2: A mixture of 6-chloro-4-(((1S,2S)-2,3-dihydroxy-1-phenylpropylamino)nicotinonitrile (0.108 g, 0.356 mmol), benzo[d]thiazol-6-amine (0.187 g, 1.244 mmol) and NMP (1.422 mL) was stirred at 150° C. for 1 hour in a microwave reactor. The vessel was cooled to room temperature, diluted with water and filtered. Following drying on a buchner funnel, 6-(benzo[d]thiazol-6-ylamino)-4-((1S,2S)-2,3-dihydroxy-1-phenylpropylamino)nicotinonitrile (0.122 g, 0.292 mmol, 82% yield) was collected as a yellowish solid. LC-MS (m/z, M+1=418), Waters sunfire 4.6×50 mm C18 Sum 4 min/1 min hold time 0-100% (A-B) A=10% MeOH-90% water-0.1% TFA, B=90% MeOH-10% water-0.1% TFA RT=2.06.

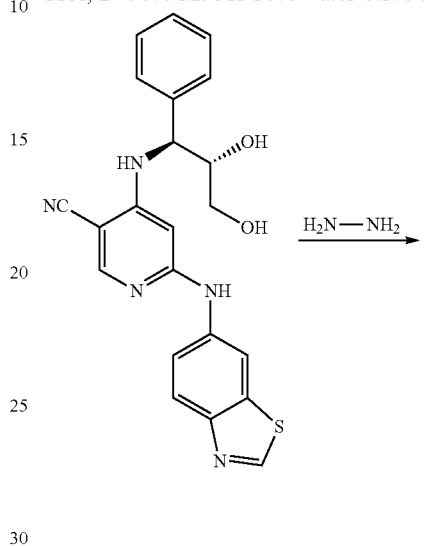

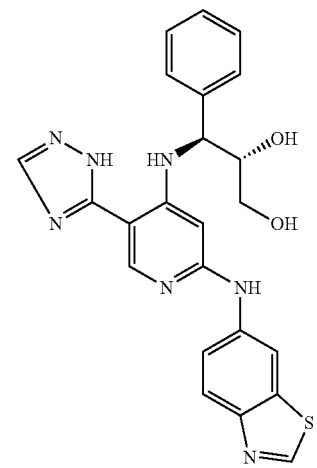

Step 3: In a tall reaction tube was added 6-(benzo[d]thiazol-6-ylamino)-4-((1S,2S)-2,3-dihydroxy-1-phenylpropylamino)nicotinonitrile (0.075 g, 0.180 mmol), THF (0.898 mL) and hydrazine (1.692 mL, 53.9 mmol). The reaction was heated to 95° C. for 16 hrs. The reaction was cooled and concentrated. MeOH (0.898 mL), formaldehyde (0.025 mL, 0.898 mmol) and trimethyl orthoformate (0.099 mL, 0.898 mmol) were added and the reaction stirred at rt overnight. The mixture was concentrated, dilute with DMF and filtered. Purification was done by HPLC using 40-100% MeOH/Water/TFA over 10 minutes. Following concentration, collected (2S,3S)-3-(2-(benzo[d]thiazol-6-ylamino)-5-(1H-1,2,4-triazol-5-yl)pyridin-4-ylamino)-3-phenylpropane-1,2-diol, TFA (0.004 g, 6.63 µmol, 3.69% yield) as a white solid. LC-MS (m/z, M+1=460), Waters sunfire 4.6×50 mm C18 Sum 4 min/1 min hold time 0-100% (A-B) A=10% MeOH-90% water-0.1% TFA, B=90% MeOH-10% water-0.1% TFA RT=2.2. $^1$H NMR (400 MHz, METHANOL-D3) d 9.32 (s, 1H), 8.64 (s, 1H), 8.44 (s, 1H), 8.09 (d, J=8.8 Hz, 1H), 7.84 (d, J=2.2 Hz, 1H), 7.39-7.22 (m, 7H), 5.98 (s, 1H), 4.75 (d, J=4.0 Hz, 1H), 4.11-4.04 (m, 1H), 3.50-3.42 (m, 1H), 3.41-3.34 (m, 1H).

Example 175

4-((5-(6-(Benzo[d]thiazol-6-ylamino)-4-(isopropylamino)pyridin-3-yl)-1,3,4-oxadiazol-2-yl)methyl)benzamide

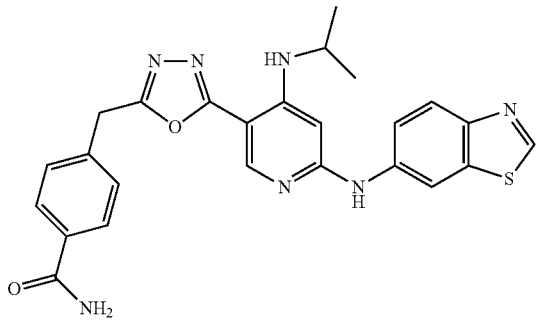 [SMILES: CC(C)Nc1cc(Nc2ccc3ncsc3c2)ncc1-c1nnc(Cc2ccc(C(N)=O)cc2)o1]

Example 175 was prepared according to the general methods outlined in Scheme 5. $^1$H NMR: 400 MHz, DMSO-$d_6$: δ 1.29 (d, J=6.40 Hz, 6H), 3.71-3.76 (m, 1H), 4.41 (s, 2H), 6.18 (s, 1H), 7.34 (s, 1H), 7.47-7.50 (m, 3H), 7.58 (dd, J=2.00, 8.80 Hz, 1H), 7.87-7.89 (m, 2H), 7.95-7.97 (m, 2H), 8.45 (s, 1H), 8.67 (d, J=2.00 Hz, 1H), 9.17 (s, 1H), 9.43 (s, 1H). LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.78 min; LCMS (ES-API), m/z 486.0 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 6.103 min; Purity: 97.6%.

Example 176

N6'-(Benzo[d]thiazol-6-yl)-N4'-isopropyl-6-methoxy-[2,3'-bipyridine]-4',6'-diamine

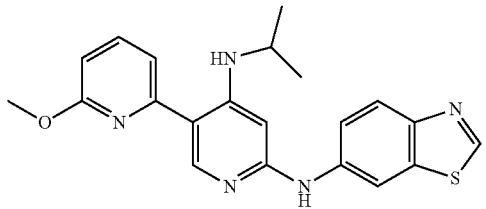 [SMILES: COc1cccc(-c2cnc(Nc3ccc4ncsc4c3)cc2NC(C)C)n1]

Step 1: 2-Chloro-5-iodo-N-isopropylpyridin-4-amine (0.25 g, 0.843 mmol), K$_2$CO$_3$ (0.350 g, 2.53 mmol), 6 methoxypyridine 2-boronic acid pinacol ester (0.396 g, 1.68 mmol) and PdCl$_2$(dppf) (0.069 g, 0.084 mmol) were taken in a sealed tube and dissolved in DMF (3 mL). The reaction mass was thoroughly purged with N$_2$ and sealed. The reaction mass was heated at 90° C. for 2 hours. The reaction was diluted with water, extracted with ethyl acetate (3×20 mL) and dried. The combined organic layers were concentrated. The residue was combined with a previously performed experiment and purified by column chromatography to obtain an off white solid (300 mg).

Step 2: 6'-Chloro-N-isopropyl-6-methoxy-[2,3'-bipyridin]-4'-amine (25 mg, 0.090 mmol), 6-aminobenzothiazole (20.28 mg, 0.135 mmol), BINAP (1.121 mg, 1.800 mmol), sodium tert-butoxide (26.0 mg, 0.270 mmol) were dissolved in Toluene (1 ml) in a sealed tube and thoroughly purged with N$_2$ for 5 minutes. Pd$_2$(dba)$_3$ (3.3 mg, 3.6 μmol) was added and the reaction mass was once again purged with N$_2$ for 5 minutes. The pressure tube was sealed and heated at 110° C. overnight. The reaction was cooled to rt and passed through a celite bed and washed with DCM. The filtrate was concentrated, dissolved in 10 mL water and extracted with DCM (3×8 mL). The combined organic layers were dried, concentrated and purified via preparative HPLC to afford Example 176. $^1$H NMR: 400 MHz, CD$_3$OD: δ 1.33 (d, J=6.40 Hz, 6H), 3.74-3.80 (m, 1H), 3.99 (s, 3H), 6.17 (s, 1H), 6.71 (d, J=8.00 Hz, 1H), 7.34 (d, J=7.60 Hz, 1H), 7.52 (dd, J=2.40, 8.80 Hz, 1H), 7.75 (t, J=8.00 Hz, 1H), 7.98 (d, J=8.80 Hz, 1H), 8.23 (s, 1H), 8.34 (s, 1H), 9.07 (s, 1H). LC/MS: ZORBAX SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.713 min; LCMS (ES-API), m/z 392.2 (M+H). HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 7.274 min; Purity: 98.1%.

Example 177

N2-(Benzo[d]thiazol-6-yl)-5-(1H-indazol-6-yl)-N4-isopropylpyridine-2,4-diamine

Step 1: 2-Chloro-5-iodo-N-isopropylpyridin-4-amine (0.15 g, 0.506 mmol) in Acetonitrile (2 mL) was added Na$_2$CO$_3$ (0.161 g, 1.518 mmol) followed by 1H-indazole-5-boronic acid pinacol ester (0.124 g, 0.508 mmol) and tetrakistriphenyl phosphine Pd(0) (0.026 g, 0.023 mmol). The reaction was thoroughly degassed and subjected to microwave radiation at 110 C for 2 hours. The reaction mixture was concentrated to remove acetonitrile, added water (10 mL) and extracted with ethyl acetate (3 times×10 mL). The combined extracts were dried purified via column chromatography. The reaction was performed 3 times to provide of 30 mg which was used directly in the next step.

Step 2: 2-Chloro-5-(1H-indazol-5-yl)-N-isopropylpyridin-4-amine (30 mg, 0.105 mmol) in Dioxane (1 ml) in a microwave vial was added Xantphos (48.4 mg, 0.084 mmol), cesium carbonate (102 mg, 0.314 mmol), 6-aminobenzothiazole (18.8 mg, 0.126 mmol) and Pd$_2$(dba)$_3$ (38.3 mg, 0.042 mmol) and purged with N$_2$ thoroughly for 10 minutes. The reaction mass was subjected to microwave radiation for 3 hours at 150° C. The crude mass was passed through a celite bed and the filtrate was concentrated to remove dioxane then added 10 mL of water and extracted with DCM (3 times×8 mL). The combined organic layers were dried and concentrated. The crude mass was purified by prep TLC first and then preparative HPLC to give Example 177. $^1$H NMR: 400 MHz, CD$_3$OD: δ 1.20 (d, J=6.40 Hz, 6H), 3.70-3.73 (m, 1H), 6.20 (s, 1H), 7.41 (dd, J=1.60, 8.80 Hz, 1H), 7.52 (dd, J=2.40, 8.80 Hz, 1H), 7.67-7.69 (m, 2H), 7.79 (dd, J=0.80, 1.20 Hz, 1H), 7.98 (d, J=9.20 Hz, 1H), 8.13 (s, 1H), 8.33 (d, J=2.00 Hz, 1H), 9.07 (s, 1H). LC/MS: ZORBAX SB C18, 4.6×50 mm, 5 μm; Solvent A=10% MeOH: 90% H₂O: 0.1% TFA; Solvent B=90% MeOH: 10% H₂O: 0.1% TFA; gradient 0-100% B over 2 min (3 min run time); retention time: 1.482 min; LCMS (ES-API), m/z 401.2 (M+H). HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 6.211 min; Purity: 99.3%.

Example 178

3-((5-(4-(Isopropylamino)-6-(quinoxalin-6-ylamino)pyridin-3-yl)-1,3,4-oxadiazol-2-yl)amino)propan-1-ol

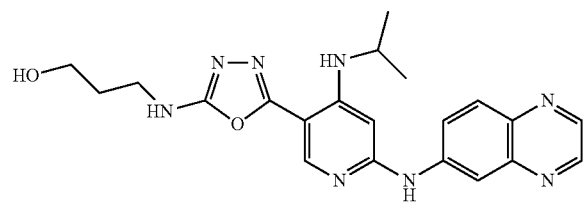 [SMILES: CC(C)Nc1cc(Nc2ccc3nccnc3c2)ncc1-c1nnc(NCCCO)o1]

Example 178 was prepared according to the general methods outlined in Scheme 5. ¹H NMR: 400 MHz, DMSO-d₆: δ 1.31 (d, J=6.40 Hz, 6H), 1.73-1.76 (m, 2H), 3.33 (2H, merged with water peak), 3.48-3.52 (m, 2H), 3.74-3.75 (m, 1H), 4.49-4.51 (m, 1H), 6.27 (s, 1H), 7.59 (d, J=7.20 Hz, 1H), 7.77 (t, J=5.60 Hz, 1H), 7.90-7.97 (m, 2H), 8.37 (s, 1H), 8.68-8.69 (m, 2H), 8.79 (d, J=2.00 Hz, 1H), 9.66 (s, 1H). LC/MS: Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.374 min; LCMS (ES-API), m/z 421.2 (M+H). HPLC: XBridge Phenyl (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 30 min (36 min run time); Flow rate: 1.0 μl/min; Retention time: 10.606 min; Purity: 97.8%.

Example 179

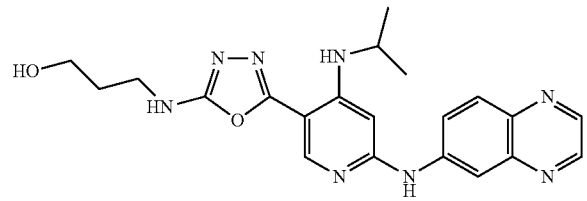 [SMILES: CC(C)Nc1cc(Nc2ccc3nccnc3c2)ncc1-c1nnc(NCCCO)o1]

Example 179 was prepared according to the general methods outlined in Scheme 5. ¹H NMR: 400 MHz, DMSO-d₆: δ 1.31 (d, J=6.40 Hz, 6H), 1.74-1.77 (m, 2H), 3.32 (2H, merged with water peak), 3.52-3.53 (m, 2H), 3.72-3.77 (m, 1H), 4.50-4.53 (m, 1H), 6.25 (s, 1H), 7.57 (d, J=7.20 Hz, 1H), 7.75 (t, J=5.60 Hz, 1H), 7.92 (d, J=9.20 Hz, 1H), 8.04-8.07 (m, 1H), 8.37 (s, 1H), 8.66 (d, J=2.40 Hz, 1H), 9.09 (s, 1H), 9.44 (s, 1H), 9.63 (s, 1H). LC/MS: Purospher@star RP-18, 4×55 mm, 3 μm; Solvent A=10% ACN: 90% H₂O: 20 mM NH₄OAc; Solvent B=90% ACN: 10% H₂O: 20 mM NH₄COOAc; gradient 0-100% B over 1.5 min (3.2 min run time); retention time: 1.337 min; LCMS (ES-API), m/z 419.2 (M−H). HPLC: Eclipse XDB C18 (150×4.6 mm) 5 micron; Solvent A=20 mM NH₄OAc in water; Solvent B=ACN; gradient 0-100% B over 23 min; Flow rate=1.0 ml/min; Retention time: 14.52 min; Purity: 95.4%.

The compounds shown in Table 13 were prepared according to the general methods used for the preparation of Example 2, appropriately substituting reagents as needed to provide the examples below.

TABLE 13

| Example No. | R₁ | R₂ |
|---|---|---|
| 180 | ![HO-pyrrolidine] | ![quinazoline-NH] |
| 181 | ![HO-pyrrolidine] | ![pyrazolo[1,5-a]pyridine-NH] |
| 182 | ![HO-pyrrolidine] | ![imidazo-pyridazine-NH] |

Example 180

(3-Hydroxypyrrolidin-1-yl)(5-(4-(isopropylamino)-6-(quinoxalin-6-ylamino)pyridin-3-yl)-1,3,4-thiadiazol-2-yl)methanone, 20 mg LC/MS: m/z 477.2 (M+H); HPLC: Eclipse XDB C18 (150×4.6 mm) 5 micron; Solvent A=20 mM NH₄OAc in water; Solvent B=ACN; gradient 0-100% B over 23 min; Flow rate=1.0 ml/min; Retention time: 14.52 min; Purity: 97%.

Example 181

(R)-(3-Hydroxypyrrolidin-1-yl)(5-(4-(isopropylamino)-6-(pyrazolo[1,5-a]pyridin-5-ylamino)pyridin-3-yl)-1,3,4-thiadiazol-2-yl)methanone, 20 mg LC/MS: m/z 465.2 (M+H); HPLC: HPLC: Sunfire C18 (150×4.6 mm), 3.5 micron; Solvent A=5% ACN: 95% H₂O: 0.05% TFA pH=2.5; Solvent B=95% ACN: 5% H₂O: 0.05% TFA pH=2.5; gradient 0-100% B over 15 min (23 min run time); Flow rate: 1.0 μl/min; Retention time: 5.30 min; Purity: 99.8%.

Example 182

(R)-(3-Hydroxypyrrolidin-1-yl)(5-(6-(imidazo[1,2-b]pyridazin-6-ylamino)-4-(isopropylamino)pyridin-3-yl)-1,3,4-thiadiazol-2-yl)methanone, 20 mg LC/MS: m/z 466.2 (M+H); HPLC: HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 7.77 min; Purity: 99.3%.

Additional compounds (Examples 183-186) were prepared according to the methods outlined for Example 2.

Example 183

(5-(4-(Cyclobutylamino)-6-(quinoxalin-6-ylamino)pyridin-3-yl)-1,3,4-thiadiazol-2-yl)(3-hydroxypyrrolidin-1-yl)methanone, 25 mg

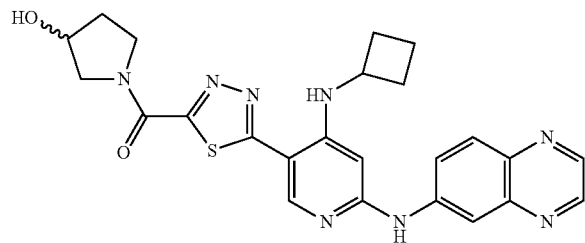 [SMILES: O=C(c1nnc(-c2cnc(Nc3ccc4nccnc4c3)cc2NC2CCC2)s1)N1CCC(O)C1]

LC/MS: m/z 489.2 (M+H); HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 5.74 min; Purity: 95.9%.

Example 184

(5-(4-(Cyclopropylamino)-6-(quinolin-6-ylamino)pyridin-3-yl)-1,3,4-thiadiazol-2-yl)(3-hydroxypyrrolidin-1-yl)methanone

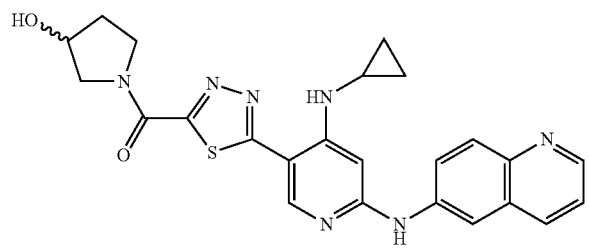 [SMILES: O=C(c1nnc(-c2cnc(Nc3ccc4ncccc4c3)cc2NC2CC2)s1)N1CCC(O)C1]

LC/MS: m/z 473.9 (M+H); HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 15 min (23 min run time); Flow rate: 1.0 μl/min; Retention time: 8.95 min; Purity: 99.1%.

Example 185

(5-(6-(Benzo[d]thiazol-6-ylamino)-4-((tetrahydro-2H-pyran-4-yl)amino)pyridin-3-yl)-1,3,4-thiadiazol-2-yl)(3-hydroxypyrrolidin-1-yl)methanone, 8 mg

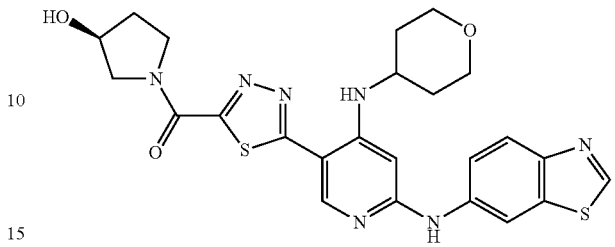

LC/MS: m/z 524.0 (M+H); HPLC: Eclipse XDB C18 (150×4 6 mm) 5 micron; Solvent A=20 mM NH$_4$OAc in water; Solvent B=ACN; gradient 0-100% B over 23 min; Flow rate=1.0 ml/min; Retention time: 7.63 min; Purity: 94.3%.

Example 186

(5-(4-((2-Fluorocyclopentyl)amino)-6-(quinoxalin-6-ylamino)pyridin-3-yl)-1,3,4-oxadiazol-2-yl)(3-hydroxypyrrolidin-1-yl)methanone, 1.5 mg

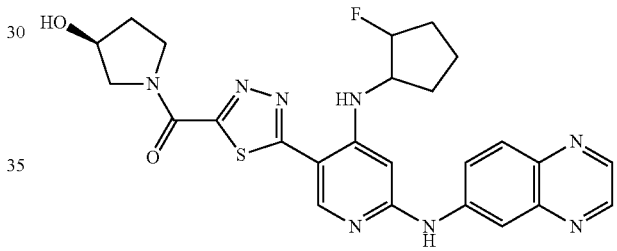

LC/MS: m/z 519.2 (M+H); HPLC: Xbridge Phenyl C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 12 min (15 min run time); Flow rate: 1.0 μl/min; Retention time: 6.63 min; Purity: 94.6%.

Example 187

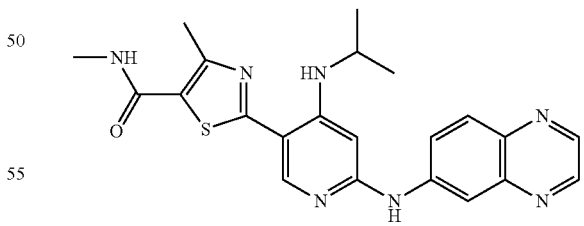

Prepared according to the method outlined for Example 21 and 22. 2-(4-(isopropylamino)-6-(quinoxalin-6-ylamino)pyridin-3-yl)-N,5-dimethylthiazole-4-carboxamide, 35 mg. LC/MS: m/z 434.5 (M+H); HPLC: Xbridge Phenyl C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 12 min (15 min run time); Flow rate: 1.0 μl/min; Retention time: 6.56 min; Purity: 96.8%.

Example 188

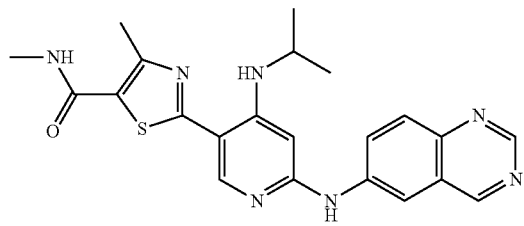 [SMILES: CNC(=O)c1sc(-c2cnc(Nc3ccc4ncncc4c3)cc2NC(C)C)nc1C]

Prepared according to the method outlined for Example 21 and 22. 2-(4-(isopropylamino)-6-(quinazolin-6-ylamino)pyridin-3-yl)-N,5-dimethylthiazole-4-carboxamide, 25 mg. LC/MS: m/z 434.2 (M+H); HPLC: Xbridge Phenyl C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 12 min (20 min run time); Flow rate: 1.0 µl/min; Retention time: 12.97 min; Purity: 91.2%.

Example 189

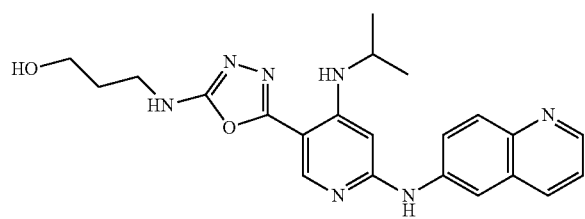 [SMILES: CC(C)Nc1cc(Nc2ccc3ncccc3c2)ncc1-c1nnc(NCCCO)o1]

Prepared according to the methods outlined for Examples 111 and 134 3-((5-(4-(cyclopropylamino)-6-(quinolin-6-ylamino)pyridin-3-yl)-1,3,4-oxadiazol-2-yl)amino)propan-1-ol, 5 mg. LC/MS: m/z 417.8 (M+H); HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 18 min (23 min run time); Flow rate: 1.0 µl/min; Retention time: 7.51 min; Purity: 96.6%.

Example 190

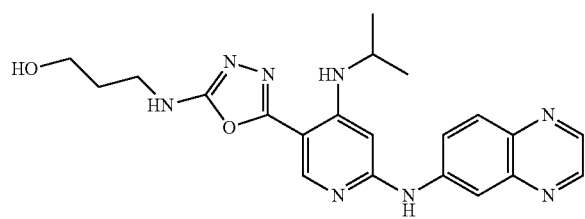 [SMILES: CC(C)Nc1cc(Nc2ccc3nccnc3c2)ncc1-c1nnc(NCCCO)o1]

Prepared according to the methods outlined for Examples 111 and 134. 3-((5-(4-(cyclopropylamino)-6-(quinoxalin-6-ylamino)pyridin-3-yl)-1,3,4-oxadiazol-2-yl)amino)propan-1-ol, 6 mg. LC/MS: m/z 418.8 (M+H); HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 18 min (23 min run time); Flow rate: 1.0 µl/min; Retention time: 9.02 min; Purity: 98.1%.

Example 191

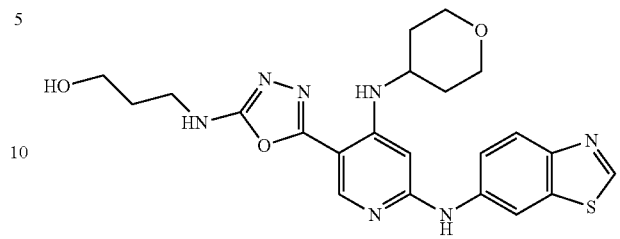

Prepared according to the methods outlined for Examples 111 and 134. 3-((5-(6-(benzo[d]thiazol-6-ylamino)-4-((tetrahydro-2H-pyran-4-yl)amino)pyridin-3-yl)-1,3,4-oxadiazol-2-yl)amino)propan-1-ol, 10 mg. LC/MS: m/z 468.2 (M+H); HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 12 min (15 min run time); Flow rate: 1.0 µl/min; Retention time: 5.14 min; Purity: 97.3%.

Example 192

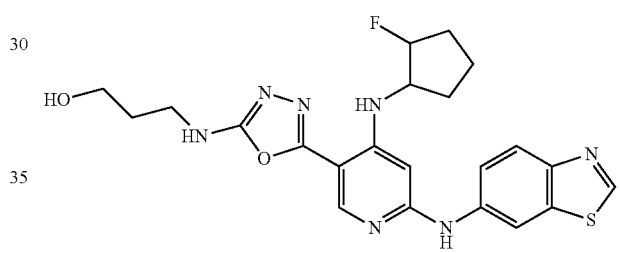

Prepared according to the methods outlined for Examples 111 and 134. 3-((5-(6-(benzo[d]thiazol-6-ylamino)-4-((2-fluorocyclopentyl)amino)pyridin-3-yl)-1,3,4-oxadiazol-2-yl)amino)propan-1-ol, 8 mg. LC/MS: m/z 470.2 (M+H); HPLC: Sunfire C18 (150×4.6 mm), 3.5 micron; Solvent A=5% ACN: 95% H$_2$O: 0.05% TFA pH=2.5; Solvent B=95% ACN: 5% H$_2$O: 0.05% TFA pH=2.5; gradient 0-100% B over 12 min (15 min run time); Flow rate: 1.0 µl/min; Retention time: 5.98 min; Purity: 93.5%.

Example 193

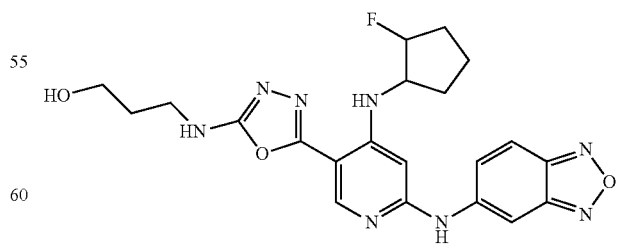

Prepared according to the methods outlined for Examples 111 and 134. 3-((5-(6-(benzo[c][1,2,5]oxadiazol-5-ylamino)-4-((2-fluorocyclopentyl)amino)pyridin-3-yl)-1,3,4-oxadiazol-2-yl)amino)propan-1-ol, 26 mg. LC/MS: m/z 453.2 (M–H); HPLC: Sunfire C18 (150×4.6 mm), 3.5 micron; Solvent A=5% ACN: 95% $H_2O$: 0.05% TFA pH=2.5; Solvent B=95% ACN: 5% $H_2O$: 0.05% TFA pH=2.5; gradient 0-100% B over 12 min (15 min run time); Flow rate: 1.0 μl/min; Retention time: 6.85 min; Purity: 96.6%.

What is claimed is:

1. A compound having the following formula:

(I)

or a stereoisomer or pharmaceutically-acceptable salt thereof, wherein

X is N;
R is —C(=O)—$R^1$, —C(=O)O—$R^1$ or —C(=O)$NR^{11}$—$R^1$;
$R^1$ is piperidinyl substituted with 0-3 $R^{1a}$;
$R^{1a}$ is hydrogen, —$OCF_3$, —CN, —$(CH_2)_rOR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$S(O)_pNR^{11}R11$, —$NR^bS(O)_pR^c$, —$S(O)_2R^c$, or $C_{1-6}$ alkyl substituted with 0-2 $R^a$;
$R^2$ is benzo[d]thiazolyl;
$R^3$ is propyl substituted with 0-3 $R^{3a}$;
$R^{3a}$ is —OH or phenyl;
$R^{11}$ at each occurrence is hydrogen;
$R^a$ is $R^d$, F, Cl, Br, $OCF_3$, $CF_3$, $CHF_2$, or CN;
$R^b$ is $R^e$, $C_{1-6}$ alkyl, or $C_{1-6}$ haloalkyl;
$R^c$ is $CH_3$;
$R^d$ is hydrogen;
$R^e$ is hydrogen;
p is 0, 1, or 2; and
r is 0, 1, or 2.

2. The compound of claim 1, or a stereoisomer or pharmaceutically-acceptable salt thereof, wherein $R^2$ is 3. The compound according to claim 1, or a stereoisomer or pharmaceutically-acceptable salt thereof, wherein $R^3$ is —$CH(CH_3)_2$.

4. The compound according to claim 1, or a stereoisomer or pharmaceutically-acceptable salt thereof, wherein $R^{1a}$ is —OH or —$NH_2$.

5. The compound according to claim 1 or a stereoisomer or pharmaceutically acceptable salt thereof, wherein:
R is —C(=O)—$R^1$;
$R^1$ is piperidinyl substituted with 0-1 $R^{1a}$; and
$R^{1a}$ is hydrogen, —OH, or —$NH_2$.

6. The compound according to claim 1, or a stereoisomer or pharmaceutically-acceptable salt thereof, wherein said compound is selected from and 7. A pharmaceutical composition comprising one or more compounds according to claim 1 and a pharmaceutically acceptable carrier or diluent.

* * * * *